(12) United States Patent
Zak et al.

(10) Patent No.: US 11,453,671 B2
(45) Date of Patent: Sep. 27, 2022

(54) PYRAZOLOPYRIMIDINE INHIBITORS OF JAK KINASES AND USES THEREOF

(71) Applicant: Genentech, Inc., South San Francisco, CA (US)

(72) Inventors: Mark Edward Zak, South San Francisco, CA (US); Naomi S. Rajapaksa, South San Francisco, CA (US); Yun-Xing Cheng, Beijing (CN); Jessica Grandner, South San Francisco, CA (US); Daniel G. M. Shore, Redwood City, CA (US); Marian C. Bryan, Fort Washington, PA (US)

(73) Assignee: Genentech, Inc., South San Francisco, CA (US)

( * ) Notice: Subject to any disclaimer, the term of this patent is extended or adjusted under 35 U.S.C. 154(b) by 98 days.

(21) Appl. No.: 16/902,499

(22) Filed: Jun. 16, 2020

(65) Prior Publication Data

US 2020/0399275 A1 Dec. 24, 2020

Related U.S. Application Data

(60) Provisional application No. 63/035,381, filed on Jun. 5, 2020.

(51) Int. Cl.
| | | |
|---|---|---|
| *A61K 31/519* | (2006.01) |
| *C07D 487/04* | (2006.01) |
| *A61P 11/06* | (2006.01) |
| *A61K 9/00* | (2006.01) |
| *A61K 9/19* | (2006.01) |

(52) U.S. Cl.
CPC .......... *C07D 487/04* (2013.01); *A61K 9/0075* (2013.01); *A61K 9/19* (2013.01); *A61P 11/06* (2018.01)

(58) Field of Classification Search
CPC ............................ A61K 31/519; C07D 487/04
USPC ........................................ 514/259.3; 544/281
See application file for complete search history.

(56) References Cited

FOREIGN PATENT DOCUMENTS

| WO | 2011/003065 A2 | 1/2011 |
| WO | 2015/177326 A1 | 11/2015 |
| WO | 2017/089390 A1 | 6/2017 |
| WO | 2017/140825 A1 | 8/2017 |
| WO | 2018/122212 A1 | 7/2018 |
| WO | 2018/166993 A2 | 9/2018 |
| WO | 2018/215389 A1 | 11/2018 |
| WO | 2018/215390 A1 | 11/2018 |
| WO | 2019/139714 A1 | 7/2019 |
| WO | WO-2019139714 A1 * | 7/2019 | .............. A61P 37/00 |
| WO | 2020/257142 A1 | 12/2020 |
| WO | 2020/257143 | 12/2020 |

OTHER PUBLICATIONS

Jordan, V. C. Nature Reviews: Drug Discovery, 2, 2003, 205.*
Hackam, et al. JAMA, 296(14), 2006, 1731-1732.*
International Search Report and Written Opinion for PCT/US2020/037853 dated Sep. 7, 2020.
ISR and Written Opinion for PCT/EP2018/063263.

* cited by examiner

*Primary Examiner* — Douglas M Willis
(74) *Attorney, Agent, or Firm* — Robert C. Hall

(57) ABSTRACT

Compounds of formula (I)

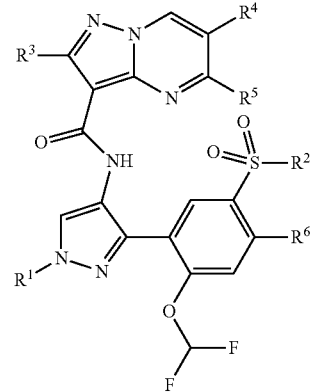

wherein $R^1$, $R^2$, $R^3$, $R^4$, $R^5$ and $R^6$ are as defined herein, and salts thereof that are useful as JAK kinse inhibitors are described herein. Also provided are pharmaceutical compositions that include such a JAK inhibitor and a pharmaceutically acceptable carrier, adjuvant or vehicle, and methods of treating or lessening the severity of a disease or condition responsive to the inhibition of a Janus kinase activity in a patient.

12 Claims, No Drawings

PYRAZOLOPYRIMIDINE INHIBITORS OF JAK KINASES AND USES THEREOF

CROSS REFERENCE TO RELATED APPLICATIONS

This application claims priority to International Application No. PCT/CN2019/091712 filed on lime 18, 2019, and US. Provisional Application No. 63/035,381 filed on Jun. 5, 2020, the disclosures of which are incorporated herein by reference.

FIELD OF THE INVENTION

The invention relates to compounds that are inhibitors of a Janus kinase, such as JAK1 and JAK2, as well as compositions containing these compounds, and methods of use including, but not limited to, diagnosis or treatment of patients suffering from a condition responsive to the inhibition of a JAK kinase.

BACKGROUND OF INVENTION

Cytokine pathways mediate a broad range of biological functions, including many aspects of inflammation and immunity. Janus kinases (JAK), including JAK1, JAK2, JAK3 and TYK2, are cytoplasmic protein kinases that associate with type I and type II cytokine receptors and regulate cytokine signal transduction. Cytokine engagement with cognate receptors triggers activation of receptor associated JAKs and this leads to JAK-mediated tyrosine phosphorylation of signal transducer and activator of transcription (STAT) proteins and ultimately transcriptional activation of specific gene sets (Schindler et al., 2007, J. Biol. Chem. 282: 20059-63). JAK1, JAK2 and TYK2 exhibit broad patterns of gene expression, while JAK3 expression is limited to leukocytes. Cytokine receptors are typically functional as heterodimers, and as a result, more than one type of JAK kinase is usually associated with cytokine receptor complexes. The specific JAKs associated with different cytokine receptor complexes have been determined in many cases through genetic studies and corroborated by other experimental evidence. Exemplary therapeutic benefits of the inhibition of JAK enzymes are discussed, for example, in International Application No. WO 2013/014567.

JAK1 was initially identified in a screen for novel kinases (Wilks A. F., 1989, Proc. Natl. Acad. Sci. U.S.A. 86:1603-1607). Genetic and biochemical studies have shown that JAK1 is functionally and physically associated with the type I interferon (e.g., IFNalpha), type II interferon (e.g., IFN-gamma), and IL-2 and IL-6 cytokine receptor complexes (Kisseleva et al., 2002, Gene 285:1-24; Levy et al., 2005, Nat. Rev. Mol. Cell Biol. 3:651-662; O'Shea et al., 2002, Cell, 109 (suppl.): S121-S131). JAK1 knockout mice die perinatally due to defects in LIE receptor signaling (Kisseleva et al., 2002, Gene 285:1-24; O'Shea et al., 2002, Cell, 109 (suppl.): S121-S131). Characterization of tissues derived from JAK1 knockout mice demonstrated critical roles for this kinase in the IFN, IL-10, IL-2/IL-4 and IL-6 pathways. A humanized monoclonal antibody targeting the IL-6 pathway (Tocilizumab) was approved by the European Commission for the treatment of moderate-to-severe rheumatoid arthritis (Scheinecker et al., 2009, Nat. Rev. Drug Discov. 8:273-274).

CD4 T cells play an important role in asthma pathogenesis through the production of TH2 cytokines within the lung, including IL-4, IL-9 and IL-13 (Cohn et al., 2004, Amur Rev. Immunol. 22:789-815). IL-4 and IL-13 induce increased mucus production, recruitment of eosinophils to the lung, and increased production of IgE (Kasaian et al., 2008, Biochem. Pharmacol. 76(2): 147-155). IL-9 leads to mast cell activation, which exacerbates the asthma symptoms (Kearley et al., 2011, Am. J. Resp. Crit. Care Med., 183(7): 865-875). The IL-4R$\alpha$ chain activates JAK1 and binds to either IL-4 or IL-13 when combined with the common gamma chain or the IL-13R$\alpha$1 chain respectively (Pernis et al., 2002, J. Clin. Invest. 109(10): 1279-1283). The common gamma chain can also combine with IL-9R$\alpha$ to bind to IL-9, and IL-9R$\alpha$ activates JAK1 as well (Demoulin et al., 1996, Mol. Cell Biol. 16(9):4710-4716). While the common gamma chain activates JAK3, it has been shown that JAK1 is dominant over JAK3, and inhibition of JAK1 is sufficient to inactivate signaling through the common gamma chain despite JAK3 activity (Haan et al., 2011, Chem. Biol. 18(3):314-323). Inhibition of IL-4, IL-13 and IL-9 signaling by blocking the JAK/STAT signaling pathway can alleviate asthmatic symptoms in pre-clinical lung inflammation models (Mathew et al., 2001, J. Exp. Med. 193(9): 1087-1096; Kudlacz et. al., 2008, Eur. J. Pharmacol. 582(1-3): 154-161).

Biochemical and genetic studies have shown an association between JAK2 and single-chain (e.g., EPO), IL-3 and interferon gamma cytokine receptor families (Kisseleva et al., 2002, Gene 285:1-24; Levy et al., 2005, Nat. Rev. Mol. Cell Biol. 3:651-662; O'Shea et al., 2002, Cell, 109 (suppl.): S121-S131). Consistent with this, JAK2 knockout mice die of anemia (O'Shea et al., 2002, Cell, 109 (suppl.): S121-S131). Kinase activating mutations in JAK2 (e.g., JAK2 V617F) are associated with myeloproliferative disorders in humans. Additionally, JAK2 associates with the receptors for cytokines such as IL-5 and Thymic stromal lymphopoietin (TSLP). IL-5 is the key cytokine responsible for eosinophil differentiation, growth, activation, survival, and recruitment to airways (Pelaia et al., 2019, Front. Physiol., 10: 1514; Stirling et al., 2001, Am. J. Respir. Crit. Care Med., 164: 1403-9; Lulkerson and Rothenberg, 2013, Nat. Rev. Drug Discov., 12: 117-9.; Varricchi and Canonica, 2016, Expert. Rev. Clin. Immunol., 12: 903-5). Three monoclonal antibody drugs targeting either IL-5 (Mepolizumab, Reslizumab) or the alpha chain of its receptor (Benralizumab) have been approved as treatments for asthma with an eosinophilic phenotype. TSLP is an epithelial-cell-derived cytokine that plays an important role in the regulation of type II immunity and serves as an alarmin upstream of TH2 cytokine production (Kitajima et al., 2011, Eur J Immunol., 41: 1862-71). Tezepelumab is an antagonist antibody to TSLP. Results from a phase 2 trial indicate it successfully reduced asthma exacerbations in patients both with and without Type 2-high signatures (Corren et al., 2017, 377: 936-46).

JAK3 associates exclusively with the gamma common cytokine receptor chain, which is present in the IL-2, IL-4, IL-7, IL-9, IL-15 and IL-21 cytokine receptor complexes. JAK3 is critical for lymphoid cell development and proliferation and mutations in JAK3 result in severe combined immunodeficiency (SCID) (O'Shea et al., 2002, Cell, 109 (suppl.): S121-S131). Based on its role in regulating lymphocytes, JAK3 and JAK3-mediated pathways have been targeted for immunosuppressive indications (e.g., transplantation rejection and rheumatoid arthritis) (Baslund et al., 2005, Arthritis & Rheumatism 52:2686-2692; Changelian et al., 2003, Science 302: 875-878).

TYK2 associates with the type I interferon (e.g., IFNalpha), IL-6, IL-10, IL-12 and IL-23 cytokine receptor complexes (Kisseleva et al., 2002, Gene 285:1-24; Watford, W. T. & O'Shea, J. J., 2006, Immunity 25:695-697). Consistent with this, primary cells derived from a TYK2 deficient human are defective in type I interferon, IL-6, IL-10, IL-12 and IL-23 signaling. A fully human monoclonal antibody targeting the shared p40 subunit of the IL-12 and IL-23 cytokines (Ustekinumab) was recently approved by the European Commission for the treatment of moderate-to-severe plaque psoriasis (Krueger et al., 2007, N. Engl. J. Med. 356:580-92; Reich et al., 2009, Nat. Rev. Drug Discov. 8:355-356). In addition, an antibody targeting the IL-12 and IL-23 pathways underwent clinical trials for treating Crohn's Disease (Mannon et al., 2004, N. Engl. J. Med. 351:2069-79).

International Patent Application Publication Numbers WO 2010/051549, WO 2011/003065, WO 2015/177326 and WO 2017/089390 discuss certain pyrazolopyrimidine compounds that are reported to useful as inhibitors of one or more Janus kinases. Data for certain specific compounds showing inhibition of JAK1 as well as JAK2, JAK3, and/or TYK2 kinases is presented therein.

Currently there remains a need for additional compounds that are inhibitors of Janus kinases. For example, there is a need for compounds that possess useful potency as inhibitors of one or more Janus kinases (e.g., JAK1 and JAK2)-in combination with other pharmacological properties that are necessary to achieve a useful therapeutic benefit. For example, there is a need for potent compounds that demonstrate selectivity for one Janus kinase over other kinases in general (e.g., selectivity for JAK1 and/or JAK2 over other kinases such as leucine-rich repeat kinase 2 (LRRK2)). There is also a need for potent compounds that demonstrate selectivity for one Janus kinase over other Janus kinases (e.g., selectivity for JAK1 and/or JAK2 over JAK3 and/or TYK2). Compounds demonstrating selectivity for both JAK1 and JAK2 over JAK3 and TYK2 could provide a therapeutic benefit, in conditions responsive to the inhibition of JAK1. Additionally there is currently a need for potent JAK1 inhibitors that possess other properties (e.g., melting point, pK, solubility, etc.) necessary for formulation and administration by inhalation. Such compounds would be particularly useful for treating conditions such as, for example, asthma.

There accordingly exists a need in the art for additional or alternative treatments of conditions mediated by JAK kinases, such as those described above. There is in particular a need for JAK1 and JAK2 kinase inhibitors usable for inhaled delivery in the treatment of airway inflammation indications such as asthma.

SUMMARY OF THE INVENTION

Provided herein are pyrazolopyrimidines that inhibit JAK kinases, such as selected from a compound of Formula (I) a stereoisomer or salt thereof, such as a pharmaceutically acceptable salt thereof. The JAK kinase may be JAK1, JAK2, or both.

One embodiment provides a compound of Formula (I):

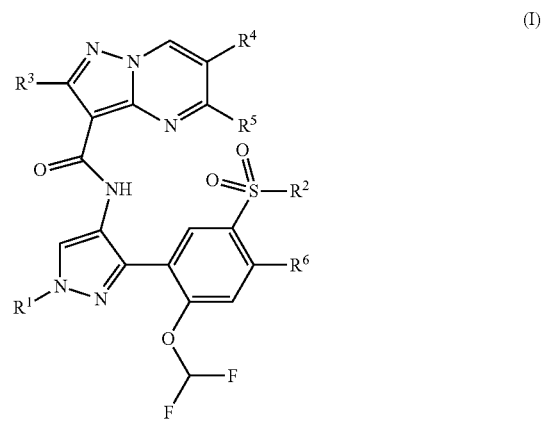

or a pharmaceutically acceptable salt thereof,
wherein:
$R^1$ is: $C_{1-6}$alkyl; cyano-$C_{1-6}$alkyl; $C_{1-6}$alkoxy-(CO)—; —(CHR$^a$)$_m$—NR$^b$R$^c$; or —(CHR$^a$)$_n$-het$^1$;
$R^2$ is: $C_{1-6}$alkyl; hydroxy-$C_{1-6}$alkyl; halo-$C_{1-6}$alkyl; $C_{1-6}$alkoxy-$C_{1-6}$alkyl; $C_{3-6}$cycloalkyl; —(CHR$^a$)$_p$—NR$^b$R$^c$; het$^2$; —(CHR$^a$)$_q$-het$^3$; or phenyl which may be unsubstituted or substituted once or twice with R$^d$;
$R^3$ is: hydrogen; amino; or $C_{1-6}$alkyl;
$R^4$ is: hydrogen; or $C_{1-6}$alkyl;
$R^5$ is: hydrogen; or $C_{1-6}$alkyl;
$R^6$ is: hydrogen; $C_{1-6}$alkyl; or $R^2$ and $R^6$ together with the atoms to which they are attached may form a six membered ring;
m is from 2 to 3;
n is from 0 to 2;
p is from 0 to 2;
each $R^a$ is independently: hydrogen; or $C_{1-6}$alkyl;
each $R^b$ is independently: hydrogen; or $C_{1-6}$alkyl;
each $R^c$ is independently: hydrogen; or $C_{1-6}$alkyl;
het$^1$ is: tetrahydrofuranyl; azetidinyl; or pyrrolidinyl, each of which may be unsubstituted or substituted once or twice with R$^e$;
het$^2$ is: pyridinyl; pyrimidinyl; pyrazolyl; imidazolyl; or isoquinolinyl which may be partially saturated; each of which may be unsubstituted or substituted once or twice with R$^f$;
het$^3$ is: azetidinyl; pyrrolidinyl; oxetanyl; or piperidinyl; each of which may be unsubstituted or substituted once with R$^g$;
each $R^d$ is independently: $C_{1-6}$alkyl; hydroxy; $C_{1-6}$alkoxy-$C_{1-6}$alkyl; —(CHR$^a$)$_q$—NR$^b$R$^c$; or phenyl;
each $R^e$ is independently: $C_{1-6}$alkyl; or oxo;
each $R^f$ is independently: $C_{1-6}$alkyl; hydroxy-$C_{1-6}$alkyl; oxo; —(CHR$^a$)$_r$—NR$^b$R$^c$; —(CHR$^a$)$_s$-het$^4$;
each $R^g$ is independently: $C_{1-6}$alkyl; or acetyl;
q is from 1 to 2;
r is from 2 to 3;
s is from 2 to 3; and
het$^4$ is: azetidin-1-yl; 1-methyl-azetidin-3-yl; quinuclidinyl; 1-methyl-pyrrolidin-2-yl; or 4-methylpiperazin-1-yl.

Also provided is a pharmaceutical composition comprising a JAK inhibitor as described herein, or a pharmaceutically acceptable salt thereof, and a pharmaceutically acceptable carrier, dilient or excipient.

Also provided is the use of a JAK inhibitor as described herein, or a pharmaceutically acceptable salt thereof in therapy, such as in the treatment of an inflammatory disease (e.g., asthma). Also provided is the use of a JAK inhibitor as described herein or a pharmaceutically acceptable salt thereof for the preparation of a medicament for the treatment of an inflammatory disease. Also provided is a method of preventing, treating or lessening the severity of a disease or condition responsive to the inhibition of a Janus kinase activity in a patient, comprising administering to the patient a therapeutically effective amount of a JAK inhibitor as described herein or a pharmaceutically acceptable salt thereof.

The most validated cytokines in asthma (IL-4, IL-5, IL-9, IL-13, and TSLP) all signal through JAK1 and/or JAK2. The compounds of the invention are active for both JAK1 and JAK2. Certain of these compounds optimally have well-balanced co-activity for both JAK1 and JAK2, or have slightly higher affinity for JAK1 over JAK2, rather than having a much greater activity for one of these kinases over the other. The subject compounds also have good selectivity against off-target kinases such as LRRK2, which has been associated with pulmonary toxicity.

While many compounds may exhibit high affinity for both JAK1 and JAK2 in simple biochemical assays, not all such compounds are effective at mediating the relevant cytokines associated with JAK1 and JAK2. Certain compounds of the invention, in addition to being active for both JAK1 and JAK2, are also shown in cell-based assays to be effective at mediation of asthma-relevant cytokines associated with JAK1 and JAK2.

Compounds of the invention also exhibit favorable pharmacokinetic (PK) properties in lung tissue and are useful for inhaled therapies. When dosed via the inhaled route using techniques such as dry powder inhalation (DPI) or intranasal (IN) delivery, certain compounds unexpectedly show sustained retention within the lung tissue, with much lower concentrations in systemic circulation. Such improved PK properties can advantageously result in smaller dosages and less frequent dosing requirements for effective therapies. Certain compounds exhibit unexpected improved solubility, again providing improved efficacy in lung. Certain compounds of the invention also exhibit unexpected reduction in cytotoxicity in comparison to other JAK inhibitors.

DETAILED DESCRIPTION OF THE INVENTION

Definitions

"Halogen" or "halo" refers to F, Cl, Br or I. Additionally, terms such as "haloalkyl," are meant to include monohaloalkyl and polyhaloalkyl, wherein one or more halogens replace a hydrogen(s) of an alkyl group.

The term "alkyl" refers to a saturated linear or branched-chain monovalent hydrocarbon radical, wherein the alkyl radical may be optionally substituted. In one example, the alkyl radical is one to eighteen carbon atoms ($C_1$-$C_{18}$). In other examples, the alkyl radical is $C_0$-$C_6$, $C_0$-$C_5$, $C_0$-$C_3$, $C_1$-$C_{12}$, $C_1$-$C_{10}$, $C_1$-$C_8$, $C_1$-$C_6$, $C_1$-$C_5$, $C_1$-$C_4$, or $C_1$-$C_3$. $C_0$ alkyl refers to a bond. Examples of alkyl groups include methyl (Me, —$CH_3$), ethyl (Et, —$CH_2CH_3$), 1-propyl (n-Pr, n-propyl, —$CH_2CH_2CH_3$), 2-propyl (i-Pr, i-propyl, —CH($CH_3$)$_2$), 1-butyl (n-Bu, n-butyl, —$CH_2CH_2CH_2CH_3$), 2-methyl-1-propyl (i-Bu, i-butyl, —$CH_2CH(CH_3)_2$), 2-butyl (s-Bu, s-butyl, —CH($CH_3$)$CH_2CH_3$), 2-methyl-2-propyl (t-Bu, t-butyl, —C($CH_3$)$_3$), 1-pentyl (n-pentyl, —$CH_2CH_2CH_2CH_2CH_3$), 2-pentyl (—CH($CH_3$)$CH_2CH_2CH_3$), 3-pentyl (—CH($CH_2CH_3$)$_2$), 2-methyl-2-butyl (—C($CH_3$)$_2CH_2CH_3$), 3-methyl-2-butyl (—CH($CH_3$)CH($CH_3$)$_2$), 3-methyl-1-butyl (—$CH_2CH_2CH(CH_3)_2$), 2-methyl-1-butyl (—$CH_2CH(CH_3)CH_2CH_3$), 1-hexyl (—$CH_2CH_2CH_2CH_2CH_2CH_3$), 2-hexyl (—CH($CH_3$)$CH_2CH_2CH_2CH_3$), 3-hexyl (—CH($CH_2CH_3$)($CH_2CH_2CH_3$)), 2-methyl-2-pentyl (—C($CH_3$)$_2CH_2CH_2CH_3$), 3-methyl-2-pentyl (—CH($CH_3$)CH($CH_3$)$CH_2CH_3$), 4-methyl-2-pentyl (—CH($CH_3$)$CH_2CH(CH_3)_2$), 3-methyl-3-pentyl (—C($CH_3$)($CH_2CH_3$)$_2$), 2-methyl-3-pentyl (—CH($CH_2CH_3$)CH($CH_3$)$_2$), 2,3-dimethyl-2-butyl (—C($CH_3$)$_2CH(CH_3)_2$), 3,3-dimethyl-2-butyl (—CH($CH_3$)C($CH_3$)$_3$), 1-heptyl and 1-octyl. In some embodiments, substituents for "optionally substituted alkyls" include one to four instances of F, Cl, Br, I, OH, SH, CN, $NH_2$, $NHCH_3$, $N(CH_3)_2$, $NO_2$, $N_3$, $C(O)CH_3$, COOH, $CO_2CH_3$, methyl, ethyl, propyl, iso-propyl, butyl, isobutyl, cyclopropyl, methoxy, ethoxy, propoxy, oxo, trifluoromethyl, difluoromethyl, sulfonylamino, methanesulfonylamino, SO, $SO_2$, phenyl, piperidinyl, piperizinyl, and pyrimidinyl, wherein the alkyl, phenyl and heterocyclic portions thereof may be optionally substituted, such as by one to four instances of substituents selected from this same list.

The term "alkenyl" refers to linear or branched-chain monovalent hydrocarbon radical with at least one site of unsaturation, i.e., a carbon-carbon double bond, wherein the alkenyl radical may be optionally substituted, and includes radicals having "cis" and "trans" orientations, or alternatively, "E" and "Z" orientations. In one example, the alkenyl radical is two to eighteen carbon atoms ($C_2$-$C_{18}$). In other examples, the alkenyl radical is $C_2$-$C_{12}$, $C_2$-$C_{10}$, $C_2$-$C_8$, $C_2$-$C_6$ or $C_2$-$C_3$. Examples include, but are not limited to, ethenyl or vinyl (—CH=$CH_2$), prop-1-enyl (—CH=$CHCH_3$), prop-2-enyl (—$CH_2$CH=$CH_2$), 2-methylprop-1-enyl, but-1-enyl, but-2-enyl, but-3-enyl, buta-1,3-dienyl, 2-methylbuta-1,3-diene, hex-1-enyl, hex-2-enyl, hex-3-enyl, hex-4-enyl and hexa-1,3-dienyl. In some embodiments, substituents for "optionally substituted alkenyls" include one to four instances of F, Cl, Br, I, OH, SH, CN, $NH_2$, $NHCH_3$, $N(CH_3)_2$, $NO_2$, $N_3$, $C(O)CH_3$, COOH, $CO_2CH_3$, methyl, ethyl, propyl, iso-propyl, butyl, isobutyl, cyclopropyl, methoxy, ethoxy, propoxy, oxo, trifluoromethyl, difluoromethyl, sulfonylamino, methanesulfonylamino, SO, $SO_2$, phenyl, piperidinyl, piperizinyl, and pyrimidinyl, wherein the alkyl, phenyl and heterocyclic portions thereof may be optionally substituted, such as by one to four instances of substituents selected from this same list.

The term "alkynyl" refers to a linear or branched monovalent hydrocarbon radical with at least one site of unsaturation, i.e., a carbon-carbon, triple bond, wherein the alkynyl radical may be optionally substituted. In one example, the alkynyl radical is two to eighteen carbon atoms ($C_2$-$C_{18}$). In other examples, the alkynyl radical is $C_2$-$C_{12}$, $C_2$-$C_{10}$, $C_2$-$C_8$, $C_2$-$C_6$ or $C_2$-$C_3$. Examples include, but are not limited to, ethynyl (—C≡CH), prop-1-ynyl (—C≡$CCH_3$), prop-2-ynyl (propargyl, —$CH_2$OCH), but-1-ynyl, but-2-ynyl and but-3-ynyl. In some embodiments, substituents for "optionally substituted alkynyls" include one to four instances of F, Cl, Br, I, OH, SH, CN, $NH_2$, $NHCH_3$, $N(CH_3)_2$, $NO_2$, $N_3$, $C(O)CH_3$, COOH, $CO_2CH_3$, methyl, ethyl, propyl, iso-propyl, butyl, isobutyl, cyclopropyl, methoxy, ethoxy, propoxy, oxo, trifluoromethyl, difluoromethyl, sulfonylamino, methanesulfonylamino, SO, $SO_2$, phenyl, piperidinyl, piperizinyl, and pyrimidinyl, wherein the alkyl, phenyl and heterocyclic portions thereof may be optionally substituted, such as by one to four instances of substituents selected from this same list.

"Alkylene" refers to a saturated, branched or straight chain hydrocarbon group having two monovalent radical centers derived by the removal of two hydrogen atoms from the same or two different carbon atoms of a parent alkane. In one example, the divalent alkylene group is one to eighteen carbon atoms ($C_1$-$C_{18}$). In other examples, the divalent alkylene group is $C_0$-$C_6$, $C_0$-$C_5$, $C_0$-$C_3$, $C_1$-$C_{12}$, $C_1$-$C_{10}$, $C_1$-$C_8$, $C_1$-$C_6$, $C_1$-$C_5$, $C_1$-$C_4$, or $C_1$-$C_3$. The group $C_0$ alkylene refers to a bond. Example alkylene groups include methylene (—$CH_2$—), 1,1-ethyl (—$CH(CH_3)$—), (1,2-ethyl (—$CH_2CH_2$—), 1,1-propyl (—$CH(CH_2CH_3)$—), 2,2-propyl (—$C(CH_3)_2$—), 1,2-propyl (—$CH(CH_3)CH_2$—), 1,3-propyl (—$CH_2CH_2CH_2$—), 1,1-dimethyleth-1,2-yl (—$C(CH_3)_2CH_2$—), 1,4-butyl (—$CH_2CH_2CH_2CH_2$—), and the like.

The term "heteroalkyl" refers to a straight or branched chain monovalent hydrocarbon radical, consisting of the stated number of carbon atoms, or, if none are stated, up to 18 carbon atoms, and from one to five heteroatoms selected from the group consisting of O, N, Si and S, and wherein the nitrogen and sulfur atoms can optionally be oxidized and the nitrogen heteroatom can optionally be quaternized. In some embodiments, the heteroatom is selected from O, N and S, wherein the nitrogen and sulfur atoms can optionally be oxidized and the nitrogen heteroatom can optionally be quaternized. The heteroatom(s) can be placed at any interior position of the heteroalkyl group, including the position at which the alkyl group is attached to the remainder of the molecule (e.g., —O—$CH_2$—$CH_3$). Examples include —$CH_2$—$CH_2$—O—$CH_3$, —$CH_2$—$CH_2$—NH—$CH_3$, —$CH_2$—$CH_2$—N($CH_3$)—$CH_3$, —$CH_2$—S—$CH_2$—$CH_3$, —S(O)—$CH_3$, —$CH_2$—$CH_2$—S(O)$_2$—$CH_3$, —Si($CH_3$)$_3$ and —$CH_2$—CH=N—$OCH_3$. Up to two heteroatoms can be consecutive, such as, for example, —$CH_2$—NH—$OCH_3$ and —$CH_2$—O—Si($CH_3$)$_3$. Heteroalkyl groups can be optionally substituted. In some embodiments, substituents for "optionally substituted heteroalkyls" include one to four instances of F, Cl, Br, I, OH, SH, CN, $NH_2$, $NHCH_3$, N($CH_3$)$_2$, $NO_2$, $N_3$, C(O)$CH_3$, COOH, $CO_2CH_3$, methyl, ethyl, propyl, iso-propyl, butyl, isobutyl, cyclopropyl, methoxy, ethoxy, propoxy, oxo, trifluoromethyl, difluoromethyl, sulfonylamino, methanesulfonylamino, SO, $SO_2$, phenyl, piperidinyl, piperizinyl, and pyrimidinyl, wherein the alkyl, phenyl and heterocyclic portions thereof may be optionally substituted, such as by one to four instances of substituents selected from this same list.

"Amino" means primary (i.e., —$NH_2$), secondary (i.e., —NRH), tertiary (i.e., —NRR) and quaternary (i.e., —N(+)RRR) amines, that are optionally substituted, in which each R is the same or different and selected from alkyl, cycloalkyl, aryl, and heterocyclyl, wherein the alkyl, cycloalkyl, aryl and heterocyclyl groups are as defined herein. Particular secondary and tertiary amines are alkylamine, dialkylamine, arylamine, diarylamine, aralkylamine and diaralkylamine, wherein the alkyl and aryl portions can be optionally substituted. Particular secondary and tertiary amines are methylamine, ethylamine, propylamine, isopropylamine, phenylamine, benzylamine, dimethylamine, diethylamine, dipropylamine and diisopropylamine. In some embodiments, R groups of a quarternary amine are each independently optionally substituted alkyl groups.

"Aryl" refers to a carbocyclic aromatic group, whether or not fused to one or more groups, having the number of carbon atoms designated, or if no number is designated, up to 14 carbon atoms. One example includes aryl groups having 6-14 carbon atoms. Another example includes aryl groups having 6-10 carbon atoms. Examples of aryl groups include phenyl, naphthyl, biphenyl, phenanthrenyl, naphthacenyl, 1,2,3,4-tetrahydronaphthalenyl, 1H-indenyl, 2,3-dihydro-1H-indenyl, and the like (see, e.g., Lang's Handbook of Chemistry (Dean, J. A., ed.) 13$^{th}$ ed. Table 7-2 [1985]). A particular aryl is phenyl. Substituted phenyl or substituted aryl means a phenyl group or aryl group substituted with one, two, three, four or five substituents, for example, 1-2, 1-3 or 1-4 substituents, such as chosen from groups specified herein (see "optionally substituted" definition), such as F, Cl, Br, I, OH, SH, CN, $NH_2$, $NHCH_3$, N($CH_3$)$_2$, $NO_2$, $N_3$, C(O)$CH_3$, COOH, $CO_2CH_3$, methyl, ethyl, propyl, iso-propyl, butyl, isobutyl, cyclopropyl, methoxy, ethoxy, propoxy, oxo, trifluoromethyl, difluoromethyl, sulfonylamino, methanesulfonylamino, SO, $SO_2$, phenyl, piperidinyl, piperizinyl, and pyrimidinyl, wherein the alkyl, phenyl and heterocyclic portions thereof may be optionally substituted, such as by one to four instances of substituents selected from this same list. Examples of the term "substituted phenyl" include a mono- or di(halo)phenyl group such as 2-chlorophenyl, 2-bromophenyl, 4-chlorophenyl, 2,6-dichlorophenyl, 2,5-dichlorophenyl, 3,4-dichlorophenyl, 3-chlorophenyl, 3-bromophenyl, 4-bromophenyl, 3,4-dibromophenyl, 3-chloro-4-fluorophenyl, 2-fluorophenyl, 2,4-difluorophenyl and the like; a mono- or di(hydroxy) phenyl group such as 4-hydroxyphenyl, 3-hydroxyphenyl, 2,4-dihydroxyphenyl, the protected-hydroxy derivatives thereof and the like; a nitrophenyl group such as 3- or 4-nitrophenyl; a cyanophenyl group, for example, 4-cyanophenyl; a mono- or di(alkyl)phenyl group such as 4-methylphenyl, 2,4-dimethylphenyl, 2-methylphenyl, 4-(isopropyl)phenyl, 4-ethylphenyl, 3-(n-propyl)phenyl and the like; a mono or di(alkoxy)phenyl group, for example, 3,4-dimethoxyphenyl, 3-methoxy-4-benzyloxyphenyl, 3-ethoxyphenyl, 4-(isopropoxy)phenyl, 4-(t-butoxy)phenyl, 3-ethoxy-4-methoxyphenyl and the like; 3- or 4-trifluoromethylphenyl; a mono- or dicarboxyphenyl or (protected carboxy)phenyl group such 4-carboxyphenyl, a mono- or di(hydroxymethyl) phenyl or (protected hydroxymethyl)phenyl such as 3-(protected hydroxymethyl)phenyl or 3,4-di(hydroxymethyl)phenyl; a mono- or di(aminomethyl)phenyl or (protected aminomethyl)phenyl such as 2-(aminomethyl)phenyl or 2,4-(protected aminomethyl)phenyl; or a mono- or di(N-(methylsulfonylamino))phenyl such as 3-(N-methylsulfonylamino))phenyl. Also, the term "substituted phenyl" represents disubstituted phenyl groups where the substituents are different, for example, 3-methyl-4-hydroxyphenyl, 3-chloro-4-hydroxyphenyl, 2-methoxy-4-bromophenyl, 4-ethyl-2-hydroxyphenyl, 3-hydroxy-4-nitrophenyl, 2-hydroxy-4-chlorophenyl, 2-chloro-5-difluoromethoxy and the like, as well as trisubstituted phenyl groups where the substituents are different, for example 3-methoxy-4-benzyloxy-6-methyl sulfonylamino, 3-methoxy-4-benzyloxy-6-phenyl sulfonylamino, and tetrasubstituted phenyl groups where the substituents are different such as 3-methoxy-4-benzyloxy-5-methyl-6-phenyl sulfonylamino. In some embodiments, a substituent of an aryl, such as phenyl, comprises an amide. For example, an aryl (e.g., phenyl) substituent may be —($CH_2$)$_{0-4}$CONR'R", wherein R' and R" each independently refer to groups including, for example, hydrogen; unsubstituted $C_1$-$C_6$alkyl; $C_1$-$C_6$alkyl substituted by halogen, OH, CN, unsubstituted $C_1$-$C_6$alkyl, unsubstituted $C_1$-$C_6$ alkoxy, oxo or NR'R"; unsubstituted $C_1$-$C_6$ heteroalkyl; $C_1$-$C_6$ heteroalkyl substituted by halogen, OH, CN, unsubstituted $C_1$-$C_6$alkyl, unsubstituted $C_1$-$C_6$ alkoxy, oxo or NR'R"; unsubstituted $C_6$-$C_{10}$ aryl; $C_6$-$C_{10}$ aryl substituted by halogen, OH, CN, unsubstituted $C_1$-$C_6$alkyl, unsubstituted $C_1$-$C_6$ alkoxy, or NR'R"; unsubstituted 3-11 membered heterocyclyl (e.g., 5-6 membered heteroaryl containing 1 to 4 heteroatoms selected from O, N and S or 4-11 membered heterocycloalkyl containing 1 to 4 heteroatoms selected from O, N and S); and 3-11 membered heterocyclyl (e.g., 5-6 membered heteroaryl containing 1 to 4 heteroatoms selected from O, N and S or 4-11 membered heterocycloalkyl containing 1 to 4 heteroatoms selected from O, N and S) substituted by halogen, OH, CN, unsubstituted $C_1$-$C_6$alkyl, unsubstituted $C_1$-$C_6$ alkoxy, oxo or NR'R"; or R' and R" can be combined with the nitrogen atom to form a 3-, 4-, 5-, 6-, or 7-membered ring wherein a ring atom is optionally substituted with N, O or S and wherein the ring is optionally substituted with halogen, OH, CN, unsubstituted $C_1$-$C_6$alkyl, unsubstituted $C_1$-$C_6$ alkoxy, oxo or NR'R".

"Cycloalkyl" refers to a non-aromatic, saturated or partially unsaturated hydrocarbon ring group wherein the cycloalkyl group may be optionally substituted independently with one or more substituents described herein. In one example, the cycloalkyl group is 3 to 12 carbon atoms ($C_3$-$C_{12}$). In other examples, cycloalkyl is $C_3$-$C_8$, $C_3$-$C_{10}$ or $C_5$-$C_{10}$. In other examples, the cycloalkyl group, as a monocycle, is $C_3$-$C_8$, $C_3$-$C_6$ or $C_5$-$C_6$. In another example, the cycloalkyl group, as a bicycle, is $C_7$-$C_{12}$. In another example, the cycloalkyl group, as a spiro system, is $C_5$-$C_{12}$. Examples of monocyclic cycloalkyl include cyclopropyl, cyclobutyl, cyclopentyl, 1-cyclopent-1-enyl, 1-cyclopent-2-enyl, 1-cyclopent-3-enyl, cyclohexyl, perdeuteriocyclohexyl, 1-cyclohex-1-enyl, 1-cyclohex-2-enyl, 1-cyclohex-3-enyl, cyclohexadienyl, cycloheptyl, cyclooctyl, cyclononyl, cyclodecyl, cycloundecyl and cyclododecyl. Exemplary arrangements of bicyclic cycloalkyls having 7 to 12 ring atoms include, but are not limited to, [4,4], [4,5], [5,5], [5,6] or [6,6] ring systems. Exemplary bridged bicyclic cycloalkyls include, but are not limited to, bicyclo[2.2.1]heptane, bicyclo[2.2.2]octane and bicyclo[3.2.2]nonane. Examples of spiro cycloalkyl include, spiro[2.2]pentane, spiro[2.3]hexane, spiro[2.4]heptane, spiro[2.5]octane and spiro[4.5]decane. In some embodiments, substituents for "optionally substituted cycloalkyls" include one to four instances of F, Cl, Br, I, OH, SH, CN, $NH_2$, $NHCH_3$, $N(CH_3)_2$, $NO_2$, $N_3$, $C(O)CH_3$, COOH, $CO_2CH_3$, methyl, ethyl, propyl, isopropyl, butyl, isobutyl, cyclopropyl, methoxy, ethoxy, propoxy, oxo, trifluoromethyl, difluoromethyl, sulfonylamino, methanesulfonylamino, SO, $SO_2$, phenyl, piperidinyl, piperizinyl, and pyrimidinyl, wherein the alkyl, aryl and heterocyclic portions thereof may be optionally substituted, such as by one to four instances of substituents selected from this same list. In some embodiments, a substituent of a cycloalkyl comprises an amide. For example, a cycloalkyl substituent may be —$(CH_2)_{0-4}$CONR'R", wherein R' and R" each independently refer to groups including, for example, hydrogen; unsubstituted $C_1$-$C_6$alkyl; $C_1$-$C_6$alkyl substituted by halogen, OH, CN, unsubstituted $C_1$-$C_6$alkyl, unsubstituted $C_1$-$C_6$ alkoxy, oxo or NR'R"; unsubstituted $C_1$-$C_6$ heteroalkyl; $C_1$-$C_6$ heteroalkyl substituted by halogen, OH, CN, unsubstituted $C_1$-$C_6$alkyl, unsubstituted $C_1$-$C_6$ alkoxy, oxo or NR'R"; unsubstituted $C_6$-$C_{10}$ aryl; $C_6$-$C_{10}$ aryl substituted by halogen, OH, CN, unsubstituted $C_1$-$C_6$alkyl, unsubstituted $C_1$-$C_6$ alkoxy, or NR'R"; unsubstituted 3-11 membered heterocyclyl (e.g., 5-6 membered heteroaryl containing 1 to 4 heteroatoms selected from O, N and S or 4-11 membered heterocycloalkyl containing 1 to 4 heteroatoms selected from O, N and S); and 3-11 membered heterocyclyl (e.g., 5-6 membered heteroaryl containing 1 to 4 heteroatoms selected from O, N and S or 4-11 membered heterocycloalkyl containing 1 to 4 heteroatoms selected from O, N and S) substituted by halogen, OH, CN, unsubstituted $C_1$-$C_6$alkyl, unsubstituted $C_1$-$C_6$ alkoxy, oxo or NR'R"; or R' and R" can be combined with the nitrogen atom to form a 3-, 4-, 5-, 6-, or 7-membered ring wherein a ring atom is optionally substituted with N, O or S and wherein the ring is optionally substituted with halogen, OH, CN, unsubstituted $C_1$-$C_6$alkyl, unsubstituted $C_1$-$C_6$ alkoxy, oxo or NR'R".

"Heterocyclic group", "heterocyclic", "heterocycle", "heterocyclyl", or "heterocyclo" are used interchangeably and refer to any mono-, bi-, tricyclic or spiro, saturated or unsaturated, aromatic (heteroaryl) or non-aromatic (e.g., heterocycloalkyl), ring system, having 3 to 20 ring atoms (e.g., 3-10 ring atoms), where the ring atoms are carbon, and at least one atom in the ring or ring system is a heteroatom selected from nitrogen, sulfur or oxygen. If any ring atom of a cyclic system is a heteroatom, that system is a heterocycle, regardless of the point of attachment of the cyclic system to the rest of the molecule. In one example, heterocyclyl includes 3-11 ring atoms ("members") and includes monocycles, bicycles, tricycles and spiro ring systems, wherein the ring atoms are carbon, where at least one atom in the ring or ring system is a heteroatom selected from nitrogen, sulfur or oxygen. In one example, heterocyclyl includes 1 to 4 heteroatoms. In one example, heterocyclyl includes 1 to 3 heteroatoms. In another example, heterocyclyl includes 3- to 7-membered monocycles having 1-2, 1-3 or 1-4 heteroatoms selected from nitrogen, sulfur or oxygen. In another example, heterocyclyl includes 4- to 6-membered monocycles having 1-2, 1-3 or 1-4 heteroatoms selected from nitrogen, sulfur or oxygen. In another example, heterocyclyl includes 3-membered monocycles. In another example, heterocyclyl includes 4-membered monocycles. In another example, heterocyclyl includes 5-6 membered monocycles, e.g., 5-6 membered heteroaryl. In another example, heterocyclyl includes 3-11 membered heterocycloyalkyls, such as 4-11 membered heterocycloalkyls. In some embodiments, a heterocycloalkyl includes at least one nitrogen. In one example, the heterocyclyl group includes 0 to 3 double bonds. Any nitrogen or sulfur heteroatom may optionally be oxidized (e.g., NO, SO, $SO_2$), and any nitrogen heteroatom may optionally be quaternized (e.g., $[NR_4]^+Cl^-$, $[NR_4]^+OH^-$). Example heterocycles are oxiranyl, aziridinyl, thiiranyl, azetidinyl, oxetanyl, thietanyl, 1,2-dithietanyl, 1,3-dithietanyl, pyrrolidinyl, dihydro-1H-pyrrolyl, dihydrofuranyl, tetrahydrofuranyl, dihydrothienyl, tetrahydrothienyl, imidazolidinyl, piperidinyl, piperazinyl, isoquinolinyl, tetrahydroisoquinolinyl, morpholinyl, thiomorpholinyl, 1,1-dioxo-thiomorpholiny 1, dihydropyranyl, tetrahydropyranyl, hexahydrothiopyranyl, hexahydropyrimidinyl, oxazinanyl, thiazinanyl, thioxanyl, homopiperazinyl, homopiperidinyl, azepanyl, oxepanyl, thiepanyl, oxazepinyl, oxazepanyl, diazepanyl, 1,4-diazepanyl, diazepinyl, thiazepinyl, thiazepanyl, tetrahydrothiopyranyl, oxazolidinyl, thiazolidinyl, isothiazolidinyl, 1,1-dioxoisothiazolidinony 1, oxazolidinonyl, imidazolidinonyl, 4,5,6,7-tetrahydro[2H]indazoly 1, tetrahydrobenzoimidazolyl, 4,5,6,7-tetrahydrobenzo[d]imidazolyl, 1,6-dihydroimidazol[4,5-d]pyrrolo[2,3-b]pyridinyl, thiazinyl, oxazinyl, thiadiazinyl, oxadiazinyl, dithiazinyl, dioxazinyl, oxathiazinyl, thiatriazinyl, oxatriazinyl, dithiadiazinyl, imidazolinyl, dihydropyrimidyl, tetrahydropyrimidyl, 1-pyrrolinyl, 2-pyrrolinyl, 3-pyrrolinyl, indolinyl, thiapyranyl, 2H-pyranyl, 4H-pyranyl, dioxanyl, 1,3-dioxolanyl, pyrazolinyl, pyrazolidinyl, dithianyl, dithiolanyl, pyrimidinonyl, pyrimidindionyl, pyrimidin-2,4-dionyl, piperazinonyl, piperazindionyl, pyrazolidinylimidazolinyl, 3-azabicyclo[3.1.0]hexanyl, 3,6-diazabicyclo[3.1.1]heptanyl, 6-azabicyclo[3.1.1]heptanyl, 3-azabicyclo[3.1.1]heptanyl, 3-azabicyclo[4.1.0]heptanyl, azabicyclo[2.2.2]hexanyl, 2-azabicyclo[3.2.1]octanyl, 8-azabicyclo[3.2.1]octanyl, 2-azabicyclo[2.2.2]octanyl, 8-azabicyclo[2.2.2]octanyl, 7-oxabicyclo[2.2.1]heptane, azaspiro[3.5]nonanyl, azaspiro[2.5]octanyl, azaspiro[4.5]decanyl, 1-azaspiro[4.5]decan-2-only, azaspiro[5.5]undecanyl, tetrahydroindolyl, octahydroindolyl, tetrahydroisoindolyl, tetrahydroindazolyl, 1,1-dioxohexahydrothiopyranyl. Examples of 5-membered heterocycles containing a sulfur or oxygen atom and one to three nitrogen atoms are thiazolyl, including thiazol-2-yl and thiazol-2-yl N-oxide, thiadiazolyl, including 1,3,4-thiadiazol-5-yl and 1,2,4-thiadiazol-5-yl, oxazolyl, for example oxazol-2-yl, and oxadiazolyl, such as 1,3,4-oxadiazol-5-yl, and 1,2,4-oxadiazol-5-yl. Example 5-membered ring heterocycles containing 2 to 4 nitrogen atoms include imidazolyl, such as imidazol-2-yl; triazolyl, such as 1,3,4-triazol-5-yl; 1,2,3-triazol-5-yl, 1,2,4-triazol-5-yl, and tetrazolyl, such as 1H-tetrazol-5-yl. Example benzo-fused 5-membered heterocycles are benzoxazol-2-yl, benzthiazol-2-yl and benzimidazol-2-yl. Example 6-membered heterocycles contain one to three nitrogen atoms and optionally a sulfur or oxygen atom, for example pyridyl, such as pyrid-2-yl, pyrid-3-yl, and pyrid-4-yl; pyrimidyl, such as pyrimid-2-yl and pyrimid-4-yl; triazinyl, such as 1,3,4-triazin-2-yl and 1,3,5-triazin-4-yl; pyridazinyl, in particular pyridazin-3-yl, and pyrazinyl. The pyridine N-oxides and pyridazine N-oxides and the pyridyl, pyrimid-2-yl, pyrimid-4-yl, pyridazinyl and the 1,3,4-triazin-2-yl groups, are other example heterocycle groups. Heterocycles may be optionally substituted. For example, substituents for "optionally substituted heterocycles" include one to four instances of F, Cl, Br, I, OH, SH, CN, $NH_2$, $NHCH_3$, $N(CH_3)_2$, $NO_2$, $N_3$, $C(O)CH_3$, COOH, $CO_2CH_3$, methyl, ethyl, propyl, iso-propyl, butyl, isobutyl, cyclopropyl, methoxy, ethoxy, propoxy, oxo, trifluoromethyl, difluoromethyl, sulfonylamino, methanesulfonylamino, SO, $SO_2$, phenyl, piperidinyl, piperizinyl, and pyrimidinyl, wherein the alkyl, aryl and heterocyclic portions thereof may be optionally substituted, such as by one to four instances of substituents selected from this same list. In some embodiments, a substituent of a heterocyclic group, such as a heteroaryl or heterocycloalkyl, comprises an amide. For example, a heterocyclic (e.g., heteroaryl or heterocycloalkyl) substituent may be $—(CH_2)_{0-4}CONR'R''$, wherein R' and R'' each independently refer to groups including, for example, hydrogen; unsubstituted $C_1$-$C_6$alkyl: $C_1$-$C_6$alkyl substituted by halogen, OH, CN, unsubstituted $C_1$-$C_6$alkyl, unsubstituted $C_1$-$C_6$ alkoxy, oxo or NR'R''; unsubstituted $C_1$-$C_6$ heteroalkyl; $C_1$-$C_6$ heteroalkyl substituted by halogen, OH, CN, unsubstituted $C_1$-$C_6$alkyl, unsubstituted $C_1$-$C_6$ alkoxy, oxo or NR'R''; unsubstituted $C_6$-$C_{10}$ aryl; $C_6$-$C_{10}$ aryl substituted by halogen, OH, CN, unsubstituted $C_1$-$C_6$alkyl, unsubstituted $C_1$-$C_6$ alkoxy, or NR'R''; unsubstituted 3-11 membered heterocyclyl (e.g., 5-6 membered heteroaryl containing 1 to 4 heteroatoms selected from O, N and S or 4-11 membered heterocycloalkyl containing 1 to 4 heteroatoms selected from O, N and S); and 3-11 membered heterocyclyl (e.g., 5-6 membered heteroaryl containing 1 to 4 heteroatoms selected from O, N and S or 4-11 membered heterocycloalkyl containing 1 to 4 heteroatoms selected from O, N and S) substituted by halogen, OH, CN, unsubstituted $C_1$-$C_6$alkyl, unsubstituted $C_1$-$C_6$ alkoxy, oxo or NR'R''; or R' and R'' can be combined with the nitrogen atom to form a 3-, 4-, 5-, 6-, or 7-membered ring wherein a ring atom is optionally substituted with N, O or S and wherein the ring is optionally substituted with halogen, OH, CN, unsubstituted $C_1$-$C_6$alkyl, unsubstituted $C_1$-$C_6$ alkoxy, oxo or NR'R''.

"Heteroaryl" refers to any mono-, bi-, or tricyclic ring system where at least one ring is a 5- or 6-membered aromatic ring containing from 1 to 4 heteroatoms selected from nitrogen, oxygen, and sulfur, and in an example embodiment, at least one heteroatom is nitrogen. See, for example, Lang's Handbook of Chemistry (Dean, J. A., ed.) 13$^{th}$ ed. Table 7-2 [1985], Included in the definition are any bicyclic groups where any of the above heteroaryl rings are fused to an aryl ring, wherein the aryl ring or the heteroaryl ring is joined to the remainder of the molecule. In one embodiment, heteroaryl includes 5-6 membered monocyclic aromatic groups where one or more ring atoms is nitrogen, sulfur or oxygen. Example heteroaryl groups include thienyl, furyl, imidazolyl, pyrazolyl, thiazolyl, isothiazolyl, oxazolyl, isoxazolyl, triazolyl, thiadiazolyl, oxadiazolyl, tetrazolyl, thiatriazolyl, oxatriazolyl, pyridyl, pyrimidyl, pyrazinyl, pyridazinyl, triazinyl, tetrazinyl, tetrazolo[1,5-b]pyridazinyl, imidazol[1,2-a]pyrimidinyl and purinyl, as well as benzo-fused derivatives, for example benzoxazolyl, benzofuryl, benzothiazolyl, benzothiadiazolyl, benzotriazolyl, benzoimidazolyl and indolyl. Heteroaryl groups can be optionally substituted. In some embodiments, substituents for "optionally substituted heteroaryls" include one to four instances of F, Cl, Br, I, OH, SH, CN, $NH_2$, $NHCH_3$, $N(CH_3)_2$, $NO_2$, $N_3$, $C(O)CH_3$, COOH, $CO_2CH_3$, methyl, ethyl, propyl, iso-propyl, butyl, isobutyl, cyclopropyl, methoxy, ethoxy, propoxy, trifluoromethyl, difluoromethyl, sulfonylamino, methanesulfonylamino, SO, $SO_2$, phenyl, piperidinyl, piperizinyl, and pyrimidinyl, wherein the alkyl, phenyl and heterocyclic portions thereof may be optionally substituted, such as by one to four instances of substituents selected from this same list. In some embodiments, a substituent of a heteroaryl comprises an amide. For example, a heteroaryl substituent may be $—(CH_2)_{0-4}CONR'R''$, wherein R' and R'' each independently refer to groups including, for example, hydrogen; unsubstituted $C_1$-$C_6$alkyl; $C_1$-$C_6$alkyl substituted by halogen, OH, CN, unsubstituted $C_1$-$C_6$alkyl, unsubstituted $C_1$-$C_6$ alkoxy, oxo or NR'R''; unsubstituted $C_1$-$C_6$ heteroalkyl; $C_1$-$C_6$ heteroalkyl substituted by halogen, OH, CN, unsubstituted $C_1$-$C_6$alkyl, unsubstituted $C_1$-$C_6$ alkoxy, oxo or NR'R''; unsubstituted $C_6$-$C_{10}$ aryl; $C_6$-$C_{10}$ aryl substituted by halogen, OH, CN, unsubstituted $C_1$-$C_6$alkyl, unsubstituted $C_1$-$C_6$ alkoxy, or NR'R''; unsubstituted 3-11 membered heterocyclyl (e.g., 5-6 membered heteroaryl containing 1 to 4 heteroatoms selected from O, N and S or 4-11 membered heterocycloalkyl containing 1 to 4 heteroatoms selected from O, N and S); and 3-11 membered heterocyclyl (e.g., 5-6 membered heteroaryl containing 1 to 4 heteroatoms selected from O, N and S or 4-11 membered heterocycloalkyl containing 1 to 4 heteroatoms selected from O, N and S) substituted by halogen, OH, CN, unsubstituted $C_1$-$C_6$alkyl, unsubstituted $C_1$-$C_6$ alkoxy, oxo or NR'R''; or R' and R'' can be combined with the nitrogen atom to form a 3-, 4-, 5-, 6-, or 7-membered ring wherein a ring atom is optionally substituted with N, O or S and wherein the ring is optionally substituted with halogen, OH, CN, unsubstituted $C_1$-$C_6$alkyl, unsubstituted $C_1$-$C_6$ alkoxy, oxo or NR'R''.

In particular embodiments, a heterocyclyl group is attached at a carbon atom of the heterocyclyl group. By way of example, carbon bonded heterocyclyl groups include bonding arrangements at position 2, 3, 4, 5, or 6 of a pyridine ring, position 3, 4, 5, or 6 of a pyridazine ring, position 2, 4, 5, or 6 of a pyrimidine ring, position 2, 3, 5, or 6 of a pyrazine ring, position 2, 3, 4, or 5 of a furan, tetrahydrofuran, thiofuran, thiophene, pyrrole or tetrahydropyrrole ring, position 2, 4, or 5 of an oxazole, imidazole or thiazole ring, position 3, 4, or 5 of an isoxazole, pyrazole, or isothiazole ring, position 2 or 3 of an aziridine ring, position 2, 3, or 4 of an azetidine ring, position 2, 3, 4, 5, 6, 7, or 8 of a quinoline ring or position 1, 3, 4, 5, 6, 7, or 8 of an isoquinoline ring.

In certain embodiments, the heterocyclyl group is N-attached. By way of example, nitrogen bonded heterocyclyl or heteroaryl groups include bonding arrangements at position 1 of an aziridine, azetidine, pyrrole, pyrrolidine, 2-pyrroline, 3-pyrroline, imidazole, imidazolidine, 2-imidazoline, 3-imidazoline, pyrazole, pyrazoline, 2-pyrazoline, 3-pyrazoline, piperidine, piperazine, indole, indoline, 1H-indazole, position 2 of a isoindole, or isoindoline, position 4 of a morpholine, and position 9 of a carbazole, or β-carboline.

The term "alkoxy" refers to a linear or branched monovalent radical represented by the formula —OR in which R is alkyl, as defined herein. Alkoxy groups include methoxy, ethoxy, propoxy, isopropoxy, mono-, di- and tri-fluoromethoxy and cyclopropoxy.

"Acyl" means a carbonyl containing substituent represented by the formula —C(O)—R in which R is hydrogen, alkyl, cycloalkyl, aryl or heterocyclyl, wherein the alkyl, cycloalkyl, aryl and heterocyclyl are as defined herein. Acyl groups include alkanoyl (e.g., acetyl), aroyl (e.g., benzoyl), and heteroaroyl (e.g., pyridinoyl).

"Optionally substituted" unless otherwise specified means that a group may be unsubstituted or substituted by one or more (e.g., 0, 1, 2, 3, 4, or 5 or more, or any range derivable therein) of the substituents listed for that group in which said substituents may be the same or different. In an embodiment, an optionally substituted group has 1 substituent. In another embodiment an optionally substituted group has 2 substituents. In another embodiment an optionally substituted group has 3 substituents. In another embodiment an optionally substituted group has 4 substituents. In another embodiment an optionally substituted group has 5 substituents.

Optional substituents for alkyl radicals, alone or as part of another substituent (e.g., alkoxy), as well as alkylenyl, alkenyl, alkynyl, heteroalkyl, heterocycloalkyl, and cycloalkyl, also each alone or as part of another substituent, can be a variety of groups, such as those described herein, as well as selected from the group consisting of halogen; oxo; CN; NO; $N_3$; —OR'; perfluoro-$C_1$-$C_4$ alkoxy; unsubstituted $C_3$-$C_7$ cycloalkyl; $C_3$-$C_7$ cycloalkyl substituted by halogen, OH, CN, unsubstituted $C_1$-$C_6$alkyl, unsubstituted $C_1$-$C_6$ alkoxy, oxo or NR'R"; unsubstituted $C_6$-$C_{10}$ aryl (e.g., phenyl); $C_6$-$C_{10}$ aryl substituted by halogen, OH, CN, unsubstituted $C_1$-$C_6$alkyl, unsubstituted $C_1$-$C_6$ alkoxy, or NR'R"; unsubstituted 3-11 membered heterocyclyl (e.g., 5-6 membered heteroaryl containing 1 to 4 heteroatoms selected from O, N and S or 4-11 membered heterocycloalkyl containing 1 to 4 heteroatoms selected from O, N and S); 3-11 membered heterocyclyl (e.g., 5-6 membered heteroaryl containing 1 to 4 heteroatoms selected from O, N and S or 4-11 membered heterocycloalkyl containing 1 to 4 heteroatoms selected from O, N and S) substituted by halogen, OH, CN, unsubstituted $C_1$-$C_6$alkyl, unsubstituted $C_1$-$C_6$ alkoxy, oxo or NR'R"; —NR'R"; —SR'; —SiR'R"R'"; —OC(O)R'; —C(O)R'; —$CO_2$R'; —CONR'R"; —OC(O)NR'R"; —NR"C(O)R'; —NR'"C(O)NR'R"; —NR"C(O)$_2$R'; —S(O)$_2$R'; —S(O)$_2$NR'R"; —NR'S(O)$_2$R"; —NR" 'S(O)$_2$NR'R"; amidinyl; guanidinyl; —(CH$_2$)$_{1-4}$—OR'; —(CH$_2$)$_{1-4}$—NR'R"; —(CH$_2$)$_{1-4}$—SR'; —(CH$_2$)$_{1-4}$—SiR'R"R'"; —(CH$_2$)$_{1-4}$—OC(O)R; —(CH$_2$)$_{1-4}$—C(O)R'; —(CH$_2$)$_{1-4}$—$CO_2$R'; and —(CH$_2$)$_{1-4}$CONR'R", or combinations thereof, in a number ranging from zero to (2m'+1), where m' is the total number of carbon atoms in such radical. R', R" and R'" each independently refer to groups including, for example, hydrogen; unsubstituted $C_1$-$C_6$alkyl; $C_1$-$C_6$alkyl substituted by halogen, OH, CN, unsubstituted $C_1$-$C_6$alkyl, unsubstituted $C_1$-$C_6$ alkoxy, oxo or NR'R"; unsubstituted $C_1$-$C_6$ heteroalkyl; $C_1$-$C_6$ heteroalkyl substituted by halogen, OH, CN, unsubstituted $C_1$-$C_6$alkyl, unsubstituted $C_1$-$C_6$ alkoxy, oxo or NR'R"; unsubstituted $C_6$-$C_{10}$ aryl; $C_6$-$C_{10}$ aryl substituted by halogen, OH, CN, unsubstituted $C_1$-$C_6$alkyl, unsubstituted $C_1$-$C_6$ alkoxy, or NR'R"; unsubstituted 3-11 membered heterocyclyl (e.g., 5-6 membered heteroaryl containing 1 to 4 heteroatoms selected from O, N and S or 4-11 membered heterocycloalkyl containing 1 to 4 heteroatoms selected from O, N and S); and 3-11 membered heterocyclyl (e.g., 5-6 membered heteroaryl containing 1 to 4 heteroatoms selected from O, N and S or 4-11 membered heterocycloalkyl containing 1 to 4 heteroatoms selected from O, N and S) substituted by halogen, OH, CN, unsubstituted $C_1$-$C_6$alkyl, unsubstituted $C_1$-$C_6$ alkoxy, oxo or NR'R". When R' and R" are attached to the same nitrogen atom, they can be combined with the nitrogen atom to form a 3-, 4-, 5-, 6-, or 7-membered ring wherein a ring atom is optionally substituted with N, O or S and wherein the ring is optionally substituted with halogen, OH, CN, unsubstituted $C_1$-$C_6$alkyl, unsubstituted $C_1$-$C_6$ alkoxy, oxo or NR'R". For example, —NR'R" is meant to include 1-pyrrolidinyl and 4-morpholinyl.

Similarly, optional substituents for the aryl and heteroaryl groups are varied. In some embodiments, substituents for aryl and heteroaryl groups are selected from the group consisting of halogen; CN; NO; $N_3$; —OR'; perfluoro-$C_1$-$C_4$ alkoxy; unsubstituted $C_3$-$C_7$ cycloalkyl; $C_3$-$C_7$ cycloalkyl substituted by halogen, OH, CN, unsubstituted $C_1$-$C_6$alkyl, unsubstituted $C_1$-$C_6$ alkoxy, oxo or NR'R"; unsubstituted $C_6$-$C_{10}$ aryl (e.g., phenyl); $C_6$-$C_{10}$ aryl substituted by halogen, OH, CN, unsubstituted $C_1$-$C_6$alkyl, unsubstituted $C_1$-$C_6$ alkoxy, or NR'R"; unsubstituted 3-11 membered heterocyclyl (e.g., 5-6 membered heteroaryl containing 1 to 4 heteroatoms selected from O, N and S or 4-11 membered heterocycloalkyl containing 1 to 4 heteroatoms selected from O, N and S); 3-11 membered heterocyclyl (e.g., 5-6 membered heteroaryl containing 1 to 4 heteroatoms selected from O, N and S or 4-11 membered heterocycloalkyl containing 1 to 4 heteroatoms selected from O, N and S) substituted by halogen, OH, CN, unsubstituted $C_1$-$C_6$alkyl, unsubstituted $C_1$-$C_6$ alkoxy, oxo or NR'R"; —NR'R"; —SR'; —SiR'R"R'"; —OC(O)R'; —C(O)R'; —$CO_2$R'; —CONR'R"; —OC(O)NR'R"; —NR"C(O)R'; —NR'"C(O)NR'R"; —NR"C(O)$_2$R'; —S(O)$_2$R'; —S(O)$_2$NR'R"; —NR'S(O)$_2$R"; —NR" 'S(O)$_2$NR'R"; amidinyl; guanidinyl; —(CH$_2$)$_{1-4}$—OR'; —(CH$_2$)$_{1-4}$—NR'R"; —(CH$_2$)$_{1-4}$—SR'; —(CH$_2$)$_{1-4}$—SiR'R"R'"; —(CH$_2$)$_{1-4}$—OC(O)R'; —(CH$_2$)$_{1-4}$—C(O)R'; —(CH$_2$)$_{1-4}$—$CO_2$R; and —(CH$_2$)$_{1-4}$CONR'R", or combinations thereof, in a number ranging from zero to (2m'+1), where m' is the total number of carbon atoms in such radical. R', R" and R'" each independently refer to groups including, for example, hydrogen; unsubstituted $C_1$-$C_6$alkyl; $C_1$-$C_6$alkyl substituted by halogen, OH, CN, unsubstituted $C_1$-$C_6$alkyl, unsubstituted $C_1$-$C_6$ alkoxy, oxo or NR'R"; unsubstituted $C_1$-$C_6$ heteroalkyl; $C_1$-$C_6$ heteroalkyl substituted by halogen, OH, CN, unsubstituted $C_1$-$C_6$alkyl, unsubstituted $C_1$-$C_6$ alkoxy, oxo or NR'R"; unsubstituted $C_6$-$C_{10}$ aryl; $C_6$-$C_{10}$ aryl substituted by halogen, OH, CN, unsubstituted $C_1$-$C_6$alkyl, unsubstituted $C_1$-$C_6$ alkoxy, or NR'R"; unsubstituted 3-11 membered heterocyclyl (e.g., 5-6 membered heteroaryl containing 1 to 4 heteroatoms selected from O, N and S or 4-11 membered heterocycloalkyl containing 1 to 4 heteroatoms selected from O, N and S); and 3-11 membered heterocyclyl (e.g., 5-6 membered heteroaryl containing 1 to 4 heteroatoms selected from O, N and S or 4-11 membered heterocycloalkyl containing 1 to 4 heteroatoms selected from O, N and S) substituted by halogen, OH, CN, unsubstituted $C_1$-$C_6$alkyl, unsubstituted $C_1$-$C_6$ alkoxy, oxo or NR'R". When R' and R" are attached to the same nitrogen atom, they can be combined with the nitrogen atom to form a 3-, 4-, 5-, 6-, or 7-membered ring wherein a ring atom is optionally substituted with N, O or S and wherein the ring is optionally substituted with halogen, OH, CN, unsubstituted $C_1$-$C_6$alkyl, unsubstituted $C_1$-$C_6$ alkoxy, oxo or NR'R". For example, —NR'R" is meant to include 1-pyrrolidinyl and 4-morpholinyl.

The term "oxo" refers to =O or (=O)$_2$.

As used herein a wavy line " " that intersects a bond in a chemical structure indicate the point of attachment of the atom to which the wavy bond is connected in the chemical structure to the remainder of a molecule, or to the remainder of a fragment of a molecule. In some embodiments, an arrow together with an asterisk is used in the manner of a wavy line to indicate a point of attachment.

In certain embodiments, divalent groups are described genetically without specific bonding configurations. It is understood that the generic description is meant to include both bonding configurations, unless specified otherwise. For example, in the group $R^3$—$R^2$—$R^3$, if the group $R^2$ is described as —$CH_2C(O)$—, then it is understood that this group can be bonded both as $R^1$—$CH_2C(O)$—$R^3$, and as $R^1$—$C(O)CH_2$—$R^3$, unless specified otherwise.

The terms "compound(s) of the invention," and "compound(s) of the present invention" and the like, unless otherwise indicated, include compounds of Formula (I) herein, such as compounds 1-18, sometimes referred to as JAK inhibitors, including stereoisomers (including atropisomers), geometric isomers, tautomers, solvates, metabolites, isotopes, salts (e.g., pharmaceutically acceptable salts), and prodrugs thereof. In some embodiments, solvates, metabolites, isotopes or prodrugs are excluded, or any combination thereof.

The phrase "pharmaceutically acceptable" refers to molecular entities and compositions that do not produce an adverse, allergic or other untoward reaction when administered to an animal, such as, for example, a human, as appropriate.

Compounds of the present invention may be in the form of a salt, such as a pharmaceutically acceptable salt. "Pharmaceutically acceptable salts" include both acid and base addition salts. "Pharmaceutically acceptable acid addition salt" refers to those salts which retain the biological effectiveness and properties of the free bases and which are not biologically or otherwise undesirable, formed with inorganic acids such as hydrochloric acid, hydrobromic acid, sulfuric acid, nitric acid, carbonic acid, phosphoric acid and the like, and organic acids may be selected from aliphatic, cycloaliphatic, aromatic, araliphatic, heterocyclic, carboxylic, and sulfonic classes of organic acids such as formic acid, acetic acid, propionic acid, glycolic acid, gluconic acid, lactic acid, pyruvic acid, oxalic acid, malic acid, maleic acid, malonic acid, succinic acid, fumaric acid, tartaric acid, citric acid, aspartic acid, ascorbic acid, glutamic acid, anthranilic acid, benzoic acid, cinnamic acid, mandelic acid, embonic acid, phenylacetic acid, methanesulfonic acid, ethanesulfonic acid, benzenesulfonic acid, p-toluenesulfonic acid, salicyclic acid and the like.

"Pharmaceutically acceptable base addition salts" include those derived from inorganic bases such as sodium, potassium, lithium, ammonium, calcium, magnesium, iron, zinc, copper, manganese, aluminum salts and the like. Particular base addition salts are the ammonium, potassium, sodium, calcium and magnesium salts. Salts derived from pharmaceutically acceptable organic nontoxic bases include salts of primary, secondary, and tertiary amines, substituted amines including naturally occurring substituted amines, cyclic amines and basic ion exchange resins, such as isopropylamine, trimethylamine, diethylamine, triethylamine, tripropylamine, ethanolamine, 2-diethylaminoethanol, tromethamine, dicyclohexylamine, lysine, arginine, histidine, caffeine, procaine, hydrabamine, choline, betaine, ethylenediamine, glucosamine, methylglucamine, theobromine, purines, piperizine, piperidine, N-ethylpiperidine, polyamine resins and the like. Particular organic non-toxic bases include isopropylamine, diethylamine, ethanolamine, tromethamine, dicyclohexylamine, choline, and caffeine.

In some embodiments, a salt is selected from a hydrochloride, hydrobromide, trifluoroacetate, sulphate, phosphate, acetate, fumarate, maleate, tartrate, lactate, citrate, pyruvate, succinate, oxalate, methanesulphonate, p-toluenesulphonate, bisulphate, benzenesulphonate, ethanesulphonate, malonate, xinafoate, ascorbate, oleate, nicotinate, saccharinate, adipate, formate, glycolate, palmitate, L-lactate, D-lactate, aspartate, malate, L-tartrate, D-tartrate, stearate, furoate (e.g., 2-furoate or 3-furoate), napadisylate (naphthalene-1,5-disulfonate or naphthalene-1-(sulfonic acid)-5-sulfonate), edisylate (ethane-1,2-disulfonate or ethane-1-(sulfonic acid)-2-sulfonate), isethionate (2-hydroxyethylsulfonate), 2-mesitylenesulphonate, 2-naphthalenesulphonate, 2,5-dichlorobenzenesulphonate, D-mandelate, L-mandelate, cinnamate, benzoate, adipate, esylate, malonate, mesitylate (2-mesitylenesulphonate), napsylate (2-naphthalenesulfonate), camsylate (camphor-10-sulphonate, for example (1 S)-(+)-10-camphorsulfonic acid salt), glutamate, glutarate, hippurate (2-(benzoylamino)acetate), orotate, xylate (p-xylene-2-sulphonate), and pamoic (2,2'-dihydroxy-1,1'-dinaphthylmethane-3,3'-dicarboxylate).

A "sterile" formulation is aseptic or free from all living microorganisms and their spores.

"Stereoisomers" refer to compounds that have identical chemical constitution, but differ with regard to the arrangement of the atoms or groups in space. Stereoisomers include diastereomers, enantiomers, conformers and the like.

"Chiral" refers to molecules which have the property of non-superimposability of the mirror image partner, while the term "achiral" refers to molecules which are superimposable on their mirror image partner.

"Diastereomer" refers to a stereoisomer with two or more centers of chirality and whose molecules are not mirror images of one another. Diastereomers have different physical properties, e.g., melting points, boiling points, spectral properties or biological activities. Mixtures of diastereomers may separate under high resolution analytical procedures such as electrophoresis and chromatography such as HPLC.

"Enantiomers" refer to two stereoisomers of a compound which are non-superimposable mirror images of one another.

Stereochemical definitions and conventions used herein generally follow S. P. Parker, Ed., McGraw-Hill Dictionary of Chemical Terms (1984) McGraw-Hill Book Company, New York; and Eliel, E. and Wilen, S., "Stereochemistry of Organic Compounds", John Wiley & Sons, Inc., New York, 1994. Many organic compounds exist in optically active forms, i.e., they have the ability to rotate the plane of plane-polarized light. In describing an optically active compound, the prefixes D and L, or R and S, are used to denote the absolute configuration of the molecule about its chiral center(s). The prefixes d and l or (+) and (−) are employed to designate the sign of rotation of plane-polarized light by the compound, with (−) or l meaning that the compound is levorotatory. A compound prefixed with (+) or d is dextrorotatory. For a given chemical structure, these stereoisomers are identical except that they are mirror images of one another. A specific stereoisomer may also be referred to as an enantiomer, and a mixture of such isomers is often called an enantiomeric mixture. A 50:50 mixture of enantiomers is referred to as a racemic mixture or a racemate, which may occur where there has been no stereoselection or stereospecificity in a chemical reaction or process. The terms "racemic mixture" and "racemate" refer to an equimolar mixture of two enantiomeric species, devoid of optical activity.

The term "tautomer" or "tautomeric form" refers to structural isomers of different energies which are interconvertible via a low energy barrier. For example, proton tautomers (also known as prototropic tautomers) include interconversions via migration of a proton, such as keto-enol and imine-enamine isomerizations. Valence tautomers include interconversions by reorganization of some of the bonding electrons.

Certain compounds of the present invention can exist in unsolvated forms as well as solvated forms, including hydrated forms. A "solvate" refers to an association or complex of one or more solvent molecules and a compound of the present invention. Examples of solvents that form solvates include water, isopropanol, ethanol, methanol, DMSO, ethyl acetate, acetic acid, and ethanolamine. Certain compounds of the present invention can exist in multiple crystalline or amorphous forms. In general, all physical forms are intended to be within the scope of the present invention. The term "hydrate" refers to the complex where the solvent molecule is water.

A "metabolite" refers to a product produced through metabolism in the body of a specified compound or salt thereof. Such products can result, for example, from the oxidation, reduction, hydrolysis, amidation, deamidation, esterification, deesterification, enzymatic cleavage, and the like, of the administered compound.

Metabolite products typically are identified by preparing a radiolabelled (e.g., $^{14}C$ or $^{3}H$) isotope of a compound of the invention, administering it in a detectable dose (e.g., greater than about 0.5 mg/kg) to an animal such as rat, mouse, guinea pig, monkey, or to a human, allowing sufficient time for metabolism to occur (typically about 30 seconds to 30 hours) and isolating its conversion products from the urine, blood or other biological samples. These products are easily isolated since they are labeled (others are isolated by the use of antibodies capable of binding epitopes surviving in the metabolite). The metabolite structures are determined in conventional fashion, e.g., by MS, LC/MS or NMR analysis. In general, analysis of metabolites is done in the same way as conventional drug metabolism studies well known to those skilled in the art. The metabolite products, so long as they are not otherwise found in vivo, are useful in diagnostic assays for therapeutic dosing of the compounds of the invention.

A "subject," "individual," or "patient" is a vertebrate. In certain embodiments, the vertebrate is a mammal. Mammals include, but are not limited to, farm animals (such as cows), sport animals, pets (such as guinea pigs, cats, dogs, rabbits and horses), primates, mice and rats. In certain embodiments, a mammal is a human. In embodiments comprising administration of a JAK inhibitor as described herein or a pharmaceutically acceptable salt thereof to a patient, the patient may be in need thereof.

The term "Janus kinase" refers to JAK1, JAK2, JAK3 and TYK2 protein kinases. In some embodiments, a Janus kinase may be further defined as one of JAK1, JAK2, JAK3 or TYK2. In any embodiment, any one of JAK1, JAK2, JAK3 and TYK2 may be specifically excluded as a Janus kinase. In some embodiments, a Janus kinase is JAK1. In some embodiments, a Janus kinase is a combination of JAK1 and JAK2.

The terms "inhibiting" and "reducing," or any variation of these terms, includes any measurable decrease or complete inhibition to achieve a desired result. For example, there may be a decrease of about, at most about, or at least about 5%, 10%, 15%, 20%, 25%, 30%, 35%, 40%, 45%, 50%, 55%, 60%, 65%, 70%, 75%, 80%, 85%, 90%, 95%, 99%, or more, or any range derivable therein, reduction of activity (e.g., JAK1 activity) compared to normal.

"Therapeutically effective amount" means an amount of a compound or a salt thereof (e.g., a pharmaceutically acceptable salt thereof) of the present invention that (i) treats or prevents the particular disease, condition or disorder, or (ii) attenuates, ameliorates or eliminates one or more symptoms of the particular disease, condition, or disorder, and optionally (iii) prevents or delays the onset of one or more symptoms of the particular disease, condition or disorder described herein. In some embodiments, the therapeutically effective amount is an amount sufficient to decrease or alleviate the symptoms of an autoimmune or inflammatory disease (e.g., asthma). In some embodiments, a therapeutically effective amount is an amount of a chemical entity described herein sufficient to significantly decrease the activity or number of B-cells. In the case of cancer, the therapeutically effective amount of the drug may reduce the number of cancer cells; reduce the tumor size; inhibit (i.e., slow to some extent and preferably stop) cancer cell infiltration into peripheral organs; inhibit (i.e., slow to some extent and preferably stop) tumor metastasis; inhibit, to some extent, tumor growth; or relieve to some extent one or more of the symptoms associated with the cancer. To the extent the drug may prevent growth or kill existing cancer cells, it may be cytostatic or cytotoxic. For cancer therapy, efficacy can, for example, be measured by assessing the time to disease progression (TTP) or determining the response rate (RR).

"Treatment" (and variations such as "treat" or "treating") refers to clinical intervention in an attempt to alter the natural course of the individual or cell being treated, and can be performed either for prophylaxis or during the course of clinical pathology. Desirable effects of treatment include preventing occurrence or recurrence of disease, alleviation of symptoms, diminishment of any direct or indirect pathological consequences of the disease, stabilized (i.e., not worsening) state of disease, decreasing the rate of disease progression, amelioration or palliation of the disease state, prolonging survival as compared to expected survival if not receiving treatment and remission or improved prognosis. In some embodiments, a compound of the invention or a salt thereof (e.g., a pharmaceutically acceptable salt thereof), is used to delay development of a disease or disorder or to slow the progression of a disease or disorder. Those in need of treatment include those already with the condition or disorder as well as those prone to have the condition or disorder, (for example, through a genetic mutation) or those in which the condition or disorder is to be prevented.

"Inflammatory disorder" refers to any disease, disorder or syndrome in which an excessive or unregulated inflammatory response leads to excessive inflammatory symptoms, host tissue damage, or loss of tissue function. "Inflammatory disorder" also refers to a pathological state mediated by influx of leukocytes or neutrophil chemotaxis.

"Inflammation" refers to a localized, protective response elicited by injury or destruction of tissues, which serves to destroy, dilute, or wall off (sequester) both the injurious agent and the injured tissue. Inflammation is notably associated with influx of leukocytes or neutrophil chemotaxis. Inflammation can result from infection with pathogenic organisms and viruses and from noninfectious means such as trauma or reperfusion following myocardial infarction or stroke, immune responses to foreign antigens, and autoimmune responses. Accordingly, inflammatory disorders amenable to treatment with a compound or a salt thereof (e.g., a pharmaceutically acceptable salt thereof) of the present invention encompass disorders associated with reactions of the specific defense system as well as with reactions of the nonspecific defense system.

"Specific defense system" refers to the component of the immune system that reacts to the presence of specific antigens. Examples of inflammation resulting from a response of the specific defense system include the classical response to foreign antigens, autoimmune diseases, and delayed type hypersensitivity responses mediated by T-cells. Chronic inflammatory diseases, the rejection of solid transplanted tissue and organs, e.g., kidney and bone marrow transplants, and graft versus host disease (GVHD), are further examples of inflammatory reactions of the specific defense system.

The term "nonspecific defense system" refers to inflammatory disorders that are mediated by leukocytes that are incapable of immunological memory (e.g., granulocytes, and macrophages). Examples of inflammation that result, at least in part, from a reaction of the nonspecific defense system include inflammation associated with conditions such as adult (acute) respiratory distress syndrome (ARDS) or multiple organ injury syndromes; reperfusion injury; acute glomerulonephritis; reactive arthritis; dermatoses with acute inflammatory components; acute purulent meningitis or other central nervous system inflammatory disorders such as stroke; thermal injury; inflammatory bowel disease; granulocyte transfusion associated syndromes; and cytokine-induced toxicity.

"Autoimmune disease" refers to any group of disorders in which tissue injury is associated with humoral or cell-mediated responses to the body's own constituents. Non-limiting examples of autoimmune diseases include rheumatoid arthritis, lupus and multiple sclerosis.

"Allergic disease" as used herein refers to any symptoms, tissue damage, or loss of tissue function resulting from allergy. "Arthritic disease" as used herein refers to any disease that is characterized by inflammatory lesions of the joints attributable to a variety of etiologies. "Dermatitis" as used herein refers to any of a large family of diseases of the skin that are characterized by inflammation of the skin attributable to a variety of etiologies. "Transplant rejection" as used herein refers to any immune reaction directed against grafted tissue, such as organs or cells (e.g., bone marrow), characterized by a loss of function of the grafted and surrounding tissues, pain, swelling, leukocytosis, and thrombocytopenia. The therapeutic methods of the present invention include methods for the treatment of disorders associated with inflammatory cell activation.

"Inflammatory cell activation" refers to the induction by a stimulus (including, but not limited to, cytokines, antigens or auto-antibodies) of a proliferative cellular response, the production of soluble mediators (including but not limited to cytokines, oxygen radicals, enzymes, prostanoids, or vasoactive amines), or cell surface expression of new or increased numbers of mediators (including, but not limited to, major histocompatability antigens or cell adhesion molecules) in inflammatory cells (including but not limited to monocytes, macrophages, T lymphocytes, B lymphocytes, granulocytes (i.e., polymorphonuclear leukocytes such as neutrophils, basophils, and eosinophils), mast cells, dendritic cells, Langerhans cells, and endothelial cells). It will be appreciated by persons skilled in the art that the activation of one or a combination of these phenotypes in these cells can contribute to the initiation, perpetuation, or exacerbation of an inflammatory disorder.

In some embodiments, inflammatory disorders which can be treated according to the methods of this invention include, but are not limited to, asthma, rhinitis (e.g., allergic rhinitis), allergic airway syndrome, atopic dermatitis, bronchitis, rheumatoid arthritis, psoriasis, contact dermatitis, chronic obstructive pulmonary disease (COPD) and delayed hypersensitivity reactions.

The terms "cancer" and "cancerous", "neoplasm", and "tumor" and related terms refer to or describe the physiological condition in mammals that is typically characterized by unregulated cell growth. A "tumor" comprises one or more cancerous cells. Examples of cancer include carcinoma, blastoma, sarcoma, seminoma, glioblastoma, melanoma, leukemia, and myeloid or lymphoid malignancies. More particular examples of such cancers include squamous cell cancer (e.g., epithelial squamous cell cancer) and lung cancer including small-cell lung cancer, non-small cell lung cancer ("NSCLC"), adenocarcinoma of the lung and squamous carcinoma of the lung. Other cancers include skin, keratoacanthoma, follicular carcinoma, hairy cell leukemia, buccal cavity, pharynx (oral), lip, tongue, mouth, salivary gland, esophageal, larynx, hepatocellular, gastric, stomach, gastrointestinal, small intestine, large intestine, pancreatic, cervical, ovarian, liver, bladder, hepatoma, breast, colon, rectal, colorectal, genitourinary, biliary passage, thyroid, papillary, hepatic, endometrial, uterine, salivary gland, kidney or renal, prostate, testis, vulval, peritoneum, anal, penile, bone, multiple myeloma, B-cell lymphoma, central nervous system, brain, head and neck, Hodgkin's, and associated metastases. Examples of neoplastic disorders include myeloproliferative disorders, such as polycythemia vera, essential thrombocytosis, myelofibrosis, such as primary myelofibrosis, and chronic myelogenous leukemia (CML).

A "chemotherapeutic agent" is an agent useful in the treatment of a given disorder, for example, cancer or inflammatory disorders. Examples of chemotherapeutic agents are well-known in the art and include examples such as those disclosed in U.S. Publ. Appl. No. 2010/0048557, incorporated herein by reference. Additionally, chemotherapeutic agents include pharmaceutically acceptable salts, acids or derivatives of any of chemotherapeutic agents, as well as combinations of two or more of them.

"Package insert" is used to refer to instructions customarily included in commercial packages of therapeutic products that contain information about the indications, usage, dosage, administration, contraindications or warnings concerning the use of such therapeutic products.

Unless otherwise stated, structures depicted herein include compounds that differ only in the presence of one or more isotopically enriched atoms. Exemplary isotopes that can be incorporated into compounds of the present invention include isotopes of hydrogen, carbon, nitrogen, oxygen, phosphorus, sulfur, fluorine, chlorine, and iodine, such as $^2H$, $^3H$, $^{11}C$, $^{13}C$, $^{14}C$, $^{13}N$, $^{15}N$, $^{15}O$, $^{17}O$, $^{18}O$, $^{32}P$, $^{33}P$, $^{35}S$, $^{18}F$, $^{36}Cl$, $^{123}I$, and $^{125}I$, respectively. Isotopically-labeled compounds (e.g., those labeled with $^3H$ and $^{14}C$) can be useful in compound or substrate tissue distribution assays. Tritiated (i.e., $^3H$) and carbon-14 (i.e., $^{14}C$) isotopes can be useful for their ease of preparation and detectability. Further, substitution with heavier isotopes such as deuterium (i.e., $^2H$) may afford certain therapeutic advantages resulting from greater metabolic stability (e.g., increased in vivo half-life or reduced dosage requirements). In some embodiments, one or more hydrogen atoms are replaced by $^2H$ or $^3H$, or one or more carbon atoms are replaced by $^{13}C$- or $^{14}C$-enriched carbon. Positron emitting isotopes such as $^{15}O$, $^{13}N$, $^{11}C$, and $^{18}F$ are useful for positron emission tomography (PET) studies to examine substrate receptor occupancy. Isotopically labeled compounds can generally be prepared by procedures analogous to those disclosed in the Schemes or in the Examples herein, by substituting an isotopically labeled reagent for a non-isotopically labeled reagent.

It is specifically contemplated that any limitation discussed with respect to one embodiment of the invention may apply to any other embodiment of the invention. Furthermore, any compound or a salt thereof (e.g., a pharmaceutically acceptable salt thereof) or composition of the invention may be used in any method of the invention, and any method of the invention may be used to produce or to utilize any compound or a salt thereof (e.g., a pharmaceutically acceptable salt thereof) or composition of the invention.

The use of the term "or" is used to mean "and/or" unless explicitly indicated to refer to alternatives only or the alternatives are mutually exclusive, although the disclosure supports a definition that refers to only alternatives and "and/or."

Throughout this application, the term "about" is used to indicate that a value includes the standard deviation of error for the device or method being employed to determine the value.

As used herein, "a" or "an" means one or more, unless clearly indicated otherwise. As used herein, "another" means at least a second or more.

Headings used herein are intended only for organizational purposes.

Inhibitors of Janus Kinases

One embodiment provides a compound of Formula (I):

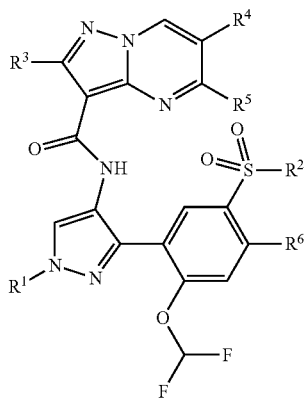

(I)

or a pharmaceutically acceptable salt thereof, wherein:
$R^1$ is: $C_{1-6}$alkyl; cyano-$C_{1-6}$alkyl; $C_{1-6}$alkoxy-(CO)—; —(CHR$^a$)$_m$—NR$^b$R$^c$; or —(CHR$^a$)$_n$-het$^1$;
$R^2$ is: $C_{1-6}$alkyl; hydroxy-$C_{1-6}$alkyl; halo-$C_{1-6}$alkyl; $C_{1-6}$alkoxy-$C_{1-6}$alkyl; $C_{3-6}$cycloalkyl; —(CHR$^a$)$_p$—NR$^b$R$^c$; het$^2$; —(CHR$^a$)$_q$-het$^3$; or phenyl which may be unsubstituted or substituted once or twice with R$^d$;
$R^3$ is: hydrogen; amino; or $C_{1-6}$alkyl;
$R^4$ is: hydrogen; or $C_{1-6}$alkyl;
$R^5$ is: hydrogen; or $C_{1-6}$alkyl;
$R^6$ is: hydrogen; $C_{1-6}$alkyl; or $R^2$ and $R^6$ together with the atoms to which they are attached may form a six membered ring;
m is from 2 to 3;
n is from 0 to 2;
p is from 0 to 2;
each R$^a$ is independently: hydrogen; or $C_{1-6}$alkyl;
each R$^b$ is independently: hydrogen; or $C_{1-6}$alkyl;
each R$^c$ is independently: hydrogen; or $C_{1-6}$alkyl;
het$^1$ is: tetrahydrofuranyl; azetidinyl; or pyrrolidinyl, each of which may be unsubstituted or substituted once or twice with R$^e$;
het$^2$ is: pyridinyl; pyrimidinyl; pyrazolyl; imidazolyl; or isoquinolinyl which may be partially saturated; each of which may be unsubstituted or substituted once or twice with R$^f$;
het$^3$ is: azetidinyl; pyrrolidinyl; oxetanyl; or piperidinyl; each of which may be unsubstituted or substituted once with R$^g$;
each R$^d$ is independently: $C_{1-6}$alkyl; hydroxy; $C_{1-6}$alkoxy-$C_{1-6}$alkyl; —(CHR$^a$)$_q$—NR$^b$R$^c$; or phenyl;
each R$^e$ is independently: $C_{1-6}$alkyl; or oxo;
each R$^f$ is independently: $C_{1-6}$alkyl; hydroxy-$C_{1-6}$alkyl; oxo; —(CHR$^a$)$_r$—NR$^b$R$^c$; —(CHR$^a$)$_s$-het$^4$;
each R$^g$ is independently: $C_{1-6}$alkyl; or acetyl;
q is from 1 to 2;
r is from 2 to 3;
s is from 2 to 3; and
het$^4$ is: azetidin-1-yl; 1-methyl-azetidin-3-yl; quinuclidinyl; 1-methyl-pyrrolidin-2-yl; or 4-methylpiperazin-1-yl.

In certain embodiments $R^3$ is hydrogen.
In certain embodiments $R^4$ is hydrogen.
In certain embodiments $R^5$ is hydrogen.
In certain embodiments $R^6$ is hydrogen.
In certain embodiments $R^1$ is cyanomethyl or methyl.
In certain embodiments $R^1$ is cyanomethyl.
In certain embodiments $R^1$ is methyl.
In certain embodiments $R^2$ is: $C_{1-6}$alkyl; hydroxy-$C_{1-6}$alkyl; halo-$C_{1-6}$alkyl; $C_{1-6}$alkoxy-$C_{1-6}$alkyl; $C_{3-6}$cycloalkyl; —(CHR$^a$)$_p$—NR$^b$R$^c$; het$^2$; —(CHR$^a$)$_q$-het$^3$; or phenyl which may be unsubstituted or substituted once with R$^d$.
In certain embodiments $R^2$ is $C_{1-6}$alkyl.
In certain embodiments $R^2$ is hydroxy-$C_{1-6}$alkyl.
In certain embodiments $R^2$ is halo-$C_{1-6}$alkyl.
In certain embodiments $R^2$ is $C_{1-6}$alkoxy-$C_{1-6}$alkyl.
In certain embodiments $R^2$ is $C_{3-6}$cycloalkyl.
In certain embodiments $R^2$ is —(CHR$^a$)$_p$—NR$^b$R$^c$.
In certain embodiments $R^2$ is het$^2$.
In certain embodiments $R^2$ is —(CHR$^a$)$_q$-het$^3$.
In certain embodiments $R^2$ is phenyl which may be unsubstituted or substituted once with R$^d$.
In certain embodiments $R^2$ is $C_{1-6}$alkyl, hydroxy-$C_{1-6}$alkyl; $C_{1-6}$alkoxy-$C_{1-6}$alkyl or halo-$C_{1-6}$alkyl.
In certain embodiments $R^2$ is —(CH$_2$)$_2$—NR$^b$R$^c$.
In certain embodiments $R^2$ is $C_{1-6}$alkyl.

In certain embodiments $R^2$ is hydroxy-$C_{1-6}$alkyl or $C_{1-6}$alkoxy-$C_{1-6}$alkyl.

In certain embodiments $R^2$ is hydroxy-$C_{1-6}$alkyl.

In certain embodiments $R^2$ is $C_{1-6}$alkoxy-$C_{1-6}$alkyl.

In certain embodiments $R^2$ is methoxy-$C_{1-6}$alkyl.

In certain embodiments $R^2$ is 2-methoxyethyl.

In certain embodiments $R^2$ is halo-$C_{1-6}$alkyl.

In certain embodiments $R^2$ is 2-hydroxy ethyl, difluoromethoxy, 3-hydroxyhenyl, -methoxyphenyl, 2-hydroxypropyl, pyridine-4-yl, methyl, azetidin-yl, 2-hydroxy-1-methyl-ethyl, methylamino, dimethylamino, 1-methyl-pyrazol-4-yl, phenyl, pyrazol-4-yl, 1-methyl-2-oxo-4-pyridyl, or 2-hydroxy-1-methyl-propyl.

In certain embodiments $R^2$ is 2-hydroxyethyl, 2-hydroxypropyl, 2-hydroxy-1-methyl-ethyl, or 2-hydroxy-1-methyl-propyl.

In certain embodiments $R^2$ is 2-hydroxyethyl.

In certain embodiments $R^2$ is 2-hydroxypropyl.

In certain embodiments $R^2$ is 2-hydroxy-1-methyl-ethyl.

In certain embodiments $R^2$ is 2-hydroxy-1-methyl-propyl.

In certain embodiments m is 2.

In certain embodiments m is 3.

In certain embodiments n is 0.

In certain embodiments n is 1.

In certain embodiments n is 2.

In certain embodiments p is 0.

In certain embodiments p is 1.

In certain embodiments p is 2.

In certain embodiments q is 1.

In certain embodiments q is 2.

In certain embodiments r is 2.

In certain embodiments r is 3.

In certain embodiments s is 2.

In certain embodiments s is 3.

In certain embodiments $R^a$ is hydrogen.

In certain embodiments $R^a$ is $C_{1-6}$alkyl.

In certain embodiments $R^b$ is hydrogen.

In certain embodiments $R^b$ is $C_{1-6}$alkyl.

In certain embodiments $R^c$ is hydrogen.

In certain embodiments $R^c$ is $C_{1-6}$alkyl.

In certain embodiments $het^1$ is 1-methyl azetidin-4-yl, 2-oxy-tetrahydrofuran-3-yl or pyrrolidinyl.

In certain embodiments $het^2$ is pyridine-4-yl, 1-methyl-pyrazol-4-yl, 1-(2-hydroxypropyl)-pyrazol-4-yl, pyrazol-4-yl, pyridine-3-yl, 6-oxo-1H-pyridin-3-yl, 1-methyl-2-oxo-pyridin-4-yl, 1-quinuclidin-3-ylpyrazol-4-yl, 1-[2-[(1-methylpyrrolidin-2-yl]ethyl]pyrazol-4-yl, 1-[2-(dimethylamino)propyl]pyrazol-4-yl, 1-methyl-azetidin-3-yl)pyrazol-4-yl, 2-methyl-1H-isoquinolin-7-yl, 2-methyl-1H-isoquinolin-6-yl, 1-methyl-imidazol-4-yl, or 1H-imidazol-4-yl, pyrimidin-5-yl, In certain embodiments $het^3$ is 1-methyl-azetidin-4-yl, azetidin-4-yl, azetidine-1-yl, pyrrolidin-3-yl, oxetan-4-yl, 1-methyl-pyrrolidin-3-yl, 1-acetyl-azetidin-4-yl, piperidin-3-yl, or 4-methylpiperazin-1-yl.

In certain embodiments the subject compounds are of formula (II)

(II)

wherein $R^1$ and $R^2$ are as defined herein.

In certain embodiments the subject compounds are of formula (III)

(III)

wherein $R^2$ is as defined herein.

In certain embodiments the compound of formula (I) is selected from:

;

-continued
25
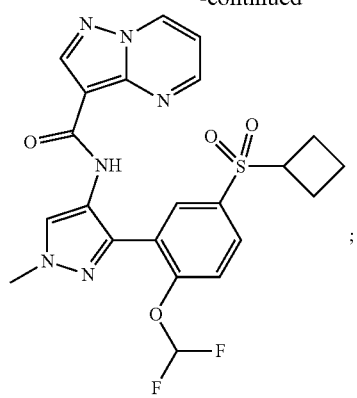
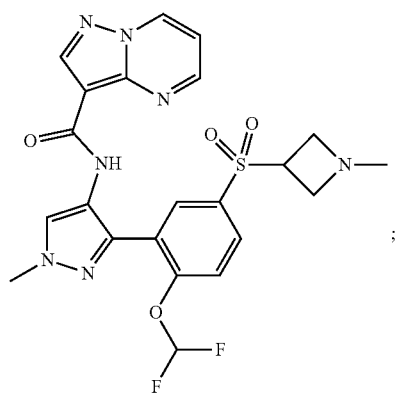
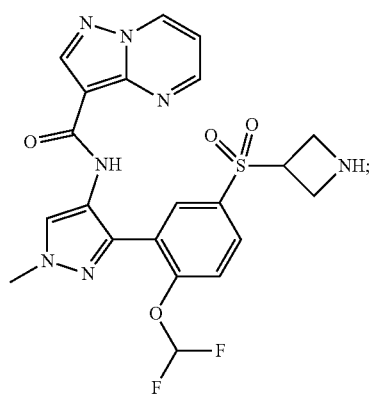
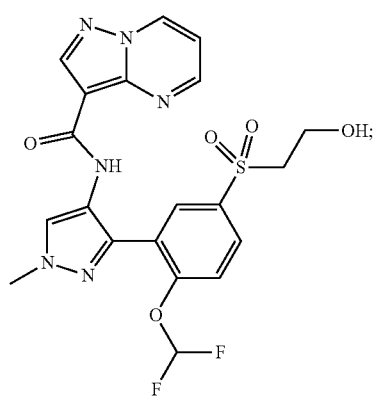
26
-continued
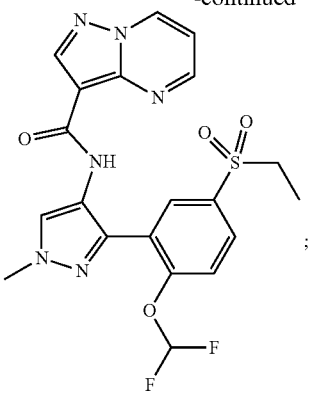
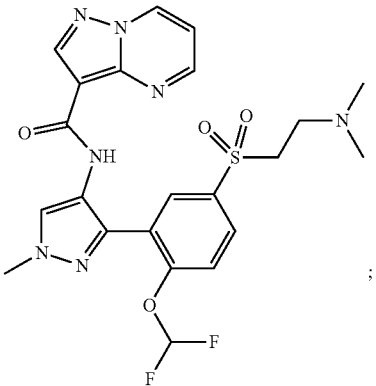
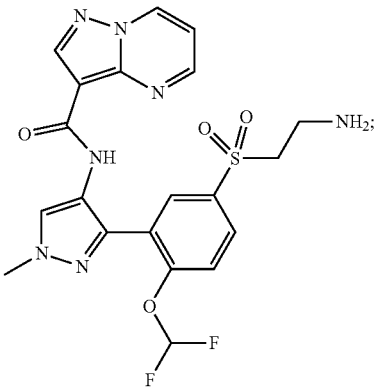
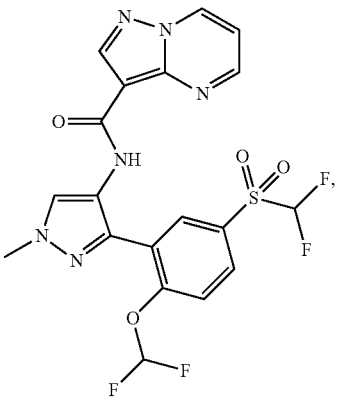

27
-continued
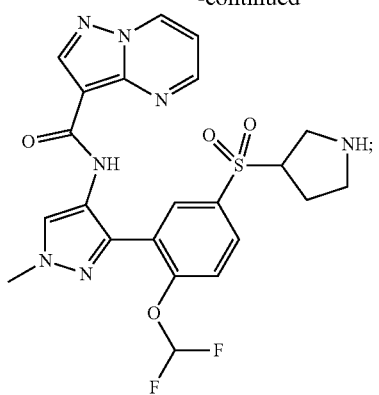
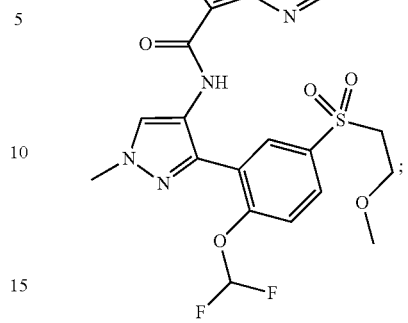
28
-continued
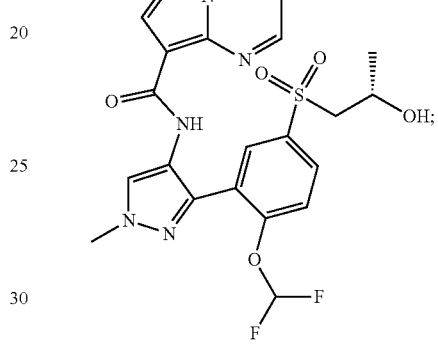
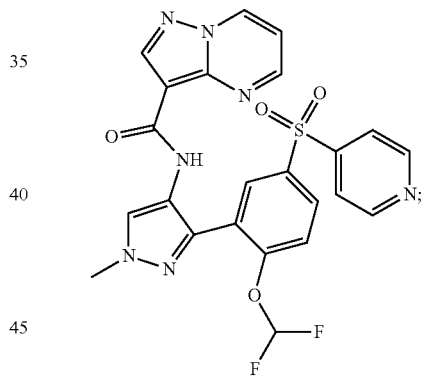
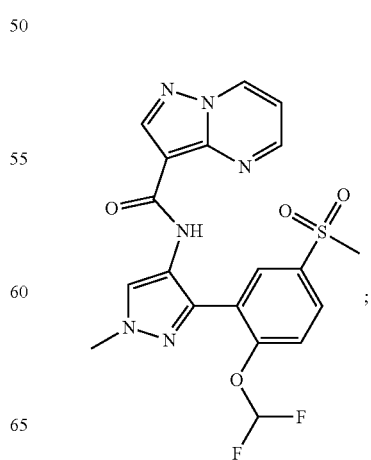

29
-continued
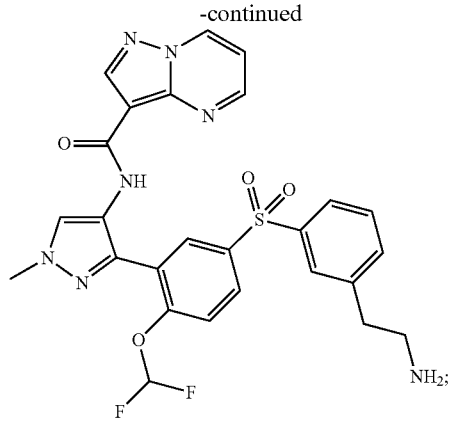
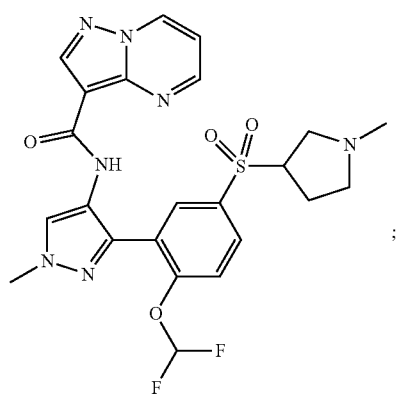
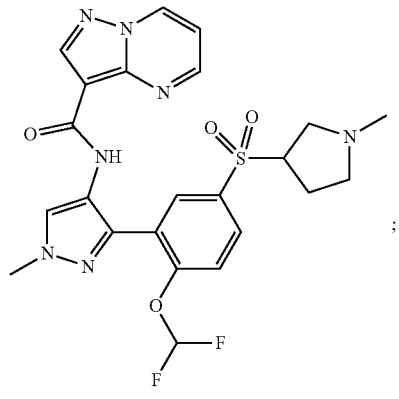
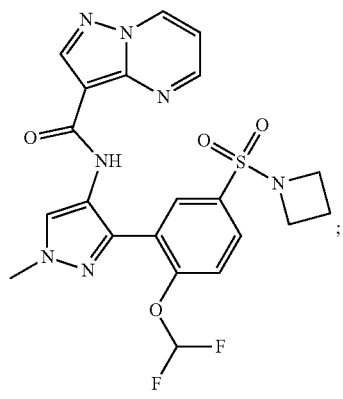
30
-continued
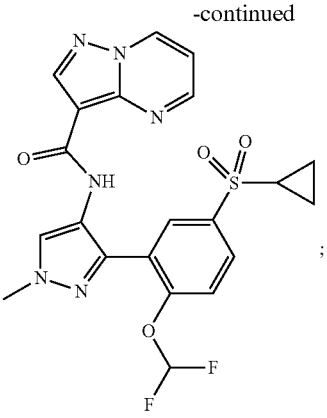
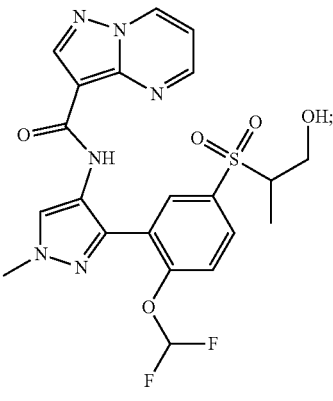
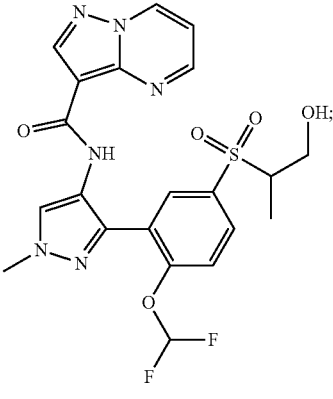
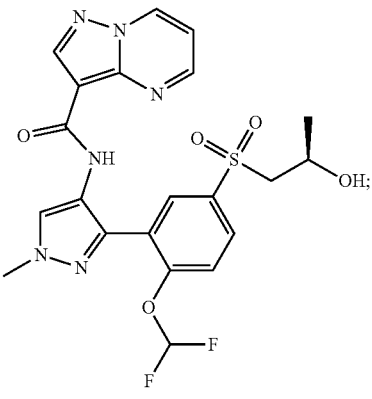

31
-continued
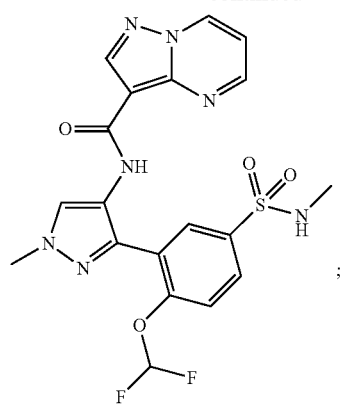
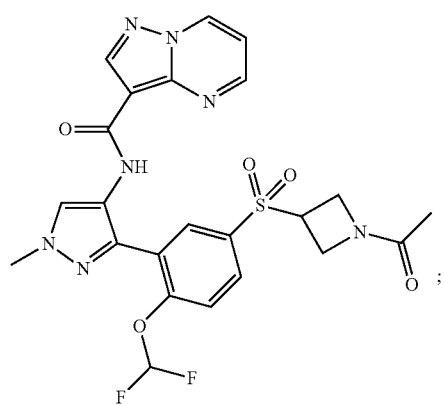
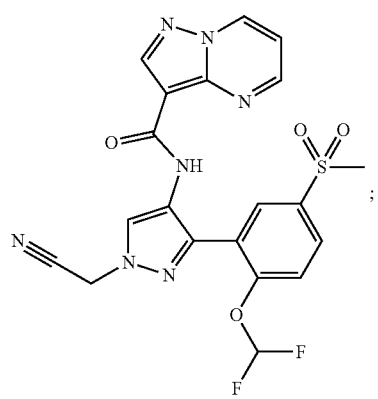
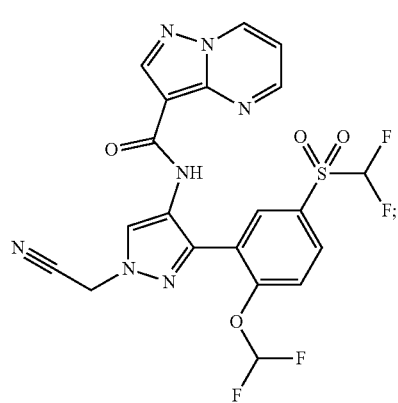
32
-continued
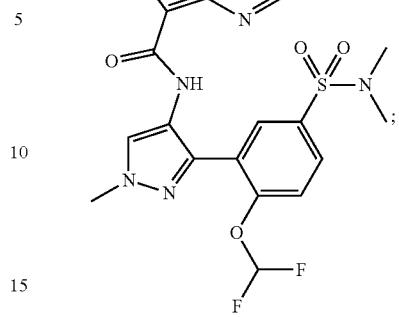
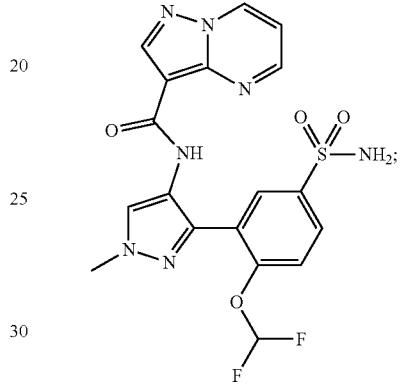
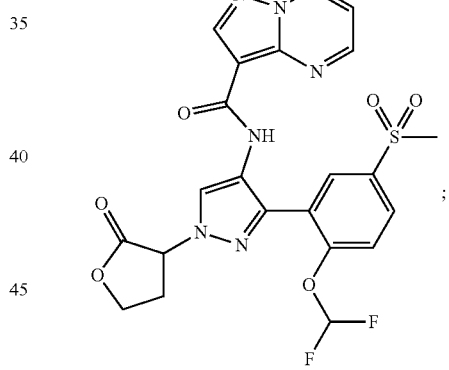
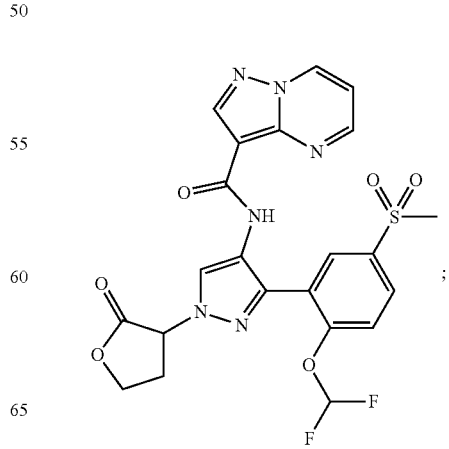

33
-continued
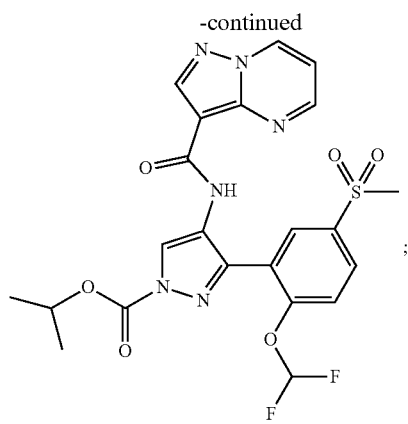
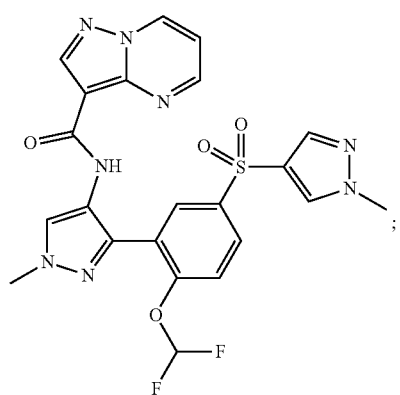
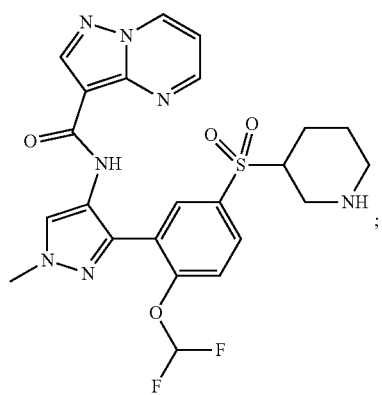
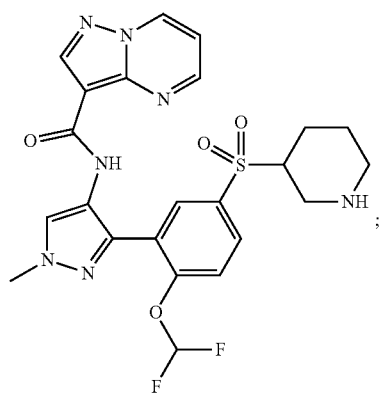
34
-continued
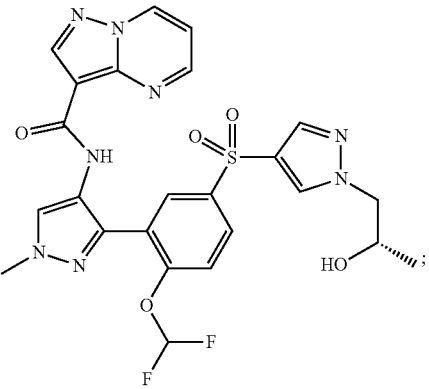
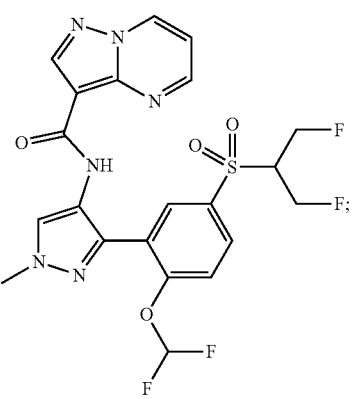
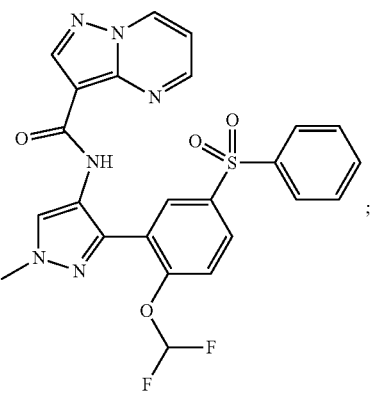
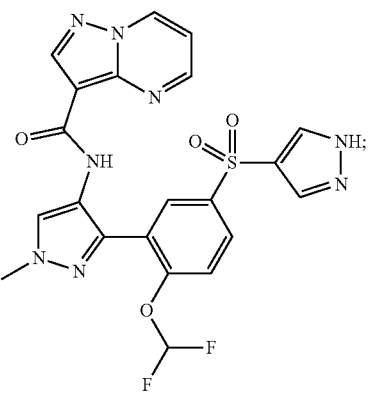

35
-continued
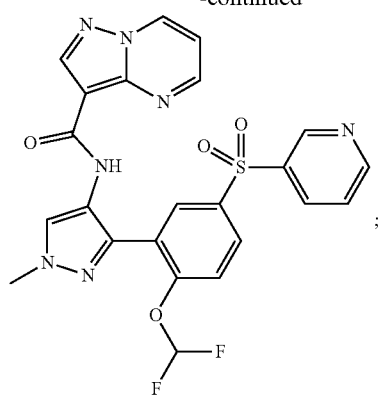
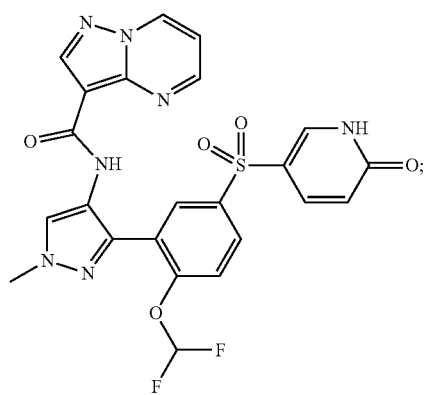
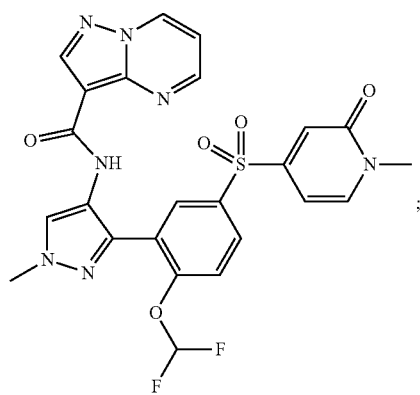
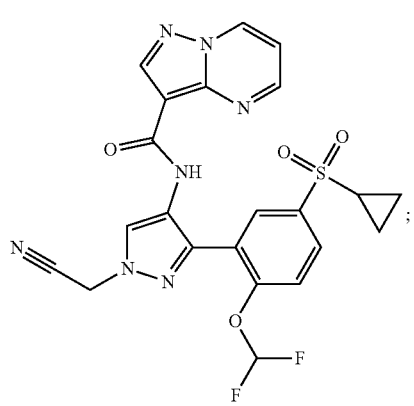
36
-continued
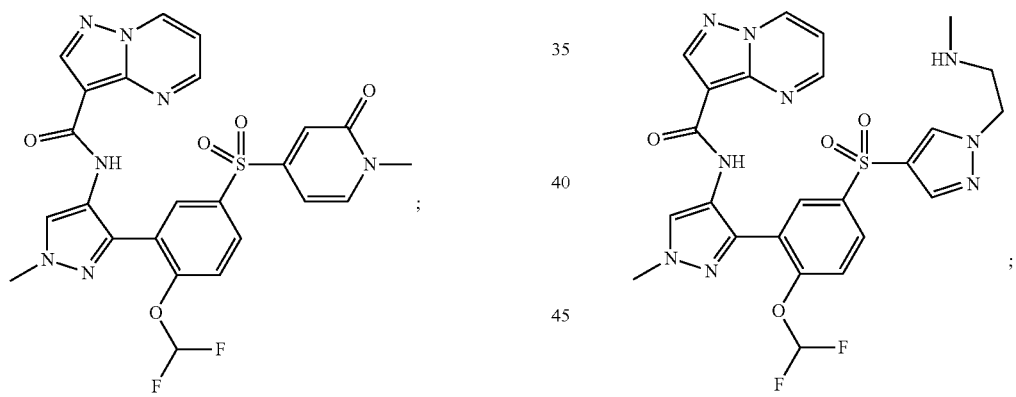
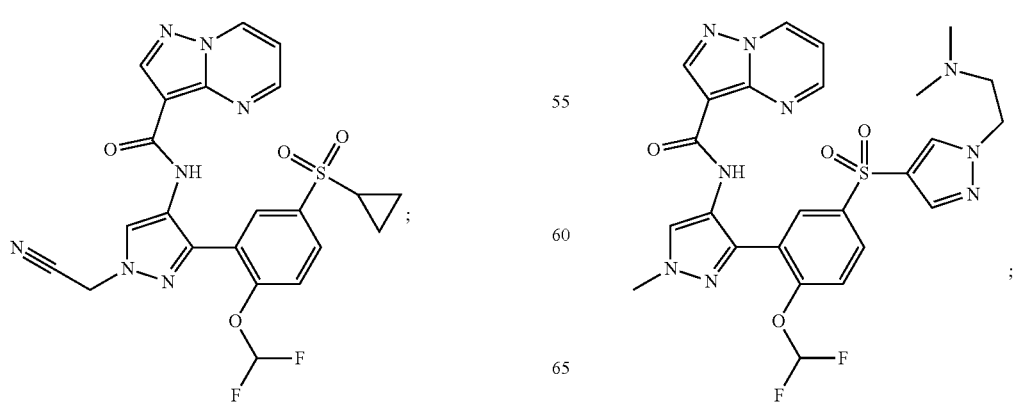

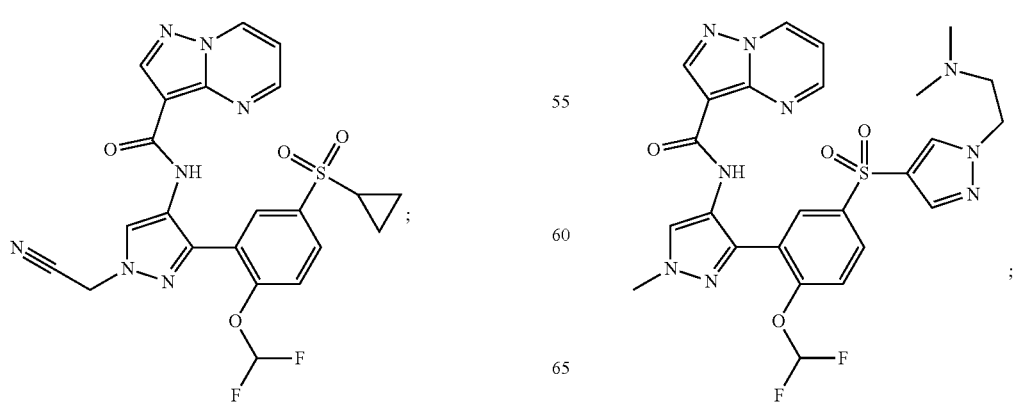

37
-continued
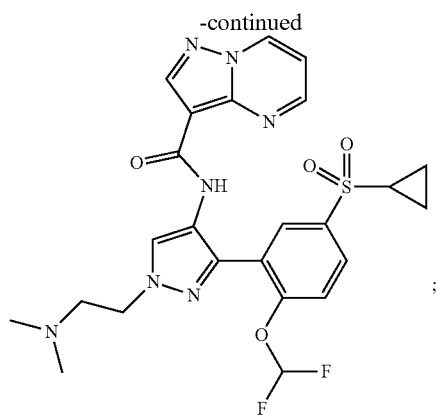
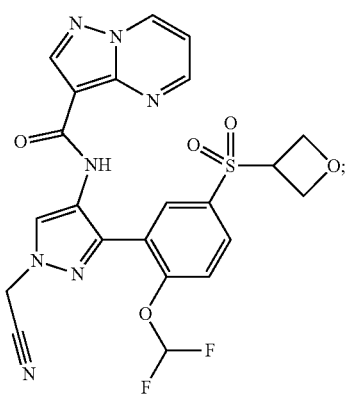
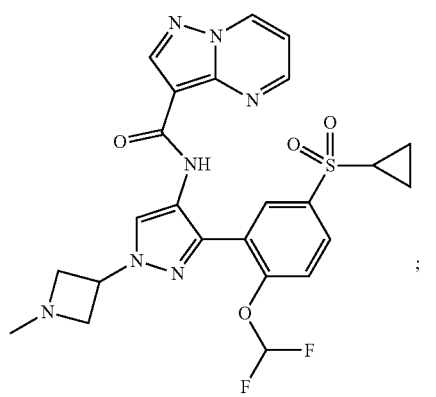
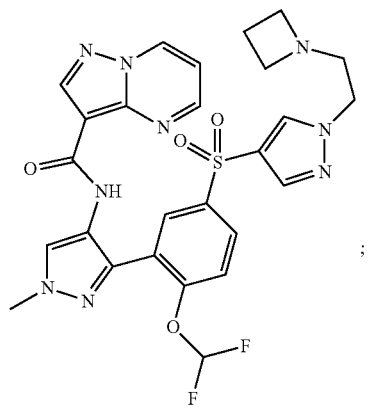
38
-continued
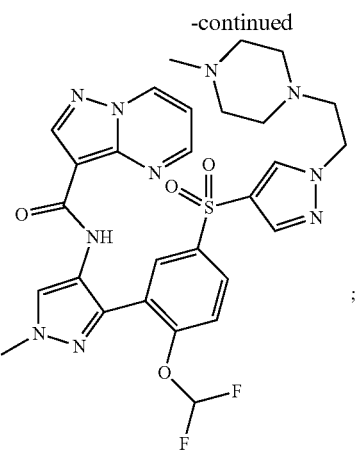
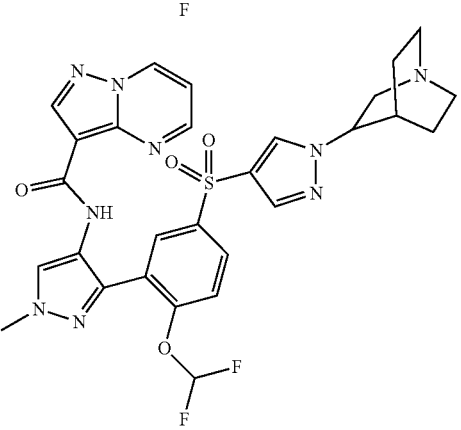
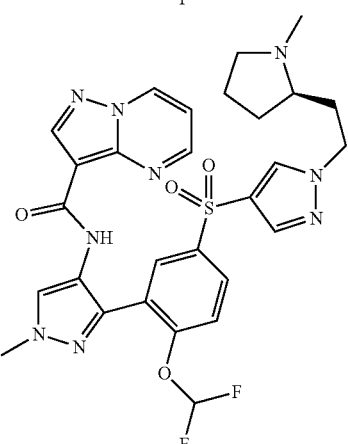
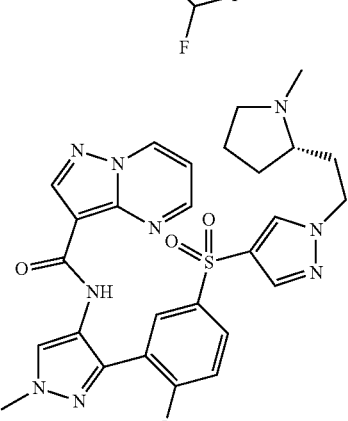

;
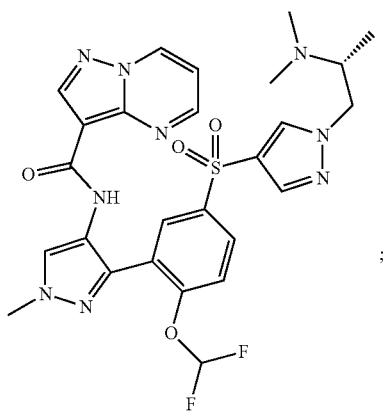
;
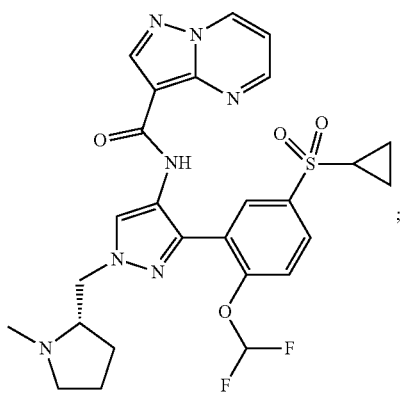
;
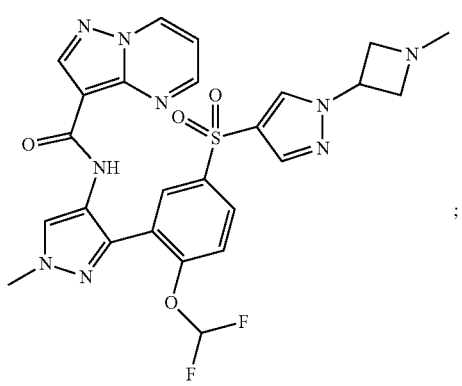
;
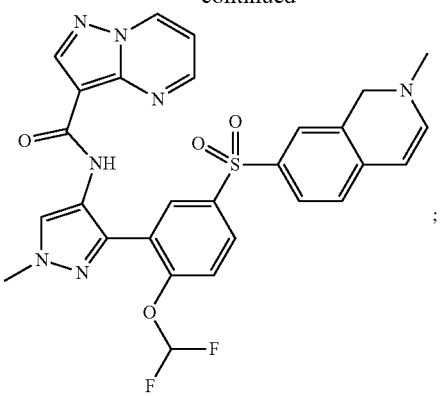
;
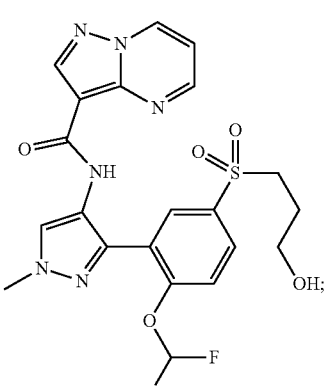
;
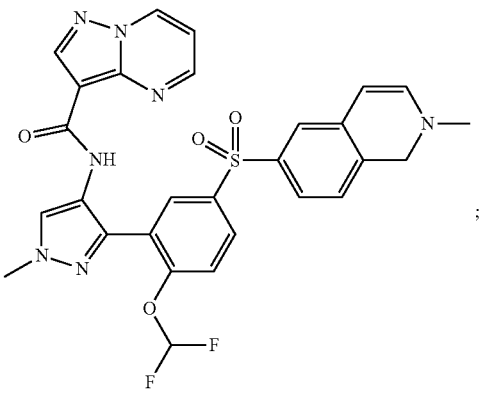
;
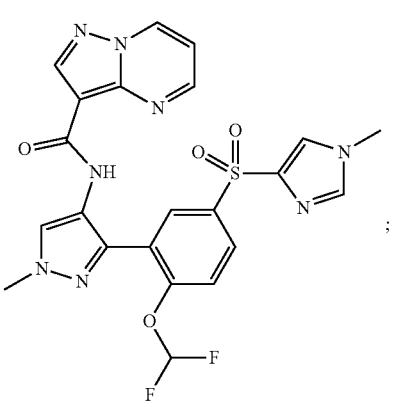
;

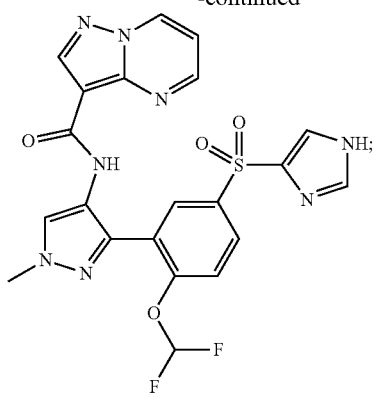
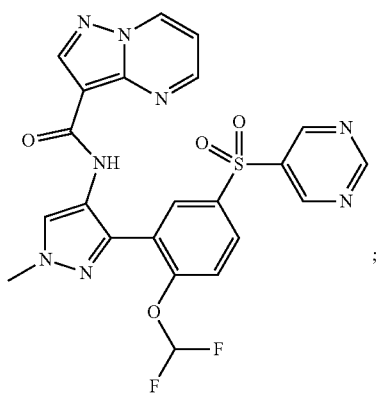
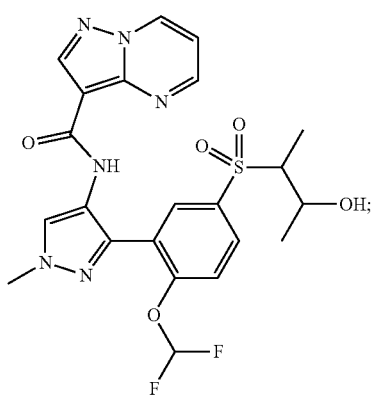
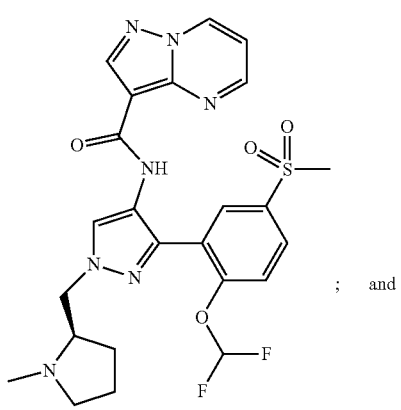
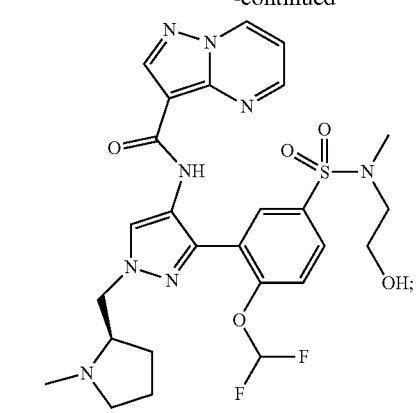
or a pharmaceutically acceptable stereoisomer or salt thereof.
In certain embodiments, the subject compound is selected from:
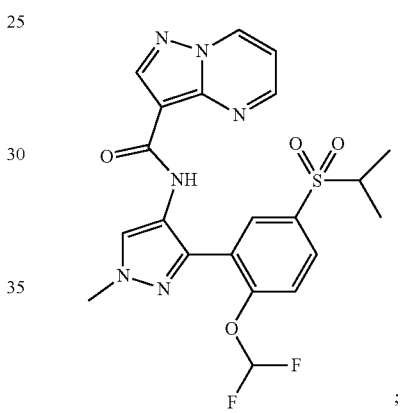
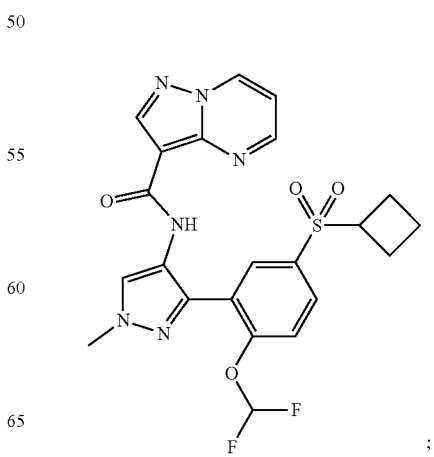

43
-continued
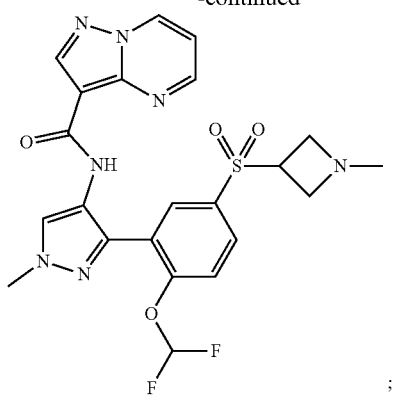
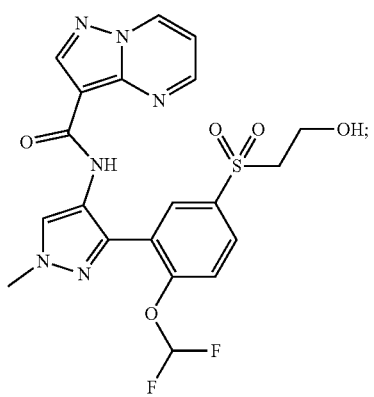
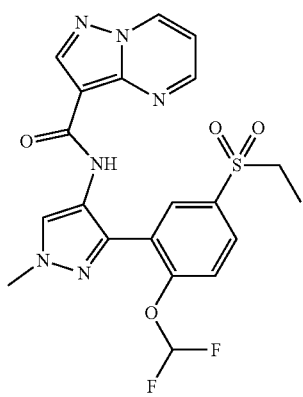
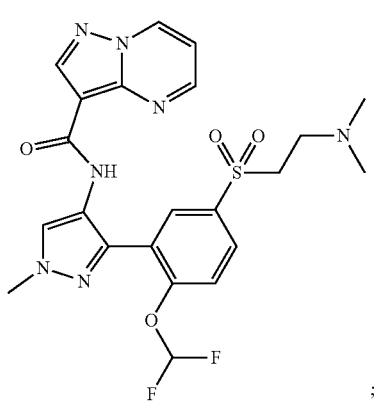
44
-continued
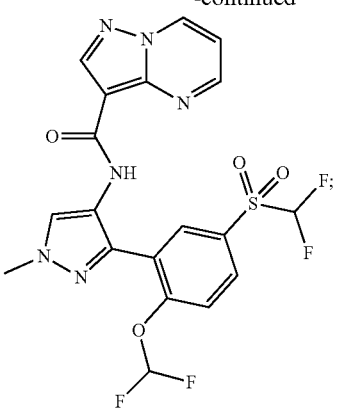
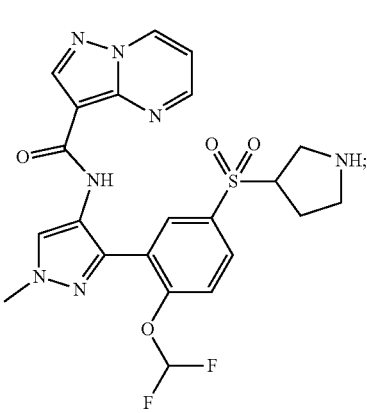
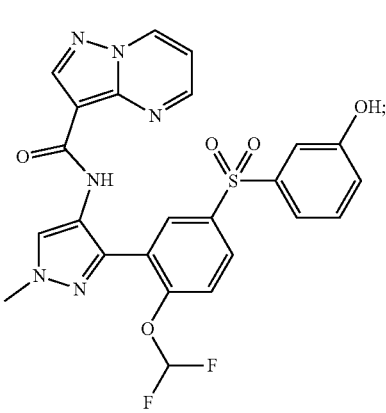
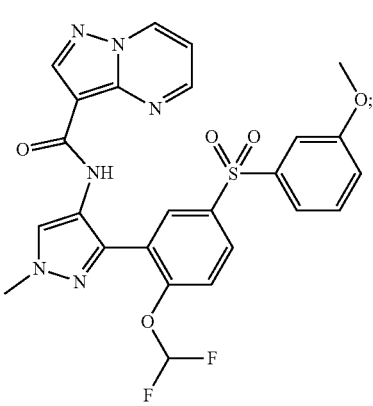

45
-continued
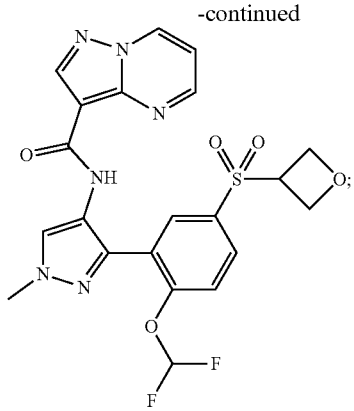
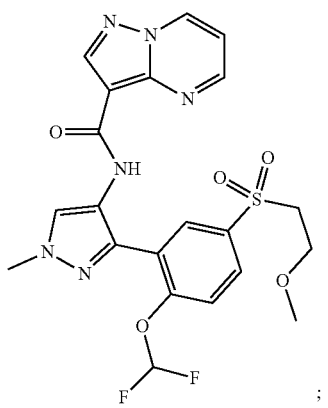
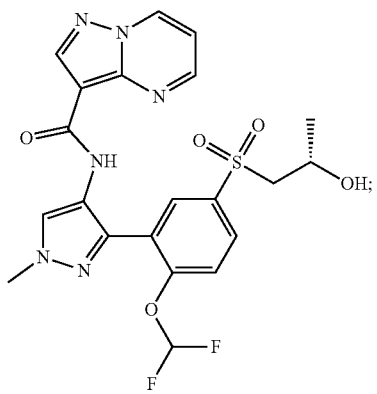
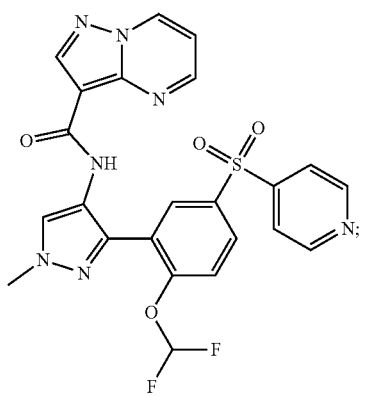
46
-continued
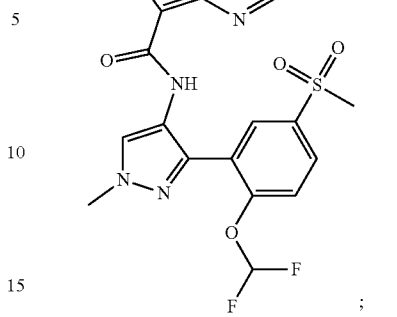
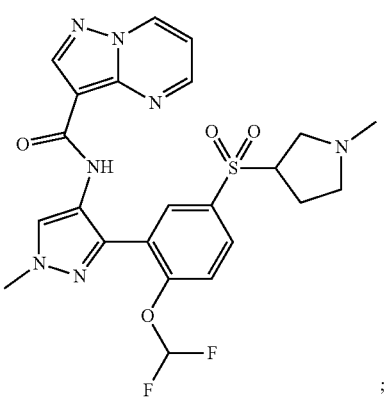
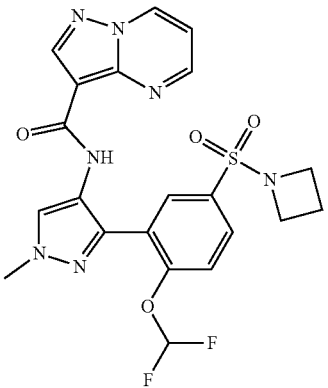
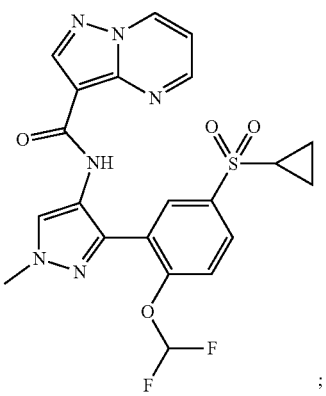

47
-continued
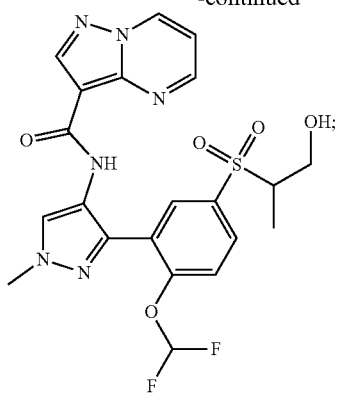
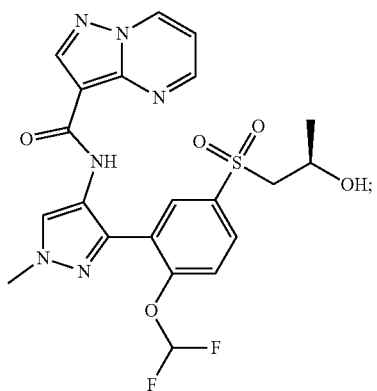
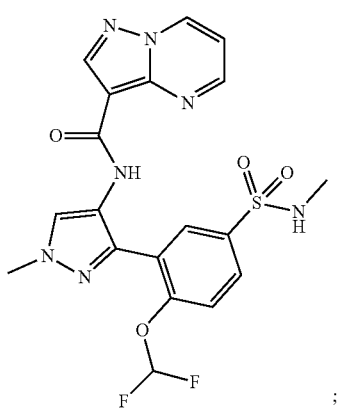
48
-continued
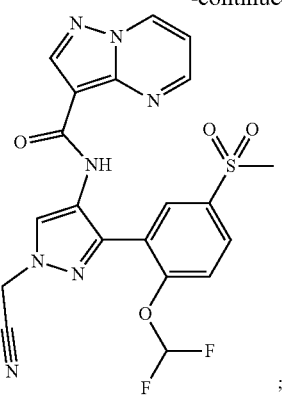
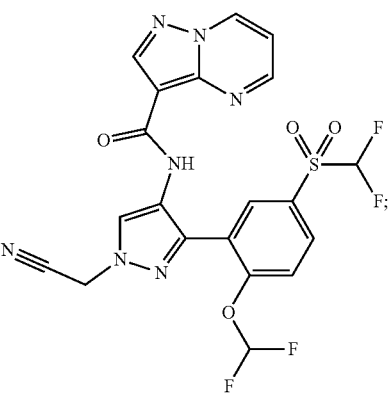
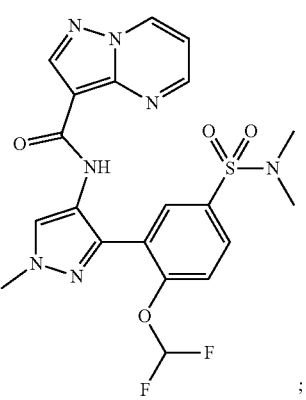
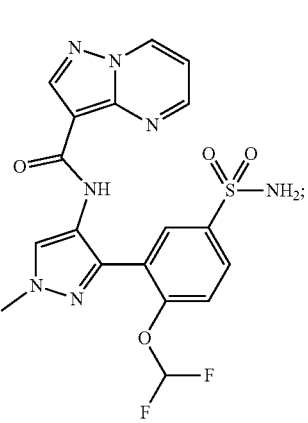

49
-continued
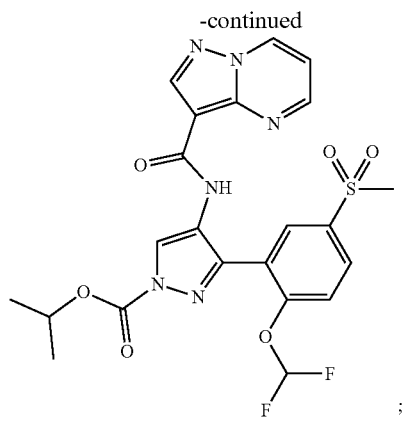
;
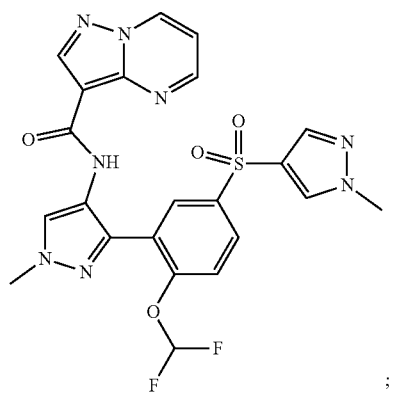
;
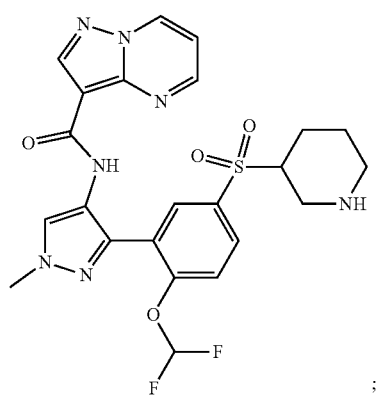
;
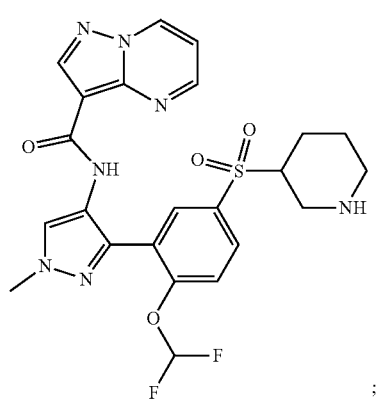
;
50
-continued
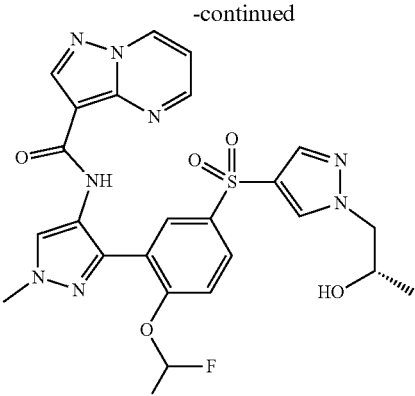
;
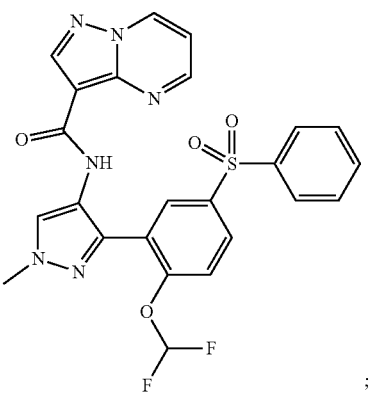
;
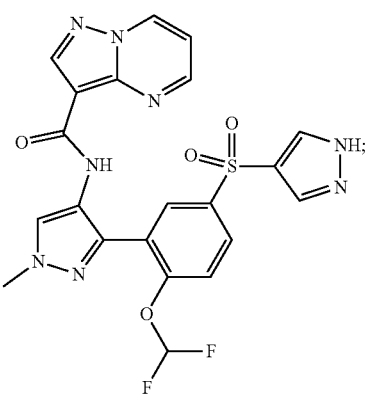
;
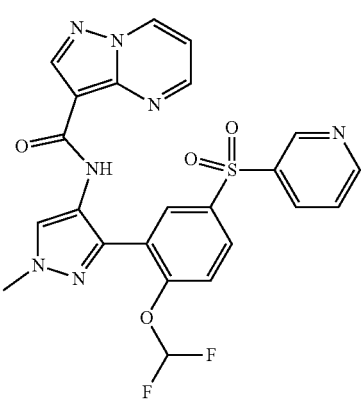
;

51
-continued
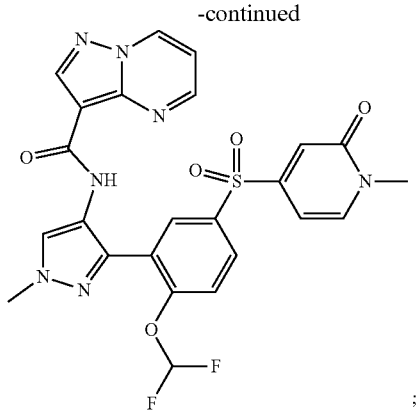
;
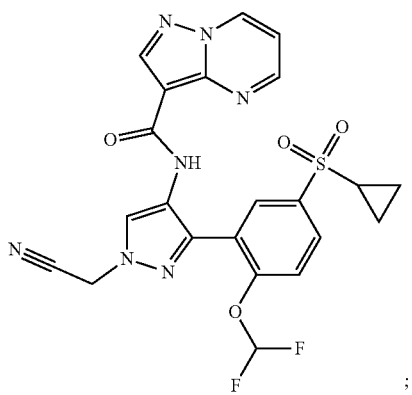
;
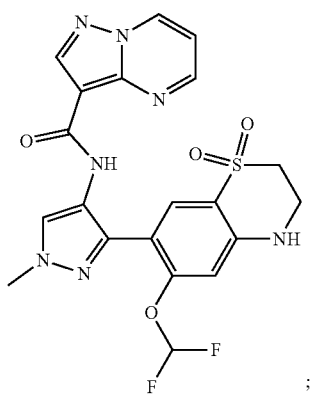
;
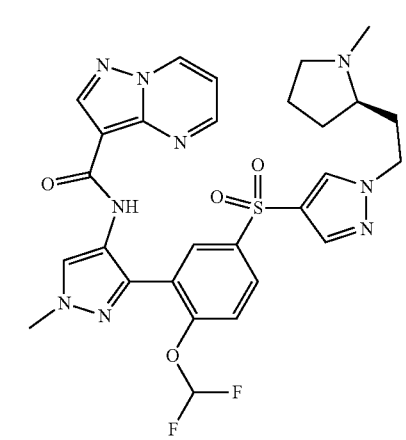
;
52
-continued
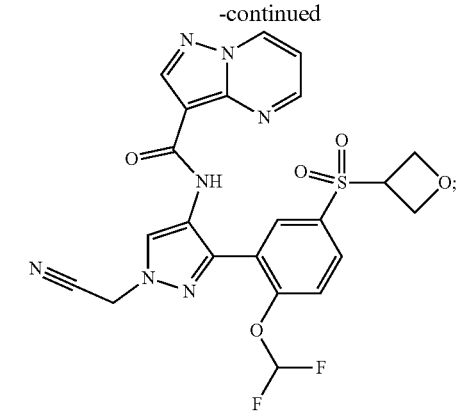
;
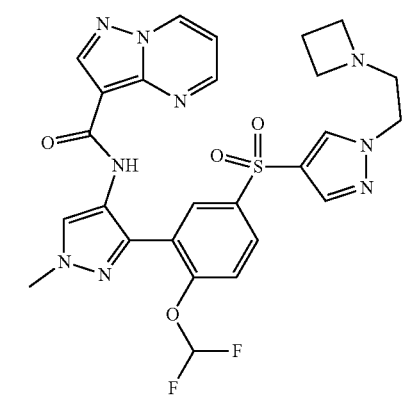
;
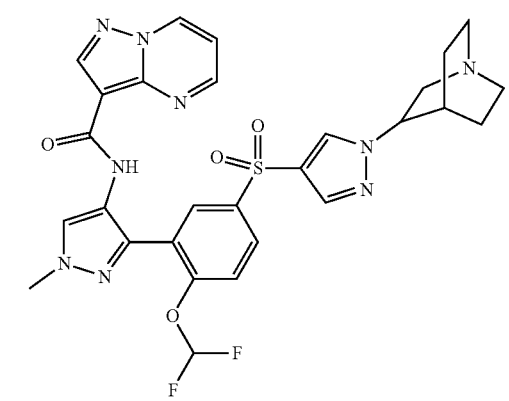
;
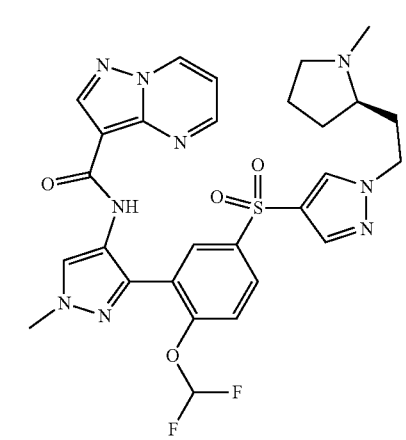
;

53
-continued
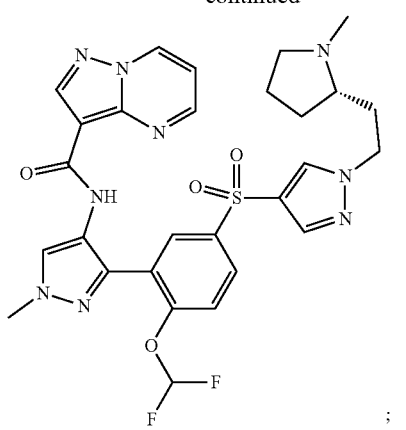
;
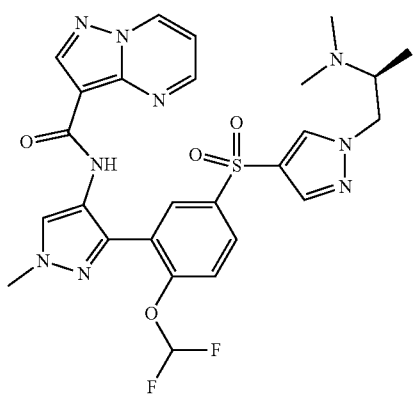
;
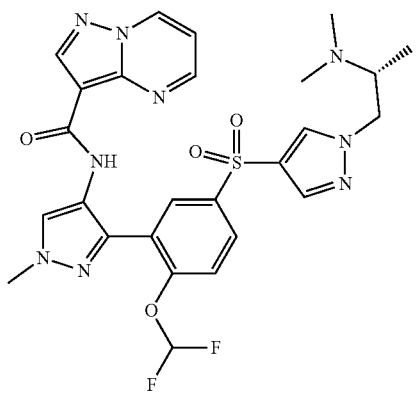
;
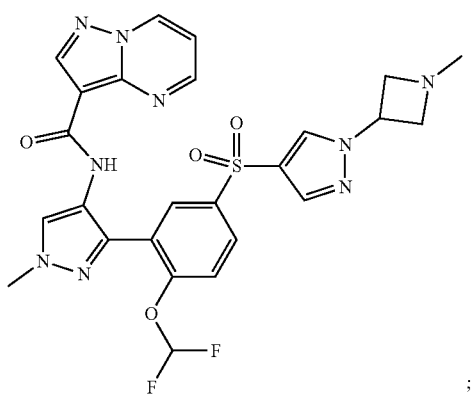
;
54
-continued
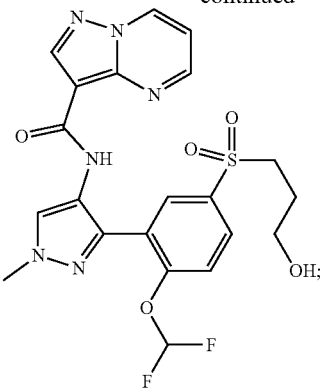
;
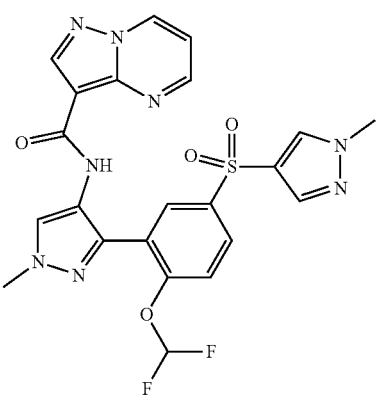
;
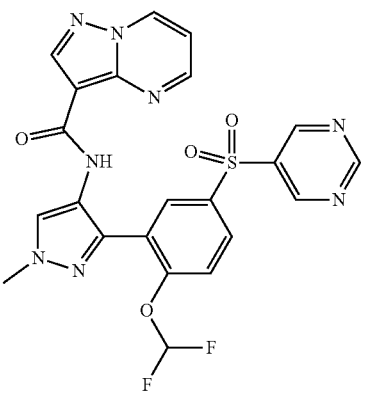
; and
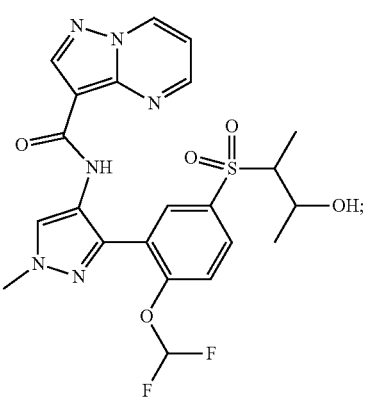
;
or a stereoisomer or pharmaceutically acceptable salt thereof.

In certain embodiments the compounds are selected from:
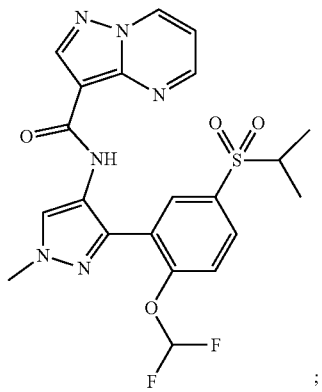
;
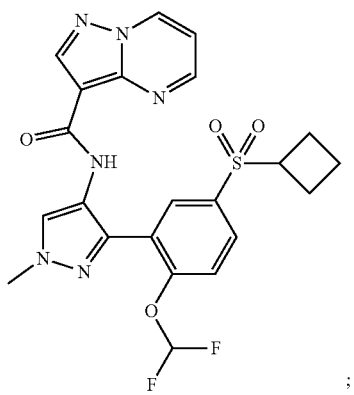
;
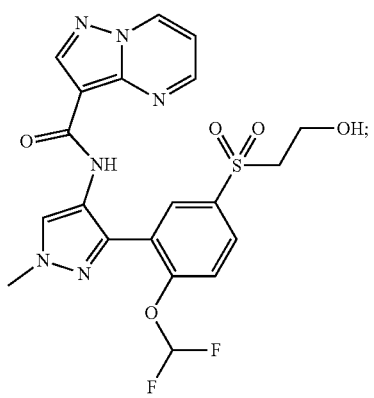
;
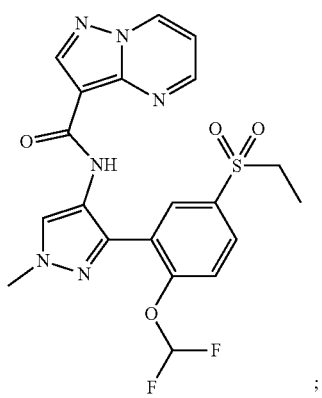
;
-continued
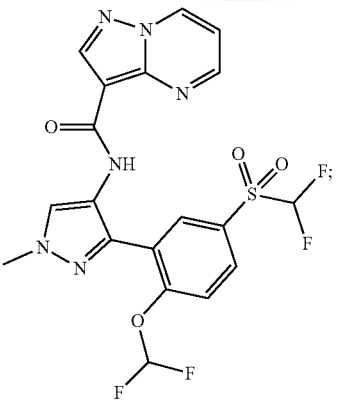
;
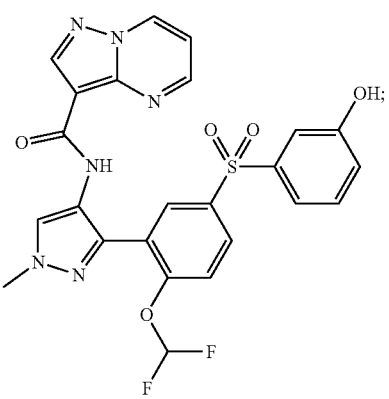
;
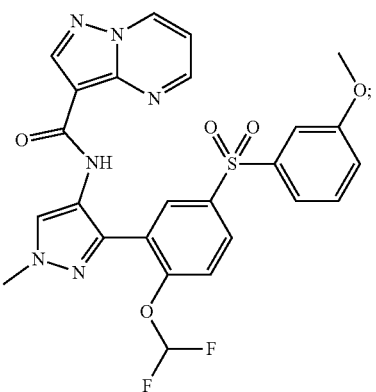
;
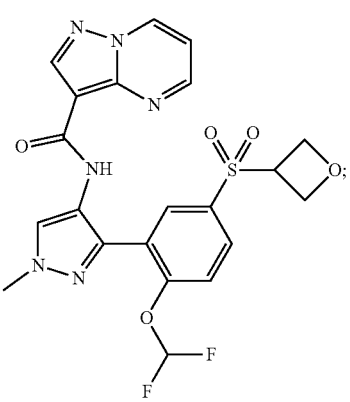
;

57
-continued
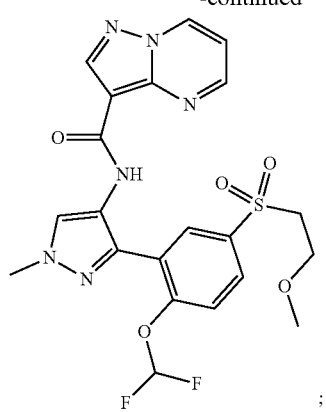
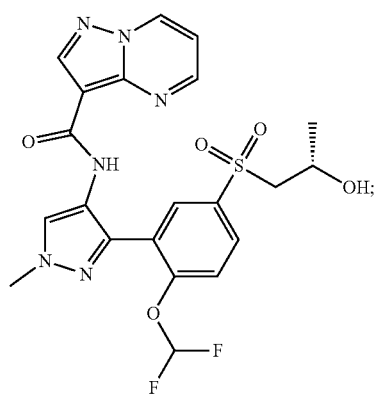
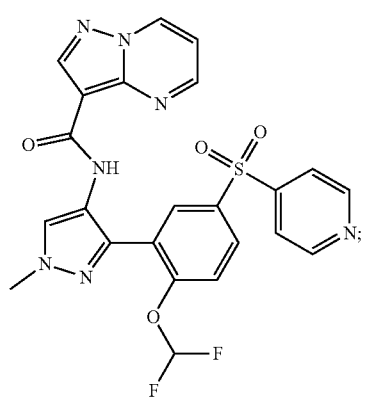
58
-continued
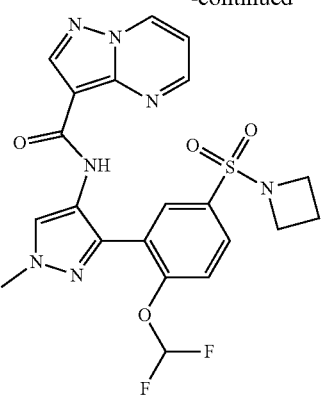
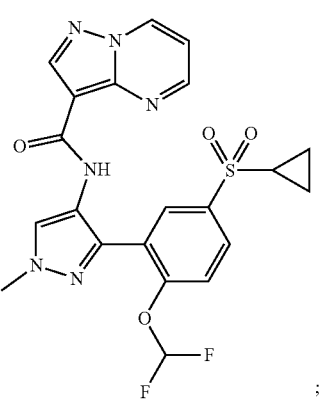
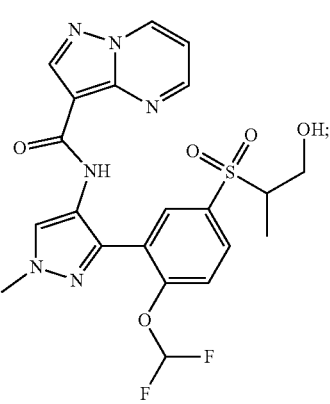
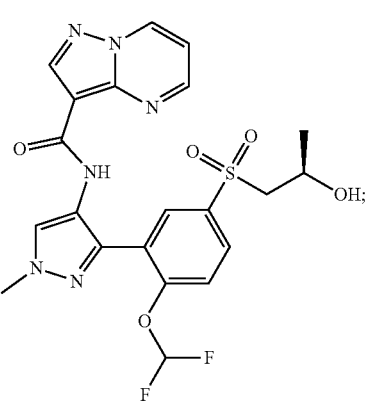

59
-continued
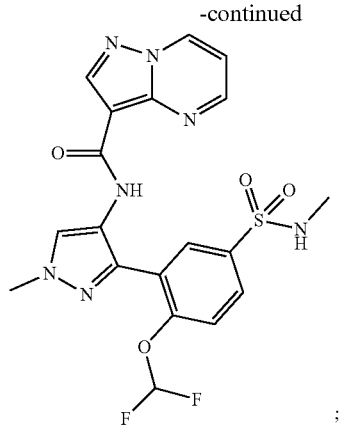
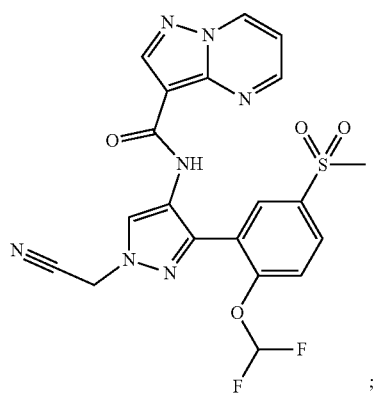
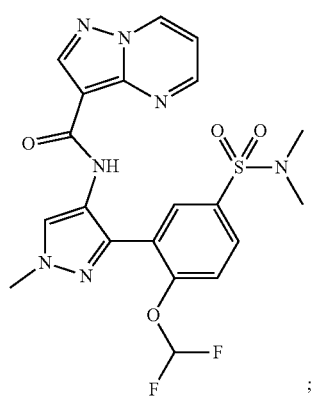
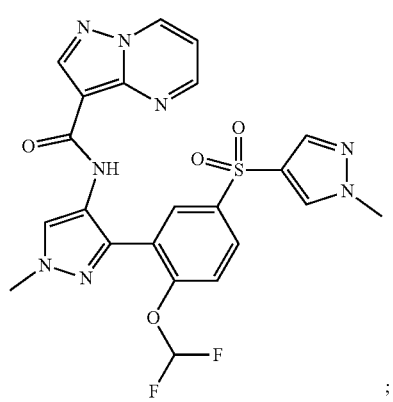
60
-continued
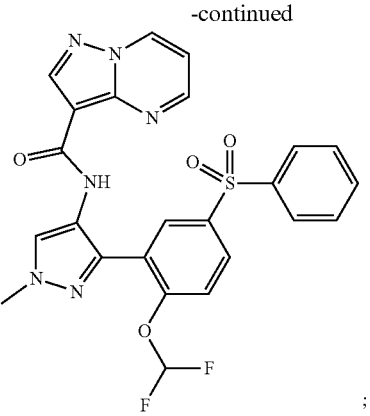
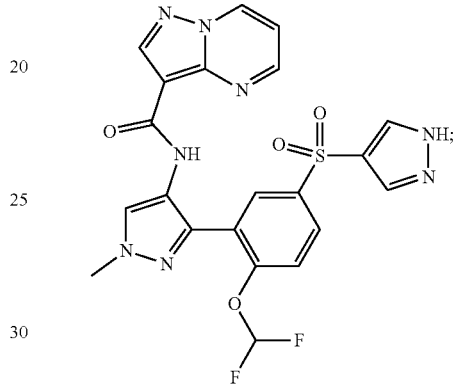
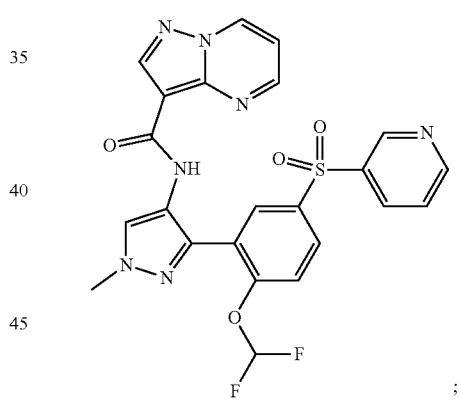
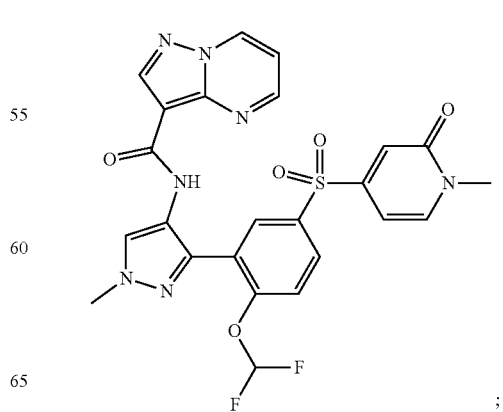

61
-continued
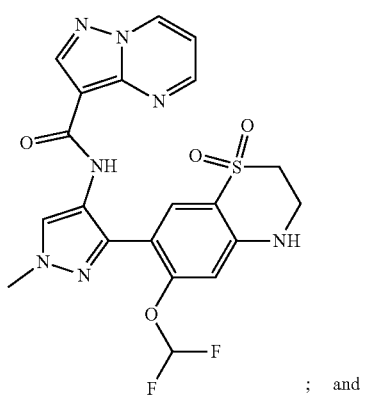
; and
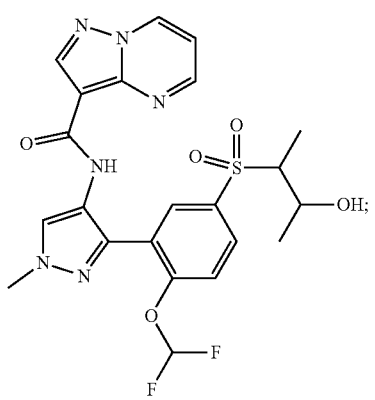
or a stereoisomer or pharmaceutically acceptable salt thereof.
In certain embodiments the subject compound is selected from:
Structure
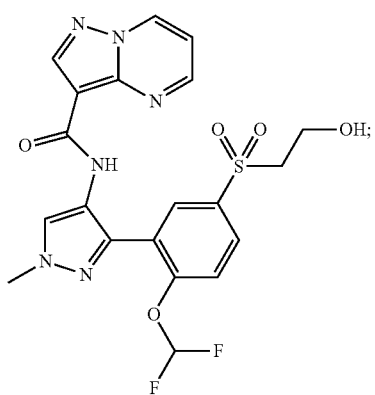
62
-continued
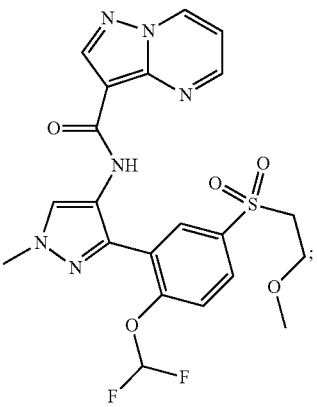
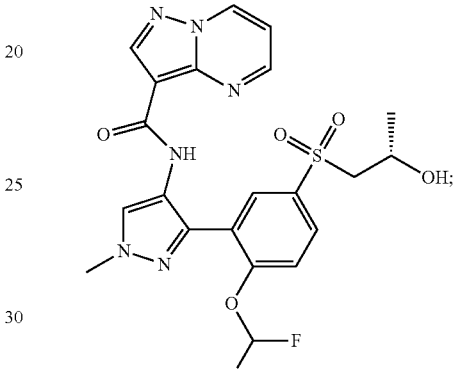
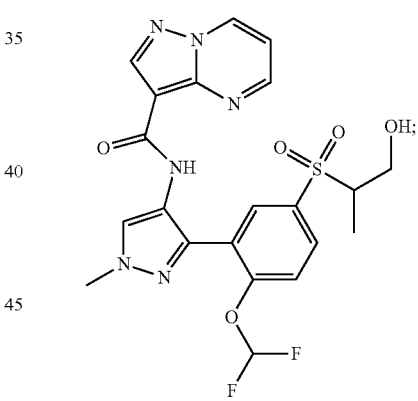
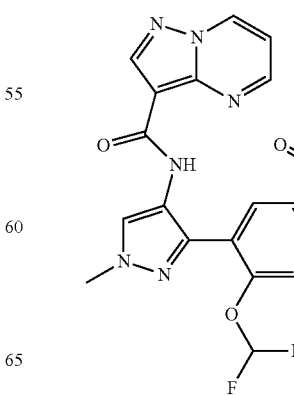

-continued

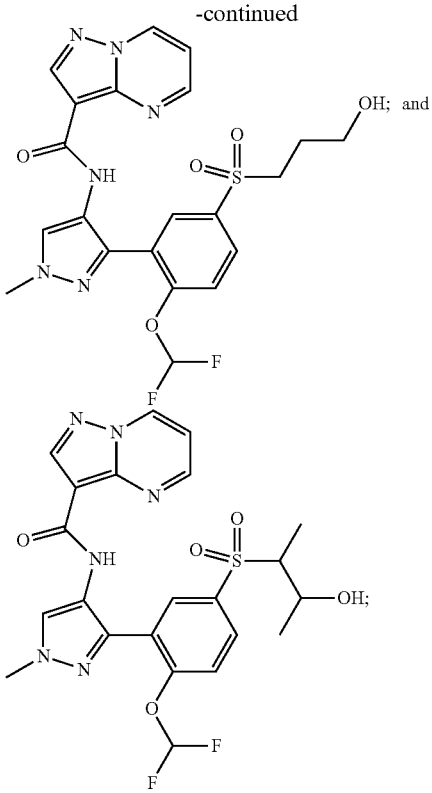

or a stereoisomer or pharmaceutically acceptable salt thereof.

Also provided is a pharmaceutical composition comprising a JAK inhibitor as described herein, or a pharmaceutically acceptable salt thereof, and a pharmaceutically acceptable carrier, dilient or excipient.

Also provided is the use of a JAK inhibitor as described herein, or a pharmaceutically acceptable salt thereof in therapy, such as in the treatment of an inflammatory disease (e.g., asthma). Also provided is the use of a JAK inhibitor as described herein or a pharmaceutically acceptable salt thereof for the preparation of a medicament for the treatment of an inflammatory disease. Also provided is a method of preventing, treating or lessening the severity of a disease or condition responsive to the inhibition of a Janus kinase activity in a patient, comprising administering to the patient a therapeutically effective amount of a JAK inhibitor as described herein or a pharmaceutically acceptable salt thereof.

In one embodiment the disease or condition for therapy is cancer, polycythemia vera, essential thrombocytosis, myelofibrosis, chronic myelogenous leukemia (CML), rheumatoid arthritis, inflammatory bowel syndrome, Crohn's disease, psoriasis, contact dermatitis or delayed hypersensitivity reactions.

In one embodiment the use of a JAK inhibitor as described herein or a pharmaceutically acceptable salt thereof, for the treatment of cancer, polycythemia vera, essential thrombocytosis, myelofibrosis, chronic myelogenous leukemia (CML), rheumatoid arthritis, inflammatory bowel syndrome, Crohn's disease, psoriasis, contact dermatitis or delayed hypersensitivity reactions is provided.

In one embodiment a composition that is formulated for administration by inhalation is provided.

In one embodiment a metered dose inhaler that comprises a compound of the present invention or a pharmaceutically acceptable salt thereof is provided.

In one embodiment a JAK inhibitor as described herein or a pharmaceutically acceptable salt thereof is at least five-times more potent as an inhibitor of JAK1 than as an inhibitor of LRRK2.

In one embodiment a JAK inhibitor as described herein or a pharmaceutically acceptable salt thereof is at least ten-times more potent as an inhibitor of JAK1 than as an inhibitor of LRRK2.

In one embodiment a method for treating hair loss in a mammal comprising administering a JAK inhibitor as described herein or a pharmaceutically acceptable salt thereof to the mammal is provided.

In one embodiment the use of a JAK inhibitor as described herein or a pharmaceutically acceptable salt thereof for the treatment of hair loss is provided.

In one embodiment the use of a JAK inhibitor as described herein or a pharmaceutically acceptable salt thereof to prepare a medicament for treating hair loss in a mammal is provided.

Compounds of the invention may contain one or more asymmetric carbon atoms. Accordingly, the compounds may exist as diastereomers, enantiomers or mixtures thereof. The syntheses of the compounds may employ racemates, diastereomers or enantiomers as starting materials or as intermediates. Mixtures of particular diastereomeric compounds may be separated, or enriched in one or more particular diastereomers, by chromatographic or crystallization methods. Similarly, enantiomeric mixtures may be separated, or enantiomerically enriched, using the same techniques or others known in the art. Each of the asymmetric carbon or nitrogen atoms may be in the R or S configuration and both of these configurations are within the scope of the invention.

In the structures shown herein, where the stereochemistry of any particular chiral atom is not specified, then all stereoisomers are contemplated and included as the compounds of the invention. Where stereochemistry is specified by a solid wedge or dashed line representing a particular configuration, then that stereoisomer is so specified and defined. Unless otherwise specified, if solid wedges or dashed lines are used, relative stereochemistry is intended.

Another aspect includes prodrugs of the compounds described herein, including known amino-protecting and carboxy-protecting groups which are released, for example hydrolyzed, to yield the compound of the present invention under physiologic conditions.

The term "prodrug" refers to a precursor or derivative form of a pharmaceutically active substance that is less efficacious to the patient compared to the parent drug and is capable of being enzymatically or hydrolytically activated or converted into the more active parent form. See, e.g., Wilman, "Prodrugs in Cancer Chemotherapy" Biochemical Society Transactions, 14, pp. 375-382, 615th Meeting Belfast (1986) and Stella et al., "Prodrugs: A Chemical Approach to Targeted Drug Delivery," Directed Drug Delivery, Borchardt et al., (ed.), pp. 247-267, Humana Press (1985). Prodrugs include, but are not limited to, phosphate-containing prodrugs, thiophosphate-containing prodrugs, sulfate-containing prodrugs, peptide-containing prodrugs, D-amino acid-modified prodrugs, glycosylated prodrugs, β-lactam-containing prodrugs, optionally substituted phenoxyacetamide-containing prodrugs or optionally substituted phenylacetamide-containing prodrugs, and 5-fluorocytosine and 5-fluorouridine prodrugs.

A particular class of prodrugs are compounds in which a nitrogen atom in an amino, amidino, aminoalkyleneamino, iminoalkyleneamino or guanidino group is substituted with a hydroxy group, an alkylcarbonyl (—CO—R) group, an alkoxycarbonyl (—CO—OR), or an acyloxyalkyl-alkoxycarbonyl (—CO—O—R—O—CO—R) group where R is a monovalent or divalent group, for example alkyl, alkylene or aryl, or a group having the Formula —C(O)—O—CP1P2-haloalkyl, where P1 and P2 are the same or different and are hydrogen, alkyl, alkoxy, cyano, halogen, alkyl or aryl. In a particular embodiment, the nitrogen atom is one of the nitrogen atoms of the amidino group. Prodrugs may be prepared by reacting a compound with an activated group, such as acyl groups, to bond, for example, a nitrogen atom in the compound to the exemplary carbonyl of the activated acyl group. Examples of activated carbonyl compounds are those containing a leaving group bonded to the carbonyl group, and include, for example, acyl halides, acyl amines, acyl pyridinium salts, acyl alkoxides, acyl phenoxides such as p-nitrophenoxy acyl, dinitrophenoxy acyl, fluorophenoxy acyl, and difluorophenoxy acyl. The reactions are generally carried out in inert solvents at reduced temperatures such as −78° C. to about 50° C. The reactions may also be carried out in the presence of an inorganic base, for example potassium carbonate or sodium bicarbonate, or an organic base such as an amine, including pyridine, trimethylamine, triethylamine, triethanolamine, or the like.

Additional types of prodrugs are also encompassed. For instance, a free carboxyl group of a JAK inhibitor as described herein can be derivatized as an amide or alkyl ester. As another example, compounds of the present invention comprising free hydroxy groups can be derivatized as prodrugs by converting the hydroxy group into a group such as, but not limited to, a phosphate ester, hemisuccinate, dimethylaminoacetate, or phosphoryloxymethyloxycarbonyl group, as outlined in Fleisher, D. et al., (1996) Improved oral drug delivery: solubility limitations overcome by the use of prodrugs Advanced Drug Delivery Reviews, 19:115. Carbamate prodrugs of hydroxy and amino groups are also included, as are carbonate prodrugs, sulfonate esters and sulfate esters of hydroxy groups. Derivatization of hydroxy groups as (acyloxy)methyl and (acyloxy)ethyl ethers, wherein the acyl group can be an alkyl ester optionally substituted with groups including, but not limited to, ether, amine and carboxylic acid functionalities, or where the acyl group is an amino acid ester as described above, are also encompassed. Prodrugs of this type are described in J. Med. Chem., (1996), 39:10. More specific examples include replacement of the hydrogen atom of the alcohol group with a group such as $(C_1-C_6)$alkanoyloxymethyl, 1-$((C_1-C_6)$alkanoyloxy)ethyl, 1-methyl-1-$((C_1-C_6)$alkanoyloxy)ethyl, (Cu $C_6$)alkoxycarbonyloxymethyl, N—$(C_1-C_6)$alkoxycarbonylaminomethyl, succinoyl, (Cu $C_6$)alkanoyl, alpha-amino$(C_1-C_4)$alkanoyl, arylacyl and alpha-aminoacyl, or alpha-aminoacyl-alpha-aminoacyl, where each alpha-aminoacyl group is independently selected from the naturally occurring L-amino acids, $P(O)(OH)_2$, —$P(O)(O(C_1-C_6)$alkyl$)_2$ or glycosyl (the radical resulting from the removal of a hydroxyl group of the hemiacetal form of a carbohydrate).

"Leaving group" refers to a portion of a first reactant in a chemical reaction that is displaced from the first reactant in the chemical reaction. Examples of leaving groups include, but are not limited to, halogen atoms, alkoxy and sulfonyloxy groups. Example sulfonyloxy groups include, but are not limited to, alkylsulfonyloxy groups (for example methyl sulfonyloxy (mesylate group) and trifluoromethylsulfonyloxy (triflate group)) and arylsulfonyloxy groups (for example p-toluenesulfonyloxy (tosylate group) and p-nitrosulfonyloxy (nosylate group)).

Synthesis of Janus Kinase Inhibitor Compounds

Compounds may be synthesized by synthetic routes described herein. In certain embodiments, processes well-known in the chemical arts can be used, in addition to, or in light of, the description contained herein. The starting materials are generally available from commercial sources such as Aldrich Chemicals (Milwaukee, Wis.) or are readily prepared using methods well known to those skilled in the art (e.g., prepared by methods generally described in Louis F. Fieser and Mary Fieser, Reagents for Organic Synthesis, v. 1-19, Wiley, N.Y. (1967-1999 ed.), Beilsteins Handbuch der organischen Chemie, 4, Aufl. ed. Springer-Verlag, Berlin, including supplements (also available via the Beilstein online database)), or Comprehensive Heterocyclic Chemistry, Editors Katrizky and Rees, Pergamon Press, 1984.

Compounds may be prepared singly or as compound libraries comprising at least 2, for example 5 to 1,000 compounds, or 10 to 100 compounds. Libraries of compounds may be prepared by a combinatorial 'split and mix' approach or by multiple parallel syntheses using either solution phase or solid phase chemistry, by procedures known to those skilled in the art. Thus according to a further aspect of the invention there is provided a compound library comprising at least 2 compounds of the present invention.

For illustrative purposes, reaction Schemes depicted below provide routes for synthesizing the compounds of the present invention as well as key intermediates. For a more detailed description of the individual reaction steps, see the Examples section below. Those skilled in the art will appreciate that other synthetic routes may be used. Although some specific starting materials and reagents are depicted in the Schemes and discussed below, other starting materials and reagents can be substituted to provide a variety of derivatives or reaction conditions. In addition, many of the compounds prepared by the methods described below can be further modified in light of this disclosure using conventional chemistry well known to those skilled in the art.

In the preparation of compounds of the present invention, protection of remote functionality (e.g., primary or secondary amine) of intermediates may be necessary. The need for such protection will vary depending on the nature of the remote functionality and the conditions of the preparation methods. Suitable amino-protecting groups include acetyl, trifluoroacetyl, benzyl, phenylsulfonyl, t-butoxycarbonyl (BOC), benzyloxycarbonyl (CBz) and 9-fluorenylmethyleneoxycarbonyl (Fmoc). The need for such protection is readily determined by one skilled in the art. For a general description of protecting groups and their use, see T. W. Greene, Protective Groups in Organic Synthesis, John Wiley & Sons, New York, 1991.

Other conversions commonly used in the synthesis of compounds of the present invention, and which can be carried out using a variety of reagents and conditions, include the following:

(1) Reaction of a carboxylic acid with an amine to form an amide. Such a transformation can be achieved using various reagents known to those skilled in the art but a comprehensive review can be found in *Tetrahedron*, 2005, 61, 10827-10852.

(2) Reaction of a primary or secondary amine with an aryl halide or pseudo halide, e.g., a triflate, commonly known as a "Buchwald-Hartwig cross-coupling," can be achieved using a variety of catalysts, ligands and bases. A review of these methods is provided in *Comprehensive Organic Name Reactions and Reagents*, 2010, 575-581.

(3) A palladium cross-coupling reaction between an aryl halide and a vinyl boronic acid or boronate ester. This transformation is a type of "Suzuki-Miyaura cross-coupling," a class of reaction that has been thoroughly reviewed in *Chemical Reviews,* 1995, 95(7), 2457-2483.
(4) The hydrolysis of an ester to give the corresponding carboxylic acid is well known to those skilled in the art and conditions include: for methyl and ethyl esters, the use of a strong aqueous base such as lithium, sodium or potassium hydroxide or a strong aqueous mineral acid such as HCl; for a tert-butyl ester, hydrolysis would be carried out using acid, for example, HCl in dioxane or trifluoroacetic acid (TFA) in dichloromethane (DCM).
(5)

Reaction Scheme 1 illustrates a synthesis for compounds of formula I. Nitropyrazole compound 1 can be arylated with 4-bromo-1-(difluoromethoxy)-2-iodobenzene under palladium catalyzed conditions to generate compound 2. The nitro group of compound 2 can be reduced with conditions such as iron and ammonium chloride to generate amino aniline 3. Amide bond coupling with commercially available pyrazolo[1,5-a]pyrimidine-3-carboxylic acid in the presence of a coupling reagent such as, but not limited to, PyAOP, with an organic base such as, but not limited to DIPEA, and DMAP in an organic solvent such as, but not limited to, DMF provides compound 4. Removal of the SEM protecting group of compound 4, using an acid such as, but not limited to HCl in a solvent such as, but not limited to, 1,4-dioxane,

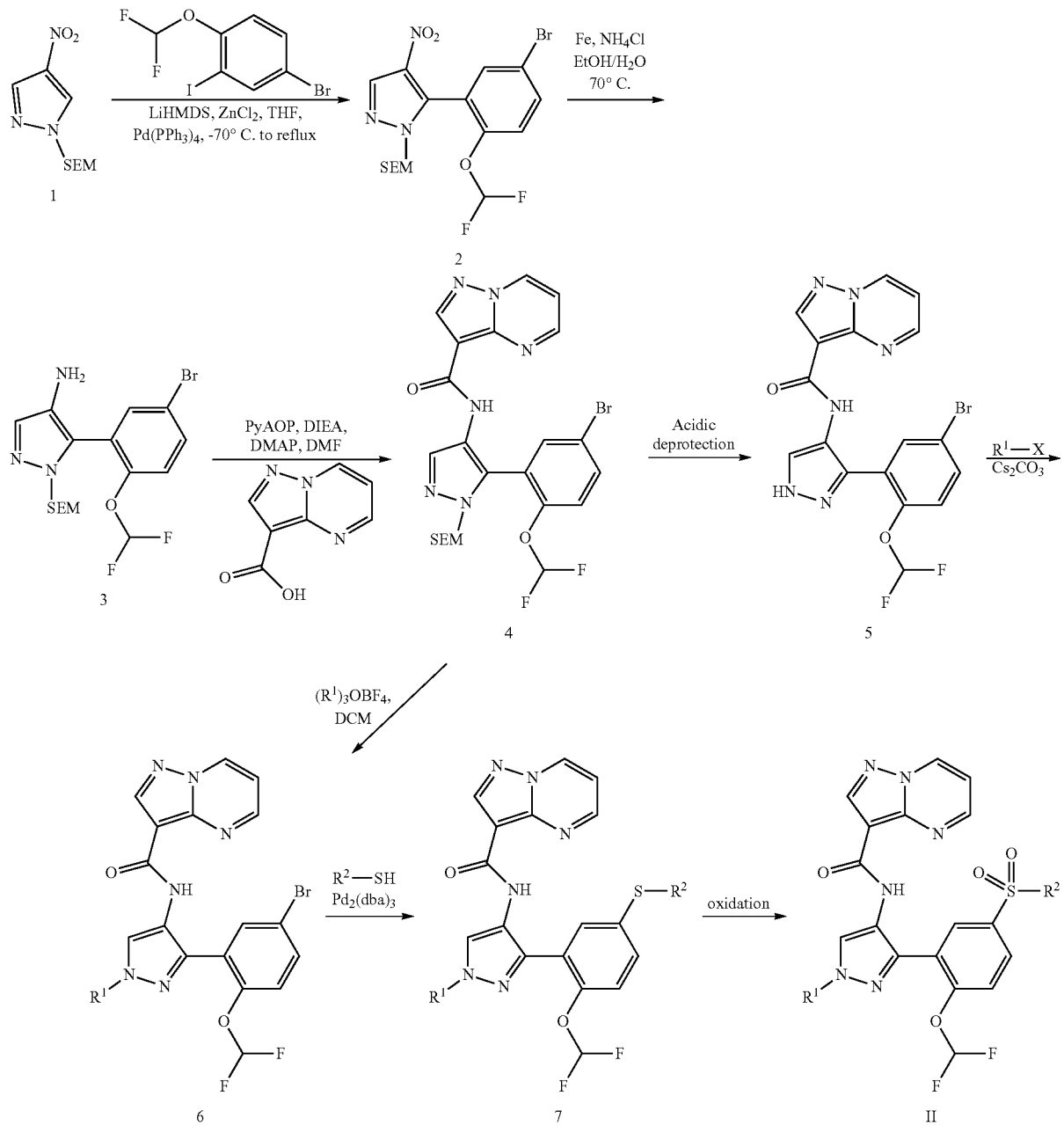

Reaction Scheme 1 results in compound 5. Compound 5 can then undergo N-alkylation with a group R¹—X wherein X is halo such as bromo, to provide compound 6. Compound 7 may be synthesized by treatment of compound 6 with an appropriate thiol reagent R²—SH under Pd catalyzed coupling conditions. Oxidation of the thio group of compound 7 provides compound 8, which is a compound of formula (II) in accordance with the invention. Alternatively, SEM protected compound 4 can undergo direct N-alkylation by treatment with a fluoroborate reagent.

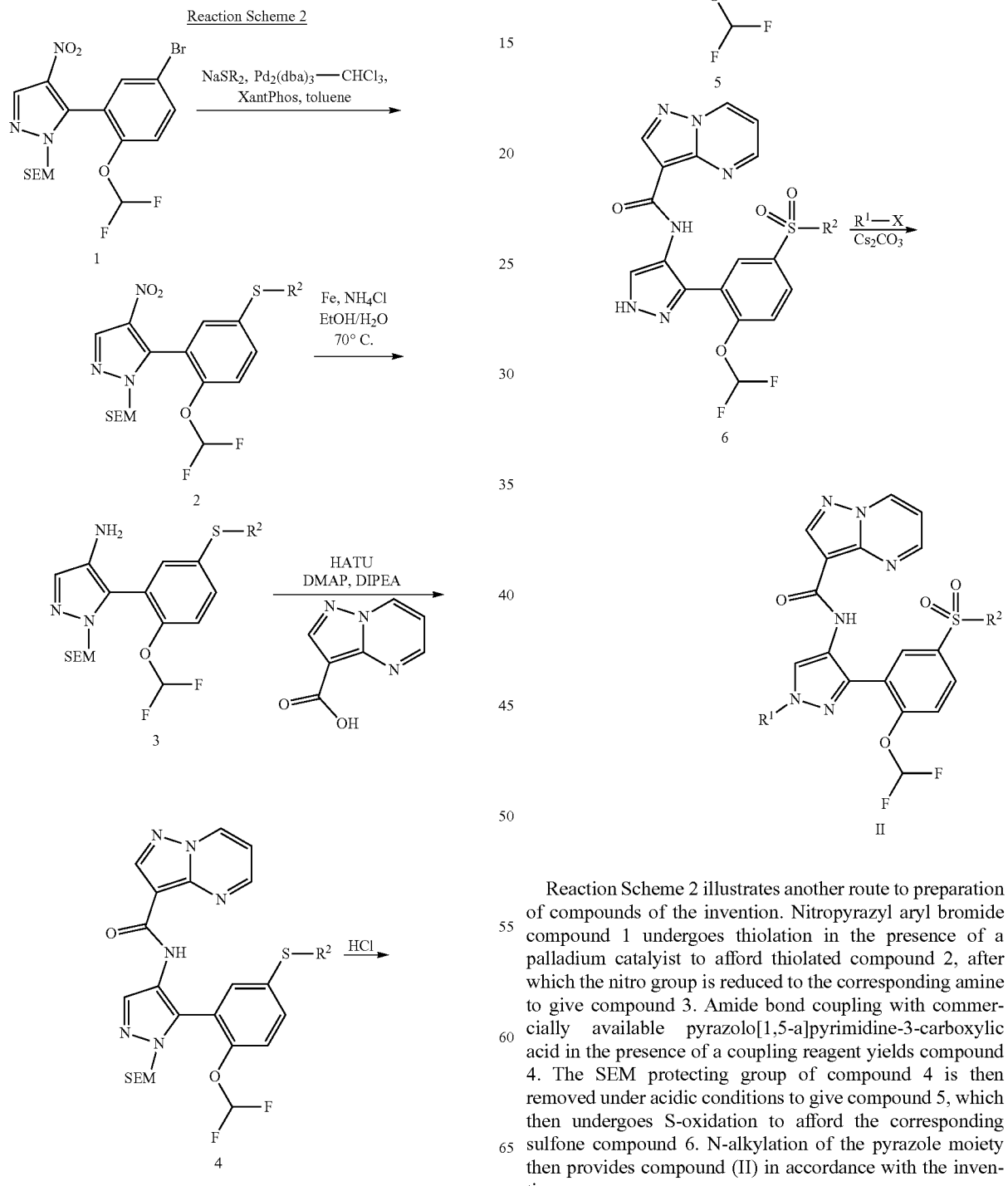

Reaction Scheme 2 illustrates another route to preparation of compounds of the invention. Nitropyrazyl aryl bromide compound 1 undergoes thiolation in the presence of a palladium catalyst to afford thiolated compound 2, after which the nitro group is reduced to the corresponding amine to give compound 3. Amide bond coupling with commercially available pyrazolo[1,5-a]pyrimidine-3-carboxylic acid in the presence of a coupling reagent yields compound 4. The SEM protecting group of compound 4 is then removed under acidic conditions to give compound 5, which then undergoes S-oxidation to afford the corresponding sulfone compound 6. N-alkylation of the pyrazole moiety then provides compound (II) in accordance with the invention.

Reaction Scheme 3
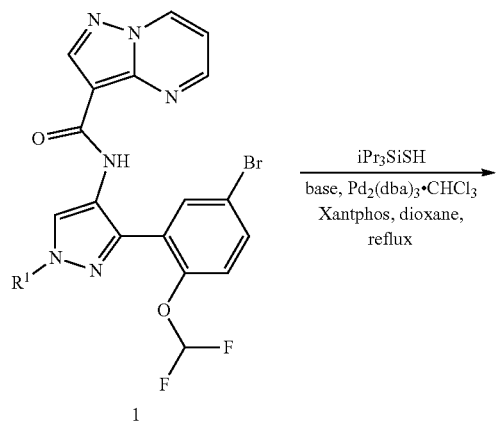
1
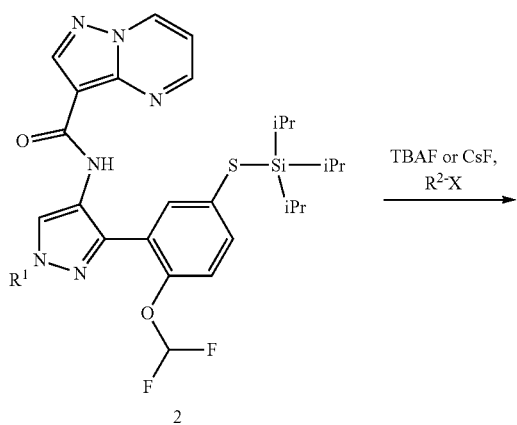
2
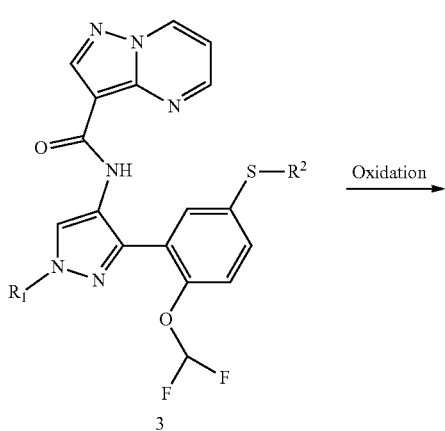
3
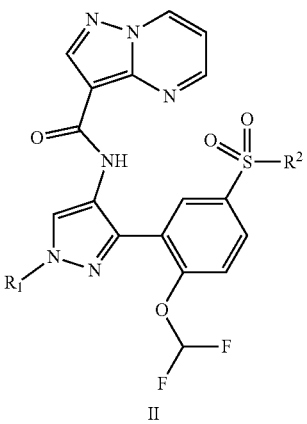
II
In reaction scheme 3 aryl bromide compound 1 is treated with a trialkylylsilanethiol such as triisopropylsilanethiol to afford thiosilyl compound 2. The thiol is deprotected and alkylated to give the sulfide compound 3, which then may undergo S-oxidation to yield compound (II) in accordance with the invention.
Reaction Scheme 4
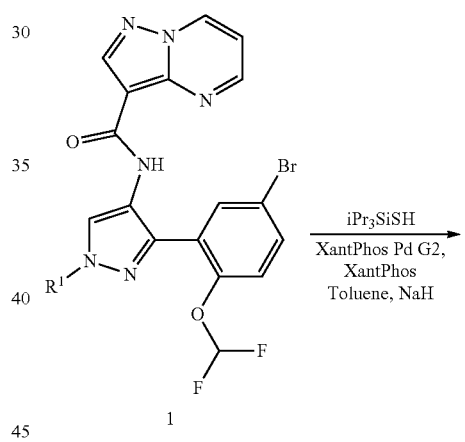
1
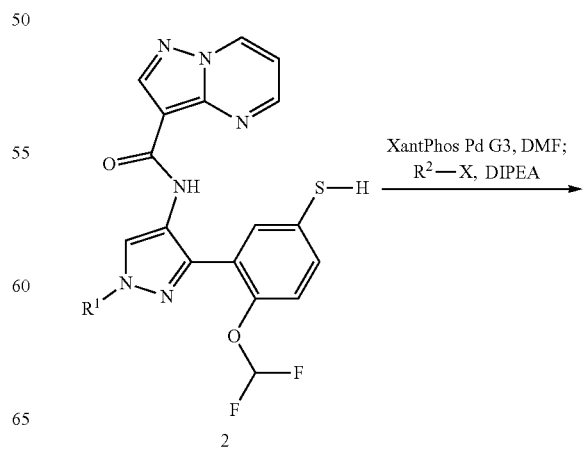
2

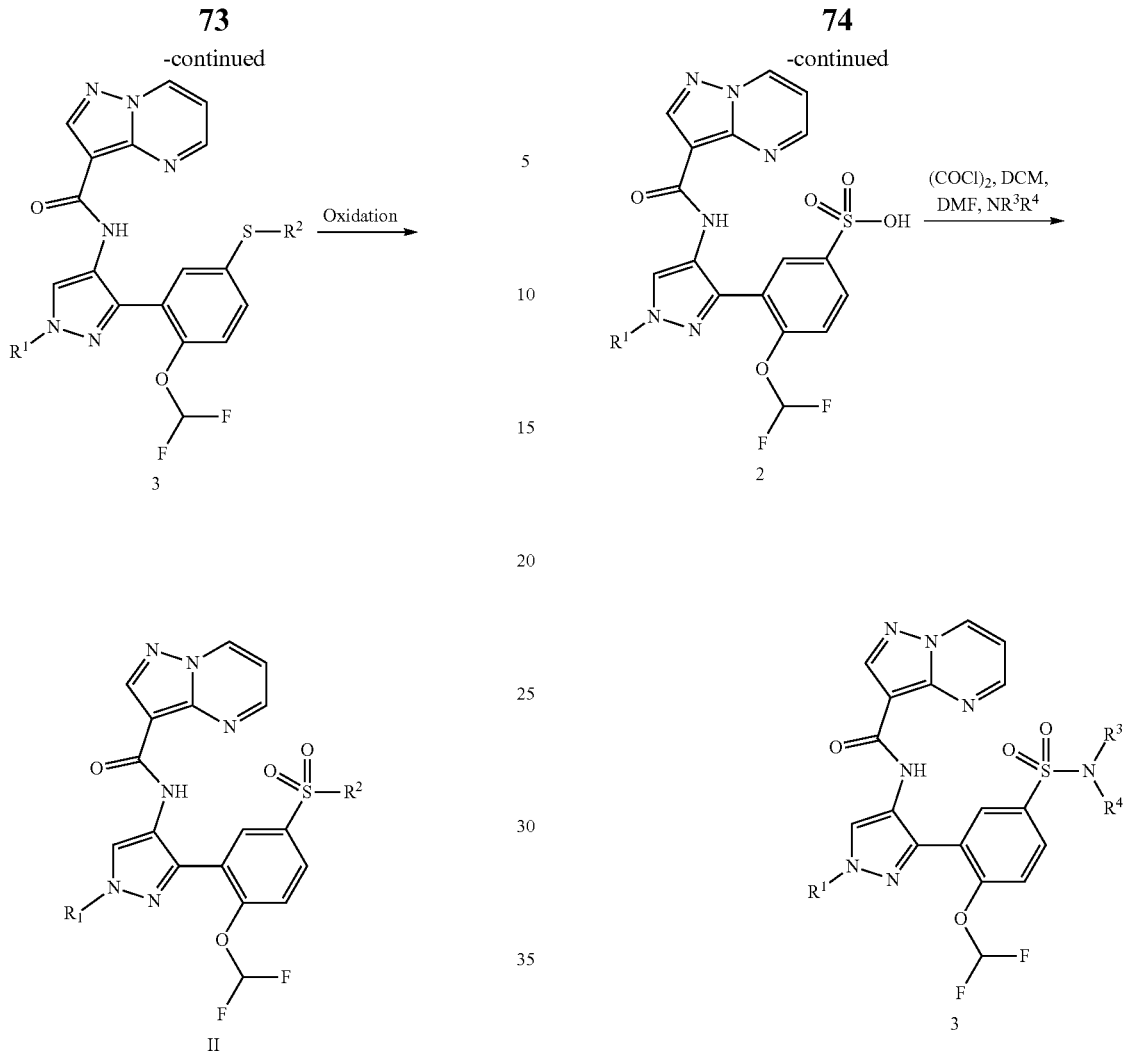

In reaction scheme 4 aryl bromide compound 1 is treated with a trialkylylsilanethiol and undergoes desilylation in situ under basic conditions to provide thiol compound 2. Compound 2 undergoes S-alkylation to provide sulfide compound 3, which in turn is oxidized to compound II in accordance with the invention.

In certain embodiments, as shown in reaction scheme 5, trialkylsilylthiol compound 1 can undergo oxidation to directly provide the sulfonic acid compound 2, which can then undergo reaction with an amine to provide sulfonamide compound 3.

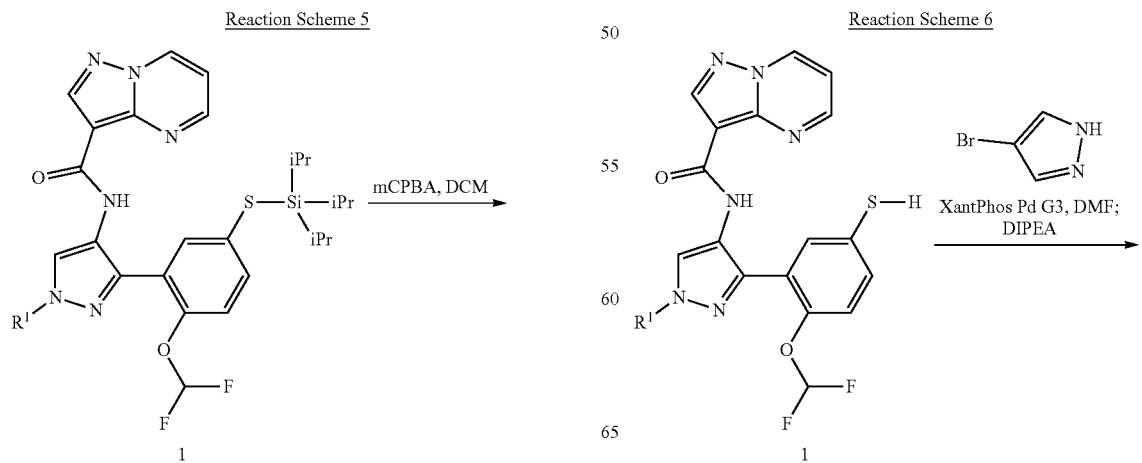

-continued

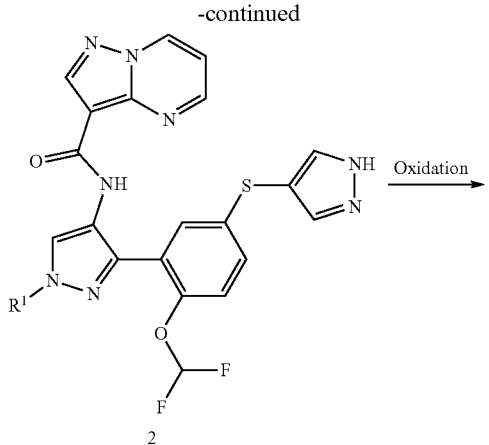

2

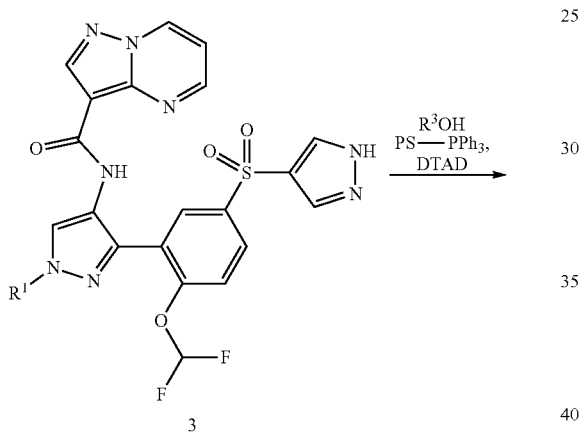

3

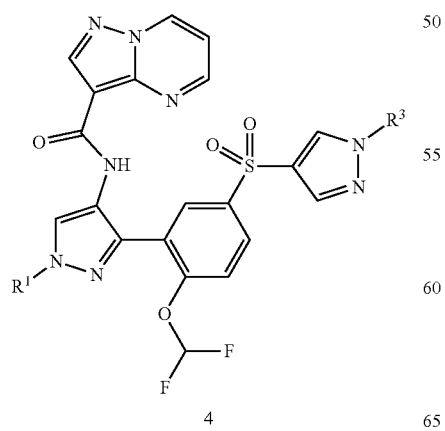

4

In certain embodiments, as shown in reaction scheme 6, thiol compound 1 is reacted with bromopyrazole to give pyrazole thioester compound 2. Compound 2 is oxidized to yield the corresponding sulfone compound, which may then undergo N-alkylation to afford compound 4.

Reaction Scheme 7

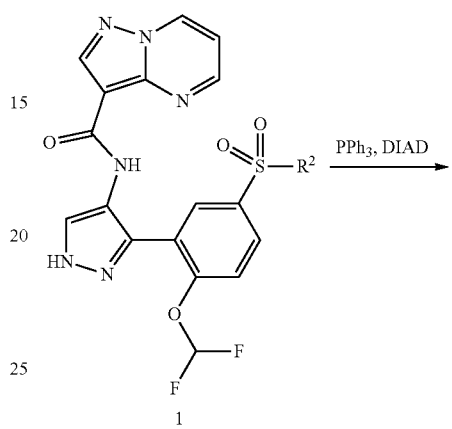

1

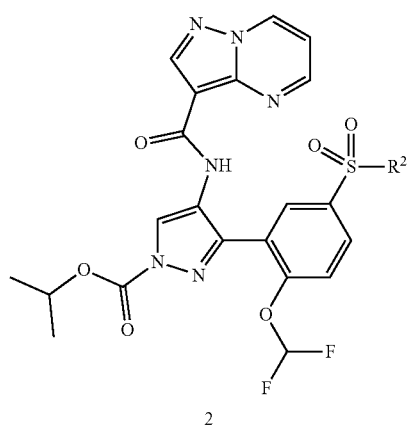

2

In reaction scheme 7 sulfone compound 1 is treated with diisopropyl azodicarboxylate to give isopropyl carboxylate compound 2.

Reaction Scheme 8
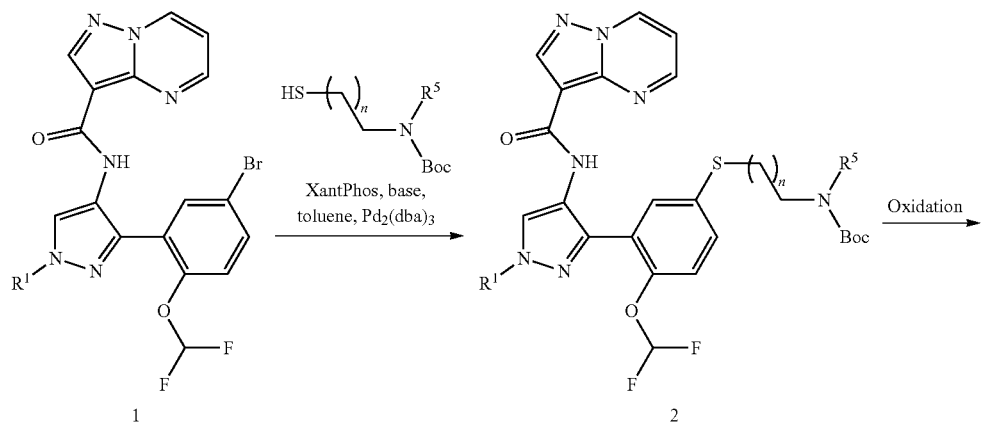
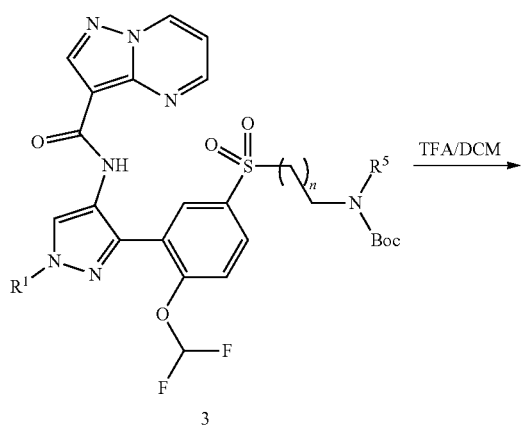
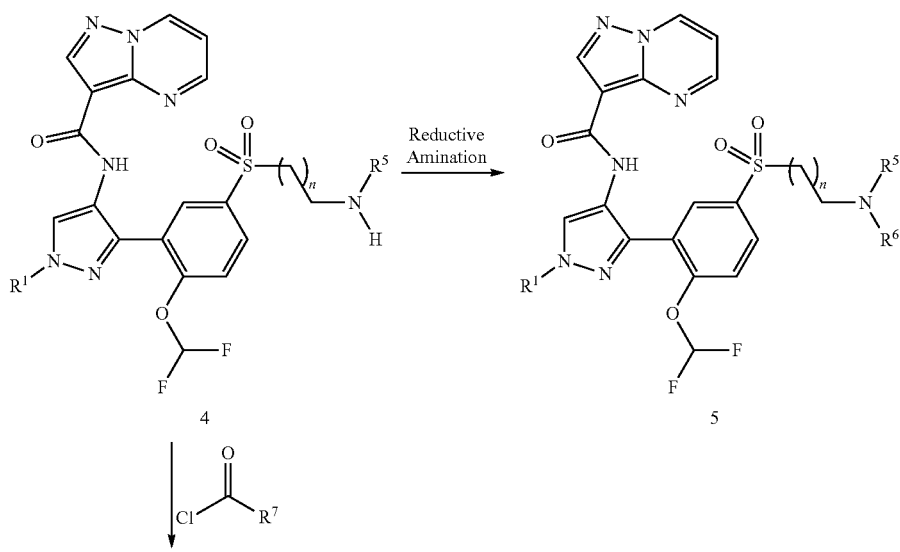

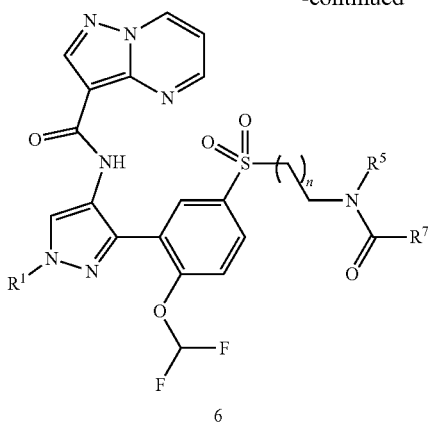

6

In reaction scheme 8 aryl bromide compound 1 is reacted with an N-protected thioalkykl amine to give aminoalkyl sulfide compound 2. Compound 2 is oxidized to give the corresponding sulfone, which is then deprotected to provide aminoalkyl sulfone compound 4. Compound 4 can undergo reductive animation to give compound 5, or alternatively be reacted with acid chloride to give carboxamide compound 6.

Reaction Scheme 9

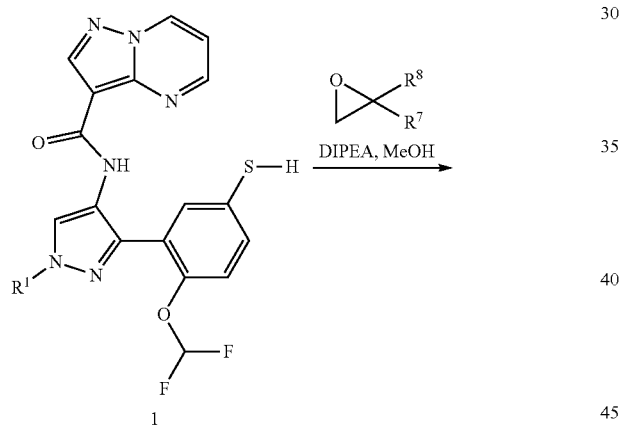

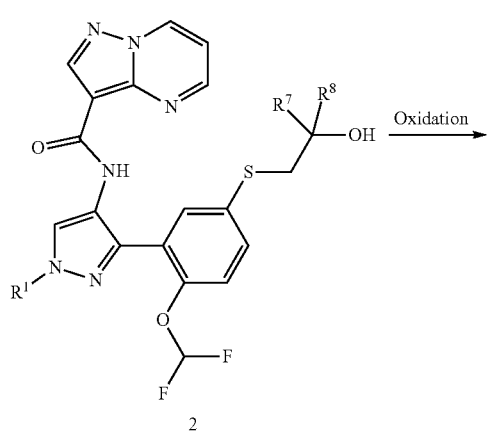

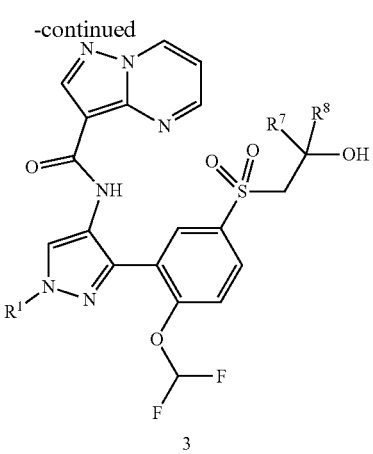

3

In reaction scheme 9 thiol compound 1 is reacted with a substituted epoxide to give hydroxy alkyl sulfide compound 2. Compound 2 is then S-oxidized to yield the corresponding hydroxy alkyl sulfone compound 3.

It will be appreciated that where appropriate functional groups exist, compounds of various formulae or any intermediates used in their preparation may be further derivatised by one or more standard synthetic methods employing condensation, substitution, oxidation, reduction, or cleavage reactions. Particular substitution approaches include conventional alkylation, arylation, heteroarylation, acylation, sulfonylation, halogenation, nitration, formylation and coupling procedures.

In a further example, primary amine or secondary amine groups may be converted into amide groups (—NHCOR' or —NRCOR') by acylation. Acylation may be achieved by reaction with an appropriate acid chloride in the presence of a base, such as triethylamine, in a suitable solvent, such as dichloromethane, or by reaction with an appropriate carboxylic acid in the presence of a suitable coupling agent such HATU (O-(7-azabenzotriazol-1-yl)-N,N,N',N'-tetramethyl-uronium hexafluorophosphate) in a suitable solvent such as dichloromethane. Similarly, amine groups may be converted into sulphonamide groups (—NHSO$_2$R' or —NR"SO$_2$R') groups by reaction with an appropriate sulphonyl chloride in the presence of a suitable base, such as triethylamine, in a suitable solvent such as dichloromethane. Primary or secondary amine groups can be converted into urea groups (—NHCONR'R" or —NRCONR'R") by reaction with an appropriate isocyanate in the presence of a suitable base such as triethylamine, in a suitable solvent, such as dichloromethane.

An amine (—$NH_2$) may be obtained by reduction of a nitro (—$NO_2$) group, for example by catalytic hydrogenation, using for example hydrogen in the presence of a metal catalyst, for example palladium on a support such as carbon in a solvent such as ethyl acetate or an alcohol e.g., methanol. Alternatively, the transformation may be carried out by chemical reduction using for example a metal, e.g., tin or iron, in the presence of an acid such as hydrochloric acid.

In a further example, amine (—$CH_2NH_2$) groups may be obtained by reduction of nitriles (—CN), for example by catalytic hydrogenation using for example hydrogen in the presence of a metal catalyst, for example palladium on a support such as carbon, or Raney nickel, in a solvent such as an ether e.g., a cyclic ether such as tetrahydrofuran, at an appropriate temperature, for example from about −78° C. to the reflux temperature of the solvent.

In a further example, amine (—$NH_2$) groups may be obtained from carboxylic acid groups (—$CO_2H$) by conversion to the corresponding acyl azide (—$CON_3$), Curtius rearrangement and hydrolysis of the resultant isocyanate (—N═C═O).

Aldehyde groups (—CHO) may be converted to amine groups (—$CH_2NR'R''$)) by reductive amination employing an amine and a borohydride, for example sodium triacetoxyborohydride or sodium cyanoborohydride, in a solvent such as a halogenated hydrocarbon, for example dichloromethane, or an alcohol such as ethanol, where necessary in the presence of an acid such as acetic acid at around ambient temperature.

In a further example, aldehyde groups may be converted into alkenyl groups (—CH═CHR') by the use of a Wittig or Wadsworth-Emmons reaction using an appropriate phosphorane or phosphonate under standard conditions known to those skilled in the art.

Aldehyde groups may be obtained by reduction of ester groups (such as —$CO_2Et$) or nitriles (—CN) using diisobutylaluminium hydride in a suitable solvent such as toluene. Alternatively, aldehyde groups may be obtained by the oxidation of alcohol groups using any suitable oxidising agent known to those skilled in the art.

Ester groups (—$CO_2R'$) may be converted into the corresponding acid group (—$CO_2H$) by acid- or base-catalused hydrolysis, depending on the nature of R. If R is t-butyl, acid-catalysed hydrolysis can be achieved for example by treatment with an organic acid such as trifluoroacetic acid in an aqueous solvent, or by treatment with an inorganic acid such as hydrochloric acid in an aqueous solvent.

Carboxylic acid groups (—$CO_2H$) may be converted into amides (CONHR' or —CONR'R'') by reaction with an appropriate amine in the presence of a suitable coupling agent, such as HATU, in a suitable solvent such as dichloromethane.

In a further example, carboxylic acids may be homologated by one carbon (i.e —$CO_2H$ to —$CH_2CO_2H$) by conversion to the corresponding acid chloride (—COCl) followed by Arndt-Eistert synthesis.

In a further example, —OH groups may be generated from the corresponding ester (e.g., —$CO_2R'$), or aldehyde (—CHO) by reduction, using for example a complex metal hydride such as lithium aluminium hydride in diethyl ether or tetrahydrofuran, or sodium borohydride in a solvent such as methanol. Alternatively, an alcohol may be prepared by reduction of the corresponding acid (—$CO_2H$), using for example lithium aluminium hydride in a solvent such as tetrahydrofuran, or by using borane in a solvent such as tetrahydrofuran.

Alcohol groups may be converted into leaving groups, such as halogen atoms or sulfonyloxy groups such as an alkylsulfonyloxy, e.g., trifluoromethylsulfonyloxy or arylsulfonyloxy, e.g., p-toluenesulfonyloxy group using conditions known to those skilled in the art. For example, an alcohol may be reacted with thioyl chloride in a halogenated hydrocarbon (e.g., dichloromethane) to yield the corresponding chloride. A base (e.g., triethylamine) may also be used in the reaction.

In another example, alcohol, phenol or amide groups may be alkylated by coupling a phenol or amide with an alcohol in a solvent such as tetrahydrofuran in the presence of a phosphine, e.g., triphenylphosphine and an activator such as diethyl-, diisopropyl-, or dimethylazodicarboxylate. Alternatively alkylation may be achieved by deprotonation using a suitable base e.g., sodium hydride followed by subsequent addition of an alkylating agent, such as an alkyl halide.

Aromatic halogen substituents in the compounds may be subjected to halogen-metal exchange by treatment with a base, for example a lithium base such as n-butyl or t-butyl lithium, optionally at a low temperature, e.g., around −78° C., in a solvent such as tetrahydrofuran, and then quenched with an electrophile to introduce a desired substituent. Thus, for example, a formyl group may be introduced by using N,N-dimethylformamide as the electrophile. Aromatic halogen substituents may alternatively be subjected to metal (e.g., palladium or copper) catalysed reactions, to introduce, for example, acid, ester, cyano, amide, aryl, heteraryl, alkenyl, alkynyl, thio- or amino substituents. Suitable procedures which may be employed include those described by Heck, Suzuki, Stille, Buchwald or Hartwig.

Aromatic halogen substituents may also undergo nucleophilic displacement following reaction with an appropriate nucleophile such as an amine or an alcohol. Advantageously, such a reaction may be carried out at elevated temperature in the presence of microwave irradiation.

Methods of Separation

In each of the exemplary Schemes it may be advantageous to separate reaction products from one another or from starting materials. The desired products of each step or series of steps is separated or purified (hereinafter separated) to the desired degree of homogeneity by the techniques common in the art. Typically such separations involve multiphase extraction, crystallization or trituration from a solvent or solvent mixture, distillation, sublimation, or chromatography. Chromatography can involve any number of methods including, for example: reverse-phase and normal phase; size exclusion; ion exchange; supercritical fluid; high, medium, and low pressure liquid chromatography methods and apparatus; small scale analytical; simulated moving bed (SMB) and preparative thin or thick layer chromatography, as well as techniques of small scale thin layer and flash chromatography.

Another class of separation methods involves treatment of a mixture with a reagent selected to bind to or render otherwise separable a desired product, unreacted starting material, reaction by product, or the like. Such reagents include adsorbents or absorbents such as activated carbon, molecular sieves, ion exchange media, or the like. Alternatively, the reagents can be acids in the case of a basic material, bases in the case of an acidic material, binding reagents such as antibodies, binding proteins, selective chelators such as crown ethers, liquid/liquid ion extraction reagents (LIX), or the like.

Selection of appropriate methods of separation depends on the nature of the materials involved. Example separation methods include boiling point, and molecular weight in distillation and sublimation, presence or absence of polar functional groups in chromatography, stability of materials in acidic and basic media in multiphase extraction, and the like. One skilled in the art will apply techniques most likely to achieve the desired separation.

Diastereomeric mixtures can be separated into their individual diastereoisomers on the basis of their physical chemical differences by methods well known to those skilled in the art, such as by chromatography or fractional crystallization. Enantiomers can be separated by converting the enantiomeric mixture into a diastereomeric mixture by reaction with an appropriate optically active compound (e.g., chiral auxiliary such as a chiral alcohol or Mosher's acid chloride), separating the diastereoisomers and converting (e.g., hydrolyzing) the individual diastereoisomers to the corresponding pure enantiomers. Also, some of the compounds of the present invention may be atropisomers (e.g., substituted biaryls) and are considered as part of this invention. Enantiomers can also be separated by use of a chiral HPLC column or supercritical fluid chromatography.

A single stereoisomer, e.g., an enantiomer, substantially free of its stereoisomer may be obtained by resolution of the racemic mixture using a method such as formation of diastereomers using optically active resolving agents (Eliel, E. and Wilen, S., Stereochemistry of Organic Compounds, John Wiley & Sons, Inc., New York, 1994; Lochmuller, C. H., J. Chromatogr., 113(3):283-302 (1975)). Racemic mixtures of chiral compounds of the invention can be separated and isolated by any suitable method, including: (1) formation of ionic, diastereomeric salts with chiral compounds and separation by fractional crystallization or other methods, (2) formation of diastereomeric compounds with chiral derivatizing reagents, separation of the diastereomers, and conversion to the pure stereoisomers, and (3) separation of the substantially pine or enriched stereoisomers directly under chiral conditions. See: Drug Stereochemistry, Analytical Methods and Pharmacology, Irving W. Wainer, Ed., Marcel Dekker, Inc., New York (1993).

Diastereomeric salts can be formed by reaction of enantiomerically pure chiral bases such as brucine, quinine, ephedrine, strychnine, α-methyl-β-phenylethylamine (amphetamine), and the like with asymmetric compounds bearing acidic functionality, such as carboxylic acid and sulfonic acid. The diastereomeric salts may be induced to separate by fractional crystallization or ionic chromatography. For separation of the optical isomers of amino compounds, addition of chiral carboxylic or sulfonic acids, such as camphorsulfonic acid, tartaric acid, mandelic acid, or lactic acid can result in formation of the diastereomeric salts.

Alternatively, the substrate to be resolved is reacted with one enantiomer of a chiral compound to form a diastereomeric pair (Eliel, E. and Wilen, S., Stereochemistry of Organic Compounds, John Wiley & Sons, Inc., New York, 1994, p. 322). Diastereomeric compounds can be formed by reacting asymmetric compounds with enantiomerically pure chiral derivatizing reagents, such as menthyl derivatives, followed by separation of the diastereomers and hydrolysis to yield the pine or enriched enantiomer. A method of determining optical purity involves making chiral esters, such as a menthyl ester, e.g., (−) menthyl chloroformate in the presence of base, or Mosher ester, α-methoxy-α-(trifluoromethyl)phenyl acetate (Jacob, J. Org. Chem. 47:4165 (1982)), of the racemic mixture, and analyzing the NMR spectrum for the presence of the two atropisomeric enantiomers or diastereomers. Stable diastereomers of atropisomeric compounds can be separated and isolated by normal- and reverse-phase chromatography following methods for separation of atropisomeric naphthyl-isoquinolines (WO 96/15111, incorporated herein by reference). By method (3), a racemic mixture of two enantiomers can be separated by chromatography using a chiral stationary phase (Chiral Liquid Chromatography W. J. Lough, Ed., Chapman and Hall, New York, (1989); Okamoto, J. of Chromatogr. 513: 375-378 (1990)). Enriched or purified enantiomers can be distinguished by methods used to distinguish other chiral molecules with asymmetric carbon atoms, such as optical rotation and circular dichroism. The absolute stereochemistry of chiral centers and enatiomers can be determined by x-ray crystallography.

Positional isomers and intermediates for their synthesis may be observed by characterization methods such as NMR and analytical HPLC. For certain compounds where the energy barrier for interconversion is sufficiently high, the E and Z isomers may be separated, for example by preparatory HPLC.

Pharmaceutical Compositions and Administration

The compounds with which the invention is concerned are JAK kinase inhibitors, such as JAK1 inhibitors, and are useful in the treatment of several diseases, for example, inflammatory diseases, such as asthma.

Accordingly, another embodiment provides pharmaceutical compositions or medicaments containing a compound of the invention or a pharmaceutically acceptable salt thereof, and a pharmaceutically acceptable carrier, diluent or excipient, as well as methods of using the compounds of the invention to prepare such compositions and medicaments.

In one example, a compound of the invention or a pharmaceutically acceptable salt thereof may be formulated by mixing at ambient temperature at the appropriate pH, and at the desired degree of purity, with physiologically acceptable carriers, i.e., carriers that are non-toxic to recipients at the dosages and concentrations employed into a galenical administration form. The pH of the formulation depends mainly on the particular use and the concentration of compound, but typically ranges anywhere from about 3 to about 8. In one example, a compound of the invention or a pharmaceutically acceptable salt thereof is formulated in an acetate buffer, at pH 5. In another embodiment, the compounds of the present invention are sterile. The compound may be stored, for example, as a solid or amorphous composition, as a lyophilized formulation or as an aqueous solution.

Compositions are formulated, dosed, and administered in a fashion consistent with good medical practice. Factors for consideration in this context include the particular disorder being treated, the particular mammal being treated, the clinical condition of the individual patient, the cause of the disorder, the site of delivery of the agent, the method of administration, the scheduling of administration, and other factors known to medical practitioners.

It will be understood that the specific dose level for any particular patient will depend upon a variety of factors including the activity of the specific compound employed, the age, body weight, general health, sex, diet, time of administration, route of administration, rate of excretion, drug combination and the severity of the particular disease undergoing treatment. Optimum dose levels and frequency of dosing will be determined by clinical trial, as is required in the pharmaceutical art. In general, the daily dose range for oral administration will lie within the range of from about 0.001 mg to about 100 mg per kg body weight of a human, often 0.01 mg to about 50 mg per kg, for example 0.1 to 10 mg per kg, in single or divided doses. In general, the daily dose range for inhaled administration will lie within the range of from about 0.1 µg to about 1 mg per kg body weight of a human, preferably 0.1 µg to 50 µg per kg, in single or divided doses. On the other hand, it may be necessary to use dosages outside these limits in some cases.

The compounds of the invention or a pharmaceutically acceptable salt thereof, may be administered by any suitable means, including oral, topical (including buccal and sublingual), rectal, vaginal, transdermal, parenteral, subcutaneous, intraperitoneal, intrapulmonary, intradermal, intrathecal, inhaled and epidural and intranasal, and, if desired for local treatment, intralesional administration. Parenteral infusions include intramuscular, intravenous, intraarterial, intraperitoneal, or subcutaneous administration. In some embodiments, inhaled administration is employed.

The compounds of the present invention or a pharmaceutically acceptable salt thereof, may be administered in any convenient administrative form, e.g., tablets, powders, capsules, lozenges, granules, solutions, dispersions, suspensions, syrups, sprays, vapors, suppositories, gels, emulsions, patches, etc. Such compositions may contain components conventional in pharmaceutical preparations, e.g., diluents (e.g., glucose, lactose or mannitol), carriers, pH modifiers, buffers, sweeteners, bulking agents, stabilizing agents, surfactants, wetting agents, lubricating agents, emulsifiers, suspending agents, preservatives, antioxidants, opaquing agents, glidants, processing aids, colorants, perfuming agents, flavoring agents, other known additives as well as further active agents.

Suitable carriers and excipients are well known to those skilled in the art and are described in detail in, e.g., Ansel, Howard C., et al., Ansel's Pharmaceutical Dosage Forms and Drug Delivery Systems. Philadelphia: Lippincott, Williams & Wilkins, 2004; Gennaro, Alfonso R., et al. Remington: The Science and Practice of Pharmacy. Philadelphia: Lippincott, Williams & Wilkins, 2000; and Rowe, Raymond C. Handbook of Pharmaceutical Excipients. Chicago, Pharmaceutical Press, 2005. For example, carriers include solvents, dispersion media, coatings, surfactants, antioxidants, preservatives (e.g., antibacterial agents, antifungal agents), isotonic agents, absorption delaying agents, salts, preservatives, drugs, drug stabilizers, gels, binders, excipients, disintegration agents, lubricants, sweetening agents, flavoring agents, dyes, such like materials and combinations thereof, as would be known to one of ordinary skill in the art (see, for example, Remington's Pharmaceutical Sciences, pp 1289-1329, 1990). Except insofar as any conventional carrier is incompatible with the active ingredient, its use in the therapeutic or pharmaceutical compositions is contemplated. Exemplary excipients include dicalcium phosphate, mannitol, lactose, starch, magnesium stearate, sodium saccharine, cellulose, magnesium carbonate or combinations thereof. A pharmaceutical composition may comprise different types of carriers or excipients depending on whether it is to be administered in solid, liquid or aerosol form, and whether it need to be sterile for such routes of administration.

For example, tablets and capsules for oral administration may be in unit dose presentation form, and may contain conventional excipients such as binding agents, for example syrup, acacia, gelatin, sorbitol, tragacanth, or polyvinylpyrrolidone; fillers, for example, lactose, sugar, maize-starch, calcium phosphate, sorbitol or glycine; tabletting lubricant, for example, magnesium stearate, talc, polyethylene glycol or silica; disintegrants, for example, potato starch, or acceptable wetting agents such as sodium lauryl sulfate. The tablets may be coated according to methods well known in normal pharmaceutical practice. Oral liquid preparations may be in the form of, for example, aqueous or oily suspensions, solutions, emulsions, syrups or elixirs, or may be presented as a dry product for reconstitution with water or other suitable vehicle before use. Such liquid preparations may contain conventional additives such as suspending agents, for example, sorbitol, syrup, methyl cellulose, glucose syrup, gelatin hydrogenated edible fats; emulsifying agents, for example, lecithin, sorbitan monooleate, or acacia; non-aqueous vehicles (which may include edible oils), for example, almond oil, fractionated coconut oil, oily esters such as glycerine, propylene glycol, or ethyl alcohol; preservatives, for example, methyl or propyl p-hydroxybenzoate or sorbic acid, and if desired conventional flavoring or coloring agents.

For topical application to the skin, a compound may be made up into a cream, lotion or ointment. Cream or ointment formulations which may be used for the drug are conventional formulations well known in the art, for example as described in standard textbooks of pharmaceutics such as the British Pharmacopoeia.

Compounds of the invention or a pharmaceutically acceptable salt thereof may also be formulated for inhalation, for example, as a nasal spray, or dry powder or aerosol inhalers. For delivery by inhalation, the compound is typically in the form of microparticles, which can be prepared by a variety of techniques, including spray-drying, freeze-drying and micronisation. Aerosol generation can be carried out using, for example, pressure-driven jet atomizers or ultrasonic atomizers, such as by using propellant-driven metered aerosols or propellant-free administration of micronized compounds from, for example, inhalation capsules or other "dry powder" delivery systems.

By way of example, a composition of the invention may be prepared as a suspension for delivery from a nebulizer or as an aerosol in a liquid propellant, for example, for use in a pressurized metered dose inhaler (PMDI). Propellants suitable for use in a PMDI are known to the skilled person, and include CFC-12, HFA-134a, HFA-227, HCFC-22 ($CCl_2F_2$) and HFA-152 ($CH_4F_2$ and isobutane).

In some embodiments, a composition of the invention is in dry powder form, for delivery using a dry powder inhaler (DPI). Many types of DPI are known.

Microparticles for delivery by administration may be formulated with excipients that aid delivery and release. For example, in a dry powder formulation, microparticles may be formulated with large carrier particles that aid flow from the DPI into the lung. Suitable carrier particles are known, and include lactose particles; they may have a mass median aerodynamic diameter of, for example, greater than 90 µm.

In the case of an aerosol-based formulation, an example is:

Compound of the invention* 24 mg/canister
Lecithin, NF Liq. Conc. 1.2 mg/canister
Trichlorofluoromethane, NF 4.025 g/canister
Dichlorodifluoromethane, NF 12.15 g/canister.
* or a pharmaceutically acceptable salt thereof A compound of the invention or a pharmaceutically acceptable salt thereof may be dosed as described depending on the inhaler system used. In addition to the compound, the administration forms may additionally contain excipients as described above, or, for example, propellants (e.g., Frigen in the case of metered aerosols), surface-active substances, emulsifiers, stabilizers, preservatives, flavorings, fillers (e.g., lactose in the case of powder inhalers) or, if appropriate, further active compounds.

For the purposes of inhalation, a large number of systems are available with which aerosols of optimum particle size can be generated and administered, using an inhalation technique which is appropriate for the patient. In addition to the use of adaptors (spacers, expanders) and pear-shaped containers (e.g., Nebulator®, Volumatic®), and automatic devices emitting a puffer spray (Autohaler®), for metered aerosols, in the case of powder inhalers in particular, a number of technical solutions are available (e.g., Diskhaler®, Rotadisk®, Turbohaler® or the inhalers, for example, as described in U.S. Pat. No. 5,263,475, incorporated herein by reference). Additionally, compounds of the invention or a pharmaceutically acceptable salt thereof, may be delivered in multi-chamber devices thus allowing for delivery of combination agents.

The compound or a pharmaceutically acceptable salt thereof, may also be administered parenterally in a sterile medium. Depending on the vehicle and concentration used, the compound can either be suspended or dissolved in the vehicle. Advantageously, adjuvants such as a local anaesthetic, preservative or buffering agent can be dissolved in the vehicle.

Targeted Inhaled Drug Delivery

Compounds of the present invention may be used for targeted inhaled delivery. Optimisation of drugs for delivery to the lung by topical (inhaled) administration has been recently reviewed (Cooper, A. E. et al. Curr. Drug Metab. 2012, 13, 457-473).

Due to limitations in delivery devices, the dose of an inhaled drug may be limited humans, which necessitates highly potent molecules with good lung pharmacokinetic properties. High potency against the target of interest is especially important for an inhaled drug due to factors such as the limited amount of drug that can be delivered in a single puff from an inhaler, and the safety concerns related to a high aerosol burden in the lung (for example, cough or irritancy). For example, in some embodiments, a Ki of about 0.5 nM or less in a JAK1 biochemical assay such as described herein, and an IC50 of about 20 nM or less in a JAK1 dependent cell based assay such as described herein, may be desirable for an inhaled JAK1 inhibitor. In other embodiments, the projected human dose of a compound of the present invention, or a pharmaceutically acceptable salt thereof, is at least two times less than the projected human dose of a compound known in the art. Accordingly, in some embodiments, compounds (or a pharmaceutically acceptable salt thereof) described herein demonstrate such potency values. The procedures below were used to evaluate the subject compounds for potential use as inhaled drugs.

IL13 signaling. IL13 signaling is strongly implicated in asthma pathogenesis. IL13 is a cytokine that requires active JAK1 in order to signal. Thus, inhibition of JAK1 also inhibits IL13 signaling, which may provide benefit to asthma patients. Inhibition of IL13 signaling in an animal model (e.g., a mouse model) may predict future benefit to human asthmatic patients. Thus, it may be beneficial for an inhaled JAK1 inhibitor to show suppression of IL13 signaling in an animal model. Methods of measuring such suppression are known in the art. For example, as discussed herein and is known in the art, JAK1-dependent STAT6 phosphorylation is known to be a downstream consequence of IL13 stimulation. Accordingly, in some embodiments, compounds (or a pharmaceutically acceptable salt thereof) described herein demonstrate inhibition of lung pSTAT6 induction. To examine pharmacodynamic effects on pSTAT6 levels, compounds of the invention were co-dosed intranasally with IL13 to female Balb/c mice Compounds were formulated in 0.2% (v:v) Tween 80 in saline and mixed 1:1 (v:v) with IL13 immediately prior to administration. The intranasal doses were administered to lightly anaesthetised (isoflurane) mice by dispensing a fixed volume (50 µL) directly into the nostrils by pipette to achieve the target dose level (3 mg/kg, 1 mg/kg, 0.3 mg/kg, 0.1 mg/kg). At 0.25 hr post dose, blood samples (ca 0.5 mL) were collected by cardiac puncture and plasma generated by centrifugation (1500 g, 10 min, +4° C.). The lungs were perfused with chilled phosphate buffer saline (PBS), weighed and snap frozen in liquid nitrogen. All samples were stored at ca. −80° C. until analysis. Defrosted lung samples were weighed and homogenised following the addition of 2 mL HPLC grade water for each gram of tissue, using an Omni-Prep Bead Ruptor at 4° C. Plasma and lung samples were extracted by protein precipitation with three volumes of acetonitrile containing Tolbutamide (50 ng/mL) and Labetalol (25 ng/mL) as analytical internal standards. Following vortex mixing and centrifugation for 30 minutes at 3200 g and 4° C., the supernatants were diluted appropriately (e.g., 1:1 v:v) with HPLC grade water in a 96-well plate. Representative aliquots of plasma and lung samples were assayed for the parent compound by LC-MS/MS, against a series of matrix matched calibration and quality control standards. The standards were prepared by spiking aliquots of control Balb/c mouse plasma or lung homogenate (2:1 in HPLC grade water) with test compound and extracting as described for the experimental samples. A lung:plasma ratio was determined as the ratio of the mean lung concentration (µM) to the mean plasma concentration (µM) at the sampling time (0.2

To measure pSTAT6 levels, mouse lungs were stored frozen at −80° C. until assay and homogenised in 0.6 ml ice-cold cell lysis buffer (Cell Signalling Technologies, catalogue #9803 S) supplemented with 1 mM PMSF and a cocktail of protease (Sigma Aldrich, catalogue #P8340) and phosphatase (Sigma Aldrich, catalogue #P5726 and P0044) inhibitors. Samples were centrifuged at 16060×g for 4 minutes at 4° C. to remove tissue debris and protein concentration of homogenates determined using the Pierce BCA protein assay kit (catalogue #23225). Samples were diluted to a protein concentration of 5 mg/ml in ice-cold distilled water and assayed for pSTAT6 levels by Me so Scale Discovery electro-chemiluminescent immuno-assay. Briefly, 5 µl/well 150 µg/ml STAT6 capture antibody (R&D Systems, catalogue #MAB 2169) was coated onto 96 well Meso Scale Discovery High Binding Plates (catalogue #L15XB-3) and air-dried for 5 hours at room temperature. Plates were blocked by addition of 150 µl/well 30 mg/ml Meso Scale Discovery Blocker A (catalogue #R93BA-4) and incubation for 2 hours at room temperature on a microplate shaker. Blocked plates were washed 4 times with Meso Scale Discovery TRIS wash buffer (catalogue #R61TX-1), followed by transfer of 50 µl/well lung homogenate to achieve a protein loading of 250 µg/well. Assay plates were incubated overnight at 4° C. and washed 4 times with TRIS wash buffer before addition of 25 µl/well 2.5 µg/ml sulfotag-labelled pSTAT6 detection antibody (BD Pharmingen, catalogue #558241) for 2 hours at room temperature on a microplate shaker. Plates were washed 4 times with TRIS wash buffer and 150 µl/well IX Meso Scale Discovery Read Buffer T (catalogue #R92TC-1) added. Lung homogenate pSTAT6 levels were quantified by detection of electrochemiluminescence on a Meso Scale Discovery SECTOR S 600 instrument.

JAK and JAK2 inhibition Compounds inhibiting both JAK1 and JAK2 are potentially useful for treatment of different types of asthma. Selectivity between JAK1 and JAK2 may also be important for an inhaled JAK1 inhibitor. For example, GMCSF (granulocyte-macrophage colony-stimulating factor) is a cytokine that signals through JAK2 exclusively. Neutralization of GMCSF activity is associated with pulmonary alveolar proteinosis (PAP) in the lung. However, submaximal JAK2 suppression does not appear to be associated with PAP. Thus, even modest JAK1 vs JAK2 selectivity, or approximately equivalent inhibition of JAK1 and JAK2, may be of benefit in avoiding full suppression of the GMCSF pathway and avoiding PAP. For example, in certain embodiments compounds that are equipotent for JAK1 and JAK 2 are desirable. In other embodiments compounds with about 2×-5× selectivity for JAK1 over JAK2 may be of benefit for an inhaled JAK1 inhibitor. Accordingly, in some embodiments, compounds (or a pharmaceutically acceptable salt thereof) described herein demonstrate such selectivity. Methods of measuring JAK1 and JAK2 selectivity are known in the art, and information can also be found in the Examples herein.

Kinase profiling. Additionally, it may be desirable for an inhaled JAK1 or JAK1/JAK2 inhibitor to be selective over one or more other kinases to reduce the likelihood of potential toxicity due to off-target kinase pathway suppression. Thus, it may also be of benefit for an inhaled JAK1 inhibitor to be selective against a broad panel of non-JAK kinases, such as in protocols available from ThermoFisher Scientific's SelectScreen™ Biochemical Kinase Profiling Service using Adapta™ Screening Protocol Assay Conditions (Revised Jul. 29, 2016), LanthaScreen™ Eu Kinase Binding Assay Screening Protocol and Assay Conditions (Revised Jun. 7, 2016), and/or Z'LYTE™ Screening Protocol and Assay Conditions (Revised Sep. 16, 2016). For example, a compound of the present invention, or a pharmaceutically acceptable salt thereof, exhibits at least 50-fold selectivity for JAK1 versus a panel of non-JAK kinases. Accordingly, in some embodiments, compounds (or a pharmaceutically acceptable salt thereof) described herein demonstrate such selectivity.

Cytotoxicity assays. Hepatocyte toxicity, general cytotoxicity or cytotoxicity of unknown mechanism is an undesirable feature for a potential drug, including inhaled drugs. It may be of benefit for an inhaled JAK1 or JAK1/JAK2 inhibitor to have low intrinsic cytotoxicity against various cell types. Typical cell types used to assess cytotoxicity include both primary cells such as human hepatocytes, and proliferating established cell lines such as Jurkat and HEK-293. Accordingly, in some embodiments, compounds (or a pharmaceutically acceptable salt thereof) described herein demonstrate such values. Methods of measuring cytotoxicity are known in the art. In some embodiments, compounds described herein were tested as follows:

(a) Jurkat and HEK293T cells were maintained at a sub confluent density in T175 flasks. Cells were plated at 450 cells/45 µl medium in Greiner 384 well black/clear tissue culture treated plates. (Greiner Catalog #781091). After dispensing cells, plates were equilibrated at room temperature for 30 minutes. After 30 minutes at room temperature, cells were incubated overnight at 37° C. in a $CO_2$ and humidity controlled incubator. The following day, cells were treated with compounds diluted in 100% DMSO (final DMSO concentration on cells=0.5%) with a 10 point dose-response curve with a top concentration of 50 µM. Cells and compounds were then incubated for 72 hours overnight at 37° C. in a $CO_2$ and humidity controlled incubator. After 72 hours of incubation, viability was measured using CellTiterGlo® (Promega Catalog #G7572) to all wells. After incubation at room temperature for 20 minutes, plates were read on EnVision™ (Perkin Elmer Life Sciences) using luminescence mode;

(b) using human primary hepatocytes: the test compound was prepared as a 10 mM solution in DMSO. Additionally, a positive control such as Chlorpromazine was prepared as a 10 mM solution in DMSO. Test compounds were typically assessed using a 7-point dose response curve with 2-fold dilutions. Typically, the maximum concentration tested was 50-100 mM. The top concentration was typically dictated by solubility of the test compound. Cryopreserved primary human hepatocytes (BioreclamationIVT)(lot IZT) were thawed in InVitroGro™ HT thawing media (BioreclamationIVT) at 37° C., pelleted and resuspended. Hepatocyte viability was assessed by Trypan blue exclusion and cells were plated in black-walled, BioCoat™ collagen 384-well plates (Corning BD) at a density of 13,000 cells/well in InVitroGro™ CP plating media supplemented with 1% Torpedo™ Antibiotic Mix (BioreclamationIVT) and 5% fetal bovine serum. Cells were incubated overnight for 18 hours (37° C., 5% $CO_2$) prior to treatment. Following 18 horns incubation, plating media was removed and hepatocytes were treated with compounds diluted in InVitroGro™ HI incubation media containing 1% Torpedo™ Antibiotic Mix and 1% DMSO (serum-free conditions). Hepatocytes were treated with test compounds at concentrations such as 0.78, 1.56, 3.12, 6.25, 12.5, 25, and 50 µM at a final volume of 50 µL. A positive control (e.g., Chlorpromazine) was included in the assay, typically at the same concentrations as the test compound. Additional cells were treated with 1% DMSO as a vehicle control. All treatments were for a 48 horn time period (at 37° C., 5% $CO_2$) and each treatment condition was performed in triplicate. Following 48 hours of compound treatment, CellTiter-Glo® cell viability assay (Promega) was used as the endpoint assay to measure ATP content as a determination of cell viability. The assay was performed according to manufacture instructions. Luminescence was determined on an EnVision™ Muliplate Reader (PerkinElmer, Waltham, Mass., USA). Luminescence data was normalized to vehicle (1% DMSO) control wells. Inhibition curves and $IC_{50}$ estimates were generated by non-linear regression of log-transformed inhibitor concentrations (7-point serial dilutions including vehicle) vs. normalized response with variable Hill slopes, with top and bottom constrained to constant values of 100 and 0, respectively (GraphPad Prism™, GraphPad Software, La Jolla, Calif., USA).

hERG Inhibition. Inhibition of the hERG (human ether-à-go-go-related gene) potassium channel may lead to long QT syndrome and cardiac arrhythmias. Although plasma levels of an inhaled JAK1 or JAK1/JAK2 inhibitor are expected to be low, lung-deposited compound exiting the lung via pulmonary absorption into the bloodstream will circulate directly to the heart. Thus, local heart concentrations of an inhaled JAK1 inhibitor may be transiently higher than total plasma levels, particularly immediately after dosing. Thus, it may be of benefit to minimize hERG inhibition of an inhaled JAK1 inhibitor. For example, in some embodiments, a hERG IC50 greater than 30× over the free-drug plasma Cmax is preferred. Accordingly, in some embodiments, compounds (or a pharmaceutically acceptable salt thereof) of the invention demonstrate minimized hERG inhibition under conditions such as:

(a) using hERG 2pt automatic patch clamp conditions to examine in vitro effects of a compound on hERG expressed in mammalizan cells, evaluated at room temperature using the QPatch HT® (Sophion Bioscience A/S, Denmark), an automatic parallel patch clamp system. In some cases, compounds were tested at only one or two concentrations such as 1 or 10 uM. In other cases a more extensive concentration response relationship was established to allow estimation of IC50. For example, test compound concentrations were selected to span the range of approximately 10-90% inhibition in half-log increments. Each test article concentration was tested in two or more cells (n≥2). The duration of exposure to each test article concentration was a minimum of 3 minutes; and/or (b) those described in WO 2014/074775, in the Examples, under "Effect on Cloned hERG Potassium Channels Expressed in Mammalian Cells," a ChanTest™, a Charles River Company, protocol with the following changes: cells stably expressing hERG were held at −80 mV. Onset and steady state inhibition of hERG potassium current due to compound were measured using a pulse pattern with fixed amplitudes (conditioning prepulse: +20 mV for 1 s; repolarizing test ramepto −90 mV (−0.5 V/s) repeated at 5 s intervals). Each recording ended with a final application of a supramaximal concentration of a reference substance, E-4021 (500 nM) (Charles River Company). The remaining uninhibited current was subtracted off-line digitially from the data to determine the potency of the test substance for hERG inhibition.

CYP (cytochrome P450) inhibition assay. CYP inhibition may not be a desirable feature for an inhaled JAK1 or JAK1/JAK2 inhibitor. For example, a reversible or time dependent CYP inhibitor may cause an undesired increase in its own plasma levels, or in the plasma levels of other co-administered drugs (drug-drug interactions). Additionally, time dependent CYP inhibition is sometimes caused by biotransformation of parent drug to a reactive metabolite. Such reactive metabolites may covalently modify proteins, potentially leading to toxicity. Thus, minimizing reversible and time dependent CYP inhibition may be of benefit to an inhaled JAK1 inhibitor. Accordingly, in some embodiments, compounds (or a pharmaceutically acceptable salt thereof) of the present invention demonstrate minimal or no reversible and/or time dependent CYP inhibition. Methods of measuring CYP inhibition are known in the art. CYP inhibition of compounds described herein were assessed over a concentration range of 0.16-10 uM of compound using pooled (n=150) human liver microsomes (Corning, Tewksbury, Mass.) using methods previously reported (Halladay et al., *DrugMetab. Lett.* 2011, 5, 220-230). Incubation duration and protein concentration was dependent on the CYP isoform and the probe substrate/metabolites assessed. The following substrate/metabolites, and incubation times and protein concentrations for each CYP were used: CYP1A2, phenacetin/acetaminophen, 30 min, 0.03 mg/ml protein; CYP2C9, warfarin/7-hydroxywarfarin, 30 min, 0.2 mg/ml protein; CYP2C19, mephenytoin/4-hydroxymephenytoin, 40 min, 0.2 mg/ml protein; CYP2D6, dextromethorphan/dextrorphan, 10 min, 0.03 mg/ml protein; CYP3A4, midazolam/1-hydroxymidazolam, 10 min, 0.03 mg/ml protein and CYP3A4 testosterone/6-hydroxytestosterone, 10 min, 0.06 mg/ml protein. These conditions were previously determined to be in the linear rate of formation for the CYP-specific metabolites. All reaction were initiated with 1 mM NADPH and terminated by the addition of 0.1% formic acid in acetonitrile containing appropriate stable labeled internal standard. Samples were analyzed by LC-MS/MS Mouse lung tissue binding. A high bound fraction or percentage of JAK1/JAK2 inhibitors to lung tissue may be undesirable since it can reduce the amount of free drug available to inhibit JAK1 or JAK2.

(a) Tissue binding experiments were performed in triplicate (n=3) using a Single-Use RED Plate by following the standard protocol. Initially, individual drugs were spiked to tissue homogenates (pH 7.4) to achieve a final concentration of 1 μM, and then 300 μL of drug-tissue homogenate mixtures were transferred to the donor wells of the RED plate which was pre-loaded with 500 μL phosphate buffer saline (133 mM) on the receiver wells. The RED plate was sealed with a gas permeable membrane and placed in a shaking incubator (450 rpm, VWR Symphony™) for 6 hr at 37° C. with 5% $CO_2$. At the end of incubation, aliquots of 30 μL samples were taken out of the RED device and matrix equalized with an equal volume of tissue homogenates or buffer, and resulting samples were then immediately quenched with ice cold acetonitrile (sample:acetonitrile 1:4) containing either propranolol or labetalol as an internal standard. After shaking for 15 min at 500 rpm on a Thermo Scientific Compact Digital MicroPlate Shaker, all samples were then subjected to centrifugation at 3700 rpm for 15 min (Beckman Coulter Allegra X 12R) to remove plasma protein. Subsequently, supernatants were collected and then diluted with an equal volume of water prior to LC-MS/MS analysis.

(b) In an alternate procedure, the extent of lung tissue binding of test compound to mouse lung homogenate may also be determined by equilibrium dialysis using Pierce RED (rapid equilibrium dialysis) devices (Fisher Scientific 89811 & 89809). A 10 mM solution of compound in DMSO was prepared and diluted to 1 mM with DMSO. An aliquot of this 1 mM (4 μL) was added into lung homogenate (dilution factor of 1:9, lung tissue:potassium phosphate buffer (0.05 M, pH 7.4)) to give a final compound incubation concentration of 5 μM with solvent accounting for 0.5% (v/v) of the final incubation volume.

For each assay, the percentage lung tissue bound was determined in triplicate. Lung homogenate (200 μL) was loaded into one side of a RED device insert, in triplicate, and 350 μL of potassium phosphate buffer was loaded into the other side. The RED devices were sealed and incubated for 4 hours at ca. 37° C. on an orbital shaker (~150 rpm).

Following incubation, an aliquot of lung homogenate (8 μL) and an aliquot of dialysate (72 μL) were matrix matched (lung homogenate with 72 μL phosphate buffer, dialysate with 8 μL lung homogenate) ahead of analysis. Protein was precipitated from the samples with the addition of 160 μL of acetonitrile containing internal standard. The same matrix matching and protein precipitation procedure was performed on lung homogenate aliquots sampled at the start of the experiment (t=0 min samples), for the assessment of the mass balance. The quenched samples were centrifuged (4000 rpm, 30 min, 4° C.) and the resultant supernatant diluted with water (3:1 (v/v), supernatant: water) and the samples analysed for parent compound by liquid chromatography mass spectrometry assay.

The unbound fraction (fu) in lung homogenate was determined from the ratio of the dialysate to homogenate peak area, corrected to take into account the lung homogenate dilution (D) to enable an estimate of whole lung tissue binding using the following equations:

Undiluted $fu=(1/D)/[((1/\text{Apparent } fu)-1)+(1/D)]$

Corrected fraction bound (%)=(1-undiluted $fu$)*100

Kinetic solubility. Good aqueous solubility for JAK1/JAK2 inhibitors for inhaled delivery may be desirable in order to reduce the amount of undissolved particulate matter in the lung. In one procedure to measure kinetic solubility, 4 µL of a 10 mM DMSO stock solution of test compound is added to 196 µL of pH 7.4 phosphate buffered saline solution in a Millipore Multiscreen® 96-well filter plate to give a test concentration of 200 µM with 2% residual DMSO. The filter plate is sealed with aluminum sealing film and shaken at room temperature for 24 hours, then the mixtures were vacuum filtered into a clean 96-well plate. The filtrate samples are diluted by a factor of two using pH 7.4 phosphate buffered saline solution, then 5 µL of the resulting solutions are analyzed by ultra-high performance liquid chromatography (UHPLC) with chemiluminescence nitrogen detection (CLND) and ultraviolet (UV) detection at a wavelength of 254 nm. Sample concentration is typically quantified by the CLND intensity, which is related to the number of nitrogens in the compound. The UV detection is used primarily to confirm sample purity except for rare cases when test compounds contained no nitrogens. In those cases, a compound-specific calibration curve is collected based on UV absorbance. This curve is then used to determine sample concentration.

Linophilicity. Lipophilicity is relevant to the solubility, absorption, tissue penetration, protein binding, distribution, and ADME and PK properties generally of potential drugs. Calculated logP (cLogP), the logarithm of partition coefficient of a compound between n-octanol and water (i.e. log(concentration of the compound in n-octanol/concentration of compound in water), thus can be an important consideration for JAK1/JAK inhibitors for inhaled delivery.

Liver Microsomal Stability. In order to minimize systemic exposure of an inhaled JAK1/JAK2 inhibitor it may be beneficial to optimize for rapid metabolism in the liver. Liver microsomal stability assay was performed on a BioCel 1200 liquid handling workstation (Agilent Technologies, Santa Clara, Calif.). Compounds (1.0 μM) were incubated for 5 min at 37° C. in 100 μL of a reaction mixture containing 100 mM phosphate buffer (pH 7.4) and 0.5 mg/mL liver microsomes and 1 mM NADPH. At different time intervals (0, 20, 40 and 60 min), aliquots of 20 μL of reaction mixtures were taken out and mixed with 4-volumes of acetonitrile (ACN) containing 0.1 μM propranolol as the internal standard to stop metabolic reaction. The samples were then centrifuged at 3250×g for 40 min to remove precipitated protein. The supernatants were subsequently transferred to a new 96-well plate and diluted 2-fold using deionized water, and were then subjected to LC-MS/MS analysis using an ABI Sciex 5500 QTRAP® mass spectrometer (Applied Biosystems, Poster City, Calif.) coupled with a Agilent 1260 HPLC (Agilent Technologies, Santa Clara, Calif.). Percent of remaining was calculated using peak area ratio of test compound to the internal standard at different time points relative to the control (T=0 min). See B. Williamson, C. Wilson, G. Dagnell, RJ Riley. Harmonised high throughput microsomal stability assay. *J. Pharmacol. Toxicol. Methods.* 2017; 84:31-36.

Solid state properties. For compounds destined to be delivered via dry powder inhalation there is also a requirement to be able to generate crystalline forms of the compound that can be micronized to 1-5 μm in size. Particle size is an important determinant of lung deposition of an inhaled compound. Particles with a diameter of less than 5 microns (μm) are typically defined as respirable. Particles with a diameter larger than 5 μm are more likely to deposit in the oropharynx and are correspondingly less likely to be deposited in the lung. Additionally, fine particles with a diameter of less than 1 μm are more likely than larger particles to remain suspended in air, and are correspondingly more likely to be exhaled from the lung. Thus, a particle diameter of 1-5 μm may be of benefit for an inhaled medication whose site of action is in the lung. Typical methods used to measure particle size include laser diffraction and cascade impaction. Typical values used to define particle size include:

- D10, D50, and D90. These are measurements of particle diameter that indicate, respectively, 10%, 50%, or 90% of the sample is below that value. For example a D50 of 3 μm indicates that 50% of the sample is below 3 μm in size.
- Mass mean aerodynamic diameter (MMAD). MMAD is the diameter at which 50% of the particles by mass are larger and 50% are smaller. MMAD is a measure of central tendency.
- Geometric Standard Deviation (GSD). GSD is a measure of the magnitude in dispersity from the MMAD, or the spread in aerodynamic particle size distribution.

A common formulation for inhaled medications is a dry powder preparation including the active pharmaceutical ingredient (API) blended with a carrier such as lactose with or without additional additives such as magnesium stearate. For this formulation and others, it may be beneficial for the API itself to possess properties that allow it to be milled to a respirable particle size of 1-5 μm. Agglomeration of particles is to be avoided, which can be measured by methods known in the art, such as examining D90 values under different pressure conditions. Accordingly, in some embodiments, compounds (or a pharmaceutically acceptable salt thereof) of the present invention can be prepared with such a respirable particle size with little or no agglomeration.

As for crystallinity, for some formulations of inhaled drugs, including lactose blends, it is important that API of a specific crystalline form is used. Crystallinity and crystalline form may impact many parameters relevant to an inhaled drug including but not limited to: chemical and aerodynamic stability over time, compatibility with inhaled formulation components such as lactose, hygroscopicity, lung retention, and lung irritancy. Thus, a stable, reproducible crystalline form may be of benefit for an inhaled drug. Additionally, the techniques used to mill compounds to the desired particle size are often energetic and may cause low melting crystalline forms to convert to other crystalline forms, or to become fully or partially amorphous. A crystalline form with a melting point of less than 150° C. may be incompatible with milling, while a crystalline form with a melting point of less than 100° C. is likely to be non-compatible with milling. Thus, it may be beneficial for an inhaled medication to have a melting point of at least greater than 100° C., and ideally greater than 150° C. Accordingly, in some embodiments, compounds (or a pharmaceutically acceptable salt thereof) described herein demonstrate such properties.

Additionally, minimizing molecular weight may help to lower the efficacious dose of an inhaled JAK1 inhibitor. Lower molecular weight results in a corresponding higher number of molecules per unit mass of the active pharmaceutical ingredient (API). Thus, it may be of benefit to find the smallest molecular weight inhaled JAK1 inhibitor that retains all the other desired properties of an inhaled drug.

Finally, the compound needs to maintain a sufficient concentration in the lung over a given time period so as to be able to exert a pharmacological effect of the desired duration, and for pharmacological targets where systemic inhibition of said target is undesired, to have a low systemic exposure. The lung has an inherently high permeability to both large molecules (proteins, peptides) as well as small molecules with concomitant short lung half-lives, thus it may be necessary to attenuate the lung absorption rate through modification of one or more features of the compounds: minimizing membrane permeability, optimized pKa, cLogP, solubility, dissolution rate. Methods of measuring such properties are known in the art.

Accordingly, in some embodiments, a compound of the present invention (or a pharmaceutically acceptable salt thereof) favourably exhibits one or more of the above features. Further, in some embodiments, a compound of the present invention favorably exhibits one or more of these features relative to a compound known in the art—this may be particularly true for compounds of the art intended as oral drugs versus inhaled. For example, compounds with rapid oral absorption are typically poorly retained in the lung on inhalation.

Methods of Treatment with and Uses of Janus Kinase Inhibitors

The compounds of the present invention or a pharmaceutically acceptable salt thereof, inhibit the activity of a Janus kinase, such as JAK1, and/or JAK2 kinase. For example, a compound or a pharmaceutically acceptable salt thereof inhibits the phosphorylation of signal transducers and activators of transcription (STATs) by JAK1 kinase as well as ST AT mediated cytokine production. Compounds of the present invention are useful for inhibiting JAK1 kinase activity in cells through cytokine pathways, such as IL-6, IL-15, IL-7, IL-2, IL-4, IL-9, IL-10, IL-13, IL-21, G-CSF, IFNalpha, IFNbeta or IFNgamma pathways. Accordingly, in one embodiment is provided a method of contacting a cell with a compound of the present invention or a pharmaceutically acceptable salt thereof, to inhibit a Janus kinase activity in the cell (e.g., JAK1 activity).

The compounds can be used for the treatment of immunological disorders driven by aberrant IL-6, IL-15, IL-7, IL-2, IL-4, IL9, IL-10, IL-13, IL-21, G-CSF, IFNalpha, IFNbeta or IFNgamma cytokine signaling.

Accordingly, one embodiment includes a compound of the present invention or a pharmaceutically acceptable salt thereof, for use in therapy.

In some embodiments, there is provided use of a compound of the present invention or a pharmaceutically acceptable salt thereof, in the treatment of an inflammatory disease. Further provided is use of a compound of the present invention or a pharmaceutically acceptable salt thereof for the preparation of a medicament for the treatment of an inflammatory disease, such as asthma. Also provided is a compound of the present invention or a pharmaceutically acceptable salt thereof for use in the treatment of an inflammatory disease, such as asthma.

Another embodiment includes a method of preventing, treating or lessening the severity of a disease or condition, such as asthma, responsive to the inhibition of a Janus kinase activity, such as JAK1 kinase activity, in a patient. The method can include the step of administering to a patient a therapeutically effective amount of a compound of the present invention or a pharmaceutically acceptable salt thereof. In one embodiment, the disease or condition responsive to the inhibition of a Janus kinase, such as JAK1 kinase, is asthma.

In one embodiment, the disease or condition is cancer, stroke, diabetes, hepatomegaly, cardiovascular disease, multiple sclerosis, Alzheimer's disease, cystic fibrosis, viral disease, autoimmune diseases, atherosclerosis, restenosis, psoriasis, rheumatoid arthritis, inflammatory bowel disease, asthma, allergic disorders, inflammation, neurological disorders, a hormone-related disease, conditions associated with organ transplantation (e.g., transplant rejection), immunodeficiency disorders, destructive bone disorders, proliferative disorders, infectious diseases, conditions associated with cell death, thrombin-induced platelet aggregation, liver disease, pathologic immune conditions involving T cell activation, CNS disorders or a myeloproliferative disorder.

In one embodiment, the inflammatory disease is rheumatoid arthritis, psoriasis, asthma, inflammatory bowel disease, contact dermatitis or delayed hypersensitivity reactions. In one embodiment, the autoimmune disease is rheumatoid arthritis, lupus or multiple sclerosis.

In another embodiment, a compound of the present invention or a pharmaceutically acceptable salt thereof may be used to treat lung diseases such as a fibrotic lung disease or an interstitial lung disease (e.g., an interstitial pneumonia). In some embodiments, a compound of the present invention or a pharmaceutically acceptable salt thereof may be used to treat idiopathic pulmonary fibrosis (IFF), systemic sclerosis interstitial lung disease (SSc-ILD)), nonspecific interstitial pneumonia (NSIP), rheumatoid arthritis-associated interstitial lung disease (RA-ILD), sarcoidosis, hypersensitivity pneumonitis, or ILD secondary to connective tissue disease beyond scleroderma (e.g., polymyositis, dermatomyositis, rheumatoid arthritis, systemic lupus erythematosus (SLE), or mixed connective tissue disease).

In one embodiment, the cancer is breast, ovary, cervix, prostate, testis, penile, genitourinary tract, seminoma, esophagus, larynx, gastric, stomach, gastrointestinal, skin, keratoacanthoma, follicular carcinoma, melanoma, lung, small cell lung carcinoma, non-small cell lung carcinoma (NSCLC), lung adenocarcinoma, squamous carcinoma of the lung, colon, pancreas, thyroid, papillary, bladder, liver, biliary passage, kidney, bone, myeloid disorders, lymphoid disorders, hairy cells, buccal cavity and pharynx (oral), lip, tongue, mouth, salivary gland, pharynx, small intestine, colon, rectum, anal, renal, prostate, vulval, thyroid, large intestine, endometrial, uterine, brain, central nervous system, cancer of the peritoneum, hepatocellular cancer, head cancer, neck cancer, Hodgkin's or leukemia.

In one embodiment, the disease is a myeloproliferative disorder. In one embodiment, the myeloproliferative disorder is polycythemia vera, essential thrombocytosis, myelofibrosis or chronic myelogenous leukemia (CML).

Another embodiment includes the use of a compound of the present invention or a pharmaceutically acceptable salt thereof, for the manufacture of a medicament for the treatment of a disease described herein (e.g., an inflammatory disorder, an immunological disorder or cancer). In one embodiment, the invention provides a method of treating a disease or condition as described herein e.g., an inflammatory disorder, an immunological disorder or cancer) by targeting inhibition of a JAK kinase, such as JAK1.

Combination Therapy

The compounds may be employed alone or in combination with other agents for treatment. The second or further (e.g., third) compound of a pharmaceutical composition or dosing regimen typically has complementary activities to the compound of this invention such that they do not adversely affect each other. Such agents are suitably present in combination in amounts that are effective for the purpose intended. The compounds may be administered together in a unitary pharmaceutical composition or separately and, when administered separately this may occur simultaneously or sequentially. Such sequential administration may be close or remote in time.

For example, other compounds may be combined with a compound of the present invention or a pharmaceutically acceptable salt thereof for the prevention or treatment of inflammatory diseases, such as asthma. Suitable therapeutic agents for a combination therapy include, but are not limited to: an adenosine A2A receptor antagonist; an anti-infective; a non-steroidal Glucocorticoid Receptor (GR Receptor) agonist; an antioxidant; an alpha 2 adrenoceptor agonist; a CCR1 antagonist; a chemokine antagonist (not CCR1); a corticosteroid; a CRTh2 antagonist; a DPI antagonist; a formyl peptide receptor antagonist; a histone deacetylase activator; a chloride channel hCLCA1 blocker; an epithelial sodium channel blocker (ENAC blocker; an inter-cellular adhesion molecule 1 blocker (ICAM blocker); an IKK2 inhibitor; a JNK inhibitor; a transient receptor potential ankyrin 1 (TRPA1) inhibitor; a Bruton's tyrosine kinase (BTK) inhibitor (e.g., fenebrutinib); a spleen tyrosine kinase (SYK) inhibitor; a tryptase-beta antibody; an ST2 receptor antibody (e.g., AMG 282); a cyclooxygenase inhibitor (COX inhibitor); a lipoxygenase inhibitor; a leukotriene receptor antagonist; a dual alpha 2 adrenoceptor agonist/M3 receptor antagonist (MABA compound); a MEK-1 inhibitor; a myeloperoxidase inhibitor (MPO inhibitor); a muscarinic antagonist; a p38 MAPK inhibitor; a phosphodiesterase PDE4 inhibitor; a phosphatidylinositol 3-kinase δ inhibitor (PI3-kinase δ inhibitor); a phosphatidylinositol 3-kinase beta inhibitor (PI3-kinase gamma inhibitor); a peroxisome proliferator activated receptor agonist (PPARgamma agonist); a protease inhibitor; a retinoic acid receptor modulator (RAR gamma modulator); a statin; a thromboxane antagonist; a TLR7 receptor agonist; or a vasodilator.

In addition, a compound of the present invention or a pharmaceutically acceptable salt thereof, may be combined with: (1) corticosteroids, such as alclometasone dipropionate, amelometasone, beclomethasone dipropionate, budesonide, butixocort propionate, biclesonide, clobetasol propionate, desisobutyrylciclesonide, dexamethasone, etiprednol dicloacetate, fluocinolone acetonide, fluticasone furoate, fluticasone propionate, loteprednol etabonate (topical) or mometasone furoate; (2) β2-adrenoreceptor agonists such as salbutamol, albuterol, terbutaline, fenoterol, bitolterol, carbuterol, clenbuterol, pirbuterol, rimoterol, terbutaline, tretoquinol, tulobuterol and long acting β2-adrenoreceptor agonists such as metaproterenol, isoproterenol, isoprenaline, salmeterol, indacaterol, formoterol (including formoterol fumarate), arformoterol, carmoterol, abediterol, vilanterol trifenate, or olodaterol; (3) corticosteroid/long acting 32 agonist combination products such as salmeterol/fluticasone propionate (Advair®, also sold as Seretide®), formoterol/budesonide (Symbicort®), formoterol/fluticasone propionate (Flutiform®), formoterol/ciclesonide, formoterol/mometasone furoate, indacaterol/mometasone furoate, vilanterol trifenate/fluticasone furoate (BREO ELLIPTA), or arformoterokciclesonide; (4) anticholinergic agents, for example, muscarinic-3 (M3) receptor antagonists such as ipratropimn bromide, tiotropium bromide, aclidinium bromide (LAS-34273), glycopyrronium bromide, or umeclidinium bromide; (5) M3-anticholinergic/β2-adrenoreceptor agonist combination products such as vilanterol/umeclidinium (Anoro® Ellipta®), olodaterol/tiotropium bromide, glycopyrronium bromide/indacaterol (Ultibro®, also sold as Xoterna®), fenoterol hydrobromide/ipratropium bromide (Berodual®), albuterol sulfate/ipratropium bromide (Combivent®), formoterol fumarate/glycopyrrolate, or aclidinium bromide/formoterol; (6) dual pharmacology M3-anticholinergic/β2-adrenoreceptor agonists such as batefenterol succinate, AZD-2115 or LAS-190792; (7) leukotriene modulators, for example, leukotriene antagonists such as montelukast, zafirulast or pranlukast or leukotriene biosynthesis inhibitors such as zileuton, or LTB4 antagonists such as amelubant, or FLAP inhibitors such as fiboflapon, GSK-2190915; (8) phosphodiesterase-IV (PDE-IV) inhibitors (oral or inhaled), such as roflumilast, cilomilast, oglemilast, rolipram, tetomilast, AVE-8112, revamilast, CHE 6001; (9) antihistamines, for example, selective histamine-1 (H1) receptor antagonists such as fexofenadine, citirizine, loratidine or astemizole or dual H1/H3 receptor antagonists such as GSK 835726, or GSK 1004723; (10) antitussive agents, such as codeine or dextramorphan; (11) a mucolytic, for example, N-acetyl cysteine or fudostein; (12) a expectorant/mucokinetic modulator, for example, ambroxol, hypertonic solutions (e.g., saline or mannitol) or surfactant; (13) a peptide mucolytic, for example, recombinant human deoxyribonoclease I (dornase-alpha and rhDNase) or helicidin; (14) antibiotics, for example azithromycin, tobramycin or aztreonam; (15) non-selective COX-1/COX-2 inhibitors, such as ibuprofen or ketoprofen; (16) COX-2 inhibitors, such as celecoxib and rofecoxib; (17) VLA-4 antagonists, such as those described in WO 97/03094 and WO 97/02289, each incorporated herein by reference; (18) FACE inhibitors and TNF-α inhibitors, for example anti-TNF monoclonal antibodies, such as Remicade® and CDP-870 and TNF receptor immunoglobulin molecules, such as Enbrel®; (19) inhibitors of matrix metalloprotease, for example MMP-12; (20) human neutrophil elastase inhibitors, such as BAY-85-8501 or those described in WO 2005/026124, WO 2003/053930 and WO 2006/082412, each incorporated herein by reference; (21) A2b antagonists such as those described in WO 2002/42298, incorporated herein by reference; (22) modulators of chemokine receptor function, for example antagonists of CCR3 and CCR8; (23) compounds which modulate the action of other prostanoid receptors, for example, a thromboxane $A_2$ antagonist; DPI antagonists such as laropiprant or asapiprant CRTH2 antagonists such as OC000459, fevipiprant, ADC 3680 or ARRY 502; (24) PPAR agonists including PPAR alpha agonists (such as fenofibrate), PPAR delta agonists, PPAR gamma agonists such as pioglitazone, rosiglitazone and balaglitazone; (25) methylxanthines such as theophylline or aminophylline and methylxanthine/corticosteroid combinations such as theophylline/budesonide, theophylline/fluticasone propionate, theophylline/ciclesonide, theophylline/mometasone furoate and theophylline/beclometasone dipropionate; (26) A2a agonists such as those described in EP1052264 and EP1241176; (27) CXCR2 or IL-8 antagonists such as AZD-5069, AZD-4721, or danirixin; (28) IL-R signalling modulators such as kineret and ACZ 885; (29) MCP-1 antagonists such as ABN-912; (30) a p38 MAPK inhibitor such as BCT197, JNJ49095397, losmapimod or PH-797804; (31) TLR7 receptor agonists such as AZD 8848; (32) PI3-kinase inhibitors such as RV1729 or GSK2269557 (nemiralisib); (33) triple combination products such as TRELEGY ELLIPTA (fluticasone furoate, umeclidinium bromide, and vilanterol); or (34) small molecule inhibitors of TRPA1, BTK, or SYK.

In some embodiments a compound of the present invention or a pharmaceutically acceptable salt thereof, can be used in combination with one or more additional drugs, for example anti-hyperproliferative, anti-cancer, cytostatic, cytotoxic, anti-inflammatory or chemotherapeutic agents, such as those agents disclosed in U.S. Publ. Appl. No. 2010/0048557, incorporated herein by reference. A compound of the present invention or a pharmaceutically acceptable salt thereof, can be also used in combination with radiation therapy or surgery, as is known in the art.

Combinations of any of the foregoing with a compound of the present invention or a pharmaceutically acceptable salt thereof are specifically contemplated.

Articles of Manufacture

Another embodiment includes an article of manufacture (e.g., a kit) for treating a disease or disorder responsive to the inhibition of a Janus kinase, such as a JAK1 kinase. The kit can comprise:

(a) a first pharmaceutical composition comprising a compound of the present invention or a pharmaceutically acceptable salt thereof; and (b) instructions for use.

In another embodiment, the kit further comprises:

(c) a second pharmaceutical composition, such as a pharmaceutical composition comprising an agent for treatment as described above, such as an agent for treatment of an inflammatory disorder, or a chemotherapeutic agent.

In one embodiment, the instructions describe the simultaneous, sequential or separate administration of said first and second pharmaceutical compositions to a patient in need thereof.

In one embodiment, the first and second compositions are contained in separate containers. In another embodiment, the first and second compositions are contained in the same container.

Containers for use include, for example, bottles, vials, syringes, blister pack, etc. The containers may be formed from a variety of materials such as glass or plastic. The container includes a compound of the present invention or a pharmaceutically acceptable salt thereof, which is effective for treating the condition and may have a sterile access port (for example the container may be an intravenous solution bag or a vial having a stopper pierceable by a hypodermic injection needle). The label or package insert indicates that the compound is used for treating the condition of choice, such as asthma or cancer. In one embodiment, the label or package inserts indicates that the compound can be used to treat a disorder. In addition, the label or package insert may indicate that the patient to be treated is one having a disorder characterized by overactive or irregular Janus kinase activity, such as overactive or irregular JAK1 activity. The label or package insert may also indicate that the compound can be used to treat other disorders.

Alternatively, or additionally, the kit may further comprise a second (or third) container comprising a pharmaceutically acceptable buffer, such as bacteriostatic water for injection (BWFI), phosphate-buffered saline, Ringer's solution or dextrose solution. It may further include other materials desirable from a commercial and user standpoint, including other buffers, diluents, filters, needles, and syringes.

In order to illustrate the invention, the following examples are included. However, it is to be understood that these examples do not limit the invention and are only meant to suggest a method of practicing the invention. Persons skilled in the art will recognize that the chemical reactions described may be readily adapted to prepare other compounds of the present invention, and alternative methods for preparing the compounds are within the scope of this invention. For example, the synthesis of non-exemplified compounds according to the invention may be successfully performed by modifications apparent to those skilled in the art, e.g., by appropriately protecting interfering groups, by utilizing other suitable reagents known in the art other than those described, or by making routine modifications of reaction conditions. Alternatively, other reactions disclosed herein or known in the art will be recognized as having applicability for preparing other compounds of the invention.

EXAMPLES

The following representative compounds of Table 1 were prepared using procedures similar to those described in the Schemes and Examples herein. Absolute stereochemistry of each compound below may not be depicted: therefore, structures may appear more than once, each representing a single stereoisomer.

TABLE 1

Exemplary JAK Inhibitors of the Invention

| | Structure | Name |
|---|---|---|
| 1 | 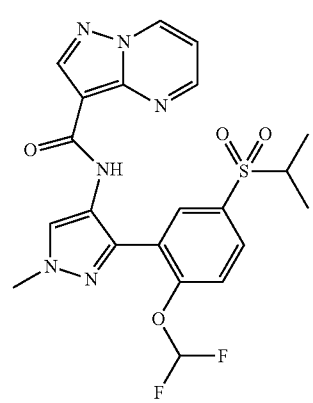 [SMILES: CC(C)S(=O)(=O)c1ccc(OC(F)F)c(-c2nn(C)cc2NC(=O)c2cnn3cccnc23)c1] | N-[3-[2-(difluoromethoxy)-5-isopropylsulfonyl-phenyl]-1-methyl-pyrazol-4-yl]pyrazolo[1,5-a]pyrimidine-3-carboxamide |

TABLE 1-continued

Exemplary JAK Inhibitors of the Invention

| | Structure | Name |
|---|---|---|
| 2 | 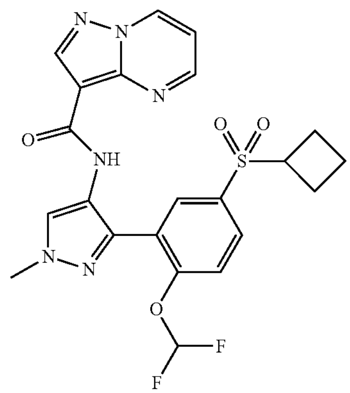 [SMILES: Cn1cc(NC(=O)c2cnn3cccnc23)c(-c2cc(S(=O)(=O)C3CCC3)ccc2OC(F)F)n1] | N-[3-[5-cyclobutylsulfonyl-2-(difluoromethoxy)phenyl]-1-methyl-pyrazol-4-yl]pyrazolo[1,5-a]pyrimidine-3-carboxamide |
| 3 | 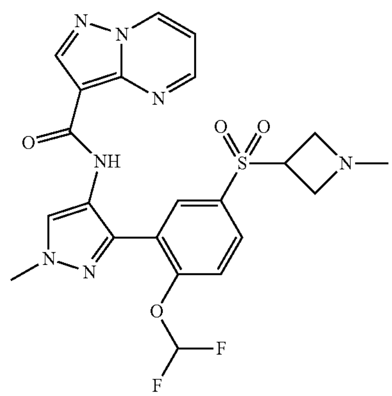 | N-[3-[2-(difluoromethoxy)-5-(1-methylazetidin-3-yl)sulfonyl-phenyl]-1-methyl-pyrazol-4-yl]pyrazolo[1,5-a]pyrimidine-3-carboxamide |
| 4 | 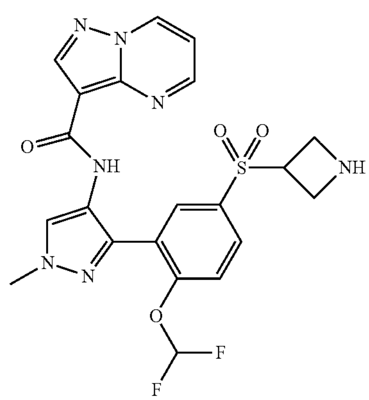 [SMILES: Cn1cc(NC(=O)c2cnn3cccnc23)c(-c2cc(S(=O)(=O)C3CNC3)ccc2OC(F)F)n1] | N-[3-[5-(azetidin-3-ylsulfonyl)-2-(difluoromethoxy)phenyl]-1-methyl-pyrazol-4-yl]pyrazolo[1,5-a]pyrimidine-3-carboxamide |
| 5 | 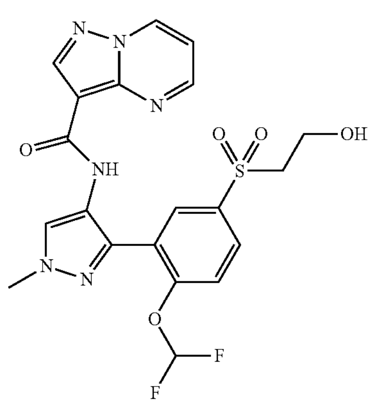 [SMILES: Cn1cc(NC(=O)c2cnn3cccnc23)c(-c2cc(S(=O)(=O)CCO)ccc2OC(F)F)n1] | N-[3-[2-(difluoromethoxy)-5-(2-hydroxyethylsulfonyl)phenyl]-1-methyl-pyrazol-4-yl]pyrazolo[1,5-a]pyrimidine-3-carboxamide |

TABLE 1-continued

Exemplary JAK Inhibitors of the Invention

| | Structure | Name |
|---|---|---|
| 6 | 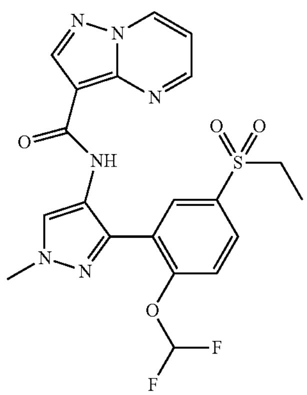 [SMILES: CCS(=O)(=O)c1ccc(OC(F)F)c(-c2nn(C)cc2NC(=O)c2cnn3cccnc23)c1] | N-[3-[2-(difluoromethoxy)-5-ethylsulfonyl-phenyl]-1-methyl-pyrazol-4-yl]pyrazolo[1,5-a]pyrimidine-3-carboxamide |
| 7 | 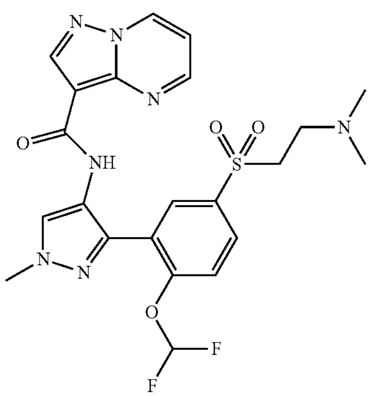 | N-[3-[2-(difluoromethoxy)-5-[2-(dimethylamino)ethylsulfonyl]phenyl]-1-methyl-pyrazol-4-yl]pyrazolo[1,5-a]pyrimidine-3-carboxamide |
| 8 | 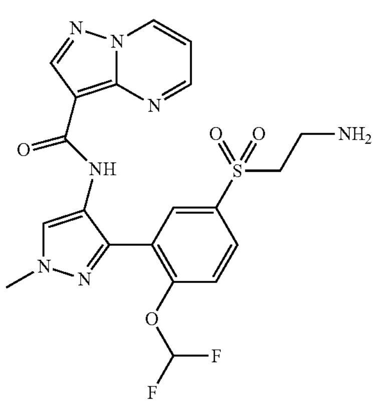 [SMILES: Cn1cc(NC(=O)c2cnn3cccnc23)c(-c2cc(S(=O)(=O)CCN)ccc2OC(F)F)n1] | N-[3-[5-(2-aminoethylsulfonyl)-2-(difluoromethoxy)phenyl]-1-methyl-pyrazol-4-yl]pyrazolo[1,5-a]pyrimidine-3-carboxamide |

TABLE 1-continued

Exemplary JAK Inhibitors of the Invention

| | Structure | Name |
|---|---|---|
| 9 | 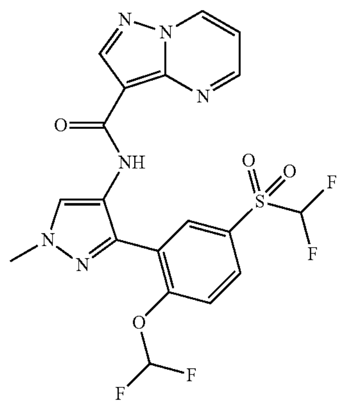 [SMILES: Cn1cc(NC(=O)c2cnn3cccnc23)c(-c2cc(S(=O)(=O)C(F)F)ccc2OC(F)F)n1] | N-[3-[2-(difluoromethoxy)-5-(difluoromethylsulfonyl)phenyl]-1-methyl-pyrazol-4-yl]pyrazolo[1,5-a]pyrimidine-3-carboxamide |
| 10 | 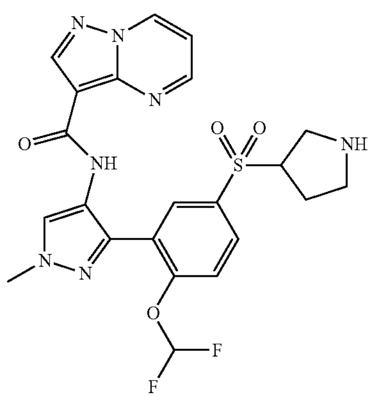 [SMILES: Cn1cc(NC(=O)c2cnn3cccnc23)c(-c2cc(S(=O)(=O)C3CCNC3)ccc2OC(F)F)n1] | N-[3-[2-(difluoromethoxy)-5-pyrrolidin-3-ylsulfonyl-phenyl]-1-methyl-pyrazol-4-yl]pyrazolo[1,5-a]pyrimidine-3-carboxamide |
| 11 | 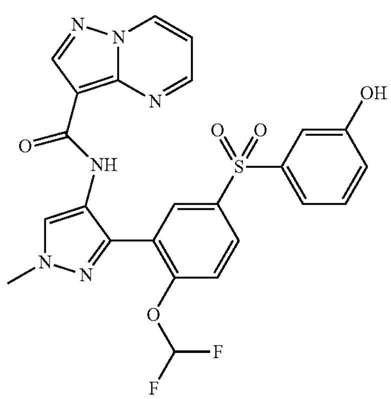 [SMILES: Cn1cc(NC(=O)c2cnn3cccnc23)c(-c2cc(S(=O)(=O)c3cccc(O)c3)ccc2OC(F)F)n1] | N-[3-[2-(difluoromethoxy)-5-(3-hydroxyphenyl)sulfonyl-phenyl]-1-methyl-pyrazol-4-yl]pyrazolo[1,5-a]pyrimidine-3-carboxamide |
| 12 | 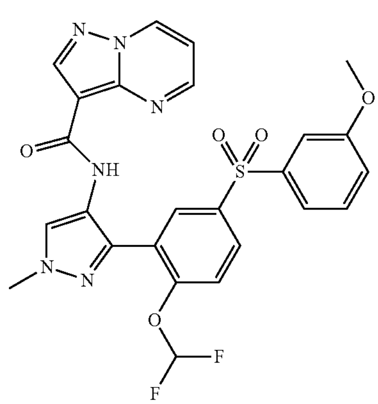 [SMILES: COc1cccc(S(=O)(=O)c2ccc(OC(F)F)c(-c3nn(C)cc3NC(=O)c3cnn4cccnc34)c2)c1] | N-[3-[2-(difluoromethoxy)-5-(3-methoxyphenyl)sulfonyl-phenyl]-1-methyl-pyrazol-4-yl]pyrazolo[1,5-a]pyrimidine-3-carboxamide |

TABLE 1-continued

Exemplary JAK Inhibitors of the Invention

| | Structure | Name |
|---|---|---|
| 13 | 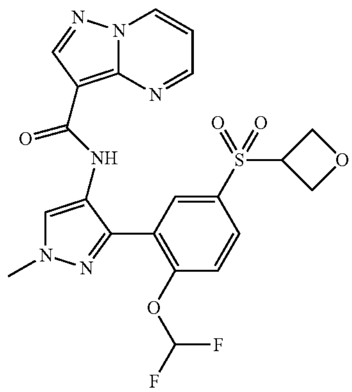 [SMILES: Cn1cc(NC(=O)c2cnn3cccnc23)c(-c2cc(S(=O)(=O)C3COC3)ccc2OC(F)F)n1] | N-[3-[2-(difluoromethoxy)-5-(oxetan-3-ylsulfonyl)phenyl]-1-methyl-pyrazol-4-yl]pyrazolo[1,5-a]pyrimidine-3-carboxamide |
| 14 | 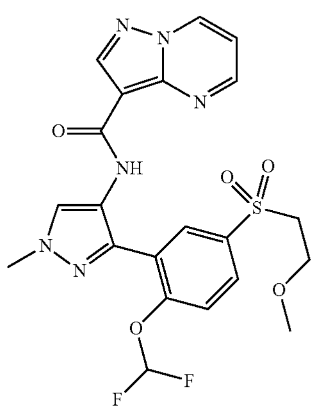 [SMILES: COCCS(=O)(=O)c1ccc(OC(F)F)c(-c2nn(C)cc2NC(=O)c2cnn3cccnc23)c1] | N-[3-[2-(difluoromethoxy)-5-(2-methoxyethylsulfonyl)phenyl]-1-methyl-pyrazol-4-yl]pyrazolo[1,5-a]pyrimidine-3-carboxamide |
| 15 | 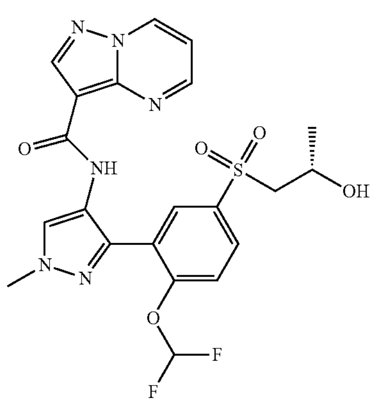 [SMILES: C[C@H](O)CS(=O)(=O)c1ccc(OC(F)F)c(-c2nn(C)cc2NC(=O)c2cnn3cccnc23)c1] | N-[3-[2-(difluoromethoxy)-5-[rac-(2S)-2-hydroxypropyl]sulfonyl-phenyl]-1-methyl-pyrazol-4-yl]pyrazolo[1,5-a]pyrimidine-3-carboxamide |

TABLE 1-continued

Exemplary JAK Inhibitors of the Invention

| | Structure | Name |
|---|---|---|
| 16 | 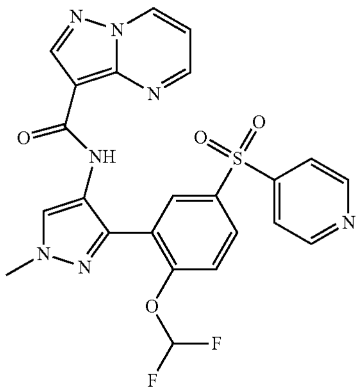 [SMILES: Cn1cc(NC(=O)c2cnn3cccnc23)c(-c2cc(S(=O)(=O)c3ccncc3)ccc2OC(F)F)n1] | N-[3-[2-(difluoromethoxy)-5-(4-pyridylsulfonyl)phenyl]-1-methyl-pyrazol-4-yl]pyrazolo[1,5-a]pyrimidine-3-carboxamide |
| 17 | 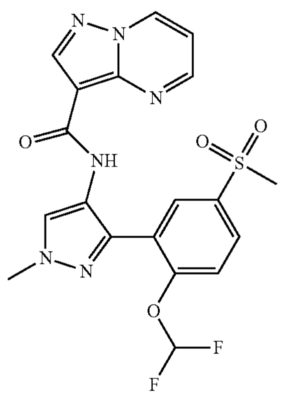 | N-[3-[2-(difluoromethoxy)-5-methylsulfonyl-phenyl]-1-methyl-pyrazol-4-yl]pyrazolo[1,5-a]pyrimidine-3-carboxamide |
| 18 | 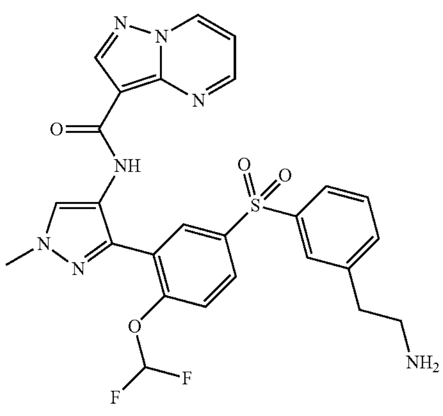 [SMILES: Cn1cc(NC(=O)c2cnn3cccnc23)c(-c2cc(S(=O)(=O)c3cccc(CCN)c3)ccc2OC(F)F)n1] | N-[3-[5-[3-(2-aminoethyl)phenyl]sulfonyl-2-(difluoromethoxy)phenyl]-1-methyl-pyrazol-4-yl]pyrazolo[1,5-a]pyrimidine-3-carboxamide |
| 19 | 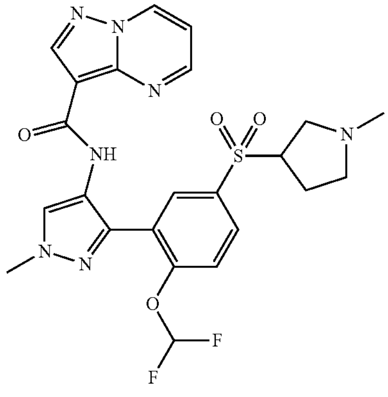 | N-[3-[2-(difluoromethoxy)-5-(1-methylpyrrolidin-3-yl)sulfonyl-phenyl]-1-methyl-pyrazol-4-yl]pyrazolo[1,5-a]pyrimidine-3-carboxamide |

TABLE 1-continued

Exemplary JAK Inhibitors of the Invention

| | Structure | Name |
|---|---|---|
| 20 | 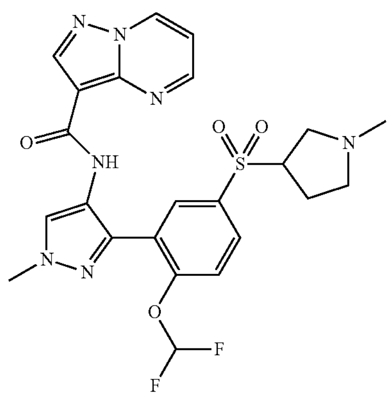 | N-[3-[2-(difluoromethoxy)-5-(1-methylpyrrolidin-3-yl)sulfonyl-phenyl]-1-methyl-pyrazol-4-yl]pyrazolo[1,5-a]pyrimidine-3-carboxamide |
| 21 | 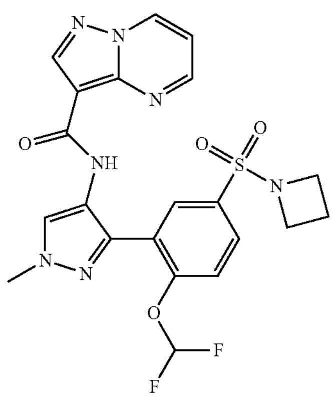 [SMILES: Cn1cc(NC(=O)c2cnn3cccnc23)c(-c2cc(S(=O)(=O)N3CCC3)ccc2OC(F)F)n1] | N-[3-[5-(azetidin-1-ylsulfonyl)-2-(difluoromethoxy)phenyl]-1-methyl-pyrazol-4-yl]pyrazolo[1,5-a]pyrimidine-3-carboxamide |
| 22 | 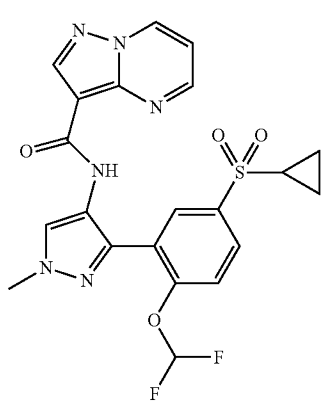 [SMILES: Cn1cc(NC(=O)c2cnn3cccnc23)c(-c2cc(S(=O)(=O)C3CC3)ccc2OC(F)F)n1] | N-[3-[5-cyclopropylsulfonyl-2-(difluoromethoxy)phenyl]-1-methyl-pyrazol-4-yl]pyrazolo[1,5-a]pyrimidine-3-carboxamide |

TABLE 1-continued

Exemplary JAK Inhibitors of the Invention

| | Structure | Name |
|---|---|---|
| 23 | 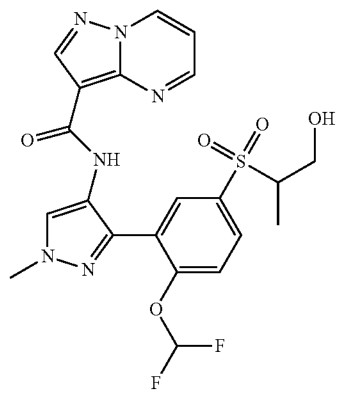 [SMILES: CC(CO)S(=O)(=O)c1ccc(OC(F)F)c(-c2nn(C)cc2NC(=O)c2cnn3cccnc23)c1] | N-[3-[2-(difluoromethoxy)-5-(2-hydroxy-1-methyl-ethyl)sulfonyl-phenyl]-1-methyl-pyrazol-4-yl]pyrazolo[1,5-a]pyrimidine-3-carboxamide |
| 24 | 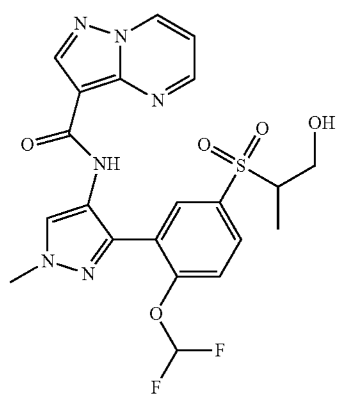 [SMILES: CC(CO)S(=O)(=O)c1ccc(OC(F)F)c(-c2nn(C)cc2NC(=O)c2cnn3cccnc23)c1] | N-[3-[2-(difluoromethoxy)-5-(2-hydroxy-1-methyl-ethyl)sulfonyl-phenyl]-1-methyl-pyrazol-4-yl]pyrazolo[1,5-a]pyrimidine-3-carboxamide |
| 25 | 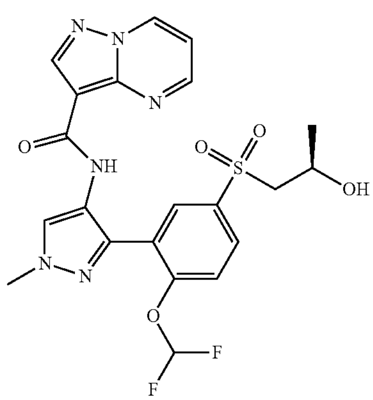 [SMILES: C[C@@H](O)CS(=O)(=O)c1ccc(OC(F)F)c(-c2nn(C)cc2NC(=O)c2cnn3cccnc23)c1] | N-[3-[2-(difluoromethoxy)-5-[rac-(2R)-2-hydroxypropyl]sulfonyl-phenyl]-1-methyl-pyrazol-4-yl]pyrazolo[1,5-a]pyrimidine-3-carboxamide |
| 26 | 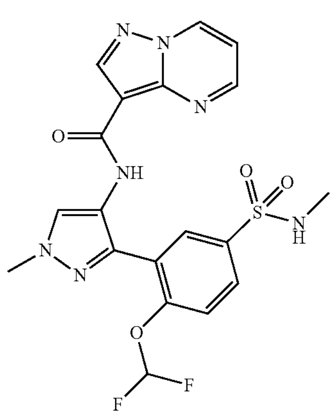 | N-[3-[2-(difluoromethoxy)-5-(methylsulfamoyl)phenyl]-1-methyl-pyrazol-4-yl]pyrazolo[1,5-a]pyrimidine-3-carboxamide |

TABLE 1-continued

Exemplary JAK Inhibitors of the Invention

| | Structure | Name |
|---|---|---|
| 27 | 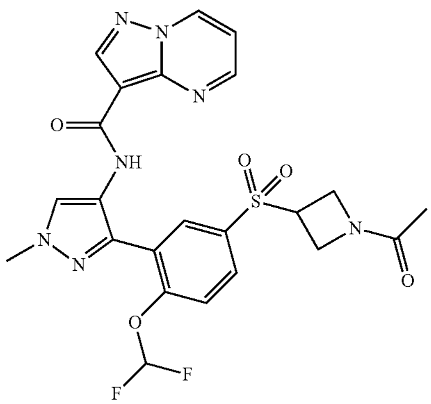 [SMILES: CC(=O)N1CC(S(=O)(=O)c2ccc(OC(F)F)c(-c3nn(C)cc3NC(=O)c3cnn4cccnc34)c2)C1] | N-[3-[5-(1-acetylazetidin-3-yl)sulfonyl-2-(difluoromethoxy)phenyl]-1-methyl-pyrazol-4-yl]pryazolo[1,5-a]pyrimidine-3-carboxamide |
| 28 | 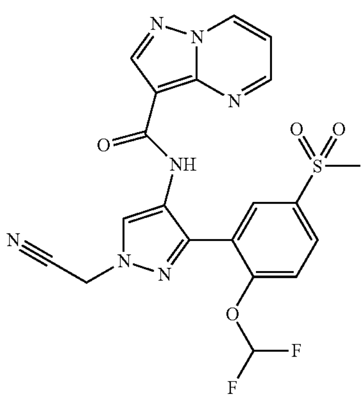 [SMILES: CS(=O)(=O)c1ccc(OC(F)F)c(-c2nn(CC#N)cc2NC(=O)c2cnn3cccnc23)c1] | N-[1-(cyanomethyl)-3-[2-(difluoromethoxy)-5-methylsulfonyl-phenyl]pyrazol-4-yl]pyrazolo[1,5-a]pyrimidine-3-carboxamide |
| 29 | 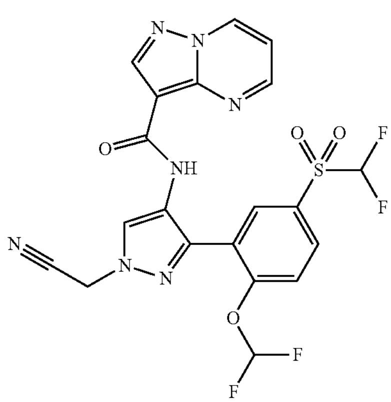 [SMILES: N#CCn1cc(NC(=O)c2cnn3cccnc23)c(-c2cc(S(=O)(=O)C(F)F)ccc2OC(F)F)n1] | N-[1-(cyanomethyl)-3-[2-(difluoromethoxy)-5-(difluoromethylsulfonyl)phenyl]pyrazol-4-yl]pyrazolo[1,5-a]pyrimidine-3-carboxamide |

TABLE 1-continued

Exemplary JAK Inhibitors of the Invention

| | Structure | Name |
|---|---|---|
| 30 | 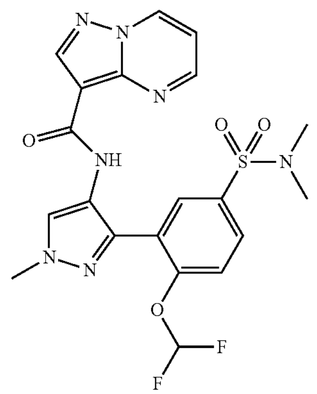 | N-[3-[2-(difluoromethoxy)-5-(dimethylsulfamoyl)phenyl]-1-methyl-pyrazol-4-yl]pyrazolo[1,5-a]pyrimidine-3-carboxamide |
| 31 | 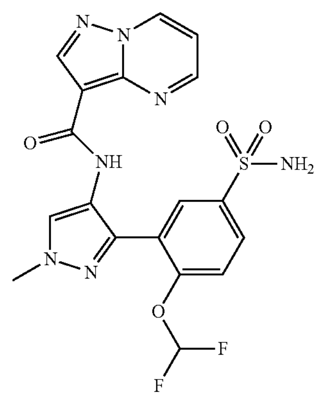 [SMILES: Cn1cc(NC(=O)c2cnn3cccnc23)c(-c2cc(S(N)(=O)=O)ccc2OC(F)F)n1] | N-[3-[2-(difluoromethoxy)-5-sulfamoyl-phenyl]-1-methyl-pyrazol-4-yl]pyrazolo[1,5-a]pyrimidine-3-carboxamide |
| 32 | 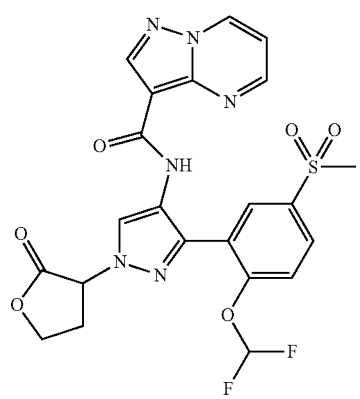 [SMILES: CS(=O)(=O)c1ccc(OC(F)F)c(-c2nn(C3CCOC3=O)cc2NC(=O)c2cnn3cccnc23)c1] | N-[3-[2-(difluoromethoxy)-5-methylsulfonyl-phenyl]-1-(2-oxotetrahydrofuran-3-yl)pyrazol-4-yl]pyrazolo[1,5-a]pyrimidine-3-carboxamide |
| 33 | 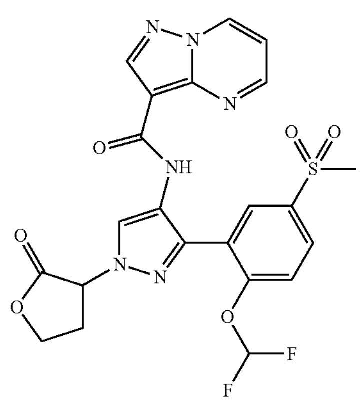 [SMILES: CS(=O)(=O)c1ccc(OC(F)F)c(-c2nn(C3CCOC3=O)cc2NC(=O)c2cnn3cccnc23)c1] | N-[3-[2-(difluoromethoxy)-5-methylsulfonyl-phenyl]-1-(2-oxotetrahydrofuran-3-yl)pyrazol-4-yl]pyrazolo[1,5-a]pyrimidine-3-carboxamide |

TABLE 1-continued

Exemplary JAK Inhibitors of the Invention

| | Structure | Name |
|---|---|---|
| 34 | 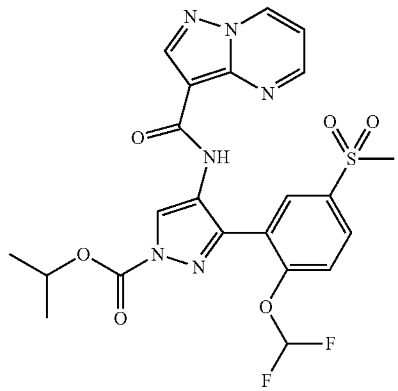 [SMILES: CC(C)OC(=O)n1cc(NC(=O)c2cnn3cccnc23)c(-c2cc(S(C)(=O)=O)ccc2OC(F)F)n1] | isopropyl 3-[2-(difluoromethoxy)-5-methylsulfonyl-phenyl]-4-(pyrazolo[1,5-a]pyrimidine-3-carbonylamino)pyrazole-1-carboxylate |
| 35 | 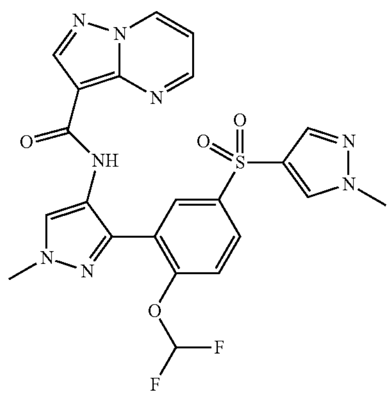 | N-[3-[2-(difluoromethoxy)-5-(1-methylpyrazol-4-yl)sulfonyl-phenyl]-1-methyl-pyrazol-4-yl]pyrazolo[1,5-a]pyrimidine-3-carboxamide |
| 36 | 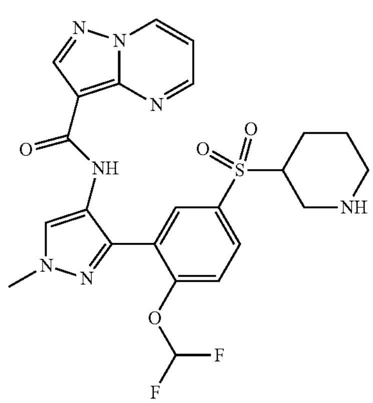 [SMILES: Cn1cc(NC(=O)c2cnn3cccnc23)c(-c2cc(S(=O)(=O)C3CCCNC3)ccc2OC(F)F)n1] | N-[3-[2-(difluoromethoxy)-5-(3-piperidylsulfonyl)phenyl]-1-methyl-pyrazol-4-yl]pyrazolo[1,5-a]pyrimidine-3-carboxamide |

TABLE 1-continued

Exemplary JAK Inhibitors of the Invention

| | Structure | Name |
|---|---|---|
| 37 | 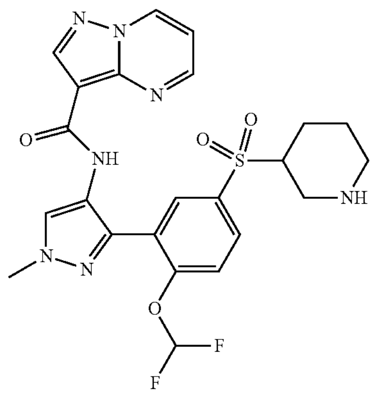 [SMILES: Cn1cc(NC(=O)c2cnn3cccnc23)c(-c2cc(S(=O)(=O)C3CCCNC3)ccc2OC(F)F)n1] | N-[3-[2-(difluoromethoxy)-5-(3-piperidylsulfonyl)phenyl]-1-methyl-pyrazol-4-yl]pyrazolo[1,5-a]pyrimidine-3-carboxamide |
| 38 | 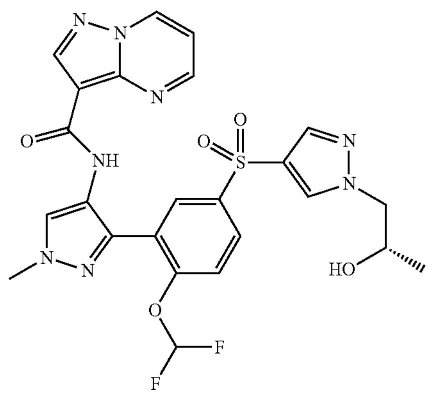 [SMILES: C[C@H](O)Cn1cc(S(=O)(=O)c2ccc(OC(F)F)c(-c3nn(C)cc3NC(=O)c3cnn4cccnc34)c2)cn1] | N-[3-[2-(difluoromethoxy)-5-[1-[(2S)-2-hydroxypropyl]pyrazol-4-yl]sulfonyl-phenyl]-1-methyl-pyrazol-4-yl]pyrazolo[1,5-a]pyrimidine-3-carboxamide |
| 39 | 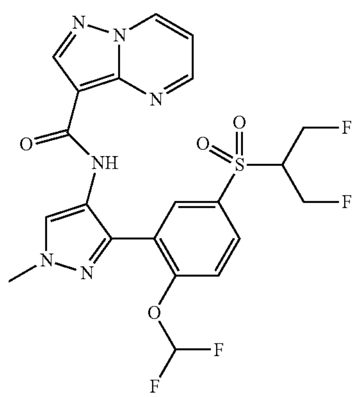 [SMILES: Cn1cc(NC(=O)c2cnn3cccnc23)c(-c2cc(S(=O)(=O)C(CF)CF)ccc2OC(F)F)n1] | N-[3-[2-(difluoromethoxy)-5-[2-fluoro-1-(fluoromethyl)ethyl]sulfonyl-phenyl]-1-methyl-pyrazol-4-yl]pyrazolo[1,5-a]pyrimidine-3-carboxamide |
| 40 | 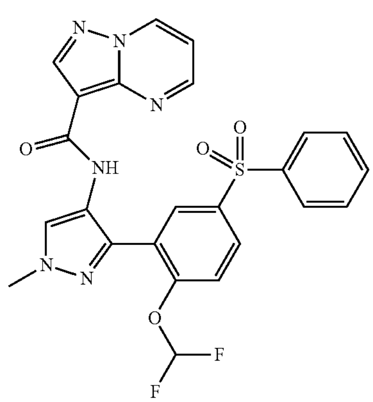 [SMILES: Cn1cc(NC(=O)c2cnn3cccnc23)c(-c2cc(S(=O)(=O)c3ccccc3)ccc2OC(F)F)n1] | N-[3-[5-(benzenesulfonyl)-2-(difluoromethoxy)phenyl]-1-methyl-pyrazol-4-yl]pyrazolo[1,5-a]pyrimidine-3-carboxamide |

TABLE 1-continued

Exemplary JAK Inhibitors of the Invention

| | Structure | Name |
|---|---|---|
| 41 | 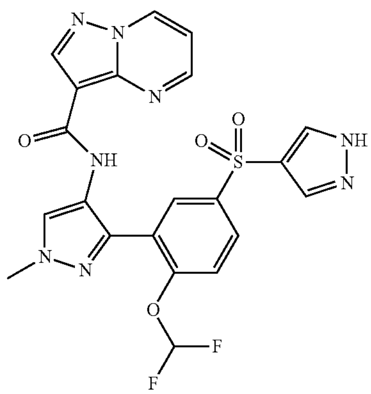 [SMILES: Cn1cc(NC(=O)c2cnn3cccnc23)c(-c2cc(S(=O)(=O)c3cn[nH]c3)ccc2OC(F)F)n1] | N-[3-[2-(difluoromethoxy)-5-(1H-pyrazol-4-ylsulfonyl)phenyl]-1-methyl-pyrazol-4-yl]pyrazolo[1,5-a]pyrimidine-3-carboxamide |
| 42 | 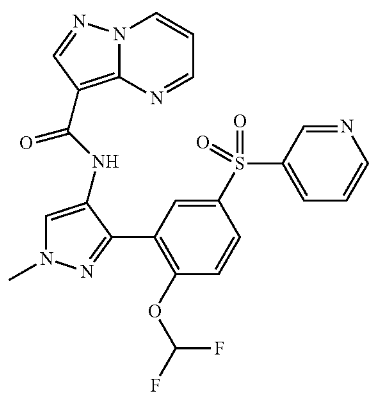 [SMILES: Cn1cc(NC(=O)c2cnn3cccnc23)c(-c2cc(S(=O)(=O)c3cccnc3)ccc2OC(F)F)n1] | N-[3-[2-(difluoromethoxy)-5-(3-pyridylsulfonyl)phenyl]-1-methyl-pyrazol-4-yl]pyrazolo[1,5-a]pyrimidine-3-carboxamide |
| 43 | 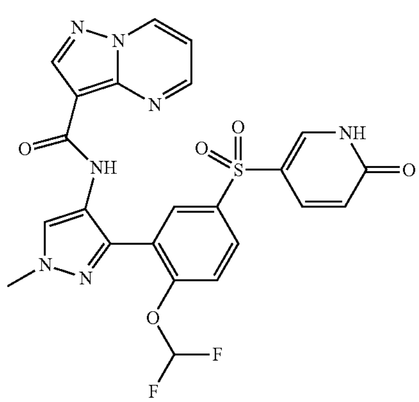 [SMILES: Cn1cc(NC(=O)c2cnn3cccnc23)c(-c2cc(S(=O)(=O)c3ccc(=O)[nH]c3)ccc2OC(F)F)n1] | N-[3-[2-(difluoromethoxy)-5-[(6-oxo-1H-pyridin-3-yl)sulfonyl]phenyl]-1-methyl-pyrazol-4-yl]pyrazolo[1,5-a]pyrimidine-3-carboxamide |

TABLE 1-continued

Exemplary JAK Inhibitors of the Invention

| | Structure | Name |
|---|---|---|
| 44 | 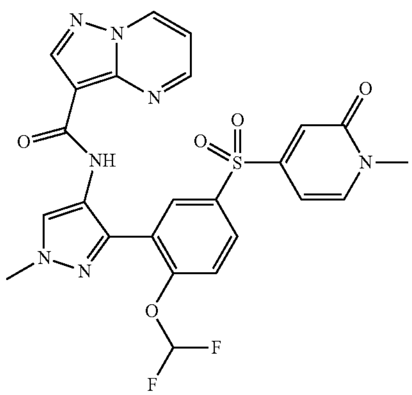 | N-[3-[2-(difluoromethoxy)-5-[(1-methyl-2-oxo-4-pyridyl)sulfonyl]phenyl]-1-methyl-pyrazol-4-yl]pyrazolo[1,5-a]pyrimidine-3-carboxamide |
| 45 | 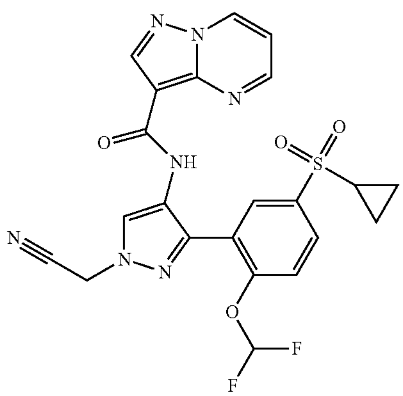 [SMILES: N#CCn1cc(NC(=O)c2cnn3cccnc23)c(-c2cc(S(=O)(=O)C3CC3)ccc2OC(F)F)n1] | N-[1-(cyanomethyl)-3-[5-cyclopropylsulfonyl-2-(difluoromethoxy)phenyl]pyrazol-4-yl]pyrazolo[1,5-a]pyrimidine-3-carboxamide |
| 46 | 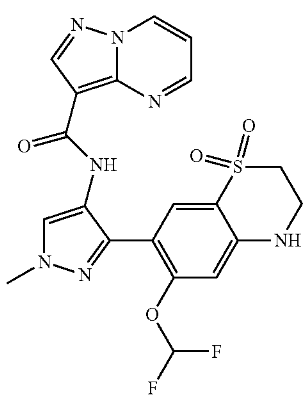 [SMILES: Cn1cc(NC(=O)c2cnn3cccnc23)c(-c2cc3c(cc2OC(F)F)NCCS3(=O)=O)n1] | N-[3-[6-(difluoromethoxy)-1,1-dioxo-3,4-dihydro-2H-1lambda6,4-benzothiazin-7-yl]-1-methyl-pyrazol-4-yl]pyrazolo[1,5-a]pyrimidine-3-carboxamide |
| 47 | 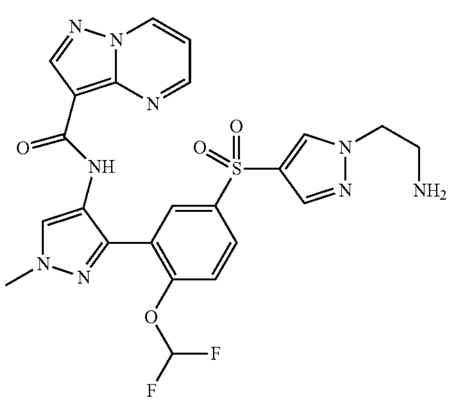 [SMILES: Cn1cc(NC(=O)c2cnn3cccnc23)c(-c2cc(S(=O)(=O)c3cnn(CCN)c3)ccc2OC(F)F)n1] | N-[3-[5-[1-(2-aminoethyl)pyrazol-4-yl]sulfonyl-2-(difluoromethoxy)phenyl]-1-methyl-pyrazol-4-yl]pyrazolo[1,5-a]pyrimidine-3-carboxamide |

TABLE 1-continued

Exemplary JAK Inhibitors of the Invention

| | Structure | Name |
|---|---|---|
| 48 | 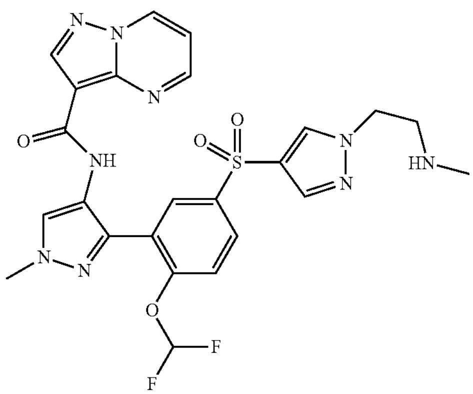 | N-[3-[2-(difluoromethoxy)-5-[1-[2-(methylamino)ethyl]pyrazol-4-yl]sulfonyl-phenyl]-1-methyl-pyrazol-4-yl]pyrazolo[1,5-a]pyrimidine-3-carboxamide |
| 49 | 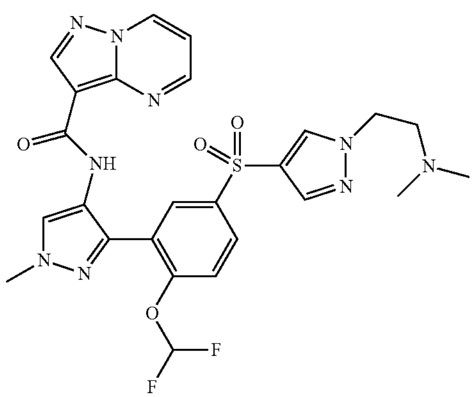 | N-[3-[2-(difluoromethoxy)-5-[1-[2-(dimethylamino)ethyl]pyrazol-4-yl]sulfonyl-phenyl]-1-methyl-pyrazol-4-yl]pyrazolo[1,5-a]pyrimidine-3-carboxamide |
| 50 | 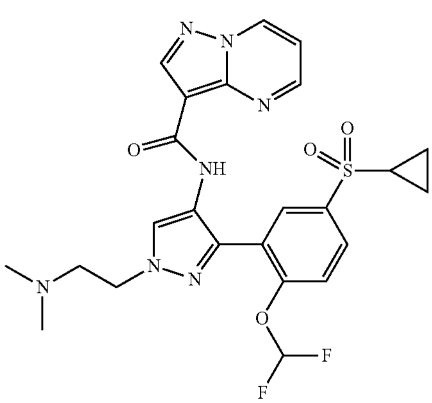 [SMILES: CN(C)CCn1cc(NC(=O)c2cnn3cccnc23)c(-c2cc(S(=O)(=O)C3CC3)ccc2OC(F)F)n1] | N-[3-[5-cyclopropylsulfonyl-2-(difluoromethoxy)phenyl]-1-[2-(dimethylamino)ethyl]pyrazol-4-yl]pyrazolo[1,5-a]pyrimidine-3-carboxamide |

TABLE 1-continued

Exemplary JAK Inhibitors of the Invention

| | Structure | Name |
|---|---|---|
| 51 | 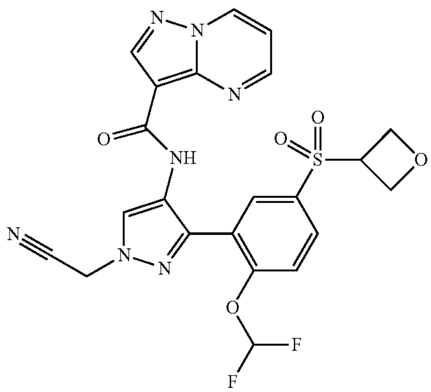 [SMILES: N#CCn1cc(NC(=O)c2cnn3cccnc23)c(-c2cc(S(=O)(=O)C3COC3)ccc2OC(F)F)n1] | N-[1-(cyanomethyl)-3-[2-(difluoromethoxy)-5-(oxetan-3-ylsulfonyl)phenyl]pyrazol-4-yl]pyrazolo[1,5-a]pyrimidine-3-carboxamide |
| 52 | 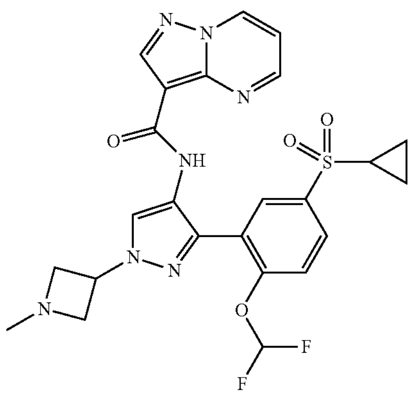 [SMILES: CN1CC(n2cc(NC(=O)c3cnn4cccnc34)c(-c3cc(S(=O)(=O)C4CC4)ccc3OC(F)F)n2)C1] | N-[3-[5-cyclopropylsulfonyl-2-(difluoromethoxy)phenyl]-1-(1-methylazetidin-3-yl)pyrazol-4-yl]pyrazolo[1,5-a]pyrimidine-3-carboxamide |
| 53 | 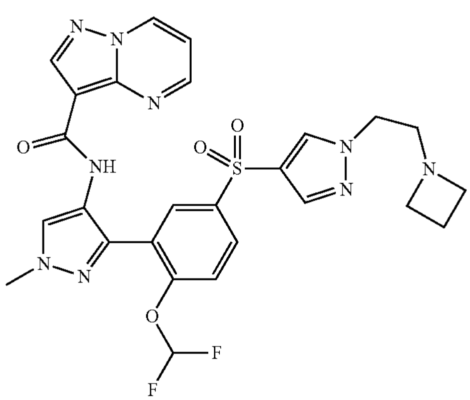 [SMILES: Cn1cc(NC(=O)c2cnn3cccnc23)c(-c2cc(S(=O)(=O)c3cnn(CCN4CCC4)c3)ccc2OC(F)F)n1] | N-[3-[5-[1-[2-(azetidin-1-yl)ethyl]pyrazol-4-yl]sulfonyl-2-(difluoromethoxy)phenyl]-1-methyl-pyrazol-4-yl]pyrazolo[1,5-a]pyrimidine-3-carboxamide |
| 54 | 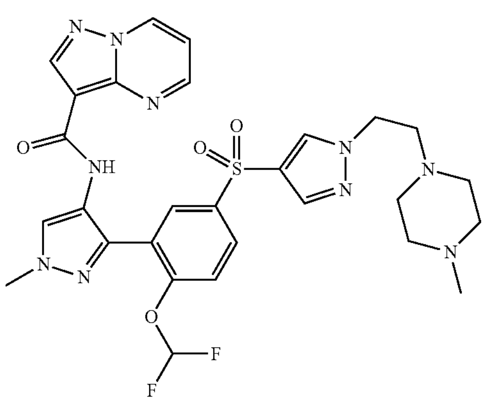 [SMILES: CN1CCN(CCn2cc(S(=O)(=O)c3ccc(OC(F)F)c(-c4nn(C)cc4NC(=O)c4cnn5cccnc45)c3)cn2)CC1] | N-[3-[2-(difluoromethoxy)-5-[1-[2-(4-methylpiperazin-1-yl)ethyl]pyrazol-4-yl]sulfonyl-phenyl]-1-methyl-pyrazol-4-yl]pyrazolo[1,5-a]pyrimidine-3-carboxamide |

TABLE 1-continued

Exemplary JAK Inhibitors of the Invention

| Structure | Name |
|---|---|
| 55 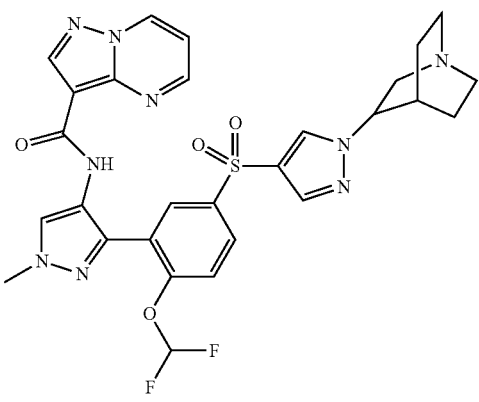 [SMILES: Cn1cc(NC(=O)c2cnn3cccnc23)c(-c2cc(S(=O)(=O)c3cnn(C4CN5CCC4CC5)c3)ccc2OC(F)F)n1] | N-[3-[2-(difluoromethoxy)-5-(1-quinuclidin-3-ylpyrazol-4-yl)sulfonyl-phenyl]-1-methyl-pyrazol-4-yl]pyrazolo[1,5-a]pyrimidine-3-carboxamide |
| 56 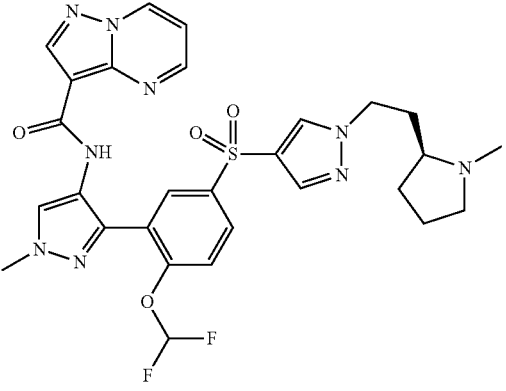 | N-[3-[2-(difluoromethoxy)-5-[1-[2-[(2R)-1-methylpyrrolidin-2-yl]ethyl]pyrazol-4-yl]sulfonyl-phenyl]-1-methyl-pyrazol-4-yl]pyrazolo[1,5-a]pyrimidine-3-carboxamide |
| 57 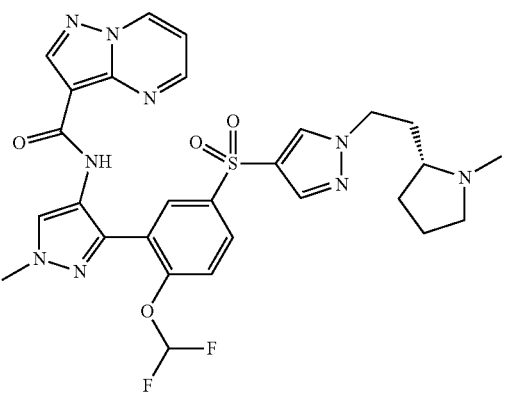 | N-[3-[2-(difluoromethoxy)-5-[1-[2-[(2S)-1-methylpyrrolidin-2-yl]ethyl]pyrazol-4-yl]sulfonyl-phenyl]-1-methyl-pyrazol-4-yl]pyrazolo[1,5-a]pyrimidine-3-carboxamide |

TABLE 1-continued

Exemplary JAK Inhibitors of the Invention

| | Structure | Name |
|---|---|---|
| 58 | 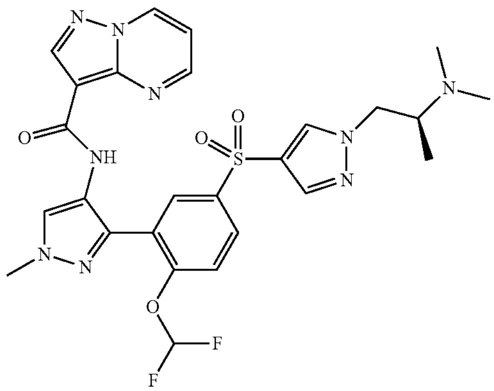 | N-[3-[2-(difluoromethoxy)-5-[1-[(2S)-2-(dimethylamino)propyl]pyrazol-4-yl]sulfonyl-phenyl]-1-methyl-pyrazol-4-yl]pyrazolo[1,5-a]pyrimidine-3-carboxamide |
| 59 | 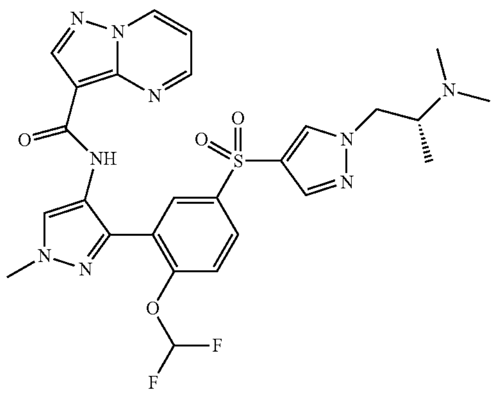 | N-[3-[2-(difluoromethoxy)-5-[1-[(2R)-2-(dimethylamino)propyl]pyrazol-4-yl]sulfonyl-phenyl]-1-methyl-pyrazol-4-yl]pyrazolo[1,5-a]pyrimidine-3-carboxamide |
| 60 | 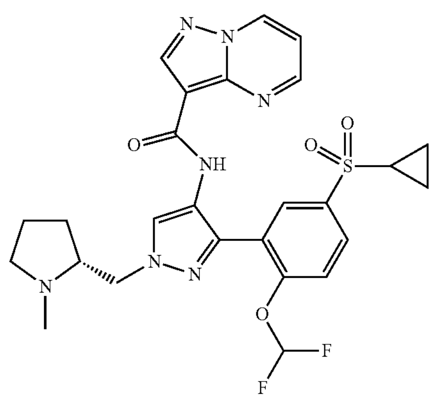 [SMILES: CN1CCC[C@@H]1Cn1cc(NC(=O)c2cnn3cccnc23)c(-c2cc(S(=O)(=O)C3CC3)ccc2OC(F)F)n1] | N-[3-[5-cyclopropylsulfonyl-2-(difluoromethoxy)phenyl]-1-[[rac-(2R)-1-methylpyrrolidin-2-yl]methyl]pyrazol-4-yl]pyrazolo[1,5-a]pyrimidine-3-carboxamide |
| 61 | 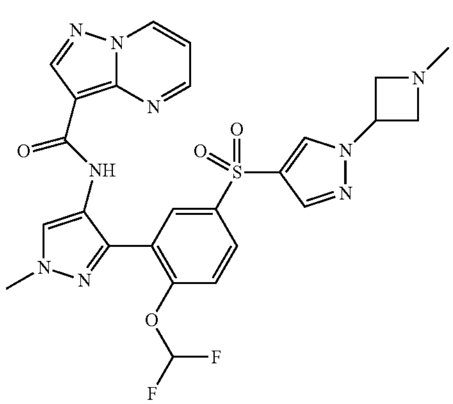 | N-[3-[2-(difluoromethoxy)-5-[1-(1-methylazetidin-3-yl)pyrazol-4-yl]sulfonyl-phenyl]-1-methyl-pyrazol-4-yl]pyrazolo[1,5-a]pyrimidine-3-carboxamide |

TABLE 1-continued

Exemplary JAK Inhibitors of the Invention

| | Structure | Name |
|---|---|---|
| 62 | 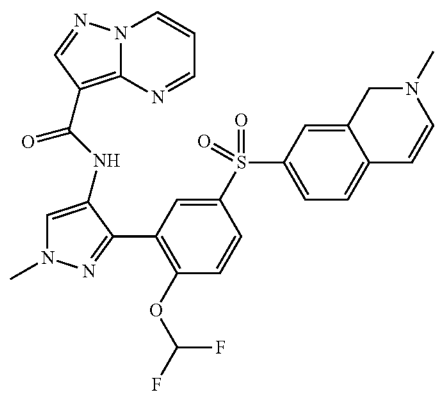 | N-[3-[2-(difluoromethoxy)-5-[(2-methyl-1H-isoquinolin-7-yl)sulfonyl]phenyl]-1-methyl-pyrazol-4-yl]pyrazolo[1,5-a]pyrimidine-3-carboxamide |
| 63 | 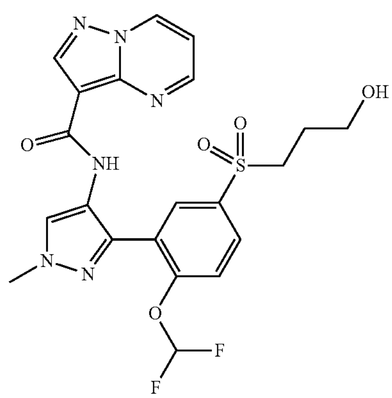 [SMILES: Cn1cc(NC(=O)c2cnn3cccnc23)c(-c2cc(S(=O)(=O)CCCO)ccc2OC(F)F)n1] | N-[3-[2-(difluoromethoxy)-5-(3-hydroxypropylsulfonyl)phenyl]-1-methyl-pyrazol-4-yl]pyrazolo[1,5-a]pyrimidine-3-carboxamide |
| 64 | 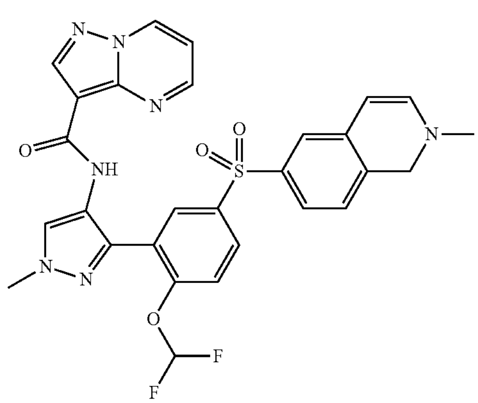 | N-[3-[2-(difluoromethoxy)-5-[(2-methyl-1H-isoquinolin-6-yl)sulfonyl]phenyl]-1-methyl-pyrazol-4-yl]pyrazolo[1,5-a]pyrimidine-3-carboxamide |

TABLE 1-continued

Exemplary JAK Inhibitors of the Invention

| | Structure | Name |
|---|---|---|
| 65 | 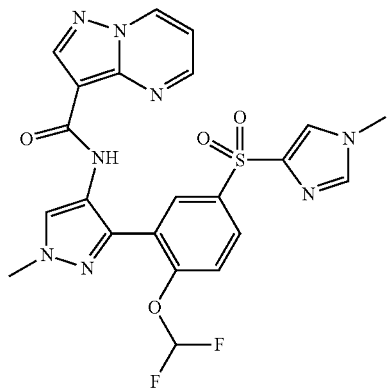 | N-[3-[2-(difluoromethoxy)-5-(1-methylimidazol-4-yl)sulfonyl-phenyl]-1-methyl-pyrazol-4-yl]pyrazolo[1,5-a]pyrimidine-3-carboxamide |
| 66 | 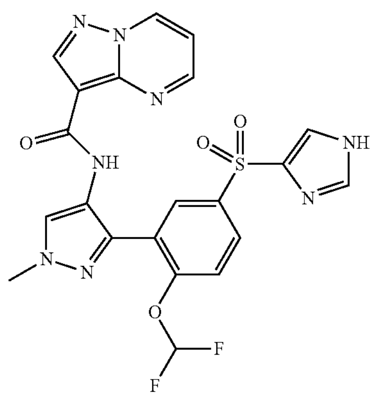 [SMILES: Cn1cc(NC(=O)c2cnn3cccnc23)c(-c2cc(S(=O)(=O)c3c[nH]cn3)ccc2OC(F)F)n1] | N-[3-[2-(difluoromethoxy)-5-(1H-imidazol-4-ylsulfonyl)phenyl]-1-methyl-pyrazol-4-yl]pyrazolo[1,5-a]pyrimidine-3-carboxamide |
| 67 | 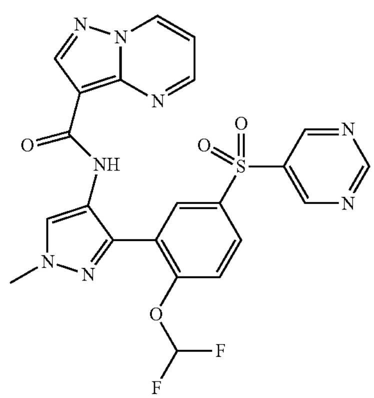 [SMILES: Cn1cc(NC(=O)c2cnn3cccnc23)c(-c2cc(S(=O)(=O)c3cncnc3)ccc2OC(F)F)n1] | N-[3-[2-(difluoromethoxy)-5-pyrimidin-5-ylsulfonyl-phenyl]-1-methyl-pyrazol-4-yl]pyrazolo[1,5-a]pyrimidine-3-carboxamide |
| 68 | 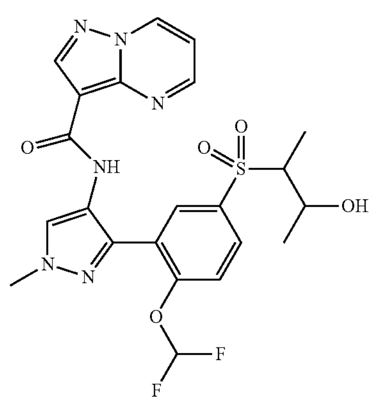 [SMILES: CC(O)C(C)S(=O)(=O)c1ccc(OC(F)F)c(-c2nn(C)cc2NC(=O)c2cnn3cccnc23)c1] | N-[3-[2-(difluoromethoxy)-5-(2-hydroxy-1-methyl-propyl)sulfonyl-phenyl]-1-methyl-pyrazol-4-yl]pyrazolo[1,5-a]pyrimidine-3-carboxamide |

TABLE 1-continued

Exemplary JAK Inhibitors of the Invention

| | Structure | Name |
|---|---|---|
| 69 | 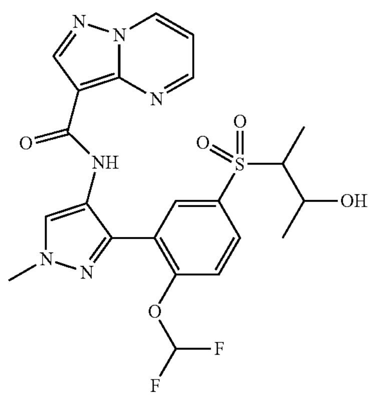 [SMILES: CC(O)C(C)S(=O)(=O)c1ccc(OC(F)F)c(-c2nn(C)cc2NC(=O)c2cnn3cccnc23)c1] | N-[3-[2-(difluoromethoxy)-5-(2-hydroxy-1-methyl-propyl)sulfonyl-phenyl]-1-methyl-pyrazol-4-yl]pyrazolo[1,5-a]pyrimidine-3-carboxamide |
| 70 | 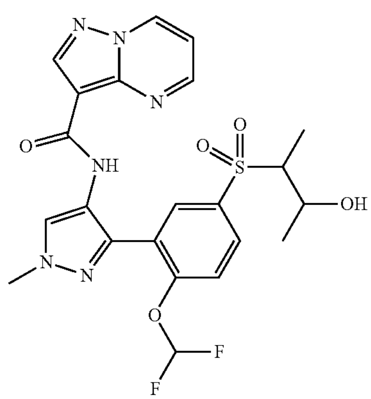 [SMILES: CC(O)C(C)S(=O)(=O)c1ccc(OC(F)F)c(-c2nn(C)cc2NC(=O)c2cnn3cccnc23)c1] | N-[3-[2-(difluoromethxoy)-5-(2-hydroxy-1-methyl-propyl)sulfonyl-phenyl]-1-methyl-pyrazol-4-yl]pyrazolo[1,5-a]pyrimidine-3-carboxamide |
| 71 | 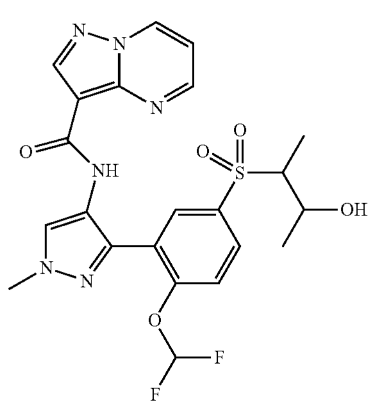 [SMILES: CC(O)C(C)S(=O)(=O)c1ccc(OC(F)F)c(-c2nn(C)cc2NC(=O)c2cnn3cccnc23)c1] | N-[3-[2-(difluoromethoxy)-5-(2-hydroxy-1-methyl-propyl)sulfonyl-phenyl]-1-methyl-pyrazol-4-yl]pyrazolo[1,5-a]pyrimidine-3-carboxamide |

TABLE 1-continued

Exemplary JAK Inhibitors of the Invention

| | Structure | Name |
|---|---|---|
| 72 | 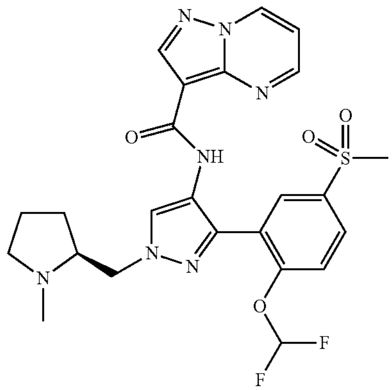 [SMILES: CN1CCC[C@H]1Cn1cc(NC(=O)c2cnn3cccnc23)c(-c2cc(S(C)(=O)=O)ccc2OC(F)F)n1] | N-[3-[2-(difluoromethoxy)-5-methylsulfonyl-phenyl]-1-[[(2S)-1-methylpyrrolidin-2-yl]methyl]pyrazol-4-yl]pyrazolo[1,5-a]pyrimidine-3-carboxamide |
| 73 | 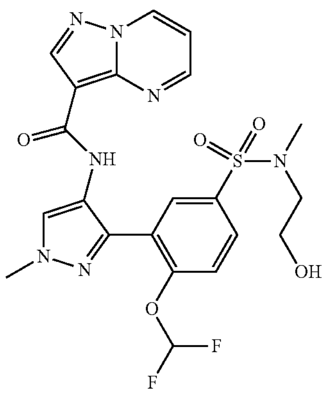 [SMILES: CN(CCO)S(=O)(=O)c1ccc(OC(F)F)c(-c2nn(C)cc2NC(=O)c2cnn3cccnc23)c1] | N-(3-(2-(difluoromethoxy)-5-(N-(2-hydroxyethyl)-N-methylsulfamoyl)phenyl)-1-methyl-1H-pyrazol-4-yl)pyrazolo[1,5-a]pyrimidine-3-carboxamide |

LCMS Conditions

Method A

Experiments were performed on a SHIMADZU LCMS-2020 with a C18-reverse-phase column (50×3 mm Shim-Pack XR-ODS, 2.2 μm particle size), elution with solvent A: water+0.05% trifluoroacetic acid; solvent B: acetonitrile+0.05% trifluoroacetic acid. Gradient:

| Gradient - Time | flow ml/min | % A | % B |
|---|---|---|---|
| 0.00 | 1.2 | 95 | 5 |
| 2.00 | 1.2 | 5 | 95 |
| 2.70 | 1.2 | 5 | 95 |
| 2.75 | 1.2 | 95 | 5 |

Detection - UV (220 and 254 nm) and ELSD

Method B

Experiments were performed on a SHIMADZU LCMS-2020 with a C18-reverse-phase column (50×3 mm Shim-Pack XR-ODS, 2.2 μm particle size), elution with solvent A: water+0.05% trifluoroacetic acid; solvent B: acetonitrile+0.05% trifluoroacetic acid. Gradient:

| Gradient - Time | flow ml/min | % A | % B |
|---|---|---|---|
| 0.00 | 1.2 | 80 | 20 |
| 3.60 | 1.2 | 40 | 60 |
| 4.00 | 1.2 | 0 | 100 |
| 4.70 | 1.2 | 0 | 100 |
| 4.75 | 1.2 | 95 | 5 |

Detection - UV (220 and 254 nm) and ELSD

Method C

Experiments were performed on a SHIMADZU LCMS-2020 with a C18-reverse-phase column (50×3 mm Shim-Pack XR-ODS, 2.2 μm particle size), elution with solvent A: water+0.05% trifluoroacetic acid; solvent B: acetonitrile+0.05% trifluoroacetic acid. Gradient:

| Gradient - Time | flow ml/min | % A | % B |
|---|---|---|---|
| 0.00 | 1.2 | 95 | 5 |
| 3.00 | 1.2 | 5 | 95 |
| 3.70 | 1.2 | 5 | 95 |
| 3.75 | 1.2 | 95 | 5 |

Detection - UV (220 and 254 nm) and ELSD

Method D

Experiments were performed on a SHIMADZU LCMS-2020 with a C18-reverse-phase column (50×3 mm Shim-Pack XR-ODS, 2.2 μm particle size), elution with solvent A: water+0.05% trifluoroacetic acid; solvent B: acetonitrile+0.05% trifluoroacetic acid. Gradient:

| Gradient - Time | flow ml/min | % A | %B |
| --- | --- | --- | --- |
| 0.00 | 1.2 | 95 | 5 |
| 3.50 | 1.2 | 30 | 70 |
| 3.70 | 1.2 | 0 | 100 |
| 4.50 | 1.2 | 0 | 100 |
| 4.75 | 1.2 | 95 | 5 |

Detection - UV (220 and 254 nm) and ELSD

Method E

Experiments were performed on a SHIMADZU LCMS-2020 with a C18-reverse-phase column (50×3 mm Shim-Pack XR-ODS, 2.2 μm particle size), elution with solvent A: water+0.05% trifluoroacetic acid; solvent B: acetonitrile+0.05% trifluoroacetic acid. Gradient:

| Gradient - Time | flow ml/min | % A | % B |
| --- | --- | --- | --- |
| 0.00 | 1.2 | 95 | 5 |
| 3.50 | 1.2 | 40 | 60 |
| 3.70 | 1.2 | 0 | 100 |
| 4.70 | 1.2 | 0 | 100 |
| 4.75 | 1.2 | 95 | 5 |

Detection - UV (220 and 254 nm) and ELSD

Method F

Experiments were performed on a SHIMADZU LCMS-2020 with a C18-reverse-phase column (50×3 mm Shim-Pack XR-ODS, 2.2 μm particle size), elution with solvent A: water+0.05% trifluoroacetic acid; solvent B: acetonitrile+0.05% trifluoroacetic acid. Gradient:

| Gradient - Time | flow ml/min | % A | % B |
| --- | --- | --- | --- |
| 0.00 | 1.2 | 70 | 30 |
| 3.50 | 1.2 | 30 | 70 |
| 3.70 | 1.2 | 0 | 100 |
| 4.50 | 1.2 | 0 | 100 |
| 4.75 | 1.2 | 95 | 5 |

Detection - UV (220 and 254 nm) and ELSD

Method G

Experiments were performed on a SHIMADZU 20 A HPLC with a C18-reverse-phase column (50×2.1 mm Ascentis Express C18, 2.7 μm particle size), elution with solvent A: water+0.05% trifluoroacetic acid; solvent B: acetonitrile+0.05% trifluoroacetic acid. Gradient:

| Gradient - Time | flow ml/min | % A | % B |
| --- | --- | --- | --- |
| 0.00 | 1.0 | 95 | 5 |
| 1.10 | 1.0 | 0 | 100 |
| 1.60 | 1.0 | 0 | 100 |
| 1.70 | 1.0 | 95 | 5 |

Detection - UV (220 and 254 nm) and ELSD

Method H

Experiments were performed on a SHIMADZU LCMS-2020 with a C18-reverse-phase column (50×3 mm Shim-Pack XR-ODS, 2.2 μm particle size), elution with solvent A: water+0.05% trifluoroacetic acid; solvent B: acetonitrile+0.05% trifluoroacetic acid. Gradient:

| Gradient - Time | flow ml/min | % A | % B |
| --- | --- | --- | --- |
| 0.00 | 1.2 | 95 | 5 |
| 1.10 | 1.2 | 0 | 100 |
| 1.70 | 1.2 | 0 | 100 |
| 1.75 | 1.2 | 95 | 5 |

Detection - UV (220 and 254 nm) and ELSD

Method I

Experiments were performed on a SHIMADZU 20A HPLC with Poroshell HPH-$C_{18}$, column (50×3 mm, 2.7 μm particle size), elution with solvent A: water/5 mM $NH_4HCO_3$; solvent B: acetonitrile. Gradient:

| Gradient - Time | flow ml/min | % A | % B |
| --- | --- | --- | --- |
| 0.00 | 1.2 | 90 | 10 |
| 1.10 | 1.2 | 5 | 95 |
| 1.60 | 1.2 | 5 | 95 |
| 1.70 | 1.2 | 90 | 10 |

Detection - UV (220 and 254 nm) and ELSD

Method J

Experiments were performed on a SHIMADZU LCMS-2020 with a C18-reverse-phase column (50×3 mm Kinetex XB-$C_{18}$, 2.6 μm particle size), elution with solvent A: water+0.05% trifluoroacetic acid; solvent B: acetonitrile+0.05% trifluoroacetic acid. Gradient:

| Gradient - Time | flow ml/min | % A | % B |
| --- | --- | --- | --- |
| 0.00 | 1.5 | 95 | 5 |
| 1.20 | 1.5 | 0 | 100 |
| 1.70 | 1.5 | 0 | 100 |
| 1.80 | 1.5 | 95 | 5 |

Detection - UV (220 and 254 nm) and ELSD

Method K

Experiments were performed on a SHIMADZU LCMS-2020 with a C18-reverse-phase column (50×3 mm Shim-Pack XR-ODS, 2.2 μm particle size), elution with solvent A: water+0.05% trifluoroacetic acid; solvent B: acetonitrile+0.05% trifluoroacetic acid. Gradient:

| Gradient - Time | flow ml/min | % A | % B |
| --- | --- | --- | --- |
| 0.00 | 1.0 | 95 | 5 |
| 2.20 | 1.0 | 0 | 100 |
| 3.20 | 1.0 | 0 | 100 |
| 3.30 | 1.0 | 95 | 5 |

Detection - UV (220 and 254 nm) and ELSD

Method L

Experiments were performed on a SHIMADZU LCMS-2020 with a C18-reverse-phase column (50×2.1 mm Kinetex XB-$C_{18}$ 100A, 2.6 μm particle size), elution with solvent A: water+0.05% trifluoroacetic acid; solvent B: acetonitrile+0.05% trifluoroacetic acid. Gradient:

| Gradient - Time | flow ml/min | % A | % B |
| --- | --- | --- | --- |
| 0.00 | 1.0 | 95 | 5 |
| 1.10 | 1.0 | 0 | 100 |
| 1.60 | 1.0 | 0 | 100 |
| 1.70 | 1.0 | 95 | 5 |

Detection - UV (220 and 254 nm) and ELSD

Method M

Experiments were performed on a SHIMADZU LCMS-2020 with a C18-reverse-phase column (30×2.1 mm Kinetex C18-100A, 1.7 μm particle size), elution with solvent A: water+0.05% trifluoroacetic acid; solvent B: acetonitrile+0.05% trifluoroacetic acid. Gradient:

| Gradient - Time | flow ml/min | % A | % B |
| --- | --- | --- | --- |
| 0.01 | 1.0 | 95 | 5 |
| 0.60 | 1.0 | 0 | 100 |
| 1.00 | 1.0 | 0 | 100 |
| 1.05 | 1.0 | 95 | 5 |

Detection - UV (220 and 254 nm) and ELSD

Method N

Experiments were performed on a SHIMADZU LCMS-2020 with a C18-reverse-phase column (50×3.0 mm Poroshell HPH-C18, 2.7 μm particle size), elution with solvent A: water+5 mM ammonium bicarbonate; solvent B: acetonitrile. Gradient:

| Gradient - Time | flow ml/min | % A | % B |
| --- | --- | --- | --- |
| 0.01 | 1.0 | 90 | 10 |
| 2.00 | 1.0 | 5 | 95 |
| 2.70 | 1.0 | 5 | 95 |
| 2.80 | 1.0 | 90 | 10 |

Detection - UV (220 and 254 nm) and ELSD

Method O

Experiments were performed on a SHIMADZU LCMS-2020 with a C18-reverse-phase column (50×3.0 mm Titank C18, 3.0 μm particle size), elution with solvent A: water+5 mM ammonium bicarbonate; solvent B: acetonitrile. Gradient:

| Gradient - Time | flow ml/min | % A | % B |
| --- | --- | --- | --- |
| 0.01 | 1.0 | 90 | 10 |
| 2.00 | 1.0 | 5 | 95 |
| 2.70 | 1.0 | 5 | 95 |
| 2.80 | 1.0 | 90 | 10 |

Detection - UV (220 and 254 nm) and ELSD

Method P

Experiments were performed on a SHIMADZU LCMS-2020 with a C18-reverse-phase column (30×2.1 mm Halo C18, 2.0 μm particle size), elution with solvent A: water+0.05% trifluoroacetic acid; solvent B: acetonitrile+0.05% trifluoroacetic acid. Gradient:

| Gradient - Time | flow ml/min | % A | % B |
| --- | --- | --- | --- |
| 0.00 | 1.0 | 95 | 5 |
| 1.30 | 1.0 | 0 | 100 |
| 1.80 | 1.0 | 0 | 100 |
| 1.90 | 1.0 | 95 | 5 |

Detection - UV (220 and 254 nm) and ELSD

Method Q

Experiments were performed on a SHIMADZU LCMS-2020 with a C18-reverse-phase column (50×3.0 mm YMC-Triart C18, 2.5 μm particle size), elution with solvent A: water+0.1% formic acid: solvent B: acetonitrile+0.1% formic acid. Gradient:

| Gradient - Time | flow ml/min | % A | % B |
| --- | --- | --- | --- |
| 0.01 | 1.0 | 95 | 5 |
| 3.00 | 1.0 | 5 | 95 |
| 3.70 | 1.0 | 5 | 95 |
| 3.75 | 1.0 | 95 | 5 |

Detection - UV (220 and 254 nm) and ELSD

Method R

Experiments were performed on a SHIMADZU LCMS-2020 with a C18-reverse-phase column (50×3 mm Shim-Pack XR-ODS, 2.2 μm particle size), elution with solvent A: water+0.05% trifluoroacetic acid; solvent B: acetonitrile+0.05% trifluoroacetic acid. Gradient:

| Gradient - Time | flow ml/min | % A | % B |
| --- | --- | --- | --- |
| 0.00 | 1.2 | 70 | 30 |
| 3.10 | 1.2 | 0 | 100 |
| 3.70 | 1.2 | 0 | 100 |
| 3.75 | 1.2 | 95 | 5 |

Detection - UV (220 and 254 nm) and ELSD

Method S

Experiments were performed on a SHIMADZU LCMS-2020 with a C18-reverse-phase column (50×3.0 mm Poroshell HPH-C18, 2.7 μm particle size), elution with solvent A: water+5 mM ammonium bicarbonate; solvent B: acetonitrile. Gradient:

| Gradient - Time | flow ml/min | % A | % B |
| --- | --- | --- | --- |
| 0.01 | 1.0 | 90 | 10 |
| 3.50 | 1.0 | 40 | 60 |
| 4.00 | 1.0 | 5 | 95 |
| 4.70 | 1.0 | 5 | 95 |
| 4.80 | 1.0 | 90 | 10 |

Detection - UV (220 and 254 nm) and ELSD

Method T

Experiments were performed on a SHIMADZU 20 A HPLC with a C18-reverse-phase column (50×2.1 mm Ascentis Express C18, 2.7 μm particle size), elution with solvent A: water+0.05% trifluoroacetic acid; solvent B: acetonitrile+0.05% trifluoroacetic acid. Gradient:

| Gradient - Time | flow ml/min | % A | % B |
| --- | --- | --- | --- |
| 0.00 | 1.0 | 95 | 5 |
| 2.00 | 1.0 | 0 | 100 |
| 2.70 | 1.0 | 0 | 100 |
| 2.80 | 1.0 | 95 | 5 |

Detection - UV (220 and 254 nm) and ELSD

Method U

Experiments were performed on a SHIMADZU LCMS-2020 with a C18-reverse-phase column (50×3 mm Shim-Pack XR-ODS, 2.2 μm particle size), elution with solvent A: water+0.05% trifluoroacetic acid; solvent B: acetonitrile+0.05% trifluoroacetic acid. Gradient:

| Gradient - Time | flow ml/min | % A | % B |
| --- | --- | --- | --- |
| 0.01 | 1.2 | 95 | 5 |
| 3.50 | 1.2 | 50 | 50 |
| 3.70 | 1.2 | 0 | 100 |

| Gradient - Time | flow ml/min | % A | % B |
|---|---|---|---|
| 4.70 | 1.2 | 0 | 100 |
| 4.75 | 1.2 | 95 | 5 |

Detection - UV (220 and 254 nm) and ELSD

Method V

Experiments were performed on a SHIMADZU LCMS-2020 with a C18-reverse-phase column (50×3.0 mm Poroshell HPH-C18, 2.7 μm particle size), elution with solvent A: water+5 mM ammonium bicarbonate; solvent B: acetonitrile. Gradient:

| Gradient - Time | flow ml/min | % A | % B |
|---|---|---|---|
| 0.01 | 1.0 | 90 | 10 |
| 3.50 | 1.0 | 60 | 40 |
| 4.00 | 1.0 | 5 | 95 |
| 4.70 | 1.0 | 5 | 95 |
| 4.80 | 1.0 | 90 | 10 |

Detection - UV (220 and 254 nm) and ELSD

Method W

Experiments were performed on a SHIMADZU LCMS-2020 with a C18-reverse-phase column (50×2.1 mm Waters Acquity BEH, 1.7 μm particle size), elution with solvent A: water+0.1% formic acid; solvent B: acetonitrile+0.1% formic acid. Gradient:

| Gradient - Time | flow ml/min | % A | % B |
|---|---|---|---|
| 0.00 | 0.8 | 95 | 5 |
| 1.60 | 0.8 | 0 | 100 |
| 1.80 | 0.8 | 0 | 100 |
| 2.00 | 0.8 | 95 | 5 |

Detection - UV (220 and 254 nm) and ELSD

Method X

Experiments were performed on an Agilent 1290 UHPLC coupled with Agilent MSD (6140) mass spectrometer using ESI as ionization source. The EC separation was using a Phenomenex XB-C18, 1.7 um, 50×2.1 mm column at a flow rate of 0.4 ml/minute. Mobile phase A was water with 0.1% formic acid and mobile phase B was acetonitrile with 0.1% formic acid. The gradient started at 2% B and ended at 98% B over 7 min and was held at 98% B for 1.5 min following equilibration for 1.5 min. LC column temperature was 40° C. UV absorbance were collected at 220 nm and 254 nm and mass spec full scan was applied to all experiments.

List of Common Abbreviations

ACN Acetonitrile
Brine Saturated aqueous sodium chloride solution
$CH_3OD$ Deuterated Methanol
$CDCl_3$ Deuterated Chloroform
DCM Dichloromethane
DIEA or DIPEA Diisopropylethylamine
DMA Dimethylacetamide
DMAP 4-Dimethylaminopyridine
DMF Dimethylformamide
DMSO Dimethylsulfoxide
DMSO-d6 Deuterated dimethylsulfoxide
DTAD Di-tert-butyl azodicarboxylate
EDC or EDCI 1-Ethyl-3-(3-dimethylaminopropyl)carbodiimide
ESI Electrospray ionization
EtOAc Ethyl acetate
EtOH Ethanol
FA Formic Acid
HOAc Acetic acid
g Gram
h hour
HATU (O-(7-azabenzotriazol-1-yl)-N,N,N',N'-tetramethyluronium hexafluorophosphate)
HCl Hydrochloric acid
HOBt Hydroxybenzo triazole
HPLC High performance liquid chromatography
IMS Industrial methylated spirits
L Liter
LCMS Liquid chromatography-mass spectrometry
LiHMDS or LHMDS Lithium hexamethydisylazide
MDAP Mass directed automated purification
MeCN Acetonitrile
MeOH Methanol
μm Micrometer
min minute
mg Milligram
mL Milliliter
mm Millimeter
M Molar
nm Nanometer
NMR Nuclear magnetic resonance spectroscopy
$Pd_2(dba)_3 \cdot CHCl_3$ Tris(dibenzylideneaeetone)dipalladium (0)-chloroform adduct
PE Petroleum ether
Prep-HPLC Preparative high performance liquid chromatography
PyAOP (7-Azabenzotriazol-1-yloxy)tripyrrolidinophosphonium hexafluorophosphate
SCX-2 Strong cation exchange
TBAF Tetra-n-butylammonium fluoride
THF Tetrahydrofuran
TFA Trifluoroacetic acid
Xantphos 4,5-Bis(diphenylphosphino)-9,9-dimethylxanthine
$ZnCl_2$ Zinc chloride

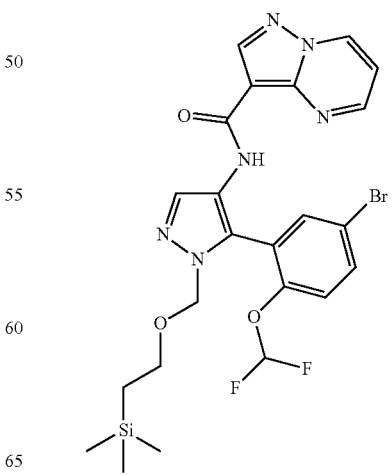

Intermediate 1

N-(5-(5-bromo-2-(difluoromethoxy)phenyl)-1-((2-(trimethylsilyl)ethoxy)methyl)-1H-pyrazol-4-yl)pyrazolo[1,5-a]pyrimidine-3-carboxamide Step 1: Synthesis of 4-bromo-1-(difluoromethoxy)-2-iodobenzene

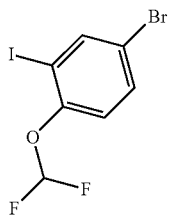

To a solution of 4-bromo-2-iodophenol (282 g, 943 mmol) in N,N-dimethyl formamide (2000 mL) and water (500 mL) was added sodium 2-chloro-2,2-difluoroacetate (216 g, 1.42 mol) and $Cs_2CO_3$ (617 g, 1.89 mol). The reaction vessel was equipped with a gas outlet for $CO_2$ release. The resulting mixture was stirred overnight at 120° C., allowed to cool to room temperature and poured into ice water (3000 mL). The resulting solution was extracted with ethyl acetate (3×1500 mL) and the organic layers were combined. The ethyl acetate extracts were washed with brine (1000 mL), dried over anhydrous sodium sulfate and concentrated under reduced pressure. The residue was purified by flash chromatography on silica gel eluting with ethyl acetate/petroleum ether (1/10) to afford 300 g (91%) of 4-bromo-1-(difluoromethoxy)-2-iodobenzene as a yellow oil. $^1$H NMR (300 MHz, $CDCl_3$) δ 7.96 (dd, J=5.7 Hz, 2.4 Hz, 1H), 7.45 (dd, J=8.7 Hz, 2.4 Hz, 1H), 7.03 (d, J=8.7 Hz, 1H), 6.39 (t, J=72.9 Hz, 1H).

Step 2: Synthesis of 5-[5-bromo-2-(difluoromethoxy)phenyl]-4-nitro-1-[[2-(trimethylsilyl)ethoxy]methyl]-1H-pyrazole

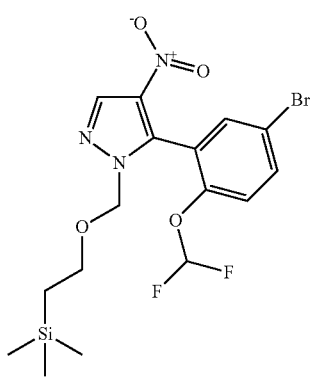

To a solution of 4-nitro-1-[[2-(trimethylsilyl)ethoxy]methyl]-1H-pyrazole (100 g, 411 mmol) in anhydrous THF (1000 mL) was added dropwise to a solution of LiHMDS (490 mL, 1.0 mol/L in THF) with stirring at −70° C. under nitrogen. The resulting solution was stirred for 1 h at −50° C. and then cooled to −70° C. $ZnCl_2$ (500 mL, 0.7 mol/L in THF) was added dropwise at −70° C. The resulting solution was allowed to warm to room temperature and stirred at room temperature for 1 h. To the mixture was added 4-bromo-1-(difluoromethoxy)-2-iodobenzene (150 g, 860 mmol), $Pd(PPh_3)_4$ (24.0 g, 20.8 mmol). The resulting solution was heated at reflux temperature overnight, allowed to cool to room temperature, and concentrated under reduced pressure. This reaction at this scale was repeated one more time, and the crude products from the two runs were combined for purification. The residue was purified by flash chromatography on silica gel eluting with ethyl acetate/petroleum ether (1/20). The appropriate fractions were combined and concentrated under reduced pressure. This resulted in 300 g (79%) of 5-[5-bromo-2-(difluoromethoxy)phenyl]-4-nitro-1-[[2-(trimethylsilyl)ethoxy]methyl]-1H-pyrazole as a light yellow solid in all. $^1$H NMR (300 MHz, $CDCl_3$) δ 8.27 (s, 1H), 7.68 (dd, J=8.7, 2.4 Hz, 1H), 7.62 (d, J=2.4 Hz, 1H), 7.19 (d, J=8.4 Hz, 1H), 6.39 (t, J=72.5 Hz, 1H), 5.44-5.19 (m, 2H), 3.72-3.54 (m, 2H), 0.94-0.89 (m, 2H), 0.02 (s, 9H).

Step 3: Synthesis of 5-(5-bromo-2-(difluoromethoxy)phenyl)-1-((2-(trimethylsilyl)ethoxy)methyl)-1H-pyrazol-4-amine

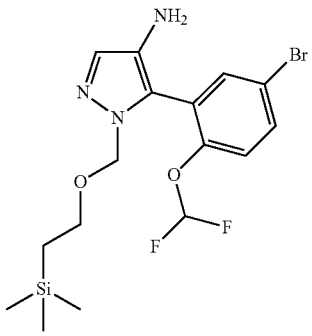 [SMILES: C[Si](C)(C)CCOCn1ncc(N)c1-c1cc(Br)ccc1OC(F)F]

To a solution of 5-(5-bromo-2-(difluoromethoxy)phenyl)-4-nitro-1-((2-(trimethylsilyl)ethoxy)methyl)-1H-pyrazole (50.1 g, 108 mmol) in ethanol (2000 mL) and water (200 mL) was added iron powder (60.1 g, 1.07 mol) and $NH_4Cl$ (28.0 g, 0.523 mol). The reaction mixture was stirred at reflux temperature for 3 h under nitrogen. The solids were filtered out, and washed with ethanol (100 mL). The filtrate was concentrated under reduced pressure. The residue was dissolved in 3000 mL of ethyl acetate. The ethyl acetate solution was washed with 1×500 mL of brine, dried over anhydrous sodium sulfate and concentrated under reduced pressure to give 50.1 g of crude 5-(5-bromo-2-(difluoromethoxy)phenyl)-1-((2-(trimethylsilyl)ethoxy)methyl)-1H-pyrazol-4-amine as a yellow oil. The crude product was used for next step without further purification. LC/MS (Method G, ESI): $[M+H]^+$=434.2, $R_T$=0.93 min.

Step 4: Synthesis of N-(5-(5-bromo-2-(difluoromethoxy)phenyl)-1-((2-(trimethylsilyl)ethoxy)methyl)-1H-pyrazol-4-yl)pyrazolo[1,5-a]pyrimidine-3-carboxamide

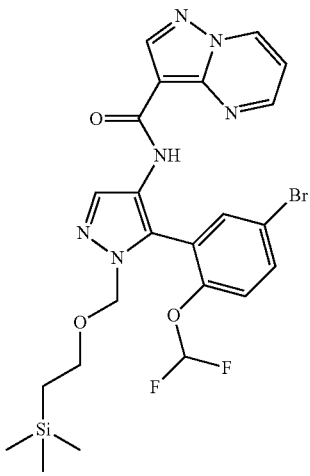 [SMILES: C[Si](C)(C)CCOCn1ncc(NC(=O)c2cnn3cccnc23)c1-c1cc(Br)ccc1OC(F)F]

To a solution of 5-(5-bromo-2-(difluoromethoxy)phenyl)-1-((2-(trimethylsilyl)ethoxy)methyl)-1H-pyrazol-4-amine (50.1 g, 115 mmol) in DMA (1500 mL) was added pyrazolo[1,5-a]pyrimidine-3-carboxylic acid (32.1 g, 196.0 mmol), PyAOP (102 g, 196 mmol), DMAP (1.41 g, 11.0 mmol) and DIPEA (44.1 g, 0.341 mol). The resulting solution was stirred for 3 h at 60° C. in an oil bath, and then allowed to cool to room temperature. The reaction mixture was then partitioned between water/ice (2000 mL) and ethyl acetate (2000 mL). The aqueous phase was extracted with ethyl acetate (2×). The organic layers were combined, washed with brine (1000 mL), dried over anhydrous sodium sulfate and concentrated under reduced pressure. The residue was purified by flash chromatography on silica gel eluting with ethyl acetate/petroleum ether (4:1). The appropriate fractions were combined and concentrated under reduced pressure. Water (150 mL) was added to the residue and the mixture was stirred in water for 1 h at room temperature. The solid was collected by filtration and air-dried to afford 60.1 g (91%) of N-(5-(5-bromo-2-(difluoromethoxy)phenyl)-1-((2-(trimethylsilyl)ethoxy)methyl)-1H-pyrazol-4-yl)pyrazolo[1,5-a]pyrimidine-3-carboxamide as a light yellow solid. LC/MS (Method G, ESI): [M+H]$^+$=579.1 & 581.1, R$_T$=1.10 min. $^1$H NMR (300 MHz, CDCl$_3$) δ 9.62 (s, 1H), 8.80 (dd, J=6.9, 1.7 Hz, 1H), 8.73 (s, 1H), 8.53 (dd, J=4.2, 1.7 Hz, 1H), 8.38 (s, 1H), 7.79 (d, J=2.4 Hz, 1H), 7.67 (dd, J=8.8, 2.5 Hz, 1H), 7.29 (d, J=1.4 Hz, 1H), 7.00 (dd, J=6.9, 4.2 Hz, 1H), 6.43 (t, J=72.6 Hz, 1H), 5.53-5.27 (m, 2H), 3.73-3.50 (m, 2H), 0.88 (ddd, J=9.5, 6.4, 4.4 Hz, 2H), 0.00 (s, 9H).

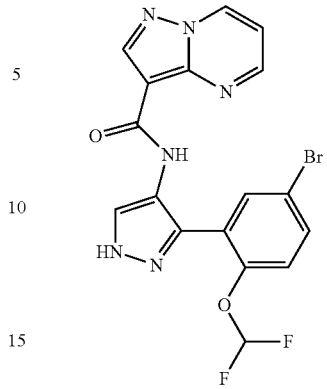

Intermediate 2

N-[3-[5-bromo-2-(difluoromethoxy)phenyl]-1H-pyrazol-4-yl]pyrazolo[1,5-a]pyrimidine-3-carboxamide N-[5-[5-bromo-2-(difluoromethoxy)phenyl]-1-[[2-(trimethylsilyl)ethoxy]methyl]-1H-pyrazol-4-yl]pyrazolo[1,5-a]pyrimidine-3-carboxamide (Intermediate 1, 5.00 g, 8.63 mmol) was treated with HCl/dioxane (150 mL, 4 M) overnight at room temperature. The resulting mixture was concentrated under reduced pressure. This resulted in 3.80 g of N-[3-[5-bromo-2-(difluoromethoxy)phenyl]-1H-pyrazol-4-yl]pyrazolo[1,5-a]pyrimidine-3-carboxamide as a yellow solid. The purity of the intermediate was sufficient for use in the next step without further purification. LC/MS (Method I, ESI): [M+H]$^+$=449.0, R$_T$=1.02 min. $^1$H NMR (400 MHz, CD$_3$OD) δ 9.11 (dd, J=6.8, 1.6 Hz, 1H), 8.67-8.64 (m, 2H), 8.32 (s, 1H), 7.80 (d, J=2.4 Hz, 1H), 7.72 (dd, J=8.8, 2.4 Hz, 1H), 7.37 (d, J=8.8 Hz, 1H), 7.23 (dd, J=7.0, 4.2 Hz, 1H), 6.81 (t, J=73.2 Hz, 1H).

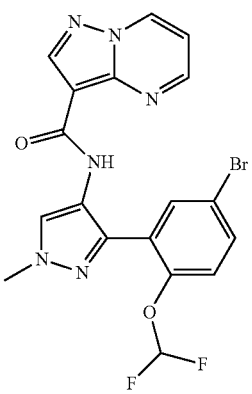

Intermediate 3

N-[3-[5-bromo-2-(difluoromethoxy)phenyl]-1-methyl-1H-pyrazol-4-yl]pyrazolo[1,5-a]pyrimidine-3-carboxamide To a solution of N-[5-[5-bromo-2-(difluoromethoxy)phenyl]-1-[[2-(trimethylsilyl)ethoxy]methyl]-1H-pyrazol-4-yl]pyrazolo[1,5-a]pyrimidine-3-carboxamide (Intermediate 1, 10.1 g, 17.3 mmol) in dichloromethane (200 mL) was added Me$_3$OBF$_4$ (2.81 g, 18.9 mmol) at room temperature. The resulting solution was stirred for 2 h at room temperature. Then EtOH was added 10 mL to the reaction mixture, and the reaction mixture was stirred for 1 h, To this solution was added 5.0 mL of HCl (conc.), and it was stirred for 1 h. The resulting mixture was concentrated under vacuum. The pH value of the solution was adjusted to 8 with sodium bicarbonate (20%). The resulting solution was extracted with 3×300 mL of ethyl acetate and the organic layers combined and dried over anhydrous sodium sulfate and concentrated under vacuum. The residue was applied onto a silica gel column eluting with ethyl acetate/petroleum ether (80%) to give 5.5 g (69%) of N-[3-[5-bromo-2-(difluoromethoxy)phenyl]-1-methyl 1H-pyrazol-4-yl]pyrazolo[1,5-a]pyrimidine-3-carboxamide as a light yellow solid. $^1$H NMR (400 MHz, CDCl$_3$): δ (ppm) 9.86 (s, 1H), 8.80 (dd, J=7.0, 1.6 Hz, 1H), 8.74 (s, 1H), 8.60 (dd, J=4.2, 1.6 Hz, 1H), 8.32 (s, 1H), 7.85 (d, J=2.4 Hz, 1H), 7.58 (dd, J=8.4, 2.4 Hz, 1H), 7.24 (d, J=8.8 Hz, 1H), 7.02 (dd, J=7.0, 4.2 Hz, 1H), 6.49 (t, J=74.0 Hz, 1H), 4.01 (s, 3H).

Intermediate 4

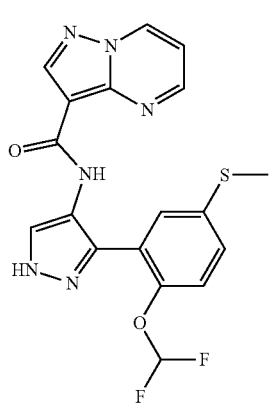

N-(3-(2-(difluoromethoxy)-5-(methylthio)phenyl)-1H-pyrazol-4-yl)pyrazolo[1,5-a]pyrimidine-3-carboxamide Step 1: Synthesis of 5-[2-(difluoromethoxy)-5-(methylsulfanyl)phenyl]-4-nitro-1-[[2-(trimethylsilyl)ethoxy]methyl]-1H-pyrazole

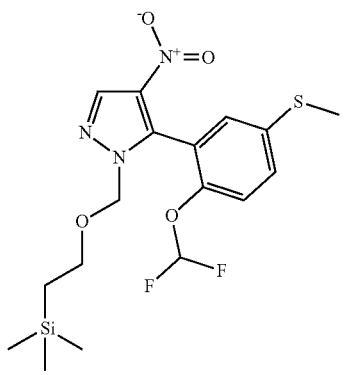

Into a 1000-mL round-bottom flask purged and maintained with an inert atmosphere of nitrogen, was placed toluene (500 mL), 5-[5-bromo-2-(difluoromethoxy)phenyl]-4-nitro-1-[[2-(trimethylsilyl)ethoxy]methyl]-1H-pyrazole (60 g, 129 mmol), NaSMe (26 g, 371 mmol), Pd$_2$(dba)$_3$.CHCl$_3$ (6.7 g, 6.47 mmol), XantPhos (7.5 g, 12.96 mmol). The resulting mixture was stirred overnight at 85° C. The resulting mixture was concentrated under vacuum. This reaction was repeated three times. The residue was applied onto a silica gel column eluting with ethyl acetate/petroleum ether (1:20). The appropriate fractions were combined and concentrated under vacuum. This resulted in 171 g of 5-[2-(difluoromethoxy)-5-(methylsulfanyl)phenyl]-4-nitro-1-[[2-(trimethylsilyl)ethoxy]methyl]-1H-pyrazole as a yellow solid in all. LC/MS (Method F, ESI): [M+H]+=432.1, RT=1.23 min; $^1$H NMR (300 MHz, CDCl3) δ: (ppm) 8.25 (s, 1H), 7.42 (dd, J=8.7, 2.4 Hz, 1H), 7.34 (d, J=2.1 Hz, 1H), 7.23 (d, J=8.7 Hz, 1H), 6.39 (t, J=72.9 Hz, 1H), 5.36-5.22 (m, 2H), 3.74-3.55 (m, 2H), 2.51 (s, 3H), 0.94-0.90 (m, 2H), 0.02 (s, 9H).

Step 2: Synthesis of N-[5-[2-(difluoromethoxy)-5-(methylsulfanyl)phenyl]-1-[[2-(trimethylsilyl)ethoxy]methyl]-1H-pyrazol-4-yl]pyrazolo[1,5-a]pyrimidine-3-carboxamide

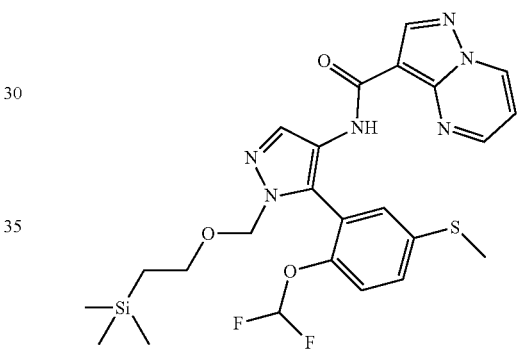

To a mixture of 5-[2-(difluoromethoxy)-5-(methylsulfanyl)phenyl]-4-nitro-1-[[2-(trimethylsilyl)ethoxy]methyl]-1H-pyrazole (171 g, 408 mmol), ethanol (2000 mL), water (200 mL) was added iron powder (228 g, 4.08 mol), NH$_4$Cl (120 g, 2.24 mol). The reaction mixture was stirred at reflux for 3 h under nitrogen, and cooled to room temperature. The solids were filtered out. The filtrate was concentrated under vacuum. The residue was dissolved in 3000 mL of ethyl acetate and washed with 1×500 mL of brine. The organic phase was dried over anhydrous sodium sulfate and concentrated under vacuum. This resulted in 148 g of 5-[2-(difluoromethoxy)-5-(methylsulfanyl)phenyl]-1-[[2-(trimethylsilyl)ethoxy]methyl]-1H-pyrazol-5-amine as yellow oil. LC/MS (Method F, ESI): [M+H]+=402.1, R$_T$=0.93 min. Into a 3000-mL 3-necked round-bottom flask, was placed DMA (1500 mL), 5-[2-(difluoromethoxy)-5-(methylsulfanyl)phenyl]-1-[[2-(trimethylsilyl)ethoxy]methyl]-1H-pyrazol-4-amine (148 g), pyrazolo[1,5-a]pyrimidine-3-carboxylic acid (102 g), HATU (325 g), 4-dimethylaminopyridine (4.5 g), DIPEA (142 g). The resulting solution was stirred for 3 h at 60° C., poured into ice water (2000 mL), extracted with 3×2000 mL of ethyl acetate and the organic layers combined. The resulting mixture was washed with 1×1000 mL of brine. The mixture was dried over anhydrous sodium sulfate and concentrated under vacuum. The residue was applied onto a silica gel column eluting with ethyl acetate/petroleum ether (4:1) to give 200 g of N-[5-[2-(difluoromethoxy)-5-(methylsulfanyl)phenyl]-1-[[2-(trimethylsilyl)ethoxy]methyl]-1H-pyrazol-4-yl]pyrazolo[1,5-a]pyrimidine-3-carboxamide as a light yellow solid. LC/MS (Method A, ESI): [M+H]+=547.2, RT=1.10 min; $^1$H NMR (300 MHz, CDCl3) δ: (ppm) 9.63 (s, 1H), 8.77 (dd, J=7.0, 1.7 Hz, 1H), 8.73 (s, 1H), 8.51 (dd, J=4.2, 1.8 Hz, 1H), 8.38 (s, 1H), 7.50 (d, J=2.4 Hz, 1H), 7.39 (dd, J=8.7, 2.4 Hz, 1H), 7.30 (d, J=8.7 Hz, 1H), 6.98 (dd, J=6.9, 4.2 Hz, 1H), 6.39 (t, J=73.2 Hz, 1H), 5.46-5.38 (m, 2H), 3.70-3.59 (m, 2H), 2.52 (s, 3H), 0.92-0.85 (m, 2H), 0.03 (s, 9H).

Step 3: Synthesis of N-(3-(2-(difluoromethoxy)-5-(methylthio)phenyl)-1H-pyrazol-4-yl)pyrazolo[1,5-a]pyrimidine-3-carboxamide

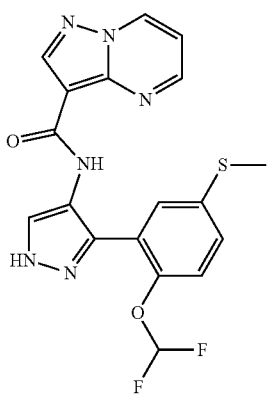 [SMILES: CSc1ccc(OC(F)F)c(-c2n[nH]cc2NC(=O)c2cnn3cccnc23)c1]

To a solution of N-[5-[2-(difluoromethoxy)-5-(methylsulfanyl)phenyl]-1-[[2-(trimethylsilyl)ethoxy]methyl]-1H-pyrazol-4-yl]pyrazolo[1,5-a]pyrimidine-3-carboxamide (60 g) in methanol (600 mL) was added concentrated HCl solution (300 mL). The resulting solution was stirred overnight at 35° C. The resulting mixture was concentrated under vacuum. The solids were collected by filtration. The solid was suspended in 200 mL of water. The pH value of the solution was adjusted to 8 with saturated sodium bicarbonate. The product was collected by filtration, dried to give 30 g (66%) N-(3-(2-(difluoromethoxy)-5-(methylthio)phenyl)-1H-pyrazol-4-yl)pyrazolo[1,5-a]pyrimidine-3-carboxamide as a light yellow solid. LC/MS (Method G, ESI): [M+H]+= 417.0, $R_T$=0.80 min; $^1$H NMR (300 MHz, DMSO-d$_6$) δ: (ppm) 13.02 (s, 1H), 9.71 (s, 1H), 9.33 (dd, J=6.9, 1.5 Hz, 1H), 8.68 (dd, J=4.1, 1.4 Hz, 1H), 8.66 (s, 1H), 8.24 (s, 1H), 7.47-7.36 (m, 3H), 7.27 (dd, J=6.9, 4.2 Hz, 1H), 7.17 (t, J=73.8 Hz, 1H), 2.51 (s, 3H).

Intermediate 5

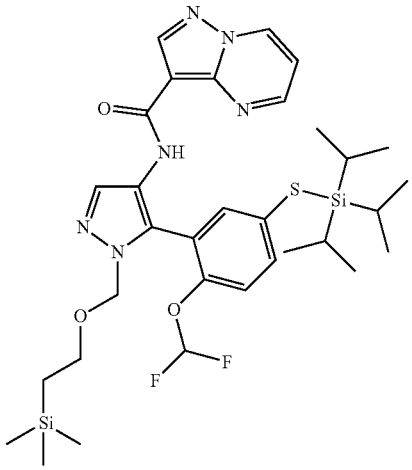

N-(5-(2-(difluoromethoxy)-5-((triisopropylsilyl)thio)phenyl)-1-((2-(trimethylsilyl)ethoxy)methyl)-1H-pyrazol-4-yl)pyrazolo[1,5-a]pyrimidine-3-carboxamide To a solution of N-(5-(5-bromo-2-(difluoromethoxy)phenyl)-1-((2-(trimethylsilyl)ethoxy)methyl)-1H-pyrazol-4-yl)pyrazolo[1,5-a]pyrimidine-3-carboxamide (Intermediate 1, 4.00 g, 6.90 mmol) in toluene (20 mL) was added sodium hydride (415 mg, 10.4 mmol, 60% in mineral oil), Pd$_2$(dba)$_3$.CHCl$_3$ (735 mg, 0.710 mmol) and XantPhos (800 mg, 1.38 mmol) and tris(propan-2-yl)silanethiol (1.97 g, 10.4 mmol) under nitrogen. The resulting solution was stirred for 20 min at 90° C. The resulting mixture was concentrated under vacuum. The residue was purified by flash chromatography on silica gel eluting with ethyl acetate/petroleum ether (80/20). The appropriate fractions were combined and concentrated under vacuum. This resulted in 3.30 g (69%) of N-(5-(2-(difluoromethoxy)-5-((triisopropylsilyl)thio)phenyl)-1-((2-(trimethylsilyl)ethoxy)methyl)-1H-pyrazol-4-yl)pyrazolo[1,5-a]pyrimidine-3-carboxamide as an off-white solid. LC/MS (Method B, ESI): [M+H]+=689.4, $R_T$=1.51 min.

Intermediate 6

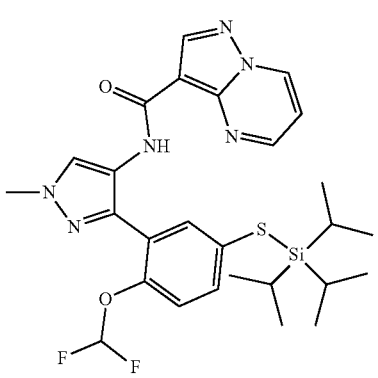

N-[3-[2-(difluoromethoxy)-5-[[tris(propan-2-yl)silyl]sulfanyl]phenyl]-1-methyl-1H-pyrazol-4-yl]pyrazolo[1,5-a]pyrimidine-3-carboxamide To a suspension of sodium hydride (260 mg, 10.8 mmol) in toluene (40 mL) was added dropwise tris(propan-2-yl)silanethiol (1.23 g, 6.47 mmol) at room temperature and under nitrogen. The mixture was stirred for 1 h at this temperature until the mixture turned clear, then N-[3-[5-bromo-2-(difluoromethoxy)phenyl]-1-methyl-1H-pyrazol-4-yl]pyrazolo[1,5-a]pyrimidine-3-carboxamide (Intermediate 3, 2.50 g, 5.40 mmol), $Pd_2(dba)_3 \cdot CHCl_3$ (184 mg, 0.178 mmol) and XantPhos (250 mg, 0.432 mmol) were added at room temperature under nitrogen atmosphere. The resulting solution was stirred for 30 min at 90° C. under $N_2$. The reaction was then quenched by the addition of 50 mL of aqueous $NH_4Cl$. The resulting solution was diluted with 100 mL of EA. The organic layer was separated and washed with 3×50 mL of water and 2×50 mL of brine. The mixture was dried over anhydrous sodium sulfate and concentrated under vacuum. The residue was applied onto a silica gel column eluting with ethyl acetate/petroleum ether (1/1) to give 2.35 g (76%) of N-[3-[2-(difluoromethoxy)-5-[[tris(propan-2-yl)silyl]sulfanyl]phenyl]-1-methyl-1H-pyrazol-4-yl]pyrazolo[1,5-a]pyrimidine-3-carboxamide as an off-white solid. TLC: PE/EA=1/1, Rf=0.4.

Intermediate 7

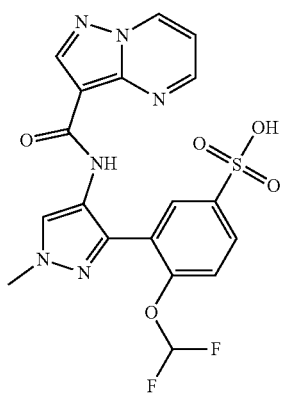

4-(difluoromethoxy)-3-(1-methyl-4-[pyrazolo[1,5-a]pyrimidine-3-amido]-1H-pyrazol-3-yl)benzene-1-sulfonic acid Into a 100-mL round-bottom flask, was placed N-[3-[2-(difluoromethoxy)-5-[[tris(propan-2-yl)silyl]sulfanyl]phenyl]-1-methyl-1H-pyrazol-4-yl]pyrazolo[1,5-a]pyrimidine-3-carboxamide (Intermediate 6, 360 mg, 0.63 mmol, 1.00 equiv.), dichloromethane (30 mL), m-CPBA (217 mg, 1.26 mmol, 2.0 equiv.). The resulting solution was stirred for 5 h at room temperature. The resulting mixture was concentrated under vacuum. The residue was applied onto a silica gel column with dichloromethane/methanol (6:4). This resulted in 210 mg (72%) of 4-(difluoromethoxy)-3-(1-methy 1-4-[pyrazolo[1,5-]pyrimidine-3-amido]-1H-pyrazol-3-yl)benzene-1-sulfonic acid as a yellow solid. LC/MS (Method I, ESI): [M+H]+=465.1, $R_T$=0.684 min.

Intermediate 8

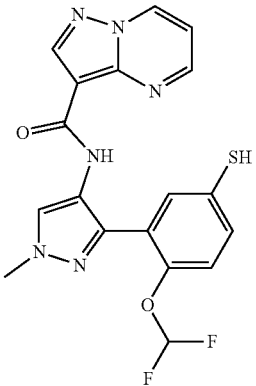

N-(3-(2-(difluoromethoxy)-5-mercaptophenyl)-1-methyl-1H-pyrazol-4-yl)pyrazolo[1,5-a]pyrimidine-3-carboxamide To a solution of N-[3-[5-bromo-2-(difluoromethoxy)phenyl]-1-methyl-pyrazol-4-yl]pyrazolo[1,5-a]pyrimidine-3-carboxamide (Intermediate 3, 3000 mg, 6.48 mmol), tris(propan-2-yl)silanethiol (1.48 g, 1.67 mL, 7.77 mmol), XantPhos Pd G2 (575 mg, 0.648 mmol) and XantPhos (375 mg, 0.648 mmol) in toluene (100 mL) and cooled to 0° C. was added NaH (518 mg, 13.0 mmol). The reaction mixture was stirred for 30 min at 0° C., at room temperature for 1 h, and then stirred at 90° C. for 1 h. The reaction mixture was diluted with dichloromethane, filtered through Celite, eluting with dichloromethane and the filtrate was concentrated in vacuo. The residue was adsorbed onto silica and purified by flash column chromatography with 10-80% 3:1 MeOH:iPrOAc in Heptane to afford N-(3-(2-(difluoromethoxy)-5-mercaptophenyl)-1-methyl-1H-pyrazol-4-yl)pyrazolo[1,5-a]pyrimidine-3-carboxamide as brown solid (2.32 g, 86%). The product was contaminated with some dimer and was used without further purification. LC/MS (Method W, ESI): [M+H]+=417.1, $R_T$=1.09 min.

Intermediate 9

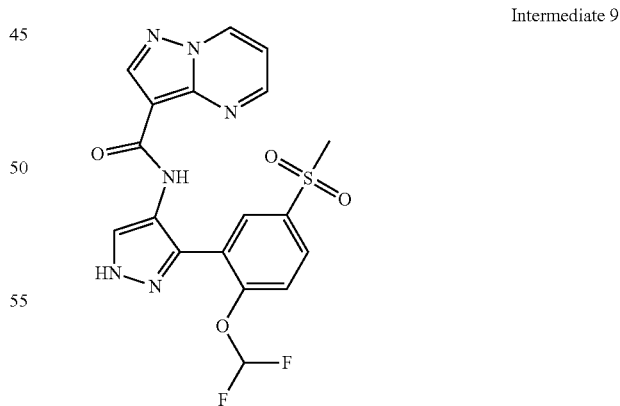

N-(3-(2-(difluoromethoxy)-5-(methylsulfonyl)phenyl)-1H-pyrazol-4-yl)pyrazolo[1,5-a]pyrimidine-3-carboxamide To a solution of N-(3-(2-(difluoromethoxy)-5-(methylthio)phenyl)-1H-pyrazol-4-yl)pyrazolo[1,5-a]pyrimidine-3- carboxamide (Intermediate 4, 500 mg, 1.20 mmol) in dichloromethane (5.0 mL) was added m-CPBA (623 mg, 3.61 mmol). The resulting solution was stirred for 5 min at room temperature and concentrated under vacuum. The residue was purified by flash chromatography on silica gel eluting with dichloromethane/methanol (25/1). The appropriate fractions were collected and concentrated under vacuum to give 523 mg (97%) of N-[3-[2-(difluoromethoxy)-5-methanesulfonylphenyl]-1H-pyrazol-4-yl]pyrazolo[1,5-a]pyrimidine-3-carboxamide as a yellow solid. LC/MS (Method G, ESI): [M+H]+=449.2, $R_T$=0.99 min; $^1$H NMR (300 MHz, DMSCO-$d_6$): δ (ppm) 13.18 (s, 1H), 9.68 (s, 1H), 9.33 (dd, J=6.9, 1.5 Hz, 1H), 8.70 (dd, J=4.2, 1.5 Hz, 1H), 8.66 (s, 1H), 8.31 (s, 1H), 8.12-8.09 (m, 2H), 7.68 (d, J=8.1 Hz, 1H), 7.47 (t, J=72.6 Hz, 1H), 7.30 (dd, 7=6.9, 4.2 Hz, 1H), 3.28 (s, 3H).

EXAMPLES

The following examples are numbered according to the examples in Table 1 above.

Example 28

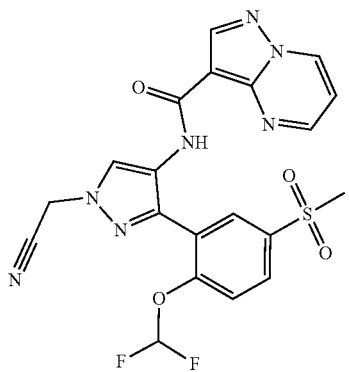 [SMILES: CS(=O)(=O)c1ccc(OC(F)F)c(-c2nn(CC#N)cc2NC(=O)c2cnn3cccnc23)c1]

N-(1-(cyanomethyl)-3-(2-(difluoromethoxy)-5-(methylsulfonyl)phenyl)-1H-pyrazol-4-yl)pyrazolo[1,5-a]pyrimidine-3-carboxamide Into a 10-mL vial, was placed N-[3-[2-(difluoromethoxy)-5-methanesulfonylphenyl]-1H-pyrazol-4-yl]pyrazolo[1,5-a]pyrimidine-3-carboxamide (Intermediate 9, 100 mg, 0.223 mmol), cesium carbonate (146 mg, 0.447 mmol, 2.00 equiv.), N,N-dimethylformamide (2 mL), and 2-bromoacetonitrile (39.8 mg, 0.332 mmol, 1.49 equiv.). The resulting solution was stirred for 3 h at room temperature. The reaction was then quenched by the addition of 3 mL of water. The resulting solution was extracted with 3×3 mL of ethyl acetate and the organic layers combined and concentrated under vacuum. The crude product (3 mL) was purified by Prep-HP LC with the following conditions (2 #-Analyse HPLC-SHIMADZU(HPLC-10)): Column, Kinetex EVO C18 Column, 30*150, 5 μm; mobile phase, water (10 mmol/L NH$_4$HCO$_3$) and ACN (19.0% ACN up to 27.0% in 7 min); Detector, UV 254/220 nm to afford 40.7 mg (37%) of N-[1-(cyanomethyl)-3-[2-(difluoromethoxy)-5-methanesulfonylphenyl]-1H-pyrazol-4-yl]pyrazolo[1,5-a]pyrimidine-3-carboxamide as a yellow solid. $^1$H NMR (300 MHz, DMSO-$d_6$): δ (ppm) 9.76 (s, 1H), 9.36 (dd, J=6.9, 1.5 Hz, 1H), 8.69-8.67 (m, 2H), 8.54 (s, 1H), 8.16 (dd, J=8.7, 2.4 Hz, 1H), 8.08 (d, J=1.6 Hz, 1H), 7.74-7.26 (m, 3H), 5.64 (s, 2H), 3.32 (s, 3H). LC/MS (Method A, ESI): [M+H]+=488.2, $R_T$=1.42 min.

Example 22

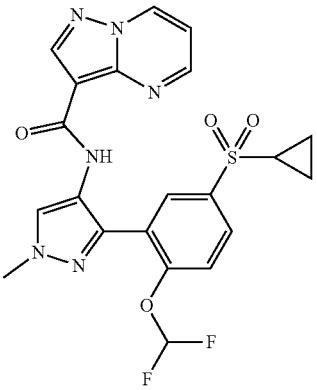 [SMILES: Cn1cc(NC(=O)c2cnn3cccnc23)c(-c2cc(S(=O)(=O)C3CC3)ccc2OC(F)F)n1]

N-(3-(5-(cyclopropylsulfonyl)-2-(difluoromethoxy) phenyl)-1-methyl-1H-pyrazol-4-yl)pyrazolo[1,5-a] pyrimidine-3-carboxamide Step 1: Synthesis of N-[5-[5-(cyclopropylsulfanyl)-2-(difluoromethoxy)phenyl]-1-[[2-(trimethylsilyl) ethoxy]methyl]-1H-pyrazol-4-yl]pyrazolo[1,5-a] pyrimidine-3-carboxamide

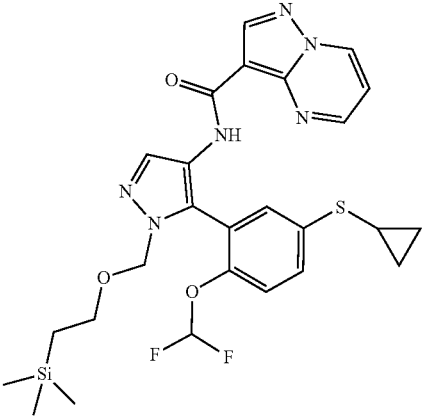 [SMILES: C[Si](C)(C)CCOCn1ncc(NC(=O)c2cnn3cccnc23)c1-c1cc(SC2CC2)ccc1OC(F)F]

Into a 250-mL round-bottom flask purged and maintained with an inert atmosphere of nitrogen, were placed N-[5-[5-bromo-2-(difluoromethoxy)phenyl]-1-[[2-(trimethylsilyl) ethoxy]methyl]-1H-pyrazol-4-yl]pyrazolo[1,5-a]pyrimidine-3-carboxamide (Intermediate 3, 4 g, 6.90 mmol), Pd$_2$(dba)$_3$ CHCl$_3$ (1.4 g, 1.35 mmol, 0.20 equiv.), XantPhos (1.6 g, 2.77 mmol, 0.401 equiv.), potassium carbonate (1.9 g, 13.7 mmol, 2.0 equiv.), toluene (100 mL), and cyclopropanethiol (2 g, 27 mmol, 3.9 equiv.). The resulting solution was stirred for 20 h at 100° C. The reaction mixture was cooled to room temperature and concentrated under vacuum. The residue was applied onto a silica gel column with ethyl acetate/hexane (1/1,4/1). The collected fractions were combined and concentrated under vacuum. This resulted in 3.5 g (89%) of N-[5-[5-(cyclopropylsulfanyl)-2-(difluoromethoxy)phenyl]-1-[[2-(trimethylsilyl)ethoxy]methyl]-1H-pyrazol-4-yl]pyrazolo[1,5-a]pyrimidine-3-carboxamide as yellow oil. LC/MS (Method J, ESI): [M+H]+=573.3, $R_T$=1.34 min.

Step 2: Synthesis of N-[3-[5-(cyclopropylsulfanyl)-2-(difluoromethoxy)phenyl]-1H-pyrazol-4-yl]pyrazolo[1,5-a]pyrimidine-3-carboxamide

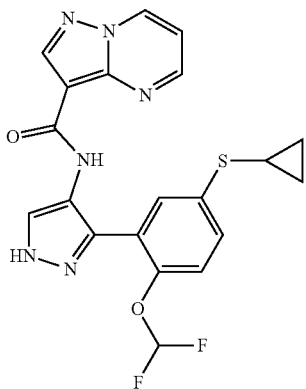 [SMILES: O=C(Nc1c[nH]nc1-c1cc(SC2CC2)ccc1OC(F)F)c1cnn2cccnc12]

Into a 100-mL round-bottom flask, was placed N-[5-[5-(cyclopropylsulfanyl)-2-(difluoromethoxy)phenyl]-1-[[2-(trimethylsilyl)ethoxy]methyl]-1H-pyrazol-4-yl]pyrazolo[1,5-a]pyrimidine-3-carboxamide (3.87 g, 6.76 mmol), dichloromethane (20 mL), and $CF_3COOH$ (10 mL). The resulting solution was stirred for 4 h at room temperature. The resulting mixture was concentrated under vacuum. The resulting solution was diluted with of ethyl acetate. The solids were collected by filtration. This resulted in 3.01 g (crude) of N-[3-[5-(cyclopropylsulfanyl)-2-(difluoromethoxy)phenyl]-1H-pyrazol-4-yl]pyrazolo[1,5-a]pyrimidine-3-carboxamide as a brown solid. LC/MS (Method H, ESI): [M+H]+=443.15, $R_T$=1.24 min.

Step 3: Synthesis of N-[3-[5-(cyclopropylsulfanyl)-2-(difluoromethoxy)phenyl]-1-methyl-1H-pyrazol-4-yl]pyrazolo[1,5-a]pyrimidine-3-carboxamide

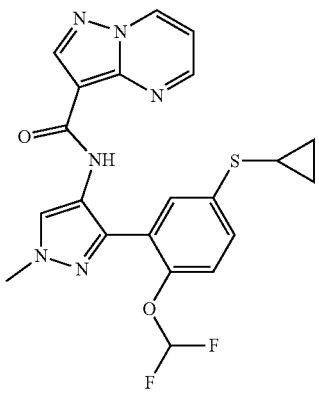 [SMILES: Cn1cc(NC(=O)c2cnn3cccnc23)c(-c2cc(SC3CC3)ccc2OC(F)F)n1]

Into a 25-mL round-bottom flask, was placed N-[3-[5-(cyclopropylsulfanyl)-2-(difluoromethoxy)phenyl]-1H-pyrazol-4-yl]pyrazolo[1,5-a]pyrimidine-3-carboxamide (250 mg, 0.565 mmol), N,N-dimethylformamide (4 mL), cesium carbonate (294 mg, 0.902 mmol, 2.00 equiv.), iodomethane (77 mg, 0.542 mmol, 1.20 equiv.). The resulting solution was stirred for 2 h at 30° C. The resulting mixture was concentrated under vacuum. The residue was applied onto a silica gel column with ethyl acetate/petroleum ether (2:1). This resulted in 150 mg (58%) of N-[3-[5-(cyclopropylsulfanyl)-2-(difluoromethoxy)phenyl]-1-methyl-1H-pyrazol-4-yl]pyrazolo[1,5-a]pyrimidine-3-carboxamide as a yellow solid. LC/MS (Method H, ESI): [M+H]+=457.2, $R_T$=1.24 min.

Step 4: Synthesis of N-[3-[5-(cyclopropanesulfonyl)-2-(difluoromethoxy)phenyl]-1-methyl-1H-pyrazol-4-yl]pyrazolo[1,5-a]pyrimidine-3-carboxamide

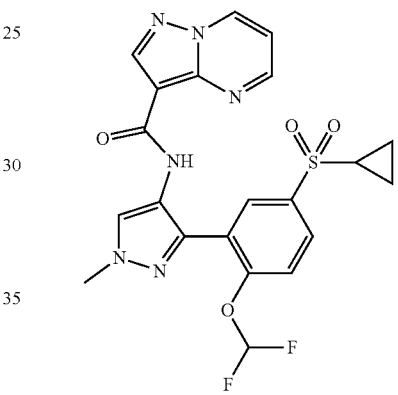

Into a 50-mL round-bottom flask, was placed N-[3-[5-(cyclopropylsulfanyl)-2-(difluoromethoxy)phenyl]-1-methyl-1H-pyralolo[1,5-a]pyrimidine-3-carboxamide (280 mg, 0.613 mmol), dichloromethane (20 mL), m-CPBA (212 mg, 1.23 mmol, 2.00 equiv.). The resulting solution was stirred for 5 h at room temperature. The resulting mixture was concentrated under vacuum. The residue was applied onto a silica gel column with dichloromethane/methanol (95:5). The crude product was purified by Prep-HPLC with the following conditions (2 #-AnalyseHPLC-SHIMADZU(HPLC-10)): Column, Kinetex EVO C18 Column, 30*150, 5 µm; mobile phase, Water (10 mmol/L $NH_4HCO_3$) and ACN (25.0% ACN up to 33.0% in 8 min); Detector, UV 254/220 nm. This resulted in 42.9 mg (14%) of N-[3-[5-(cyclopropanesulfonyl)-2-(difluoromethoxy)phenyl]-1-methyl-1H-pyrazol-4-yl]pyrazolo[1,5-a]pyrimidine-3-carboxamide as a white solid. $^1$H NMR (400 MHz, DMSO-O: δ (ppm) 9.68 (s, 1H), 9.34 (dd, J=6.8, 1.4 Hz, 1H), 8.70-8.67 (m, 2H), 8.33 (s, 1H), 8.07 (dd, J=8.8, 2.4 Hz, 1H), 8.02 (d, J=2.4 Hz, 1H), 7.69-7.28 (m, 3H), 3.96 (s, 3H), 3.01-2.95 (m, 1H), 1.16-1.12 (m, 2H), 1.08-1.06 (m, 2H). LC/MS (Method A, ESI): [M+H]+=489.2, $R_T$=1.47 min.

Example 52

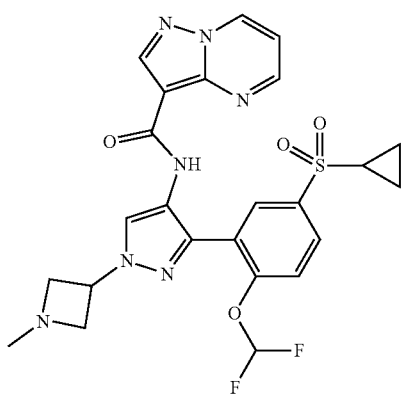 [SMILES: CN1CC(n2cc(NC(=O)c3cnn4cccnc34)c(-c3cc(S(=O)(=O)C4CC4)ccc3OC(F)F)n2)C1]

N-(3-(5-(cyclopropylsulfonyl)-2-(difluoromethoxy)phenyl)-1-(1-methylazetidin-3-yl)-1H-pyrazol-4-yl)pyrazolo[1,5-a]pyrimidine-3-carboxamide

Step 1: tert-butyl 3-(3-(5-(cyclopropylsulfonyl)-2-(difluoromethoxy)phenyl)-4-(pyrazolo[1,5-a]pyrimidine-3-carboxamido)-1H-pyrazol-1-yl)azetidine-1-carboxylate

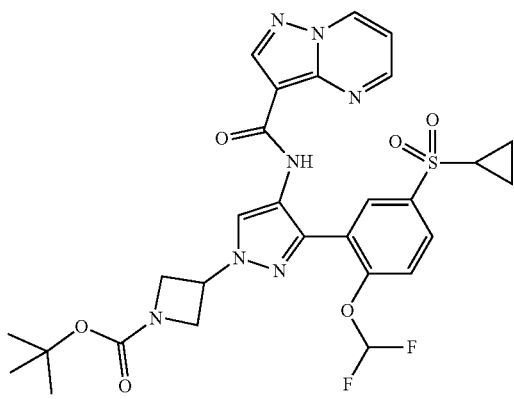 [SMILES: CC(C)(C)OC(=O)N1CC(n2cc(NC(=O)c3cnn4cccnc34)c(-c3cc(S(=O)(=O)C4CC4)ccc3OC(F)F)n2)C1]

To a vial was added N-[3-[5-cyclopropylsulfonyl-2-(difluoromethoxy)phenyl]-1H-pyrazol-4-yl]pyrazolo[1,5-a]pyrimidine-3-carboxamide (51 mg, 0.11 mmol) and cesium carbonate (105 mg, 0.32 mmol) followed by N,N-dimethylformamide (1.1 mL) and tert-butyl-3-iodoazetidine-1-carboxylate (107 mg, 0.065 mL, 0.38 mmol) and the reaction mixture was heated to 60° C. for 16 h. The reaction was quenched by the addition of saturated aqueous ammonium chloride and extracted with EtOAc (3×). The combined organic layers were washed with brine, dried over sodium sulfate, filtered and concentrated in vacuo. The residue was adsorbed onto silica and purified by flash column chromatography with 10-80% 3:1 MeOH:iPrOAc in heptane to afford the desired compound as yellow oil (35.6 mg, 53%).

Step 2: N-(1-(azetidin-3-yl)-3-(5-(cyclopropylsulfonyl)-2-(difluoromethoxy)phenyl)-1H-pyrazol-4-yl)pyrazolo[1,5-a]pyrimidine-3-carboxamide

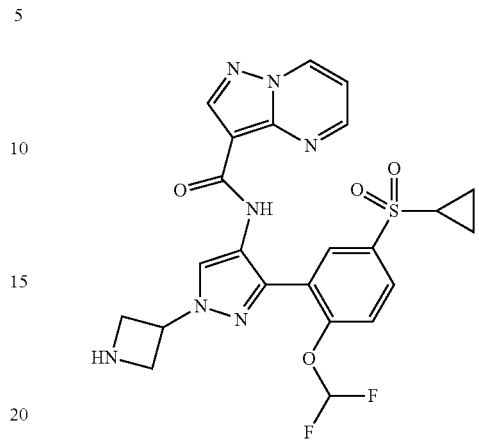

To a solution of tert-butyl 3-[3-[5-cyclopropylsulfonyl-2-(difluoromethoxy)phenyl]-4-(pyrazolo[1,5-a]pyrimidine-3-carbonylamino)pyrazol-1-yl]azetidine-1-carboxylate (35.6 mg, 0.057 mmol) in dichloromethane (1 mL) was added trifluoroacetic acid (0.25 mL) and the reaction was stirred at room temperature for 2 h. The reaction mixture was concentrated in vacuo then taken up in 2 mL of dichloromethane. MP-carbonate (180 mg, 0.57 mmol) was added and the reaction mixture was stirred for 2 h. The reaction mixture was filtered and the filtrate was concentrated in vacuo to afford the desired compound as a white solid. Assumed full conversion and carried as crude into next step. LC/MS (Method W, ESI): [M+H]+=530.2, $R_T$=0.83 min.

Step 3: N-(3-(5-(cyclopropylsulfonyl)-2-(difluoromethoxy)phenyl)-1-(1-methylazetidin-3-yl)-1H-pyrazol-4-yl)pyrazolo[1,5-a]pyrimidine-3-carboxamide

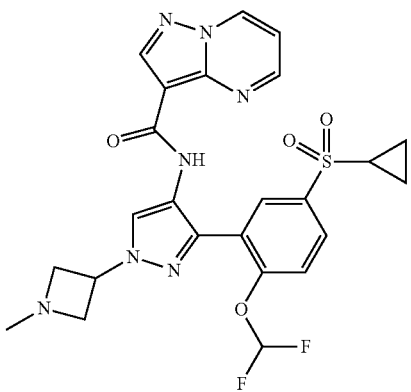 [SMILES: CN1CC(n2cc(NC(=O)c3cnn4cccnc34)c(-c3cc(S(=O)(=O)C4CC4)ccc3OC(F)F)n2)C1]

To a solution of N-[1-(azetidin-3-yl)-3-[5-cyclopropylsulfonyl-2-(difluoromethoxy)phenyl]pyrazol-4-yl]pyrazolo[1,5-a]pyrimidine-3-carboxamide (29.9 mg, 0.057 mmol) in 1,2-dichloroethane (1.88 mL) was added formaldehyde (1.28 mol/L in water) (6.87 mg, 0.0063 mL, 0.085 mmol) and sodium cyanoborohydride (3.62 mg, 0.0031 mL, 0.058 mmol) and the reaction mixture was stirred for 1 h at room temperature. Another portion of formaldehyde (1.28 mol/L in water) (6.87 mg, 0.0063 mL, 0.085 mmol and sodium cyanoborohydride (3.62 mg, 0.0031 mL, 0.058 mmol) were added, and the reaction mixture was stirred overnight. The mixture was diluted with dichloromethane and poured into a separatory funnel containing saturated aqueous sodium bicarbonate. The layers were separated and the aqueous layer was extracted with dichloromethane (2×). The combined organic layers were dried over sodium sulfate, filtered and concentrated in vacuo. The residue was purified by RP-HPLC to yield the title compound (2.1 mg, 7%) as a white solid. LC/MS (Method X, ESI): [M+H]+=544.2, $R_T$=3.06 min.

Example 9

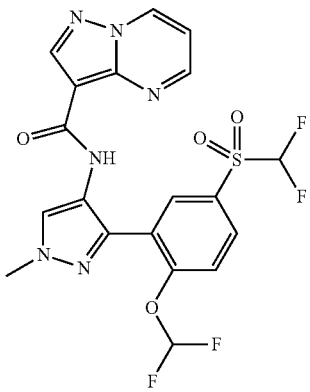 [SMILES: Cn1cc(NC(=O)c2cnn3cccnc23)c(-c2cc(S(=O)(=O)C(F)F)ccc2OC(F)F)n1]

N-(3-(2-(difluoromethoxy)-5-((difluoromethyl)sulfonyl)phenyl)-1-methyl-1H-pyrazol-4-yl)pyrazolo[1,5-a]pyrimidine-3-carboxamide Step 1: N-(3-(2-(difluoromethoxy)-5-((difluoromethyl)thio)phenyl)-1-methyl-1H-pyrazol-4-yl)pyrazolo[1,5-a]pyrimidine-3-carboxamide

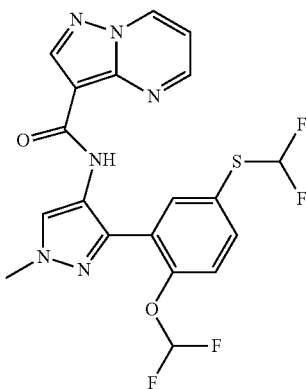 [SMILES: Cn1cc(NC(=O)c2cnn3cccnc23)c(-c2cc(SC(F)F)ccc2OC(F)F)n1]

Into a 50-mL round-bottom flask, was placed sodium 2-chloro-2,2-difluoroacetate (617 mg, 4.05 mmol, 1.00 equiv.), N,N-dimethylformamide (10 mL, 129 mmol, 1.00 equiv.), cesium carbonate (704 mg, 2.16 mmol, 2.00 equiv.), N-[3-[2-(difluoromethoxy)-5-[[tris(propan-2-yl)silyl]sulfanyl]phenyl]-1-methyl-1H-pyrazol-4-yl]pyrazolo[1,5-a]pyrimidine-3-carboxamide (Intermediate 6, 328 mg, 0.59 mmol, 2.00 equiv.). The resulting solution was stirred at 100° C. The resulting mixture was concentrated under vacuum. The residue was applied onto a silica gel column with ethyl acetate/petroleum ether (1:1). This resulted in 100 mg (5%) of N-[3-[2-(difluoromethoxy)-5-[(difluoromethyl)sulfanyl]phenyl]-1-methyl-1H-pyrazol-4-yl]pyrazolo[1,5-a]pyrimidine-3-carboxamide as a yellow solid. LC/MS (Method H, ESI): [M+H]+=467.2, $R_T$=1.20 min.

Step 2: N-(3-(2-(difluoromethoxy)-5-((difluoromethyl)sulfonyl)phenyl)-1-methyl-1H-pyrazol-4-yl)pyrazolo[1,5-a]pyrimidine-3-carboxamide

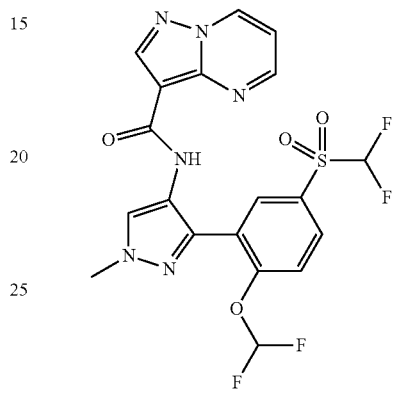

Into a 25-mL round-bottom flask, was placed N-[3-[2-(difluoromethoxy)-5-[(difluoromethyl)sulfanyl]phenyl]-1-methyl-1H-pyrazol-4-yl]pyrazolo[1,5-a]pyrimidine-3-carboxamide (100 mg, 0.22 mmol, 1.00 equiv.), dichloromethane (4 mL, 62.9 mmol, 1.00 equiv.), m-CPBA (74.4 mg, 0.43 mmol, 2.00 equiv.). The resulting solution was stirred for 4 h at room temperature. The resulting mixture was concentrated under vacuum. The residue was applied onto a silica gel column with dichloromethane/methanol (20:1). This resulted in 6.2 mg (6%) of N-[3-[5-(difluoromethane)sulfonyl-2-(difluoromethoxy)phenyl]-1-methyl-1H-pyrazol-4-yl]pyrazolo[1,5-a]pyrimidine-3-carboxamide as a yellow solid. $^1$H NMR (300 MHz, DMSO-<4): δ (ppm) 9.66 (s, 1H), 9.35 (dd, J=6.9, 1.5 Hz, 1H), 8.70-8.67 (m, 2H), 8.35 (s, 1H), 8.18 (dd, J=8.7, 2.4 Hz, 1H), 8.07 (d, J=2.4 Hz, 1H), 7.81-7.22 (m, 4H), 3.97 (s, 1H). LC/MS (Method A, ESI): [M+H]+=499.2, $R_T$=1.56 min.

Example 4

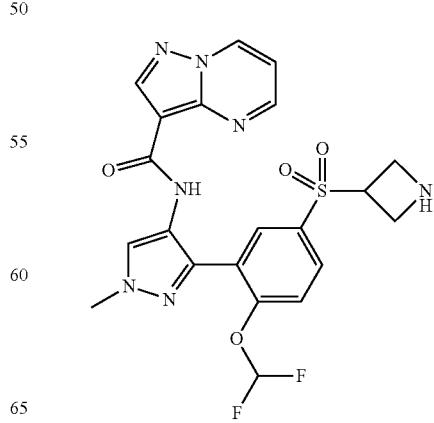

N-(3-(5-(azetidin-3-ylsulfonyl)-2-(difluoromethoxy)phenyl)-1-methyl-1H-pyrazol-4-yl)pyrazolo[1,5-a]pyrimidine-3-carboxamide Step 1: Synthesis of tert-butyl 3-((4-(difluoromethoxy)-3-(1-methyl-4-(pyrazolo[1,5-a]pyrimidine-3-carboxamido)-1H-pyrazol-3-yl)phenyl)sulfonyl)azetidine-1-carboxylate

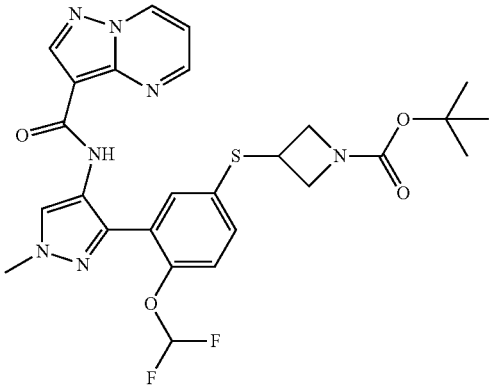 [SMILES: Cn1cc(NC(=O)c2cnn3cccnc23)c(-c2cc(SC3CN(C(=O)OC(C)(C)C)C3)ccc2OC(F)F)n1]

Into a 30-mL sealed tube purged and maintained with an inert atmosphere of nitrogen, were placed N-[3-[5-bromo-2-(difluoromethoxy)phenyl]-1-methyl-1H-pyrazol-4-yl]pyrazolo[1,5-a]pyrimidine-3-carboxamide (Intermediate 3, 1.00 g, 2.16 mmol), $Pd_2(dba)_3$ (104 mg, 0.114 mmol, 0.053 equiv.), tert-butyl 3-sulfanylazetidine-1-carboxylate (500 mg, 2.64 mmol, 1.22 equiv.), XantPhos (116 mg, 0.20 mmol, 0.093 equiv.), potassium carbonate (552 mg, 3.99 mmol, 1.85 equiv.), and toluene (15 mL). The resulting solution was stirred overnight at 100° C. and then concentrated under vacuum. The residue was applied onto a silica gel column with dichloromethane/methanol (94/6). The collected fractions were combined and concentrated under vacuum. This resulted in 1.5 g (122%) of tert-butyl 3-[[4-(difluoromethoxy)-3-(1-methyl-4-[pyrazolo[1,5-a]pyrimidine-3-amido]-1H-pyrazol-3-yl)phenyl]sulfanyl]azetidine-1-carboxylate as a red solid. LC/MS (Method A, ESI): [M+H]+=572.3, $R_T$=1.28 min.

Step 2: Synthesis of tert-butyl 3-[[4-(difluoromethoxy)-3-(1-methyl-4-[pyrazolo[1,5-a]pyrimidine-3-amido]-1H-pyrazol-3-yl)benzene]sulfonyl]azetidine-1-carboxylate

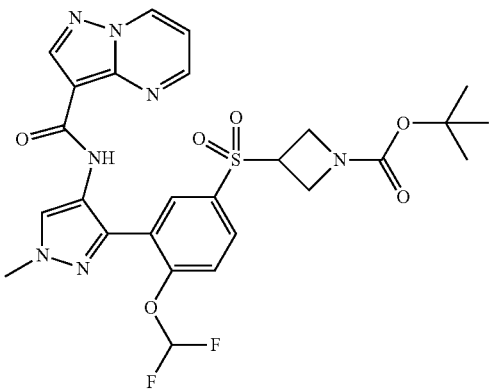 [SMILES: Cn1cc(NC(=O)c2cnn3cccnc23)c(-c2cc(S(=O)(=O)C3CN(C(=O)OC(C)(C)C)C3)ccc2OC(F)F)n1]

Into a 50-mL round-bottom flask, were placed tert-butyl 3-[[4-(difluoromethoxy)-3-(1-methyl-4-[pyrazolo[1,5-a]pyrimidine-3-amido]-1H-pyrazol-3-yl)phenyl]sulfanyl]azetidine-1-carboxylate (100 mg, 0.175 mmol), dichloromethane (10 mL), and 3-chlorobenzene-1-carboperoxoic acid (60 mg, 0.35 mmol, 2.0 equiv.). The resulting solution was stirred for 2 h at room temperature. The resulting mixture was concentrated under vacuum. The residue was applied onto a silica gel column with dichloromethane/methanol (92/8). The collected fractions were combined and concentrated under vacuum. This resulted in 100 mg (95%) of tert-butyl 3-[[4-(difluoromethoxy)-3-(1-methyl-4-[pyrazolo[1,5-a]pyrimidine-3-amido]-1H-pyrazol-3-yl)benzene]sulfonyl]azetidine-1-carboxylate as a brown solid. LC/MS (Method I, ESI): [M+H]+=604.3, $R_T$=1.05 min.

Step 3: Synthesis of N-(3-(5-(azetidin-3-ylsulfonyl)-2-(difluoromethoxy)phenyl)-1-methyl-1H-pyrazol-4-yl)pyrazolo[1,5-a]pyrimidine-3-carboxamide

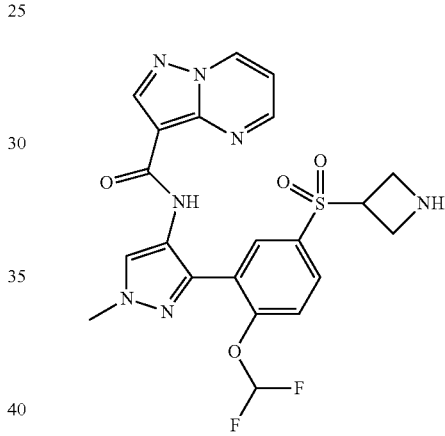

Into a 50-mL round-bottom flask, were placed tert-butyl 3-[[4-(difluoromethoxy)-3-(1-methyl-4-[pyrazolo[1,5-a]pyrimidine-3-amido]-1H-pyrazol-3-yl)benzene]sulfonyl]azetidine-1-carboxylate (100 mg, 0.166 mmol, 1.00 equiv.), trifluoroacetic acid (1 mL, 13.5 mmol, 82 equiv.), and dichloromethane (10 mL). The resulting solution was stirred for 6 h at room temperature. The resulting mixture was concentrated under vacuum. The crude product (5 mL) was purified by Flash-Prep-HPLC with the following conditions (IntelFlash-1): Column, silica gel; mobile phase, $H_2O$ $(NH_4HCO_3)/CH_3CN$=90/10 increasing to $H_2O(NH_4HCO_3)/CH_3CN$=50/50 within 10 min; Detector, UV 254 nm. This resulted in 11.6 mg (14%) of N-[3-[5-(azetidine-3-sulfonyl)-2-(difluoromethoxy)phenyl]-1-methyl-1H-pyrazol-4-yl]pyrazolo[1,5-a]pyrimidine-3-carboxamide as an off-white solid. $^1$H NMR (400 MHz, DMSO-$d_6$): δ (ppm) 9.67 (s, 1H), 9.35 (dd, J=6.8, 1.6 Hz, 1H), 8.70-8.66 (m, 2H), 8.34 (s, 1H), 8.07 (dd, J=4.4, 1.6 Hz, 1H), 8.00 (s, J=2.4 Hz, 1H), 7.70-7.29 (m, 3H), 4.67-4.59 (m, 1H), 3.97 (s, 3H), 3.80-3.77 (m, 2H), 3.60-3.56 (m, 2H). LC/MS (Method A, ESI): [M+H]+=504.2, $R_T$=1.12 min.

Example 3

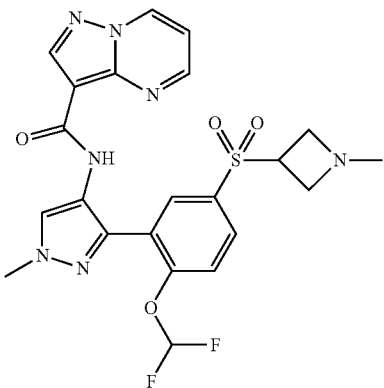

N-(3-(2-(difluoromethoxy)-5-((1-methylazetidin-3-yl)sulfonyl)phenyl)-1-methyl-1H-pyrazol-4-yl)pyrazolo[1,5-a]pyrimidine-3-carboxamide Into a 50-mL round-bottom flask, were placed N-[3-[5-(azetidine-3-sulfonyl)-2-(difluoromethoxy)phenyl]-1-methyl-1H-pyrazol-4-yl]pyrazolo[1,5-a]pyrimidine-3-carboxamide (50 mg, 0.099 mmol, 1.00 equiv.), methanol (1 mL), NaBH(AcO)$_3$ (200 mg, 0.94 mmol, 9.5 equiv.), and dichloromethane (10 mL). The resulting solution was stirred overnight at room temperature. The resulting mixture was concentrated under vacuum. The crude product (5 mL) was purified by Flash-Prep-HPLC with the following conditions (IntelFlash-1): Column, silica gel; mobile phase, H$_2$O (NH$_4$HCO$_3$)/CH$_3$CN=90/10 increasing to H$_2$O(NH$_4$HCO$_3$)/CH$_3$CN=50/50 within 10 min; Detector, UV 254 nm. This resulted in 18.1 mg (35%) of N-[3-[2-(difluoromethoxy)-5-(1-methylazetidine-3-sulfonyl)phenyl]-1-methyl-1H-pyrazol-4-yl]pyrazolo[1,5-a]pyrimidine-3-carboxamide as an off-white solid. $^1$H NMR (400 MHz, DMSO-d$_6$): δ (ppm) 9.67 (s, 1H), 9.35 (dd, J=6.8, 1.6 Hz, 1H), 8.70-8.66 (m, 2H), 8.34 (s, 1H), 8.07 (dd, J=4.4, 1.6 Hz, 1H), 8.00 (s, J=2.4 Hz, 1H), 7.70-7.29 (m, 3H), 4.67-4.59 (m, 1H), 3.97 (s, 3H), 3.80-3.77 (m, 2H), 3.60-3.56 (m, 2H). LC/MS (Method A, ESI): [M+H]+=518.3, R$_T$=1.14 min.

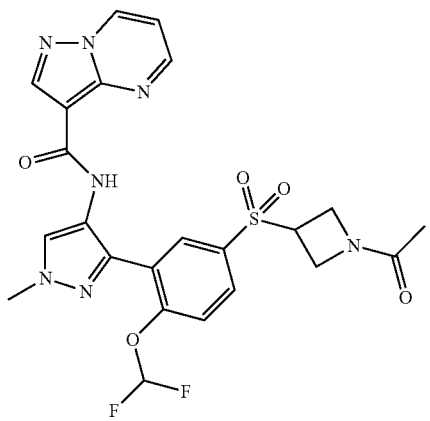 [SMILES: CC(=O)N1CC(S(=O)(=O)c2ccc(OC(F)F)c(-c3nn(C)cc3NC(=O)c3cnn4cccnc34)c2)C1]

N-(3-(5-((1-acetylazetidin-3-yl)sulfonyl)-2-(difluoromethoxy)phenyl)-1-methyl-1H-pyrazol-4-yl)pyrazolo[1,5-a]pyrimidine-3-carboxamide Into a 50-mL round-bottom flask, was placed N-[3-[5-(azetidine-3-sulfonyl)-2-(difluoromethoxy)phenyl]-1-methyl-1H-pyrazol-4-yl]pyrazolo[1,5-a]pyrimidine-3-carboxamide (80 mg, 0.159 mmol), dichloromethane (15 mL), pyridine (60 mg, 0.76 mmol, 4.8 equiv.). Acetyl chloride (15 mg, 0.19 mmol, 1.20 equiv.) was added into the solution at 0° C. The resulting solution was stirred for 30 min at room temperature. The reaction was then quenched by the addition of 10 mL of water. The resulting solution was extracted with 2×20 mL of dichloromethane and the organic layers combined, dried, and concentrated under vacuum. The residue was applied onto a silica gel column with dichloromethane/methanol (93:7). The crude product was purified by Prep-HPLC with the following conditions (2 #-AnalyseHPLC-SHIMADZU(HPLC-10)): Column, Kinetex EVO C18 Column, 30*150, 5 μm; mobile phase, Water (10 mmol/L NH$_4$HCO$_3$) and ACN (21.0% ACN up to 25.0% in 8 min); Detector, UV 254/220 nm. This resulted in 5.8 mg (7%) of N-[3-[5-(1-acetylazetidine-3-sulfonyl)-2-(difluoromethoxy)phenyl]-1-methyl-1H-pyrazol-4-yl]pyrazolo[1,5-a]pyrimidine-3-carboxamide as a white solid. $^1$H NMR (400 MHz, DMSO-d$_6$): δ (ppm) 9.68 (s, 1H), 9.36 (dd, J=6.8, 1.6 Hz, 1H), 8.70-8.68 (m, 2H), 8.34 (s, 1H), 8.16 (dd, J=6.8, 2.4 Hz, 1H), 8.07 (d, J=2.4 Hz, 1H), 7.72-7.30 (m, 3H), 4.62-4.55 (m, 1H), 4.38-4.34 (m, 2H), 4.07-3.98 (m, 2H), 3.97 (s, 3H), 2.08 (s, 3H). LC/MS (Method A, ESI): [M+H]+=546.2, R$_T$=1.32 min.

Example 26

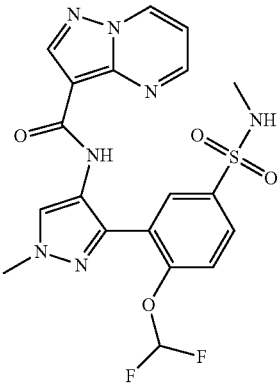 [SMILES: CNS(=O)(=O)c1ccc(OC(F)F)c(-c2nn(C)cc2NC(=O)c2cnn3cccnc23)c1]

N-[3-[2-(difluoromethoxy)-5-(methylsulfamoyl)phenyl]-1-methyl-1H-pyrazol-4-yl]pyrazolo[1,5-a]pyrimidine-3-carboxamide Into a 25-mL 2-necked round-bottom flask pinged and maintained with an inert atmosphere of nitrogen, were placed 4-(difluoromethoxy)-3-(1-methyl-4-[pyrazolo[1,5-a]pyrimidine-3-amido]-1H-pyrazol-3-yl (benzene-1-sulfonic acid (Intermediate 7, 150 mg, 0.323 mmol), dichloromethane (10 mL), N,N-dimethylformamide (0.05 mL, 0.646 mmol, 2.00 equiv.), oxalyl chloride (0.50 mL, 5.87 mmol, 18.2 equiv.), pyridine (100 mg, 1.26 mmol, 3.91 equiv.), and methylamine (0.50 mL, 14.4 mmol, 44.7 equiv.). The resulting solution was stirred for 1 h at room temperature. The reaction was then quenched by the addition of 10 mL of water. The resulting solution was extracted with 2×20 mL of dichloromethane and the organic layers combined and dried over anhydrous sodium sulfate and concentrated under vacuum. The residue was applied onto a silica gel column with dichloromethane/methanol (93:7). The crude product (20 mg) was purified by Prep-HPLC with the following conditions (2 #-AnalyseHPLC-SHIMADZU(HPLC-10)): Column, Kinetex EVO C18 Column, 30*150, 5 μm; mobile phase, Water (10 MMOL/L NH4HCO3) and ACN (20% ACN up to 35% in 7 min); Detector, UV 254/220 nm. This resulted in 8.6 mg (6%) of N-[3-[2-(difluoromethoxy)-5-(methylsulfamoyl)phenyl]-1-methyl-1H-pyrazol-4-yl]pyrazolo[1,5-a]pyrimidine-3-carboxamide as a white solid. $^1$H NMR (400 MHz, DMSO-d$_6$): δ (ppm) 9.70 (s, 1H), 9.35 (dd, J=7.2, 1.6 Hz, 1H), 8.70-8.68 (m, 2H), 8.34 (s, 1H), 7.96-7.93 (m, 2H), 7.66-7.26 (m, 4H), 3.96 (s, 3H), 2.44 (s, 3H). LC/MS (Method A, ESI): [M+H]+=478.2, R$_T$=1.39 min.

Example 5

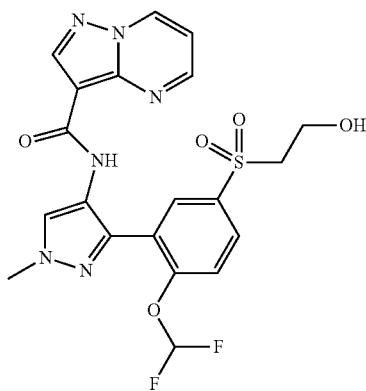 [SMILES: Cn1cc(NC(=O)c2cnn3cccnc23)c(-c2cc(S(=O)(=O)CCO)ccc2OC(F)F)n1]

N-(3-(2-(difluoromethoxy)-5-((2-hydroxyethyl) sulfonyl)phenyl)-1-methyl-1H-pyrazol-4-yl)pyrazolo [1,5-a]pyrimidine-3-carboxamide Step 1: Synthesis of N-(3-(2-(difluoromethoxy)-5-((2-hydroxyethyl)thio)phenyl)-1-methyl-1H-pyrazol-4-yl)pyrazolo[1,5-a]pyrimidine-3-carboxamide

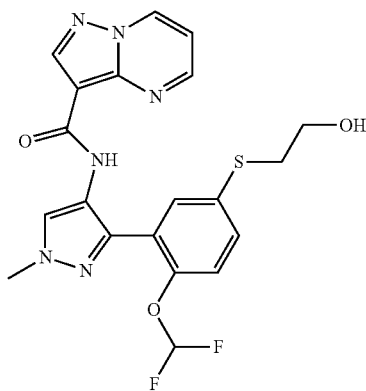 [SMILES: Cn1cc(NC(=O)c2cnn3cccnc23)c(-c2cc(SCCO)ccc2OC(F)F)n1]

To a solution of N-[3-[5-bromo-2-(difluoromethoxy)phenyl]-1-methyl-pyrazol-4-yl]pyrazolo[1,5-a]pyrimidine-3-carboxamide (Intermediate 3, 20.0 g, 43.2 mmol), DIEA (11.2 g, 86.5 mmol), Pd$_2$(dba)$_3$CH$_3$Cl (2.24 g, 2.16 mmol) and XantPhos (2.5 g, 4.32 mmol) in 1,4-dioxane (200 mL) and under nitrogen, was added 2-mercaptoethanol (3.19 mL, 45.3 mmol) at room temperature. The resulting solution was stirred for 4 h at 95° C. The resulting mixture was cooled to room temperature and filtered. The filtrate was concentrated under vacuum. The crude residue was purified by flash chromatography on silica gel eluting with MeOH/DCM (3%) to afford N-(3-(2-(difluoromethoxy)-5-((2-hydroxyethyl)thio)phenyl)-1-methyl-1H-pyrazol-4-yl)pyrazolo[1,5-a]pyrimidine-3-carboxamide (16.8 g, 36.5 mmol, 84.5% yield) as an off-white solid. LC/MS (Method A, ESI): [M+H]+=461.1, R$_T$=1.02 min.

Step 2: Synthesis of N-[3-[2-(difluoromethoxy)-5-(2-hydroxyethylsulfonyl)phenyl]-1-methyl-pyrazol-4-yl]pyrazolo[1,5-a]pyrimidine-3-carboxamide

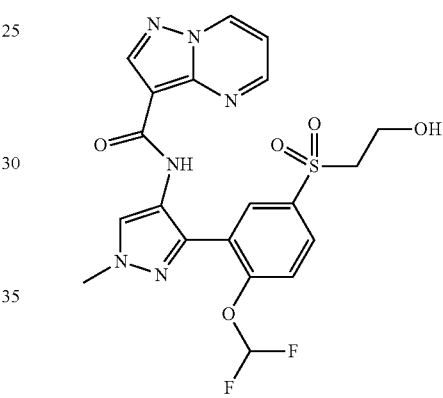

Potassium peroxomonosulfate (125 g, 204 mmol) was dissolved in water (450 mL) at 25° C. while stirring and then added into a suspension of N-(3-(2-(difluoromethoxy)-5-((2-hydroxy ethyl)thio)phenyl)-1-methyl-1H-pyrazol-4-yl) pyrazolo[1,5-a]pyrimidine-3-carboxamide (45 g, 97 mmol) in methanol (900 mL). The resulting suspension was stirred over 6 h at room temperature. Water (1 L) was added, and the resulting suspension was concentrated under vacuum to remove methanol. After filtration, the solids were collected and washed with water (100 mL). The solid was dried under 50° C. and slurried with water (500 mL). After filtration, the solids were collected and washed with water (50 mL). The solid was dried at 50° C. overnight to afford 44 g. The solid was slurried with EtOH (400 mL) at 80° C. over 3 h and then cooled down to room temperature in oil bath. After filtration, the solids were collected and washed by EtOH (20 mL). The solid was slurried with EtOH (300 mL) at 80° C. over 3 h and then cooled down to room temperature in oil bath and stirred overnight. After filtration, the solids were collected and washed by EtOH (50 mL). The solid was dried under 50° C. overnight to afford N-[3-[2-(difluoromethoxy)-5-(2-hydroxy ethylsulfonyl)phenyl]-1-methyl-pyrazol-4-yl]pyrazolo[1,5-a]pyrimidine-3-carboxamide (43.3 g, 87.9 mmol, 90.4% yield) as an off-white solid. $^1$H NMR (400 MHz, DMSO-d6) 9.68 (s, 1H), 9.34 (dd, J=7.0, 1.6 Hz, 1H), 8.68 (dd, J=4.2, 1.6 Hz, 1H), 8.66 (s, 1H), 8.33 (s, 1H), 8.11-8.01 (m, 2H), 7.67-7.29 (m, 3H), 4.89 (t, J=5.3 Hz, 1H), 3.96 (s, 3H), 3.71 (m, 2H), 3.53 (t, J=6.2 Hz, 2H). LC/MS (Method A, ESI): [M+H]+=493.2, R$_T$=1.27 min.

Example 34

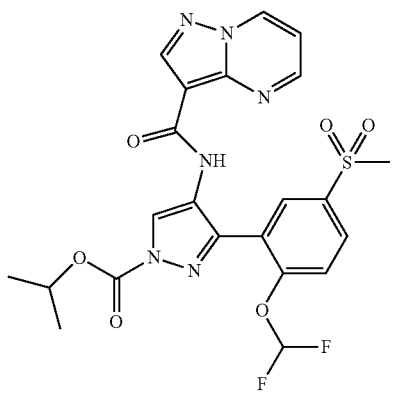 [SMILES: CC(C)OC(=O)n1cc(NC(=O)c2cnn3cccnc23)c(-c2cc(S(C)(=O)=O)ccc2OC(F)F)n1]

Isopropyl 3-(2-(difluoromethoxy)-5-(methylsulfonyl)phenyl)-4-(pyrazolo[1,5-a]pyrimidine-3-carboxamido)-1H-pyrazole-1-carboxylate Into a 100-mL 3-necked round-bottom flask, were placed N-[3-[2-(difluoromethoxy)-5-methanesulfonylphenyl]-1H-pyrazol-4-yl]pyrazolo[1,5-a]pyrimidine-3-carboxamide (100 mg, 0.223 mmol), triphenylphosphine (76 mg, 0.29 mmol, 1.3 equiv.), DIAD (58.6 mg, 0.290 mmol, 1.30 equiv.), and toluene (6 mL). The resulting solution was stirred overnight at 95° C. The resulting mixture was concentrated under vacuum. The residue was applied onto a silica gel column with ethyl acetate/petroleum ether (4:1). This resulted in 20 mg (17%) of isopropyl 3-(2-(difluoromethoxy)-5-(methylsulfonyl)phenyl)-4-(pyrazolo[1,5-a]pyrimidine-3-carboxamido)-1H-pyrazole-1-carboxylate as a white solid. $^1$H NMR (300 MHz, DMSO-d6) 9.87 (s, 1H), 9.37 (dd, J=7.2, 1.5 Hz, 1H), 8.78 (s, 1H), 8.71 (s, 1H), 8.64 (dd, J=4.2, 1.8 Hz, 1H), 8.25 (dd, J=8.9, 2.7 Hz, 1H), 8.16 (d, J=2.4 Hz, 1H), 7.80-7.26 (m, 3H), 5.26-5.18 (m, 1H), 3.33 (s, 1H), 1.42 (d, J=6.3 Hz, 1H). LC/MS (Method A, ESI): [M+H]+=535.2, R$_T$=1.68 min.

Example 12

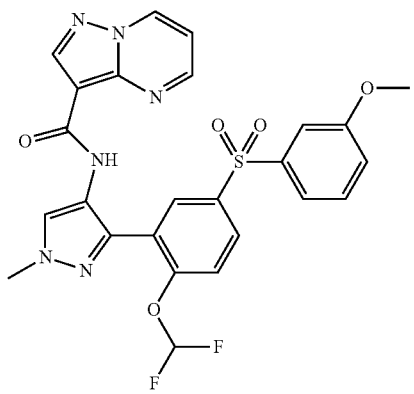

N-(3-(2-(difluoromethoxy)-5-((3-methoxyphenyl)sulfonyl)phenyl)-1-methyl-1H-pyrazol-4-yl)pyrazolo[1,5-a]pyrimidine-3-carboxamide Step 1: Synthesis of N-[3-[2-(difluoromethoxy)-5-[(3-methoxyphenyl)sulfanyl]phenyl]-1-methyl-1H-pyrazol-4-yl]pyrazolo[1,5-a]pyrimidine-3-carboxamide

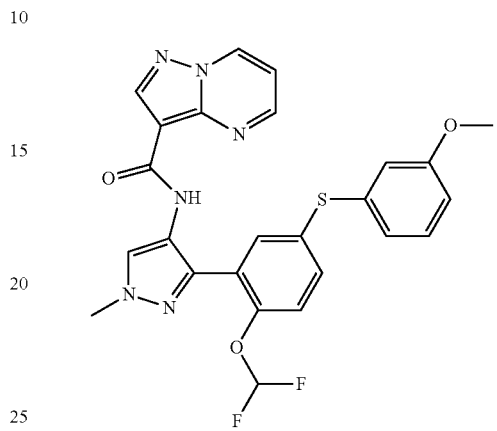

Into a 30-mL sealed tube purged and maintained with an inert atmosphere of nitrogen, was placed N-[3-[2-(difluoromethoxy)-5-[[tris(propan-2-yl)silyl]sulfanyl]phenyl]-1-methyl-1H-pyrazol-4-yl]pyrazolo[1,5-a]pyrimidine-3-carboxamide (Intermediate 6, 1.10 g, 1.92 mmol, 1.00 equiv.), cesium fluoride (658 mg, 4.33 mmol, 2.26 equiv.), isopropanol (20 mL), 1-bromo-3-methoxybenzene (809 mg, 4.33 mmol, 2.25 equiv.), Pd$_2$(dba)$_3$.CHCl$_3$ (117 mg, 0.113 mmol, 0.059 equiv.), cesium carbonate (1.40 g, 4.30 mmol, 2.24 equiv.). The resulting solution was stirred for 6 h at 90° C. The resulting mixture was concentrated under vacuum. The residue was applied onto a silica gel column with dichloromethane/methanol (95/5). The collected fractions were combined and concentrated under vacuum. This resulted in 1.2 g (120%) of N-[3-[2-(difluoromethoxy)-5-[(3-methoxyphenyl)sulfanyl]phenyl]-1-methyl-1H-pyrazol-4-yl]pyrazolo[1,5-a]pyrimidine-3-carboxamide as a red solid.

Step 2: Synthesis of N-(3-(2-(difluoromethoxy)-5-((3-methoxyphenyl)sulfonyl)phenyl)-1-methyl-1H-pyrazol-4-yl)pyrazolo[1,5-a]pyrimidine-3-carboxamide

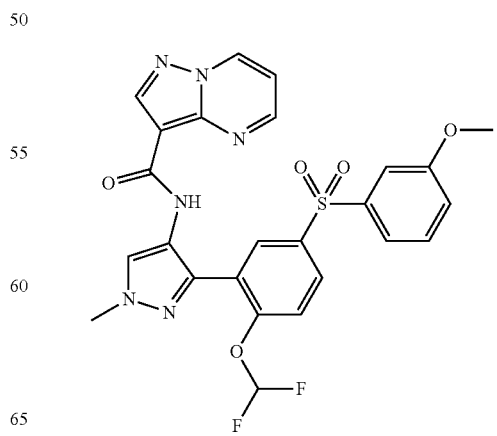

Into a 50-mL round-bottom flask, was placed N-[3-[2-(difluoromethoxy)-5-[(3-methoxyphenyl)sulfanyl]phenyl]-1-methyl-1H-pyrazol-4-yl]pyrazolo[1,5-a]pyrimidine-3-carboxamide (800 mg, 1.53 mmol), dichloromethane (10 mL), 3-chlorobenzene-1-carboperoxoic acid (753 mg, 4.36 mmol, 1.00 equiv.). The resulting solution was stirred for 2 h at room temperature. The mixture was concentrated and the crude product was purified by column chromatography to afford N-(3-(2-(difluoromethoxy)-5-((3-methoxyphenyl)sulfonyl)phenyl)-1-methyl-1H-pyrazol-4-yl)pyrazolo[1,5-a]pyrimidine-3-carboxamide. $^1$H NMR (300 MHz, DMSO-$d_6$): δ (ppm) 9.67 (s, 1H), 9.32 (dd, J=7.2, 1.5 Hz, 1H), 8.65-8.60 (m, 2H), 8.31 (s, 1H), 8.20 (dd, J=8.7, 2.4 Hz, 1H), 8.08-7.20 (m, 7H), 3.95 (s, 3H), 3.81 (s, 3H). LC/MS (Method A, ESI): [M+H]+=555.3, $R_T$=1.65 min.

Example 11

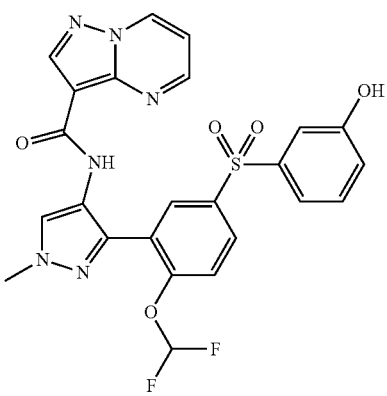 [SMILES: Cn1cc(NC(=O)c2cnn3cccnc23)c(-c2cc(S(=O)(=O)c3cccc(O)c3)ccc2OC(F)F)n1]

N-(3-(2-(difluoromethoxy)-5-((3-hydroxyphenyl)sulfonyl)phenyl)-1-methyl-1H-pyrazol-4-yl)pyrazolo[1,5-a]pyrimidine-3-carboxamide Into a 50-mL round-bottom flask purged and maintained with an inert atmosphere of nitrogen, was placed N-[3-[2-(difluoromethoxy)-5-[(3-methoxybenzene)sulfonyl]phenyl]-1-methyl-1H-pyrazol-4-yl]pyrazolo[1,5-a]pyrimidine-3-carboxamide (410 mg, 0.739 mmol), dichloromethane (10 mL), and tribromoborane (1.5 mL, 12.0 mmol, 16.2 equiv.). The resulting solution was stirred for 3 h at room temperature. The resulting mixture was concentrated under vacuum and purified by column chromatography. This resulted in 76.5 mg (19%) of N-[3-[2-(difluoromethoxy)-5-[(3-hydroxybenzene)sulfonyl]phenyl]-1-methyl-1H-pyrazol-4-yl]pyrazolo[1,5-a]pyrimidine-3-carboxamide as an off-white solid. $^1$H NMR (400 MHz, DMSO-$d_6$): δ (ppm) 10.26 (s, 1H), 9.67 (s, 1H), 9.32 (dd, J=7.2, 1.5 Hz, 1H), 8.66-8.63 (m, 2H), 8.33 (s, 1H), 8.12 (dd, J=8.8, 2.4 Hz, 1H), 8.02 (d, J=2.4 Hz, 1H), 7.66-7.26 (m, 6H), 7.06-7.01 (m, 1H), 3.96 (s, 3H). LC/MS (Method A, ESI): [M+H]+=541.3, $R_T$=1.51 min.

Example 35

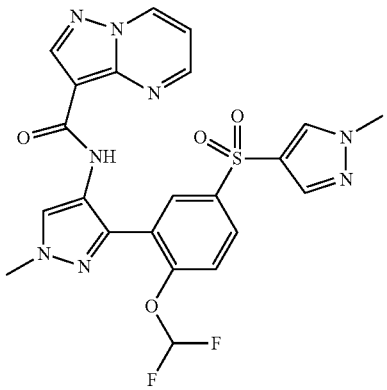

N-(3-(2-(difluoromethoxy)-5-((l-methyl-1H-pyrazol-4-yl)sulfonyl)phenyl)-1-methyl-1H-pyrazol-4-yl)pyrazolo[1,5-a]pyrimidine-3-carboxamide Step 1: Synthesis of N-[3-[2-(difluoromethoxy)-5-(1-methylpyrazol-4-yl)sulfanyl-phenyl]-1-methyl-pyrazol-4-yl]pyrazolo[1,5-a]pyrimidine-3-carboxamide

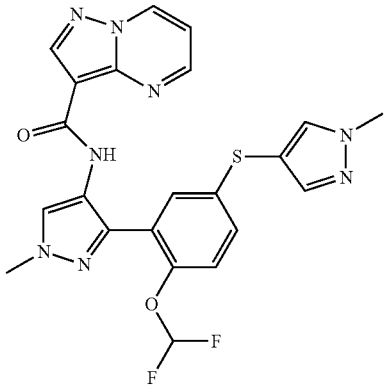

To a vial were added N-[3-[2-(difluoromethoxy)-5-sulfanyl-phenyl]-1-methyl-pyrazol-4-yl]pyrazolo[1,5-a]pyrimidine-3-carboxamide (Intermediate 8, 1.05 g, 2.52 mmol) and XantPhos Pd G3 (201 mg, 0.202 mmol). N,N-dimethylformamide (16.8 mL) was added followed by 4-bromo-1-methyl-1H-pyrazole (837 mg, 0.537 mL, 5.04 mmol) and N,N-diisopropylethylamine (978 mg, 1.32 mL, 7.56 mmol), and nitrogen was bubbled through the reaction mixture for 3 min. The reaction mixture was heated to 180° C. in a microwave reactor for 30 min. The reaction mixture was quenched by the addition of saturated aqueous ammonium chloride and extracted with ethyl acetate (3×). The combined organic layers were washed with brine, dried over sodium sulfate, filtered and concentrated in vacuo. The residue was adsorbed onto silica and purified by flash column chromatography with 10-80% 3:1 MeOH:iPrOAc in heptane to afford N-[3-[2-(difluoromethoxy)-5-(1-methylpyrazol-4-yl)sulfanyl-phenyl]-1-methyl-pyrazol-4-yl]pyrazolo[1,5-a]py- Step 2: Synthesis of N-(3-(2-(difluoromethoxy)-5-((1-methyl-1H-pyrazol-4-yl)sulfonyl)phenyl)-1-methyl-1H-pyrazol-4-yl)pyrazolo[1,5-a]pyrimidine-3-carboxamide

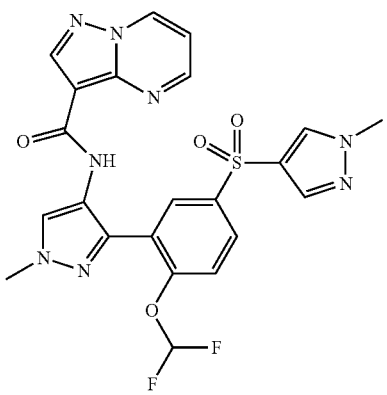

To a solution of N-[3-[2-(difluoromethoxy)-5-(1-methylpyrazol-4-yl)sulfanyl-phenyl]-1-methyl-pyrazol-4-yl]pyrazolo[1,5-a]pyrimidine-3-carboxamide (651 mg, 1.31 mmol) in dichloromethane (16.4 mL) was added 3-chloroperbenzoic acid (1.18 g, 5.25 mmol) and the reaction was stirred at room temperature for 30 min. The reaction mixture was concentrated in vacuo and the residue was dissolved in ethyl acetate and washed with saturated aqueous ammonium chloride. The aqueous layer was extracted with EtOAc (2×), and the combined organic layers were washed with brine, dried over sodium sulfate, filtered and concentrated in vacuo. This reaction was repeated scaling to N-[3-[2-(difluoromethoxy)-5-(1-methylpyrazol-4-yl)sulfanyl-phenyl]-1-methyl-pyrazol-4-yl]pyrazolo[1,5-a]pyrimidine-3-carboxamide (555 mg), and the two portions were combined for recrystallization. The combined lots were fully dissolved in 410 mL of boiling EtOH. Heating was stopped and the solution was allowed to cool to room temperature slowly, with stirring, then cooled in an ice bath. The precipitate was filtered, collected and dried under vacuum to afford N-(3-(2-(difluoromethoxy)-5-((1-methyl-1H-pyrazol-4-yl)sulfonyl)phenyl)-1-methyl-1H-pyrazol-4-yl)pyrazolo[1,5-a]pyrimidine-3-carboxamide (372 mg, 29%). $^1$H NMR (400 MHz, DMSO-$d_6$) δ 9.64 (s, 1H), 9.33 (dd, J=7.0, 1.7 Hz, 1H), 8.67-8.61 (m, 2H), 8.51 (s, 1H), 8.32 (s, 1H), 8.10 (dd, J=8.8, 2.5 Hz, 1H), 8.03 (d, J=2.5 Hz, 1H), 7.97 (d, J=0.9 Hz, 1H), 7.64 (d, J=8.8 Hz, 1H), 7.42 (t, J=72.5 Hz, 1H), 7.28 (dd, J=7.0, 4.3 Hz, 1H), 3.95 (s, 3H), 3.83 (s, 3H). LC/MS (Method X, ESI): [M+H]+=529.1 $R_T$=3.96 min.

Example 41

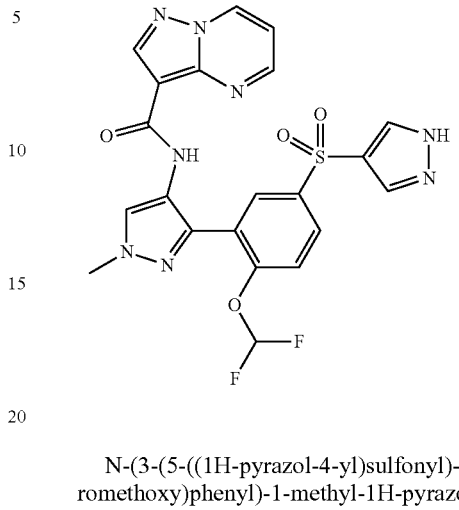

N-(3-(5-((1H-pyrazol-4-yl)sulfonyl)-2-(difluoromethoxy)phenyl)-1-methyl-1H-pyrazol-4-yl)pyrazolo[1,5-a]pyrimidine-3-carboxamide Step 1: Synthesis of N-[3-[2-(difluoromethoxy)-5-(1H-pyrazol-4-ylsulfanyl)phenyl]-1-methyl-pyrazol-4-yl]pyrazolo[1,5-a]pyrimidine-3-carboxamide

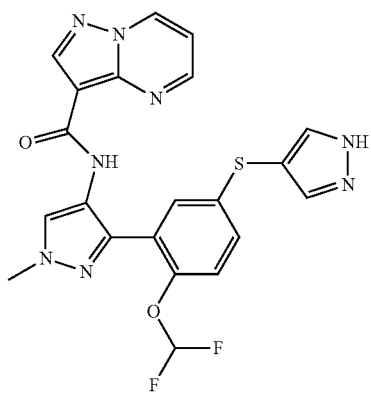 [SMILES: Cn1cc(NC(=O)c2cnn3cccnc23)c(-c2cc(Sc3cn[nH]c3)ccc2OC(F)F)n1]

To a vial was added N-[3-[2-(difluoromethoxy)-5-sulfanyl-phenyl]-1-methyl-pyrazol-4-yl]pyrazolo[1,5-a]pyrimidine-3-carboxamide (Intermediate 8, 1000 mg, 2.40 mmol), 4-bromo-1H-pyrazole (706 mg, 4.80 mmol), and XantPhos Pd G3 (240 mg, 0.240 mmol). N,N-Dimethylformamide (16.0 mL) was added followed by N,N-diisopropylethylamine (931 mg, 1.26 mL, 7.20 mmol), and nitrogen was bubbled through the reaction mixture for 3 min. The reaction mixture was heated to 180° C. in a microwave reactor for 45 min. The reaction mixture was quenched by the addition of saturated aqueous ammonium chloride and extracted with EtOAc (3×). The combined organic layers were washed with brine, dried over sodium sulfate, filtered and concentrated in vacuo. The residue was adsorbed onto silica and purified by flash column chromatography with 10-80% 3:1 MeOH:iPrOAc in heptane to afford N-[3-[2-(difluoromethoxy)-5-(1H-pyrazol-4-ylsulfanyl)phenyl]-1-methyl-pyrazol-4-yl]pyrazolo[1,5-a]pyrimidine-3-carboxamide as an orange solid (517 mg, 45%).

Step 2: Synthesis of N-(3-(5-((1H-pyrazol-4-yl)sulfonyl)-2-(difluoromethoxy)phenyl)-1-methyl-1H-pyrazolo-4-yl)pyrazolo[1,5-a]pyrimidine-3-carboxamide

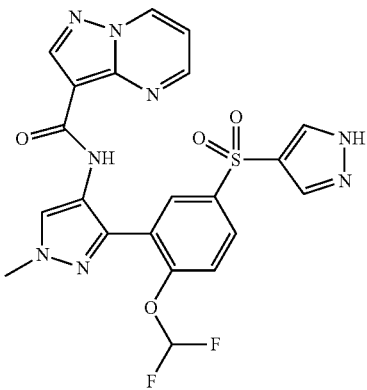 [SMILES: Cn1cc(NC(=O)c2cnn3cccnc23)c(-c2cc(S(=O)(=O)c3cn[nH]c3)ccc2OC(F)F)n1]

To a solution of N-[3-[2-(difluoromethoxy)-5-(1H-pyrazol-4-ylsulfanyl)phenyl]-1-methyl-pyrazol-4-yl]pyrazolo[1,5-a]pyrimidine-3-carboxamide (517 mg, 1.07 mmol) in dichloromethane (10 mL) was added 3-chloroperbenzoic acid (961 mg, 4.29 mmol) and the reaction was stirred at room temperature for 30 min. The reaction mixture was diluted with dichloromethane and poured into a separatory funnel containing saturated aqueous sodium bicarbonate. The layers were separated and the aqueous layer was extracted with dichloromethane (2×). The combined organic layers were dried over sodium sulfate, filtered and concentrated in vacuo. The residue was adsorbed onto silica and purified by flash column chromatography with 10-80% 3:1 MeOH IPrOAc in heptane to afford N-(3-(5-((1H-pyrazol-4-yl)sulfonyl)-2-(difluoromethoxy)phenyl)-1-methyl-1H-pyrazol-4-yl)pyrazolo[1,5-a]pyrimidine-3-carboxamide as brown solid (383 mg, 69%). $^1$H NMR (400 MHz, DMSO-$d_6$) δ 13.78 (s, 1H), 9.64 (s, 1H), 9.32 (dd, J=7.0, 1.7 Hz, 1H), 8.65 (s, 1H), 8.63 (dd, J=4.3, 1.7 Hz, 1H), 8.40-8.18 (m, 3H), 8.11 (dd, J=8.8, 2.5 Hz, 1H), 8.05 (d, J=2.5 Hz, 1H), 7.63 (d, J=8.7 Hz, 1H), 7.41 (t, J=72.5 Hz, 1H), 7.27 (dd, J=7.0, 4.2 Hz, 1H), 3.95 (s, 3H). LC/MS (Method X, ESI): [M+H]+=515.1 $R_T$=3.71 min.

Example 53

N-(3-(5-((1-(2-(azetidin-1-yl)ethyl)-1H-pyrazol-4-yl)sulfonyl)-2-(difluoromethoxy)phenyl)-1-methyl-1H-pyrazol-4-yl)pyrazolo[1,5-a]pyrimidine-3-carboxamide To a solution of N-[3-[2-(difluoromethoxy)-5-(1H-pyrazol-4-ylsulfonyl)phenyl]-1-methyl-pyrazol-4-yl]pyrazolo[1,5-a]pyrimidine-3-carboxamide (50 mg, 0.097 mmol), PS-triphenylphosphine (85.0 mg, 0.20 mmol), di-tert-butyl azodicarboxylate (49.2 mg, 0.21 mmol) in tetrahydrofuran (1.5 mL) was added 2-(azetidin-1-yl)ethanol (20.3 mg, 0.019 mL, 0.19 mmol) and the reaction mixture was heated to 60° C. for 90 min. The reaction mixture was filtered and the filtrate was concentrated in vacuo. The crude mixture was taken up in dichloromethane (3 mL) and HCl (2.0 mol/L in diethyl ether, 0.73 mL, 1.46 mmol) and the reaction mixture was stirred at room temperature for 1 h. The reaction mixture was concentrated in vacuo and taken up in dichloromethane. MP-carbonate (464 mg, 1.458 mmol) was added and the reaction mixture was stirred overnight. The mixture was filtered and concentrated in vacuo and purified by reverse-phase HPLC to yield the title compound (25.4 mg, 44%) as a white solid. $^1$H NMR (400 MHz, DMSO-$d_6$) δ 9.64 (s, 1H), 9.33 (dd, J=7.0, 1.6 Hz, 1H), 8.66-8.63 (m, 2H), 8.52 (s, 1H), 8.31 (s, 1H), 8.24 (s, 2H), 8.11 (dd, J=8.7, 2.5 Hz, 1H), 8.03 (d, J=2.5 Hz, 1H), 7.99-7.94 (m, 1H), 7.64 (d, J=8.7 Hz, 1H), 7.42 (t, J=72.5 Hz, 1H), 7.28 (dd, J=7.0, 4.3 Hz, 1H), 4.02 (t, J=6.0 Hz, 2H), 3.95 (s, 3H), 2.97 (t, J=7.0 Hz, 4H), 1.87-1.76 (m, 2H). LC/MS (Method X, ESI): [M+H]+=598.2 $R_T$=3.07 min.

Example 40

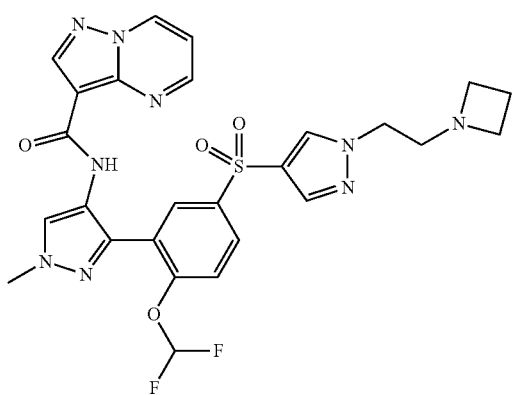 [SMILES: Cn1cc(NC(=O)c2cnn3cccnc23)c(-c2cc(S(=O)(=O)c3cnn(CCN4CCC4)c3)ccc2OC(F)F)n1]

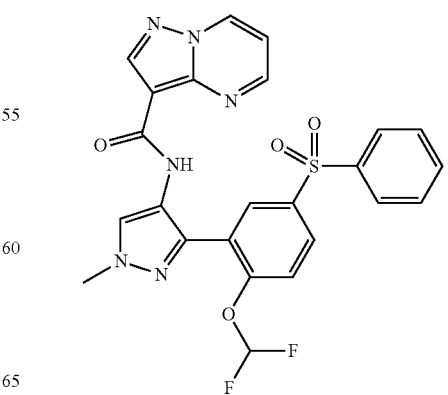

N-(3-(2-(difluoromethoxy)-5-(phenylsulfonyl)phenyl)-1-methyl-1H-pyrazol-4-yl)pyrazolo[1,5-a]pyrimidine-3-carboxamide Step 1: Synthesis of N-(3-(2-(difluoromethoxy)-5-(phenylthio)phenyl)-1-methyl-1H-pyrazol-4-yl)pyrazolo[1,5-a]pyrimidine-3-carboxamide

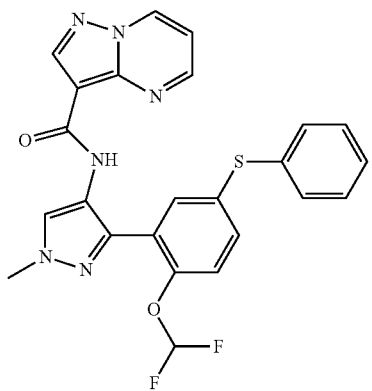 [SMILES: Cn1cc(NC(=O)c2cnn3cccnc23)c(-c2cc(Sc3ccccc3)ccc2OC(F)F)n1]

To a solution of N-[3-[5-bromo-2-(difluoromethoxy)phenyl]-1-methyl-pyrazol-4-yl]pyrazolo[1,5-a]pyrimidine-3-carboxamide (Intermediate 3, 200 mg, 0.43 mmol), thiophenol (57 mg, 0.053 mL, 0.52 mmol), XantPhos Pd G2 (38.3 mg, 0.0432 mmol) and XantPhos (25 mg, 0.0432 mmol) in toluene (11 mL) cooled to 0° C. was added NaH (34.5 mg, 0.86 mmol) and the reaction mixture was stirred for 30 min at 0° C. 1 h at room temperature, and then heated to 90° C. for 2 h. The reaction mixture was diluted with dichloromethane, filtered through Celite, eluting with dichloromethane, and the filtrate was concentrated in vacuo. The crude N-(3-(2-(difluoromethoxy)-5-(phenylthio)phenyl)-1-methyl-1H-pyrazol-4-yl)pyrazolo[1,5-a]pyrimidine-3-carboxamide was used without further purification. LC/MS (Method W, ESI): [M+H]+=593.1 $R_T$=1.34 min.

Step 2: Synthesis of N-(3-(2-(difluoromethoxy)-5-(phenylsulfonyl)phenyl)-1-methyl-1H-pyrazol-4-yl)pyrazolo[1,5-a]pyrimidine-3-carboxamide

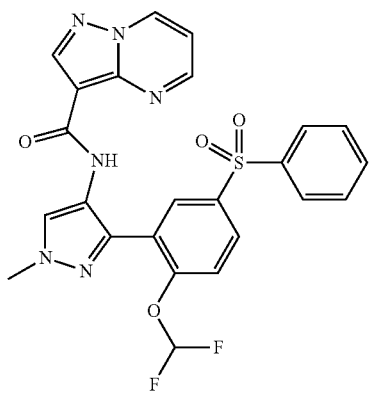 [SMILES: Cn1cc(NC(=O)c2cnn3cccnc23)c(-c2cc(S(=O)(=O)c3ccccc3)ccc2OC(F)F)n1]

To a solution of N-[3-[2-(difluoromethoxy)-5-phenylsulfanyl-phenyl]-1-methyl-pyrazol-4-yl]pyrazolo[1,5-a]pyrimidine-3-carboxamide (213 mg, 0.432 mmol) in dichloromethane (4.0 mL) was added 3-chloroperbenzoic acid (203 mg, 0.91 mmol) and the reaction was stirred at room temperature for 2 d. 3-chloroperbenzoic acid (68 mg, 0.302 mmol) was added, and after 1 h a second portion was added (25 mg). After 1 h, the reaction mixture was diluted with dichloromethane and poured into a separatory funnel containing saturated aqueous sodium bicarbonate. The layers were separated and the aqueous layer was extracted with dichloromethane (2×). The combined organic layers were dried over sodium sulfate, filtered and concentrated in vacuo. The residue was purified by reverse-phase HPLC to yield the title compound (107.2 mg, 47%) as a white solid. $^1$H NMR (400 MHz, DMSO-d$_6$) δ 9.61 (s, 1H), 9.32 (dd, J=7.0, 1.5 Hz, 1H), 8.64 (s, 1H), 8.62 (dd, J=4.3, 1.7 Hz, 1H), 8.31 (s, 1H), 8.15 (dd, J=8.8, 2.5 Hz, 1H), 8.06 (d, J=2.5 Hz, 1H), 8.03-7.93 (m, 2H), 7.71-7.22 (m, 6H), 3.95 (s, 3H). LC/MS (Method X, ESI): [M+H]+=525.1 $R_T$=4.58 min.

Example 44

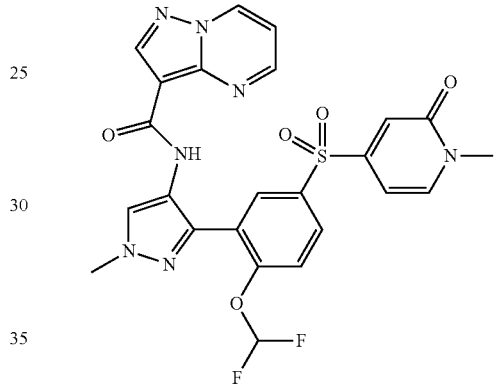

N-(3-(2-(difluoromethoxy)-5-((1-methyl-2-oxo-1,2-dihydropyridin-4-yl)sulfonyl)phenyl)-1-methyl-1H-pyrazol-4-yl)pyrazolo[1,5-a]pyrimidine-3-carboxamide Step 1: Synthesis of N-[3-[2-(difluoromethoxy)-5-[(1-methyl-2-oxo-4-pyridyl)sulfanyl]phenyl]-1-methyl-pyrazol-4-yl]pyrazolo[1,5-a]pyrimidine-3-carboxamide

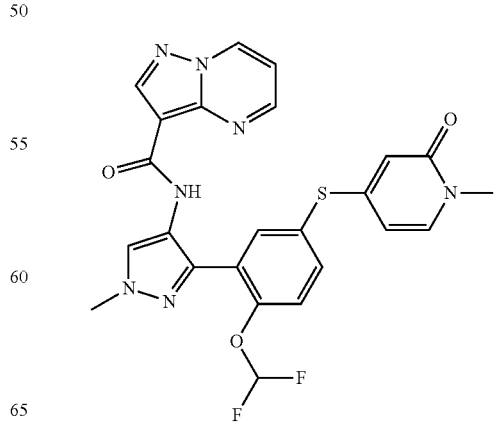

To a vial was added N-[3-[2-(difluoromethoxy)-5-sulfanyl-phenyl]-1-methy 1-pyrazol-4-yl]pyrazolo[1,5-a]pyrimidine-3-carboxamide (Intermediate 3, 50 mg, 0.12 mmol) and XantPhos Pd G3 (9.60 mg, 0.0096 mmol). N,N-dimethylformamide (1.5 mL) was added followed by 4-bromo-1-methylpyridin-2(1H)-one (47.5 mg, 0.240 mmol) and N,N-diisopropylethylamine (46.6 mg, 0.0628 mL, 0.360 mmol), and nitrogen was bubbled through the reaction mixture for 3 min. The reaction mixture was heated to 180° C. in a microwave reactor for 30 min. The reaction mixture was quenched by the addition of saturated aqueous ammonium chloride and extracted with EtOAc (3×). The combined organic layers were washed with brine, dried over sodium sulfate, filtered and concentrated in vacuo to give N-[3-[2-(difluoromethoxy)-5-[(1-methyl-2-oxo-4-pyridyl)sulfanyl]phenyl]-1-methyl-pyrazol-4-yl]pyrazolo[1,5-a]pyrimidine-3-carboxamide.

Step 2: Synthesis of N-(3-(2-(difluoromethoxy)-5-((1-methyl-2-oxo-1,2-dihydropyridin-4-yl)sulfonyl)phenyl)-1-methyl-1H-pyrazol-4-yl)pyrazolo[1,5-a]pyrimidine-3-carboxamide

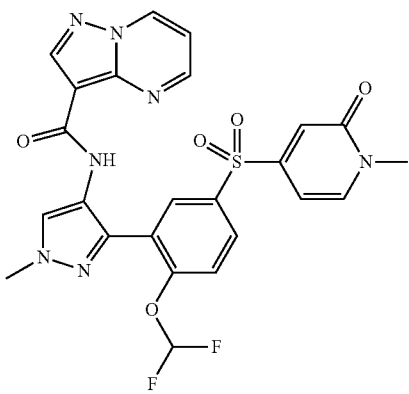

To a solution of N-[3-[2-(difluoromethoxy)-5-[(1-methyl-2-oxo-4-pyridyl)sulfanyl]phenyl]-1-methyl-pyrazol-4-yl]pyrazolo[1,5-a]pyrimidine-3-carboxamide (63 mg, 0.120 mmol) in dichloromethane (2.0 mL) was added 3-chloroperbenzoid acid (108 mg, 0.48 mmol) and the reaction was stirred at room temperature for 15 min. The reaction mixture was diluted with dichloromethane and poured into a separatory funnel containing saturated aqueous sodium bicarbonate. The layers were separated and the aqueous layer was extracted with dichloromethane (2×). The combined organic layers were dried over sodium sulfate, filtered and concentrated in vacuo. The residue was further purified by RP-HPLC to yield the title compound (29.2 mg, 44%) as a white solid. $^1$H NMR (400 MHz, DMSO-d$_6$) δ 9.63 (s, 1H), 9.33 (dd, J=6.9, 1.6 Hz, 1H), 8.66-8.63 (m, 2H), 8.32 (s, 1H), 8.22 (dd, J=8.8, 2.5 Hz, 1H), 8.09 (d, J=2.5 Hz, 1H), 7.90 (d, J=7.1 Hz, 1H), 7.68 (d, J=8.7 Hz, 1H), 7.48 (t, J=72.3 Hz, 1H), 7.28 (dd, J=7.0, 4.3 Hz, 1H), 6.94 (d, J=2.2 Hz, 1H), 6.60 (dd, J=7.1, 2.1 Hz, 1H), 3.96 (s, 3H), 3.40 (s, 3H). LC/MS (Method X, ESI): [M+H]+=556.1 R$_T$=3.18 min.

Example 15

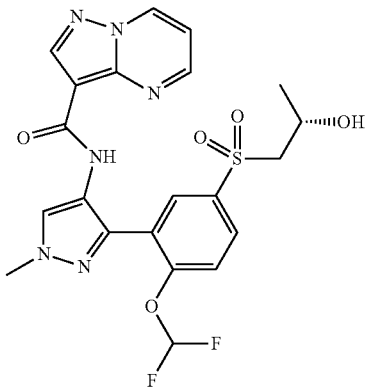 [SMILES: C[C@H](O)CS(=O)(=O)c1ccc(OC(F)F)c(-c2nn(C)cc2NC(=O)c2cnn3cccnc23)c1]

(S)—N-(3-(2-(difluoromethoxy)-5-((2-hydroxypropyl)sulfonyl)phenyl)-1-methyl-1H-pyrazol-4-yl)pyrazolo[1,5-a]pyrimidine-3-carboxamide Step 1: Synthesis of (S)—N-(3-(2-(difluoromethoxy)-5-((2-hydroxypropyl)thio)phenyl)-1-methyl-1H-pyrazol-4-yl)pyrazolo[1,5-a]pyrimidine-3-carboxamide

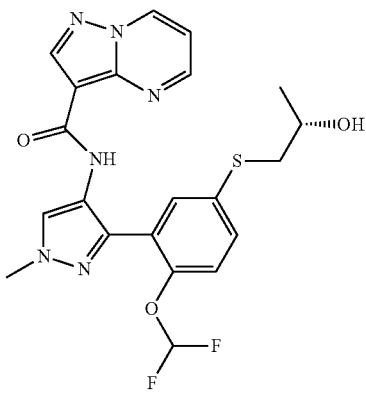 [SMILES: C[C@H](O)CSc1ccc(OC(F)F)c(-c2nn(C)cc2NC(=O)c2cnn3cccnc23)c1]

To a solution of N-[3-[2-(difluoromethoxy)-5-sulfanylphenyl]-1-methyl-pyrazol-4-yl]pyrazolo[1,5-a]pyrimidine-3-carboxamide (Intermediate 8, 950 mg, 2.28 mmol) in methanol (10 mL) was added (S)-(−)-propylene oxide (250 mg, 4.3 mmol) and DIEA (900 mg, 6.98 mmol) and the mixture was stirred at 80° C. for 3 h. After cooling to room temperature, the reaction mixture was concentrated under vacuum. The residue was purified by reverse phase HPLC [mobile phase A: water (0.1% NH$_4$HCO$_3$), mobile phase B: acetonitrile; gradient: 10% B to 40% B in 50 min] to give N-[3-[2-(difluoromethoxy)-5-[(2S)-2-hydroxypropyl]sulfanyl-phenyl]-1-methyl-pyrazol-4-yl]pyrazolo[1,5-a]pyrimidine-3-carboxamide (730 mg, 1.54 mmol, 67% yield) as a light yellow solid. LC/MS (Method O, ESI): [M+H]+=475.2 R$_T$=1.43 min.

Step 2: Synthesis of (S)—N-(3-(2-(difluoromethoxy)-5-((2-hydroxypropyl)sulfonyl)phenyl)-1-methyl-1H-pyrazol-4-yl)pyrazolo[1,5-a]pyrimidine-3-carboxamide

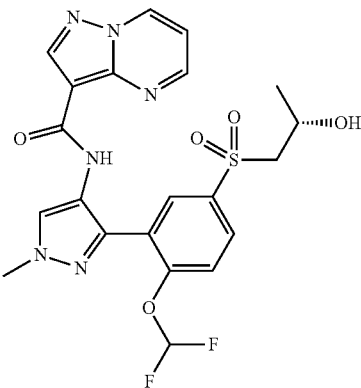 [SMILES: C[C@H](O)CS(=O)(=O)c1ccc(OC(F)F)c(-c2nn(C)cc2NC(=O)c2cnn3cccnc23)c1]

To a solution of N-[3-[2-(difluoromethoxy)-5-[(2S)-2-hydroxypropyl]sulfanyl-phenyl]-1-methyl-pyrazol-4-yl]pyrazolo[1,5-a]pyrimidine-3-carboxamide (730 mg, 1.54 mmol) in methanol (10 mL) was added a solution of oxone (2.0 g, 3.25 mmol) in water (5.0 mL) and the mixture was stirred at room temperature for 3 h. The organic solvent was removed under vacuum and 10 mL of water was added. The solid was collected by filtration. The filter cake was washed with water (5.0 mL×5) and dried under vacuum. The residue was purified by preparatory HPLC (column: XBridge Prep OBD C18 Column, 30×150 mm 5um; mobile phase A:water (10 mmol/L NH$_4$HCO$_3$), mobile phase B: ACN; flow rate:60 mL/min; gradient: 16% B to 37% B in 8 min; 254 nm; R$_T$ 1:7.45 min). The product was stirred in 3.0 mL of ethanol overnight at room temperature to give N-[3-[2-(difluoromethoxy)-5-[(2S)-2-hydroxypropyl]sulfonyl-phenyl]-1-methyl-pyrazol-4-yl]pyrazolo[1,5-a]pyrimidine-3-carboxamide (783 mg, 1.52 mmol) as an off-white solid. $^1$H NMR (400 MHz, DMSO-d$_6$) δ 9.69 (s, 1H), 9.35 (dd, J=6.8, 1.6 Hz, 1H), 8.70-8.68 (m, 2H), 8.34 (s, 1H), 8.09-8.04 (m, 2H), 7.68-7.29 (m, 3H), 4.90 (d, J=5.6 Hz, 1H), 4.10-4.04 (m, 1H), 3.97 (s, 3H), 3.50-3.40 (m, 2H), 1.12 (d, J=6.0 Hz, 3H). LC/MS (Method O, ESI): [M+H]+=507.2 R$_T$=1.26 min.

Example 25

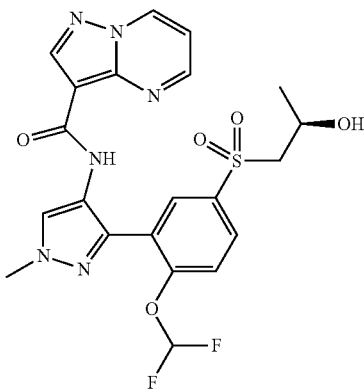 [SMILES: C[C@@H](O)CS(=O)(=O)c1ccc(OC(F)F)c(-c2nn(C)cc2NC(=O)c2cnn3cccnc23)c1]

(R)—N-(3-(2-(difluoromethoxy)-5-((2-hydroxypropyl)sulfonyl)phenyl)-1-methyl-1H-pyrazol-4-yl)pyrazolo[1,5-a]pyrimidine-3-carboxamide Step 1: Synthesis of (R)—N-(3-(2-(difluoromethoxy)-5-((2-hydroxypropyl)thio)phenyl)-1-methyl-1H-pyrazol-4-yl)pyrazolo[1,5-a]pyrimidine-3-carboxamide

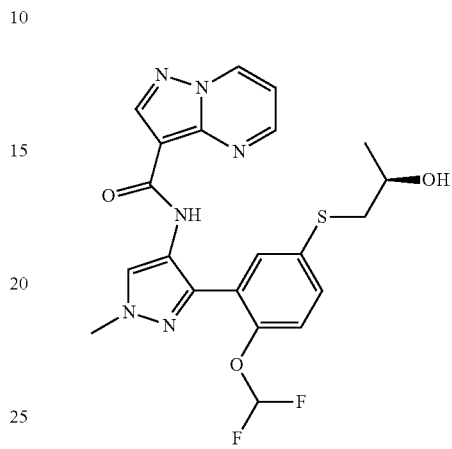

To a solution of N-[3-[2-(difluoromethoxy)-5-sulfanyl-phenyl]-1-methyl-pyrazol-4-yl]pyrazolo[1,5-a]pyrimidine-3-carboxamide (1.10 g, 2.64 mmol) in methanol (10 mL) was added (R)-(+)-propylene oxide (300 mg, 5.17 mmol) and DIEA (1.00 g, 7.75 mmol) and the reaction mixture was stirred at 80° C. for 3 h. After cooling to room temperature, the solvent was removed under vacuum. The residue was purified by reverse phase HPLC [mobile phase A: water (0.1% NH$_4$HCO$_3$), mobile phase B: acetonitrile; gradient: 10% B to 40% B in 50 min] to give N-[3-[2-(difluoromethoxy)-5-[(2R)-2-hydroxypropyl]sulfanyl-phenyl]-1-methyl-pyrazol-4-yl]pyrazolo[1,5-a]pyrimidine-3-carboxamide (780 mg, 1.64 mmol, 62% yield) as an off-white solid. LC/MS (Method O, ESI): [M+H]+=475.2 R$_T$=1.43 min.

Step 2: Synthesis of (R)—N-(3-(2-(difluoromethoxy)-5-((2-hydroxypropyl)sulfonyl)phenyl)-1-methyl-1H-pyrazol-4-yl)pyrazolo[1,5-a]pyrimidine-3-carboxamide

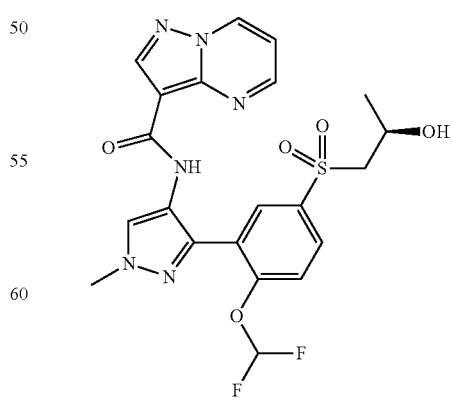

To a solution of N-[3-[2-(difluoromethoxy)-5-[(2R)-2-hydroxypropyl]sulfanyl-phenyl]-1-methyl-pyrazol-4-yl]

pyrazolo[1,5-a]pyrimidine-3-carboxamide (780 mg, 1.64 mmol) in methanol (10 mL) was added a solution of oxone (2.0 g, 3.26 mmol) in water (5.0 mL), and the mixture was stirred at room temperature for 3 h. The organic solvent was removed under vacuum. Water (10 mL) was added and the solid was collected by filtration. The filter cake was washed with water (5.0 mL×5) and then dried under vacuum. The residue was purified by prep. HPLC (column: XBridge Prep OBD C18 Column, 30×150 mm 5um; mobile phase A:water (10 mmol/L NH$_4$HCO$_3$), mobile phase B:ACN; flow rate:60 mL/min; gradient: 16% B to 37% B in 8 min; 254 nm; $R_T$ 1:7.45 min). The product was stirred in 3.0 mL of ethanol overnight at room temperature to give N-[3-[2-(difluoromethoxy)-5-[(2S)-2-hydroxypropyl]sulfonyl-phenyl]-1-methyl-pyrazol-4-yl]pyrazolo[1,5-a]pyrimidine-3-carboxamide (771 mg, 1.51 mmol, 92% yield) as an off-white solid. LC/MS (Method O, ESI): [M+H]+=507.2 $R_T$=1.26 min. $^1$H NMR (400 MHz, DMSO-d$_6$) δ 9.69 (s, 1H), 9.35 (dd, J=6.8, 1.6 Hz, 1H), 8.70-8.68 (m, 2H), 8.34 (s, 1H), 8.10-8.04 (m, 2H), 7.68-7.29 (m, 3H), 4.90 (d, J=5.6 Hz, 1H), 4.10-4.04 (m, 1H), 3.97 (s, 3H), 3.50-3.40 (m, 2H), 1.12 (d, J=6.0 Hz, 3H).

Examples 23 & 24

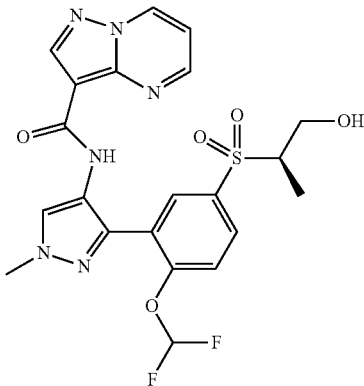

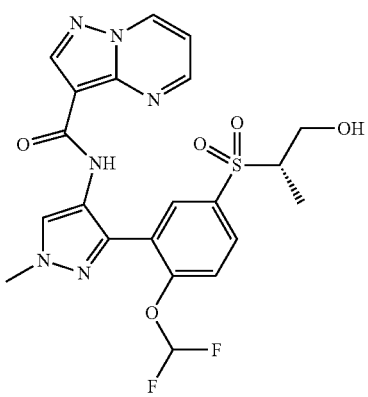

(R)—N-(3-(2-(difluoromethoxy)-5-((1-hydroxypropan-2-yl)sulfonyl)phenyl)-1-methyl-1H-pyrazol-4-yl)pyrazolo[1,5-a]pyrimidine-3-carboxamide & (S)—N-(3-(2-(difluoromethoxy)-5-((1-hydroxypropan-2-yl)sulfonyl)phenyl)-1-methyl-1H-pyrazol-4-yl)pyrazolo[1,5-a]pyrimidine-3-carboxamide Step 1: Synthesis of N-(3-(2-(difluoromethoxy)-5-((1-hydroxypropan-2-yl)thio)phenyl)-1-methyl-1H-pyrazol-4-yl)pyrazolo[1,5-a]pyrimidine-3-carboxamide

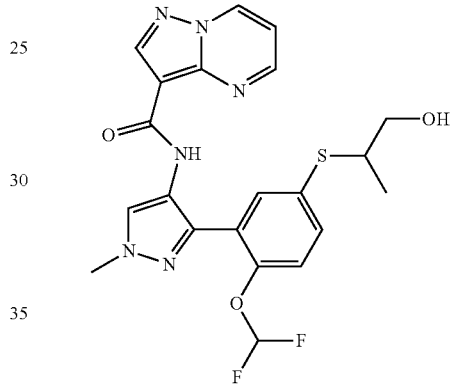

To a solution of N-[3-[5-bromo-2-(difluoromethoxy)phenyl]-1-methyl-pyrazol-4-yl]pyrazolo[1,5-a]pyrimidine-3-carboxamide (2.00 g, 4.32 mmol) in 1,4-dioxane (100 mL) was added Pd$_2$(dba)$_3$ (396 mg, 0.431 mmol), Xantphos (500 mg, 0.864 mmol) and DIPEA (1.67 g, 13.0 mmol) at room temperature under nitrogen. The resulting solution was stirred for 15 minutes at RT and heated to 90° C. 2-Sulfanylpropan-1-ol (580 mg, 6.29 mmol) was added to the reaction mixture and the resulting mixture was stirred at 90° C. for 10 h. The reaction was cooled to room temperature and the suspension was filtrated through Celite. The filtrate was concentrated under vacuum. The residue was purified by flash chromatography on silica gel eluting with DCM/EA (0%~100%) to afford N-[3-[2-(difluoromethoxy)-5-(2-hydroxy-1-methyl-ethyl)sulfanyl-phenyl]-1-methyl-pyrazol-4-yl]pyrazolo[1,5-a]pyrimidine-3-carboxamide (1.74 g, 3.67 mmol, 85% yield) as an off-white solid. LC/MS (Method I, ESI): [M+H]+=507.2 $R_T$=0.97 min.

Step 2: Synthesis of N-(3-(2-(difluoromethoxy)-5-((1-hydroxypropan-2-yl)sulfonyl)phenyl)-1-methyl-1H-pyrazol-4-yl)pyrazolo[1,5-a]pyrimidine-3-carboxamide

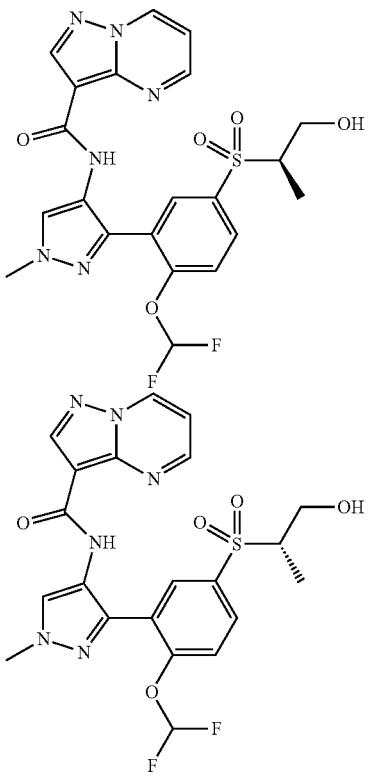

A solution of N-[3-[2-(difluoromethoxy)-5-(2-hydroxy-1-methyl-ethyl)sulfanyl-phenyl]-1-methyl-pyrazol-4-yl]pyrazolo[1,5-a]pyrimidine-3-carboxamide (850 mg, 1.79 mmol) in methanol (8.0 mL) was stirred at 0° C. for 5 min. Then a solution of oxone (2.20 g, 3.58 mmol) in water (8.0 mL) was added at 0° C. The reaction solution was stirred at room temperature for 1 h. The reaction mixture was concentrated and filtered. The filter cake was mixed with DCM (10 mL) and filtered. The filtrate was concentrated under vacuum to afford the product (779 mg, 1.54 mmol, 86% yield). This reaction was repeated on the same scale and combined to afford 1.10 g (61% yield of racemate). The combined product was purified by chiral-SFC with the following conditions: column: Lux Sum Cellulose-4, 5*25 cm, 5 µm; mobile phase A: $CO_2$, mobile phase B: EtOH:ACN=2:1 (2 mM $NH_3$-MeOH); flow rate: 150 mL/min; gradient: 40% B; 220 nm; $R_T1$: 9.03 min; $R_T2$: 10.79 min. Fractions containing the two enantiomers were combined and concentrated, and both were recrystallized by stirring in 2 mL isopropanol over 2 days at room temperature. The products were isolated by filtration to afford the title compounds, with stereochemical assignments made arbitrarily.

Peak1: (R)—(N-[3-[2-(difluoromethoxy)-5-(2-hydroxy-1-methyl-ethyl)sulfonyl-phenyl]-1-methyl-pyrazol-4-yl]pyrazolo[1,5-a]pyrimidine-3-carboxamide, 341 mg) was obtained as an off-white solid. $^1$H NMR (400 MHz, DMSO-<4) δ 9.67 (s, 1H), 9.34 (dd, J=7.0, 1.6 Hz, 1H), 8.79-8.55 (m, 1H), 8.66 (s, 1H), 8.32 (s, 1H), 8.17-7.85 (m, 2H), 7.79-7.16 (m, 3H), 4.96 (t, J=5.6 Hz, 1H), 3.96 (s, 3H), 3.70 (m, 1H), 3.60-3.27 (m, 2H), 1.22 (d, J=6.7 Hz, 3H). LC/MS (Method X, ESI): [M+H]+=507.1 $R_T$=3.59 min.

Peak2: (S)—(N-[3-[2-(difluoromethoxy)-5-(2-hydroxy-1-methyl-ethyl)sulfonyl-phenyl]-1-methyl-pyrazol-4-yl]pyrazolo[1,5-a]pyrimidine-3-carboxamide, 411 mg) was obtained as an off-white. $^1$H NMR (400 MHz, DMSO-d$_6$) δ 9.67 (s, 1H), 9.34 (dd, J=7.0, 1.6 Hz, 1H), 8.79-8.45 (m, 2H), 8.32 (s, 1H), 8.17-7.86 (m, 2H), 7.86-7.16 (m, 3H), 4.96 (t, J=5.5 Hz, 1H), 3.96 (s, 3H), 3.70 (m, 1H), 3.60-3.28 (m, 2H), 1.22 (d, J=6.7 Hz, 3H). LC/MS (Method X, ESI): [M+H]+=507.1 $R_T$=3.56 min.

Assays

Test Agents

Test agent samples were provided as solutions at a concentration of 10 mM in dimethyl sulfoxide (DMSO) and were stored in the dark at room temperature before use.

JAK1 and JAK2 Biochemical Assays

The in vitro biochemical assays quantify JAK-catalyzed phosphorylation of a synthetic peptide, as detected using a LabChip® EZ Reader II microfluidic mobility shift instrument (PerkinElmer; Waltham, Mass.). The substrate peptide Y-1B has the sequence 5-FAM-VALVDGYFRLTT-NH$_2$. Y-1B is fluorescently labeled on the N-terminus with 5-FAM (5-carboxyfluorescein) and contains a single tyrosine residue (Y) that can be phosphorylated by JAK activity. The substrate peptide stock is prepared in DMSO at 5 mM. Purified recombinant human JAK1 kinase domain protein (Residues 854-1154) was expressed in insect cells and procured from Proteros Biostructures GmbH (Martinsried, Germany). Recombinant human JAK2 kinase domain protein (Residues 812-1132) was expressed in insect cells and purified at Genentech, Inc. (South San Francisco, Calif.).

The kinase reaction mixtures contained 100 mM 4-(2-hydroxyethyl)-1-piperazineethanesulfonic acid (HEPES) buffer (pH 7.2), 10 mM magnesium chloride, 0.015% Brij® 35, 4 mM dithiothreitol, 1.5 µM Y-1B peptide substrate, 25 µM adenosine triphosphate (ATP), 1 nM total JAK1 or 0.2 nM total JAK2, and up to 1000 nM test compound in a final concentration of 2% (volume to volume [v/v]) DMSO. In each titration experiment, test compound was tested in duplicate at each of the twelve concentrations. Blank reactions contained ATP, peptide, and DMSO, but no JAK or test compound, whereas uninhibited control reactions contained ATP, peptide, JAK, and DMSO, but no test compound.

Peptide plus ATP mixture (24 µL) was added to 1 µL of test compound in DMSO (or DMSO alone). The reactions were initiated by adding 25 µL of JAK enzyme to the inhibitor/peptide/ATP mixture before thoroughly mixing the resultant solution. Reactions were incubated at room temperature (22° C.-23° C.) in a final volume of 50 µL per well in 384-well plates. After a 30-minute incubation, the reactions were stopped by adding 25 µL of 150 mM ethylenediaminetetraacetic acid in 100 mM HEPES buffer (pH 7.2) containing 0.015% Brij 35 to each well.

In each reaction, the residual Y-1B substrate and the phospho-peptide product generated were separated using the EZ Reader II instrument. Electrophoretic separation of molecules of product from molecules of substrate was achieved using downstream and upstream voltages of −500 and −2600 V, respectively, at an operating pressure of −1.3 psi. The 5-FAM group present on both the substrate and product peptides was excited at 488 nm, the fluorescence was detected at 530 nm, and the peak heights were reported.

Data Analysis

The extent (or percent) of conversion of substrate to product was calculated from the corresponding peak heights in the electropherogram using HTS Well Analyzer software, Version 5.2 (PerkinElmer), and the following equation (Equation 1):

$$\% \text{ conversion} = [P \div (S+P)] \times 100 \qquad \text{Equation 1}$$

where S and P represent the peak heights of the substrate and product, respectively. After any baseline signal from blank wells containing no JAK was subtracted from the signal of all test wells, the % conversion data were converted to fractional activity as shown in Equation 2, where $v_i$ and $v_o$ are the % conversion in the presence and absence of test compound, respectively. The % conversion observed in the uninhibited control reactions containing JAK and DMSO vehicle, but no test compound, was defined to have fractional activity=1 (with no inhibitor present, $v_i = v_o$), whereas blank wells with no JAK were defined as having fractional activity=0. Fractional activity was plotted against test compound concentration and the data were fitted using XLfit software (IDBS; Guildford, United Kingdom) to a tight-binding apparent inhibition constant ($K_i^{app}$) quadratic equation (see Equation 2) (Williams J W, Morrison J F. The kinetics of reversible tight-binding inhibition. *Methods Enzymol* 1979; 63:437-67.), which was used to calculate fractional activity and $K_i^{app}$ $$\text{Fractional activity} = \frac{v_i}{v_o} = 1 - \frac{([E]_T + [I]_T + K_i^{app}) - \sqrt{([E]_T + [I]_T + K_i^{app})^2 - 4[E]_T[I]_T}}{2[E]_T} \qquad \text{Equation 2}$$

where $[E]_T$ and $[I]_T$ are the total concentrations of active enzyme (initial estimates of 0.15 nM for JAK1 and 0.048 nM for JAK2) and inhibitor (the varied parameter), respectively. Finally, the $K_i$ was calculated from the $K_i^{app}$ by applying the competitive inhibition relationship (Equation 3)

$$K_i = K_i^{app} / (1 + [ATP]/K_m^{app}) \qquad \text{Equation 3}$$

where [ATP] is the concentration of ATP=25 µM, $K_m^{app}$ is the apparent ATP Michaelis constant=32.1 µM for JAK1, and $K_m^{app}$=11.7 µM for JAK2. By applying the tight-binding Equation 2 to account for any depletion of inhibitor, and the competitive-inhibition relationship Equation 3, the sensitivity of the assay can extend at least to a calculated K of 0.008 nM for JAK1 and 0.0015 nM for JAK2.

Kinase Selectivity

The in vitro kinase selectivity of test agents was assessed at a concentration of 1 µM in a panel of recombinant human kinase activity and binding assays, including cytoplasmic and receptor tyrosine kinases, serine/threonine kinases, and lipid kinases (SelectScreen® Kinase Profiling Services, ThermoFisher Scientific, Madison, Wis.). The kinase activity assays measure peptide phosphorylation (Z'-LYTE®) or ADP production (Adapta®) while the binding assays monitor displacement of ATP site binding probes (LanthaScreen®). The ATP concentrations used in the activity assays were typically within 2-fold of the experimentally determined apparent Michaelis constant ($K_m^{app}$) value for each kinase while the competitive binding tracer concentrations used in the binding assays were generally within 3-fold of the experimentally determined dissociation constant ($K_d$) values. Inhibitors were tested in duplicate against each kinase and the mean % Inhibition values are reported. For kinases that were inhibited by close to or greater than 50% at the initial 1-µM test concentration, 10-point inhibitor titrations using the same assays were carried out in order to determine the inhibitor concentrations that caused 50% inhibition ($IC_{50}$). The total JAK1 concentration used in this assay panel was 75 nM. If 100% of the 75 nM JAK1 protein were catalytically active, the limit of JAK1 inhibitor sensitivity from the vendor's JAK1 assay would theoretically be an $IC_{50}$ value of 37.5 nM (one-half of the total enzyme concentration). However, the SelectScreen® JAK1 assay generated JAK1 $IC_{50}$ values for several inhibitors that are much lower than 37.5 nM and which are in agreement with our internal determinations. Thus, the active JAK1 enzyme concentration in the SelectScreen® assay must be much lower than the total nominal JAK1 protein concentration of 75 nM used in the assay, and the observed sensitivity of this assay is much better than the theoretical sensitivity $IC_{50}$ limit of 37.5 nM.

Data Analysis

For fitting the data in concentration-kinase inhibition plots, the SelectScreen® Kinase Profiling Services used XFfit software (IDBS), Model No. 205 (sigmoidal concentration-response model), which is a four-parameter logistic fit model described by Equation 4

$$y = A + \{(B-A) \div [1 + (C \div x)^D]\} \qquad \text{Equation 4}$$

where x is the inhibitor concentration, y is the observed % inhibition, A is the minimum y-value, B is the maximum y-value, C is the $IC_{50}$ value, and D is the Hill slope. In certain cases, a three-parameter logistic fit was used. For example, if the plateau of the curve at infinitely low inhibitor concentration did not fit between −20% and 20% inhibition, that lower plateau was set to 0% inhibition, whereas if the plateau of the curve at infinite inhibitor concentration did not fit between 70% and 130% inhibition, that upper plateau was set to 100% inhibition.

TF-1 Cell Line Phospho-STAT JAK1 and JAK2 Pathway Selectivity Assays

TF-1 human erythroleukemia cells (ATCC®; Manassas, Va.; Catalog No. CRL-2003™) were grown in Roswell Park Memorial Institute (RPMI) medium supplemented with 10% heat-inactivated fetal bovine serum (FBS), 2 ng/mL granulocyte-macrophage colony-stimulating factor, 1×non-essential amino acids (NEAA), and 1 mM sodium pyruvate. The day before the assay, the cultures were transferred to Opti-MEM™, 1×NEAA, 1 mM sodium pyruvate, and 0.5% charcoal-stripped FBS (starve medium). Inhibitor stock solutions (5 mM in DMSO) were serially diluted 1:2 in DMSO to generate a 10-point concentration titration (at 500×test concentration), which was further diluted by a 50-fold dilution in Assay Medium (RPMI containing 1×NEAA and 1 mM sodium pyruvate) to generate a 10×concentration titration (in 2% DMSO). The cells (300,000 cells/well in 35 µL of Assay Medium) were seeded in 384-well Greiner plates. Diluted inhibitor at 10×concentration (5 µL) was added to the cells and the plates were incubated for 30 minutes at 37° C. in a humidified incubator. Cells were stimulated with the human recombinant cytokine at the respective $EC_{90}$ concentrations, as previously determined for each individual lot. For the phosphorylated signal transducer and activator of transcription 6 (P-STAT6) TF-1+ Interleukin-13 (IL-13) assay, 10 µL of 250 ng/mL IL-13 (R&D Systems; Minneapolis, Minn.) was added to the cells, which were then incubated for 10 minutes at 37° C. For the P-STAT5 TF-1+Erythropoietin (EPO) assay, 10 µL of 110

IU/mL EPO (Gibco Life Technologies, Catalog No. PHC2054) was added to the cells, which were then incubated for 30 min at 37° C. For both assays, the incubation was followed by addition to the cells of 5 µL of ice-cold 10× cell lysis buffer (Cell Signaling Technologies; Danvers, Mass.; Catalog No. 9803S) containing 1 mM phenylmethylsulfonyl fluoride (PMSF). Assay plates were frozen at −80° C. for a minimum of 1 hour. In the IL-13 assay, P-STAT6 was measured by coating goat anti-rabbit (GAR) plates (Meso Scale Discovery [MSD]; Rockville, Md.; Catalog No. MSD L21RA-1) with rabbit anti-human total STAT6 antibody (Cell Signaling Technologies; Catalog No. 9362S), incubating the cell lysates in the coated plates overnight at 4° C., and then detecting with mouse anti-P-STAT6 (Tyr641) Clone 16E12 antibody (MilliporeSigma; Burlington, Mass.; Catalog No. 05-590, custom labeled by MSD with SULFO-tag) using standard MSD plate processing, washing, and detection protocols. In the EPO assay, P-STAT5 was detected using the phospho-STAT5a,b Whole Cell Lysate Kit (MSD; Catalog No. K150IGD-1). The electrochemiluminescence (ECL) signal of wells was read on the MESO SECTOR S600 (MSD) reader.

Data Analysis

Data analysis was performed by subtracting the negative control (cytokine stimulated and 20 µM control inhibitor-treated cells) mean ECL value from the ECL value of all wells, determining percent of control for test compound well ECL values relative to the positive control (cytokine stimulated and DMSO-treated cells) mean ECL value, and determining the $IC_{50}$ for test compounds with a four-parameter logistic fit model as shown in Equation 4.

P-STAT6 BEAS-2B+IL-13 Cell Assay

In order to study the effect of JAK1 inhibitors in a cell line that is relevant to the cell biology of human asthma, an IL-13-stimulated STAT6 phosphorylation assay in the human lung bronchial epithelial BEAS-2B cell line was developed.

BEAS-2B cells (ATCC® CRL-9609™) were grown in Bronchial Epithelial Growth Medium (BEGM) (Lonza Catalog No. CC-3170; Walkersville, Md.; or PromoCell Catalog No. C-21060; Heidelberg, Germany). Test compound stock solutions (0.5 mM in DMSO) were serially diluted 1:2 in DMSO to generate a 10-point concentration curve (at 500×test concentration), which was further diluted by a 50-fold dilution step in BEGM to generate a 10× concentration curve (in 2% DMSO). Cells were plated at 100,000 cells/well in 200 µL of BEGM in 96-well plates and incubated for 48 hours at 37° C. in a humidified incubator. Medium was aspirated from the cells and replaced with 70 µL of fresh BEGM. Diluted test compound (10 µL; or 2% DMSO in assay medium) was added to the cells, and the plates were incubated for 1 hour at 37° C. in a humidified incubator. Twenty µL of 250 ng/mL human recombinant IL-13 (Bio Techne Catalog No. 213-ILB) was then added to the cells and incubated for 15 minutes at 37° C. Medium was aspirated from the cells and 60 µL of ice-cold 1×cell lysis buffer (Cell Signaling Technologies; Catalog No. 9803S) containing 1 mM PMSF was added to the cells. Assay plates were incubated at −80° C. for at least 1 hour. P-STAT6 was measured by coating GAR plates (MSD; Catalog No. L45RA-1) with rabbit anti-human total STAT6 antibody (Cell Signaling Technologies; Catalog No. 9362S), incubating the cell lysates in the coated plates overnight at 4° C., and then detecting with mouse anti-phospho-STAT6 (Tyr641) Clone 16E12 antibody (Millipore; Catalog No. 05-590, custom labeled by MSD with SULFO-tag) using standard MSD plate processing, washing, and detection protocols. Plates were read on the MESO SECTOR S600.

Data Analysis

Data analysis was performed by subtracting negative control values from all wells and determining percent of control using the positive control values; the $IC_{50}$ was determined with a four-parameter logistic fit model as shown in Equation 4.

Cell Cytotoxicity Assays

A549 (ATCC® CCL-185™), Jurkat clone E6-1 (ATCC® TIB-152™) and HEK-293T (ATCC® CRL-1573™) cells maintained at a sub-confluent density in T175 flasks were used. Cells in exponential growth phase were plated (450 cells in 45 µL of medium) in Greiner 384-well black/clear tissue culture treated plates (Greiner Catalog No. 781091). After dispensing cells, plates were allowed to equilibrate at room temperature for 30 minutes, after which time the cell plates were placed overnight in a 37° C. $CO_2$ and humidity-controlled incubator. The following day, cells were treated with test agent diluted in 100% DMSO (0.5% final DMSO concentration on cells) with a 10-point titration and a top concentration of 50 µM. Cells and compounds were then incubated for 72 hours in a 37° C. $CO_2$ and humidity-controlled incubator, after which time cell viability was measured by adding CellTiter-Glo® (Promega G7572) reagent to all wells. Plates were incubated at room temperature for 20 minutes and then the well luminescence was read on an EnVision plate reader (Perkin Elmer Life Sciences).

Data from the above JAK1 and JAK2 assays for the compounds of Table 1 are shown in Table 2 below.

TABLE 2

| | Enzyme JAK1 Ki (nM) | Enzyme JAK2 Ki (nM) | Cellular JAK1 PSTAT6 BEAS2B + IL13 $IC_{50}$ (nM) | Cellular JAK1 PSTAT6 TF-1 + IL13 $IC_{50}$ (nM) | Cellular JAK2 PSTAT5 TF-1 + EPO $IC_{50}$ (nM) | LC/MS method | Ret. Time (min) | m/z |
|---|---|---|---|---|---|---|---|---|
| 1 | 0.56 | 0.25 | 31 | 6.3 | 12 | D | 2.44 | 491.2 |
| 2 | 0.5 | 0.2 | 15 | 14 | 12 | A | 1.53 | 503.2 |
| 3 | 2 | 0.66 | 58 | | | A | 1.15 | 518.3 |
| 4 | 1.4 | 0.6 | 180 | | | A | 1.13 | 504.2 |
| 5 | 0.43 | 0.19 | 35 | 16 | 29 | A | 1.27 | 493.2 |
| 6 | 0.48 | 0.22 | 18 | | | A | 1.42 | 477.2 |
| 7 | 0.88 | 0.49 | 32 | 21 | 22 | A | 1.13 | 520.3 |
| 8 | 0.82 | 0.48 | 92 | | | A | 1.12 | 492.2 |
| 9 | 0.27 | 0.18 | 15 | | | A | 1.56 | 499.2 |
| 10 | 0.95 | 0.6 | 52 | | | A | 1.15 | 518.3 |
| 11 | 0.21 | 0.12 | 17 | | | A | 1.52 | 541.3 |
| 12 | 0.24 | 0.14 | 18 | 8.7 | 9.1 | A | 1.65 | 555.3 |

TABLE 2-continued

|    | Enzyme JAK1 Ki (nM) | Enzyme JAK2 Ki (nM) | Cellular JAK1 PSTAT6 BEAS2B + IL13 IC$_{50}$ (nM) | Cellular JAK1 PSTAT6 TF-1 + IL13 IC$_{50}$ (nM) | Cellular JAK2 PSTAT5 TF-1 + EPO IC$_{50}$ (nM) | LC/MS method | Ret. Time (min) | m/z |
|----|------|-------|------|------|------|---|------|-------|
| 13 | 0.4  | 0.19  | 33   | 34   | 28   | D | 2.1  | 505.2 |
| 14 | 0.49 | 0.22  | 23   |      |      | A | 1.4  | 507.2 |
| 15 | 0.43 | 0.16  | 20   |      |      | T | 0.94 | 507.2 |
| 16 | 0.32 | 0.19  | 15   |      |      | A | 1.47 | 526.3 |
| 17 | 0.22 | 0.1   | 14   |      |      | A | 1.36 | 463.1 |
| 18 | 0.43 | 0.4   | 290  |      |      | B | 2.14 | 568.2 |
| 19 | 4    | 1.7   | 120  |      |      | A | 1.15 | 532.3 |
| 20 | 1.5  | 0.65  | 65   |      |      | A | 1.16 | 532.3 |
| 21 | 0.22 | 0.16  | 14   |      |      | A | 1.49 | 504.3 |
| 22 | 0.46 | 0.19  | 23   | 4.6  | 14   | A | 1.47 | 489.2 |
| 23 | 0.26 | 0.13  | 14   | 20   | 22   | A | 1.33 | 507.2 |
| 24 | 0.46 | 0.19  | 30   |      |      | A | 1.33 | 507.2 |
| 25 | 0.48 | 0.2   | 20   | 20   | 39   | A | 1.33 | 507.2 |
| 26 | 0.16 | 0.097 | 11   |      |      | A | 1.39 | 478.2 |
| 27 | 0.59 | 0.26  | 99   |      |      | A | 1.13 | 546.2 |
| 28 | 0.24 | 0.14  | 9.5  | 3.1  | 26   | A | 1.43 | 488.2 |
| 29 | 0.58 | 0.37  | 25   |      |      | A | 1.61 | 524.1 |
| 30 | 0.22 | 0.14  | 11   |      |      | D | 2.47 | 492.1 |
| 31 | 0.84 | 0.38  | 51   |      |      | B | 2.2  | 464.1 |
| 32 | 1.1  | 0.62  | 120  |      |      | B | 2.41 | 533.2 |
| 33 | 0.4  | 0.23  | 99   |      |      | B | 2.41 | 533.2 |
| 34 | 0.31 | 0.29  | 21   |      |      | A | 1.68 | 535.2 |
| 35 | 0.3  | 0.19  | 24   | 5.8  | 14   | X | 3.96 | 529.2 |
| 36 | 1.8  | 1.1   |      | 71   | 120  | U | 2.22 | 532.1 |
| 37 | 0.69 | 0.54  | 46   | 51   | 38   | U | 2.22 | 532.1 |
| 38 | 0.34 | 0.25  | 89   |      |      | X | 3.98 | 573.2 |
| 39 | 1.5  | 0.53  | 230  |      |      | X | 4.33 | 533.1 |
| 40 | 0.21 | 0.11  | 24   | 3.1  | 6.4  | X | 4.67 | 525.1 |
| 41 | 0.18 | 0.1   | 37   | 15   | 34   | X | 3.71 | 515.1 |
| 42 | 0.42 | 0.24  | 30   | 2.6  | 21   | X | 4.15 | 526.1 |
| 43 | 0.5  | 0.27  | 1000 |      |      | X | 3.75 | 542.1 |
| 44 | 0.52 | 0.34  | 29   | 14   | 15   | X | 3.18 | 556.1 |
| 45 | 0.71 | 0.35  | 35   | 10   | 38   | D | 2.49 | 514.1 |
| 46 | 0.26 | 0.087 | 49   | 27   | 61   | B | 2.19 | 490.1 |
| 47 | 0.31 | 0.33  | 210  |      |      | X | 2.98 | 558.2 |
| 48 | 0.52 | 0.39  | 130  |      |      | X | 3.11 | 572.2 |
| 49 | 0.5  | 0.37  | 28   | 20   | 34   | X | 3.02 | 586.2 |
| 50 | 1.7  | 1.9   | 50   | 27   | 160  | X | 2.97 | 546.2 |
| 51 | 0.39 | 0.21  | 100  |      |      | X | 3.82 | 530.1 |
| 52 | 2.2  | 1     | 96   |      |      | X | 3    | 544.2 |
| 53 | 0.94 | 0.19  | 50   |      |      | X | 3.07 | 598.2 |
| 54 | 1.2  | 0.21  | 140  |      |      | X | 3.1  | 641.2 |
| 55 | 0.93 | 0.98  | 71   |      |      | X | 3.19 | 624.2 |
| 56 | 0.71 | 0.76  | 56   |      |      | X | 3.16 | 626.2 |
| 57 | 0.57 | 0.54  | 54   |      |      | X | 3.15 | 626.2 |
| 58 | 0.89 | 0.86  | 40   | 24   | 32   | X | 3.12 | 600.2 |
| 59 | 0.53 | 0.54  | 32   | 13   | 28   | X | 3.09 | 600.2 |
| 60 | 1.1  | 2.5   | 44   | 24   | 170  | X | 3.06 | 572.2 |
| 61 | 0.81 | 0.77  | 34   | 190  | 200  | X | 3.06 | 584.2 |
| 62 | 2    | 0.93  | 150  |      |      | X | 3.83 | 592.1 |
| 63 | 0.58 | 0.28  | 71   |      |      | X | 3.53 | 507.1 |
| 64 | 1.9  | 0.84  | 210  |      |      | X | 3.8  | 592.2 |
| 65 | 0.72 | 0.24  | 72   |      |      | X | 3.66 | 529.1 |
| 66 | 0.55 | 0.18  | 380  |      |      | X | 3.5  | 515.1 |
| 67 | 0.48 | 0.24  | 25   |      |      | X | 2.97 | 527.1 |
| 68 | 0.6  | 0.25  | 62   |      |      | X | 3.78 | 521.2 |
| 69 |      |       | 77   |      |      | X | 3.72 | 521.2 |
| 70 | 1    | 0.33  | 75   |      |      | X | 3.79 | 521.2 |
| 71 | 1.4  | 0.46  | 110  |      |      | X | 3.78 | 521.2 |
| 72 | 0.94 | 1.5   | 31   |      |      | X | 2.89 | 546.2 |
| 73 | 0.63 | 0.21  | 53   |      |      | A | 1.32 | 522.2 |

As can be seen from Table 2, the compounds of the invention are all highly active in the biochemical JAK1 and JAK2 assays as well as, in most instances, one or more of the cell-based assays for JAK1 and JAK2. Several of the compounds are substantially equipotent for JAK1 and JAK2.

Table 3 below provides mouse lung tissue binding (LTB) data (% bound) and cytotoxicity data for selected compounds of Table 1.

TABLE 3

| | Mouse LTB % | Cytotox K-293 EC$_{50}$ (µM) | Cytotox Jurkat EC$_{50}$ (µM) | Cytotox A549 EC$_{50}$ (µM) |
|---|---|---|---|---|
| 2 | 88.1 | 27.5 | 38.5 | 25.5 |
| 5 | 80.1 | 10.2 | 23 | 45.5 |
| 6 | | 6.05 | 21.5 | 6.75 |
| 7 | 78.8 | 6.9 | 2.1 | 4.1 |
| 9 | | 2.2 | 3.5 | 1.66 |
| 11 | | 3.7 | 5.5 | 6.4 |
| 12 | 97.1 | 36 | 50 | 50 |
| 13 | 85 | 31 | 50 | 44 |
| 14 | 80.1 | 32 | 50 | 50 |
| 15 | 85.7 | 25 | 35 | 25 |
| 16 | 87.3 | 7.6 | 6.2 | 7.4 |
| 17 | 85.8 | 7.3 | 11 | 8.7 |
| 21 | 83 | 4.8 | 11 | 7.5 |
| 22 | 88.7 | 43 | 50 | 50 |
| 23 | 82.1 | 11 | 24 | 28 |
| 24 | 81.7 | 22 | 37 | 50 |
| 25 | 85 | 48 | 50 | 50 |
| 26 | 86.9 | 5.8 | 12 | 11 |
| 28 | 70.8 | 24 | 39 | 50 |
| 30 | 83.1 | 2.4 | 9.2 | 6.1 |
| 35 | 86.2 | 17 | 21 | 22 |
| 37 | 90.1 | 31 | 50 | 50 |
| 40 | 95.6 | 50 | 50 | 50 |
| 41 | 91.2 | 28 | 35 | 50 |
| 44 | 86.5 | 7 | 11 | 24 |
| 45 | 87.9 | 50 | 50 | 50 |
| 46 | 89.9 | 50 | 50 | 50 |
| 48 | 91.3 | | | |
| 49 | 84.4 | 14 | 24 | 33 |
| 68 | | 19 | 32 | 50 |
| 56 | 91.4 | 10 | 24 | 50 |
| 59 | | 14 | 30 | 43 |
| 63 | 80.5 | 20 | 35 | 50 |
| 69 | 78.4 | | | |
| 72 | | 20 | 49 | 50 |
| 73 | 81.8 | 2.9 | 8.4 | 50 |

From the data in Table 3, it was discovered that 1-methy 1-pyrazole compounds (i.e., R$^1$ in Formulas (I)-(III) is methyl) have surprisingly lower cytotoxicity across K-293, Jurkat and A549 cell line assays when compared to the corresponding desmethyl (R$^1$ is hydrogen) analogs. Table 4 below provides comparisons of methyl-desmethyl analog pairs (R$^1$=methyl vs R$^1$=hydrogen) for Examples 6, 9 and 17 of Tables 1 and 2.

TABLE 4

| | | Cytotox K-293 EC50 (µM) | Cytotox Jurkat EC50 (µM) | Cytotox A549 EC50 (µM) |
|---|---|---|---|---|
| Example 6 in Table 1. | | 6.05 | 21.5 | 6.75 |
| Example. 192 in WO2017089390 | | 0.436667 | 0.79 | 2.366667 |

TABLE 4-continued
| | | Cytotox K-293 EC50 (μM) | Cytotox Jurkat EC50 (μM) | Cytotox A549 EC50 (μM) |
|---|---|---|---|---|
| Example 9 in Table 1. | 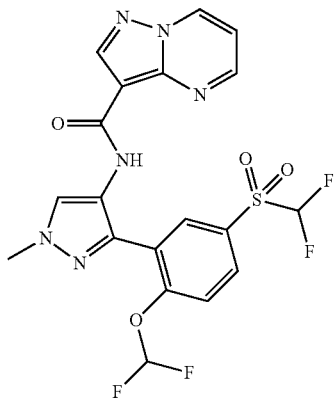 [SMILES: Cn1cc(NC(=O)c2cnn3cccnc23)c(-c2cc(S(=O)(=O)C(F)F)ccc2OC(F)F)n1] | 2.2 | 3.5 | 1.66 |
| | 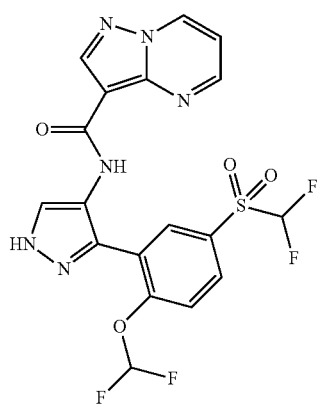 [SMILES: O=C(Nc1c[nH]nc1-c1cc(S(=O)(=O)C(F)F)ccc1OC(F)F)c1cnn2cccnc12] | 0.038 | 0.16 | 0.26 |
| Example 17 in Table 1 | 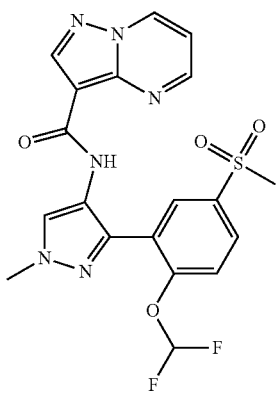 | 7.3 | 11 | 8.7 |

TABLE 4-continued

| | | Cytotox K-293 EC50 (μM) | Cytotox Jurkat EC50 (μM) | Cytotox A549 EC50 (μM) |
|---|---|---|---|---|
| Example 4 in WO201708 9390 | 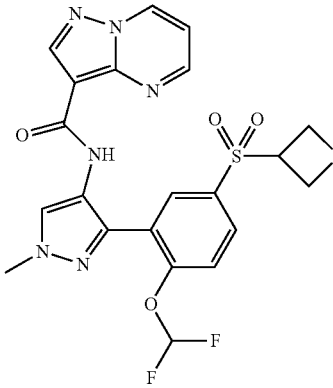 | 2.1 | 6.2 | 22 |

From the data in Table 3, it was also discovered that the sulfone compounds of the invention exhibit surprisingly improved lung tissue binding when compared to corresponding sulfide analogs. Table 5 below provides comparisons of sulfone-sulfide analog pairs ($R^1$=methyl vs $R^1$=hydrogen) for Examples 13, 28 and 35 of Tables 1 and 2

TABLE 5

| | | Lung tissue binding, % |
|---|---|---|
| Example 13 in Table 1 | | 85.8 |
| | | 97.4 |
| Example 28 in Table 1 | | 70.8 |
| | | 96.9 |

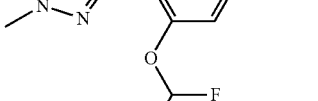

TABLE 5-continued

| | Lung tissue binding, % |
|---|---|
| Example 35 in Table 1 | 86.2 |
| | 97 |

The sulfone compounds of the invention also exhibit lower LogD, and increased kinetic solubility compared to the corresponding sulfide analogs.

From the data in Tables 2 and 3, it was also discovered that compounds of the invention wherein $R^1$ is methyl and $R^2$ is hydroxy alkyl or alkoxy alkyl exhibit good, balanced affinity for both JAK1 and JAK2, and also have relatively low lung tissue binding and cytotoxicity.

Animal Models

Mouse House Dust Mite (HDM) Model

Seven to eight week old female C57BL/6J mice purchased from Jackson West. Mice are immunized on day 0 & 14 with intraperitoneal administration of House Dust Mite (HDM, D. *Pteronyssinus*, purchased from Greer Laboratories, normalized to 0.918 ug DerP1 content per mouse) mixed with 2 mg of alum (Thermo Scientific) diluted in sterile PBS. On days 21 & 24, mice were challenged with HDM (again normalized for 0.918 ug DerP1 content) in PBS, dosed by intra-tracheal inhalation. Prior to each inhaled HDM challenge (and in a subset of groups, also on days 22 & 23), animals receive test compound via nose-only inhalation (using dry powder inhalation equipment from Electro-Medical Measurement Systems (EMMS), including a Wright dust feeder and a 4-layer/24-port or 2-layer/12-port, directed flow, nose-only inhalation tower) ending 1 hour prior to challenge. Control animals receive air-only nose only inhalation. 24 horns after the final treatment, mice are bled retro-orbitally for plasma PK, and then euthanized by CO2 inhalation. Post-euthanasia, BAL fluid is collected for total (by FACS, using a known quantity of spike-in reference beads) and differential (by Wright Giemsa-stained cytospin) cell counts. Lungs and spleens are collected, weighed, and frozen for PK. There were 5 or 6 animals per group.

In addition, to validate lung-delivered dose, PK satellite groups of 3 naïve animals each are dosed with test compound via nose-only inhalation for a single day or for four consecutive days. Directly after the final inhalation dosing, PK satellite animals are bled retro-orbitally for plasma PK, and then euthanized by $CO_2$ inhalation. Lungs and spleens are collected and weighed for PK analysis.

Rat OVA Model

Six week old male Brown Norway rats from Charles River-Kingston. Rats are immunized on day 0 with intraperitoneal administration of 150 ug OVA (Sigma) mixed with 40 mg of alum (Thermo Scientific) diluted in sterile PBS. 28 days after sensitization, rats are challenged with 2% OVA in PBS aerosolized via a nebulizer for 30 minutes for three consecutive days. Prior to each OVA challenge, animals receive JAK1/JAK2 test compound via nose-only inhalation (using dry powder inhalation equipment from Electro-Medical Measurement Systems (EMMS), including a Wright dust feeder and a 4-layer, 24-port, directed flow, nose-only inhalation tower) ending 1 horn prior to challenge. Control animals receive either MCT buffer orally, or air-only nose only inhalation. 24 horns after the final treatment, rats are euthanized by $CO_2$ inhalation. They are bled from the abdominal aorta for plasma PK and whole blood FACS analysis. Post-euthanasia, BAL fluid is collected for total (by FACS, using a known quantity of spike-in reference beads) and differential (by Wright Giemsa-stained cytospin) cell counts. Lungs are collected, weighed, and frozen for PK. Spleens are weighed and cut in half for PK and for FACS analysis. Blood and spleen samples are analyzed by FACS for total cell counts and % NK cells (CD161a positive). There are 6 animals per group, except for the naïve control group, which contains 5 animals.

In addition, to validate lung-delivered dose, PK satellite groups of 3 naïve animals each received JAK1/JAK2 test compound via nose-only inhalation for a single day or for three days. Directly after the final inhalation dosing, PK satellite animals are euthanized by $CO_2$ inhalation. They are bled from the abdominal aorta for plasma PK. Lungs and spleens wae collected and weighed for PK analysis.

Plasma and lung levels of test compounds and ratios thereof are determined in the following manner. BALB/c mice from Charles River Laboratories are used in the assay. Test compounds are individually formulated in 0.2% Tween 80 in saline and the dosing solution is introduced into the trachea of a mouse by oral aspiration. At various time points (typically 0.167, 2, 6, 24 hr) post dosing, blood samples are removed via cardiac puncture and intact lungs are excised from the mice. Blood samples are centrifuged (Eppendorf centrifuge, 5804R) for 4 minutes at approximately 12,000 rpm at 4° C. to collect plasma. Lungs are padded dry, weighed, and homogenized at a dilution of 1:3 in sterile water. Plasma and lung levels of test compound are determined by LC-MS analysis against analytical standards constructed into a standard curve in the test matrix. A lung to plasma ratio is determined as the ratio of the lung AUC in micro g hr/g to the plasma AUC in micro g hr/mL, where AUC is conventionally defined as the area under the curve of test compound concentration vs. time.

Pharmacokinetics in Plasma and Lung in Mouse

The pharmacokinetics of a compound is determined in female Balb/c mice following administration of a target dose of 0.3 mg/kg formulated in 0.2% Tween 80 in saline by single intra-nasal (IN) bolus solution/suspension administration. 7-8 Week old female Balb/c mice may be purchased from Charles River. Mice are housed under specific pathogen-free conditions until used in a study.

Animals are not fasted before dosing. Blood samples are taken from 3 animals per time-point at 0.083, 2, 7 and 24 hours post-dose, under anesthesia (intraperitoneal injection of pentobarbitone), via cardiac puncture into EDTA-coated microtainers. Blood samples are centrifuged (1500 g, 10 min at 4° C.) to separate plasma. Plasma samples frozen at approximately −80° C. After intra-nasal dosing, prior to lung perfusion, the spleens are removed, weighed and snap frozen. Following confirmation of death, the lungs of the dosed animals are perfused with chilled PBS to remove residual blood from the pulmonary vasculature. The lungs are then excised and weighed (all weights recorded). All tissue samples are frozen by immersion in liquid nitrogen. Tissue samples are stored frozen (ca. −80° C.) until analysis.

Prior to PK analysis defrosted tissue samples (spleen and lung) are weighed and homogenised following the addition of 4 mL HPLC grade water for each gram of tissue, using an Omni-Prep Bead Ruptor (Omni Inc., Kennesaw, Ga.) at 4° C. Plasma and tissue homogenate samples are extracted using protein precipitation with four volumes of acetonitrile containing Tolbutamide (200 ng/mL) or Labetalol (100 ng/mL) as internal standard. Samples are mixed and centrifuged at 3200 g and 4° C. for 30 minutes to remove precipitated proteins, and the supernatant diluted appropriately (e.g. 1:1, v/v) with HPLC grade water in a 96-well plate. Representative aliquots of plasma, spleen and lung samples are assayed for compound concentrations by LC-MS/MS in positive ion mode using a Waters Xevo TQ-S (Waters, Elstree, UK) against matrix matched calibration curves and quality control standards. The standards are prepared by spiking aliquots of control plasma, spleen and lung tissue homogenate with compound and extracted as described for the experimental samples. The assay limit of detection 0.168 mg/mL-4000 ng/mL in all matrices. Concentrations below the lower limit of quantitation (LLOQ) are treated as zero for the calculation of mean and SD. Mean concentrations measured in samples are used to construct semi-logarithmic concentration-time curve profiles. Pharmacokinetic (PK) analysis is performed using non-compartmental methods in Biobook (E-WorkbookIDBS).

Murine Model of *Alternaria alternata*-Induced Eosinophilic Inflammation of the Lung Airway eosinophilia is a hallmark of human asthma. *Alternaria alternata* is a fungal aeroallergen that can exacerbate asthma in humans and induces eosinophilic inflammation in the lungs of mice (Havaux et al. Clin Exp Immunol. 2005, 139(2): 179-88). In mice, it has been demonstrated that *alternaria* indirectly activates tissue resident type 2 innate lymphoid cells in the lung, which respond to (e.g. IL-2 and IL-7) and release JAK-dependent cytokines (e.g. IL-5 and IE-13) and coordinate eosinophilic inflammation (Bartemes et al. J Immunol. 2012, 188(3): 1503-13).

Seven- to nine-week old male C57 mice from laconic are used in the study. On the day of study, animals are lightly anesthetized with isoflurane and administered either vehicle or test compound via oropharyngeal aspiration. Animals are placed in lateral recumbency post dose and monitored for full recovery from anesthesia before being returned to their home cage. One hour later, animals are once again briefly anesthetized and challenged with either vehicle or *Alternaria* extract via oropharyngeal aspiration before being monitored for recovery from anesthesia and returned to their home cage. Forty-eight hours after *alternaria* administration, bronchoalveolar lavage fluid (BALE) is collected and eosinophils are counted in the BALE using the Advia 120 Hematology System (Siemens).

Compound activity in the model is evidenced by a decrease in the level of eosinophils present in the BALE of treated animals at forty-eight hours compared to the vehicle treated, *Alternaria* challenged control animals. Data are expressed as percent inhibition of the vehicle treated, *alternaria* challenged BALE eosinophils response. To calculate percent inhibition, the number of BALE eosinophils for each condition is converted to percent of the average vehicle treated, *alternaria* challenged BALE eosinophils and subtracted from one-hundred percent.

What is claimed is:

1. A compound or a stereoisomer thereof, wherein the compound, or stereoisomer thereof, is selected from the group consisting of:

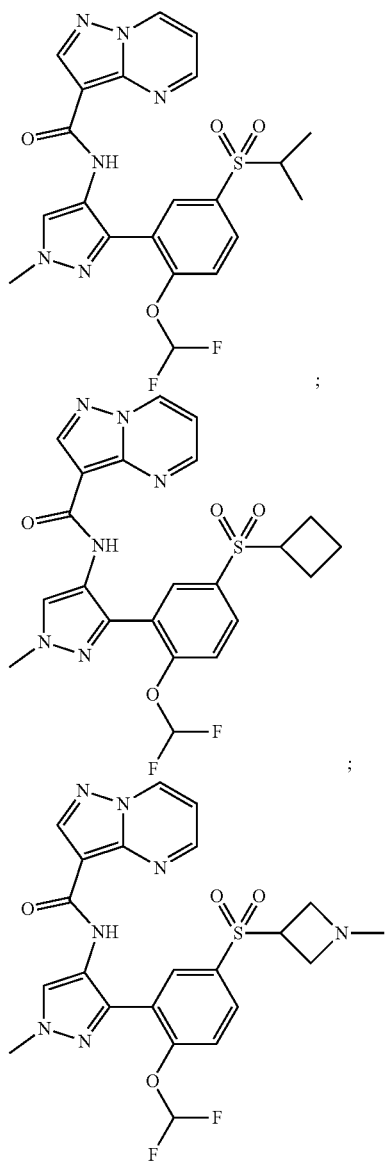

207
-continued
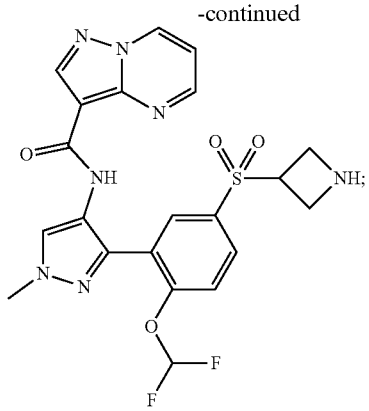
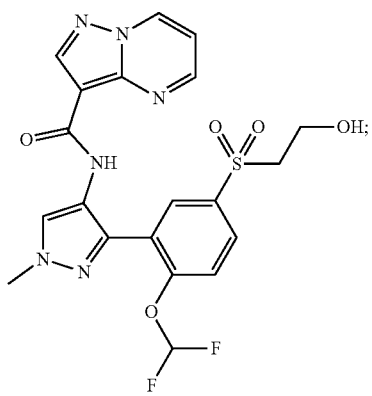
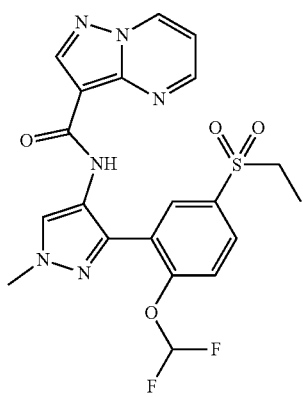
208
-continued
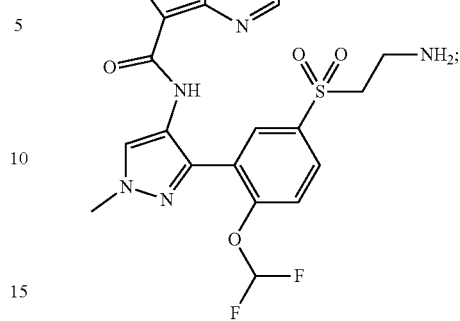
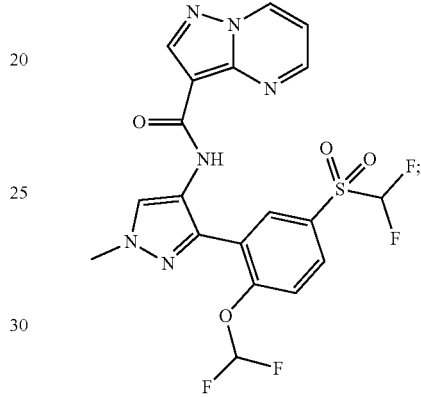
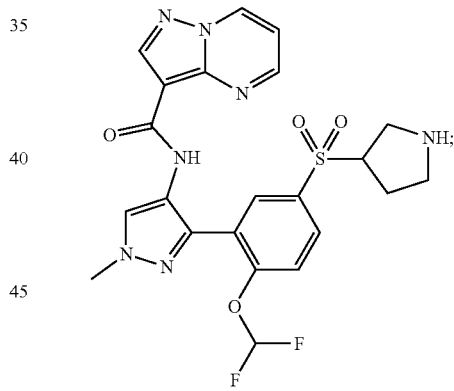
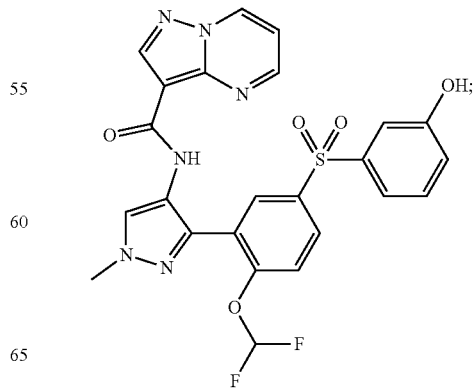

209
-continued
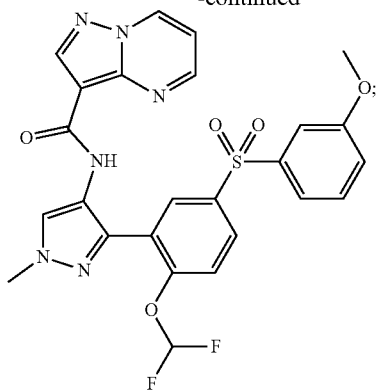
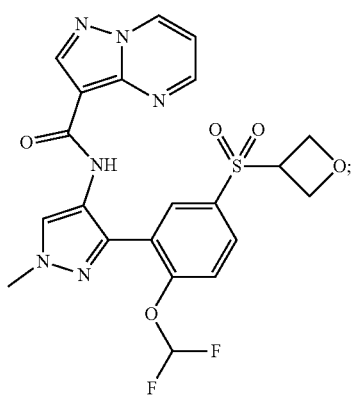
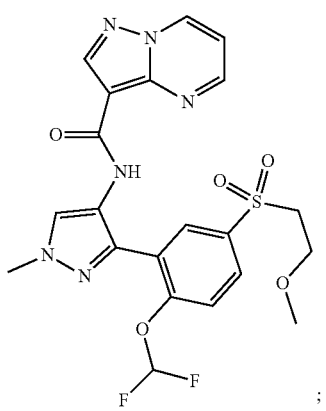
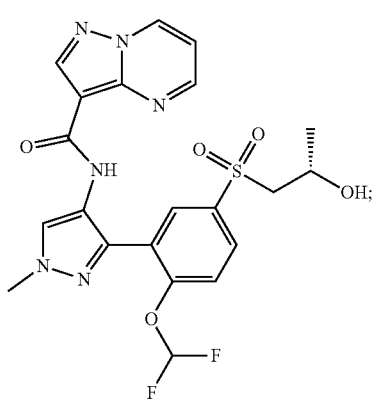
210
-continued
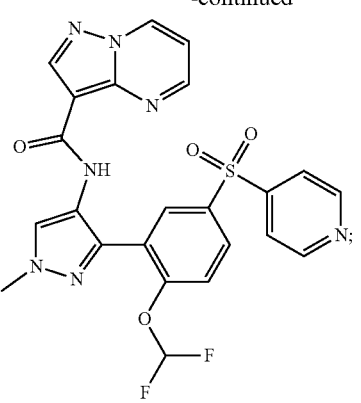
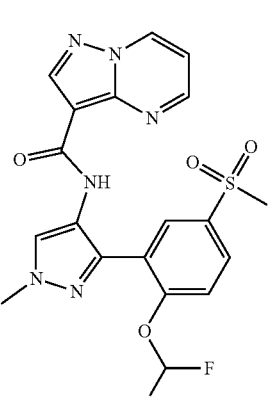
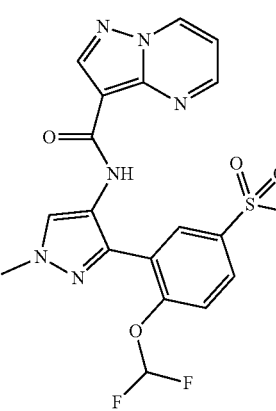
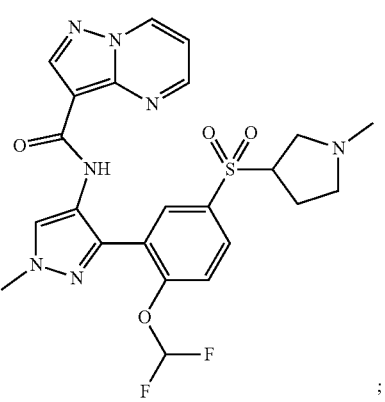

211
-continued
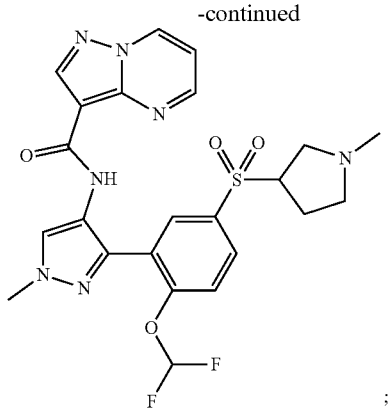
;
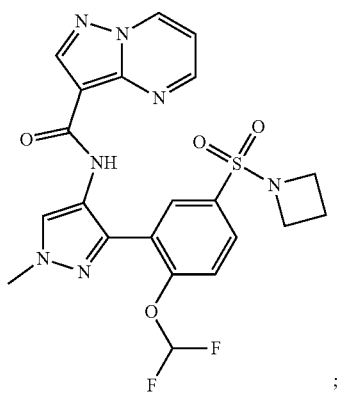
;
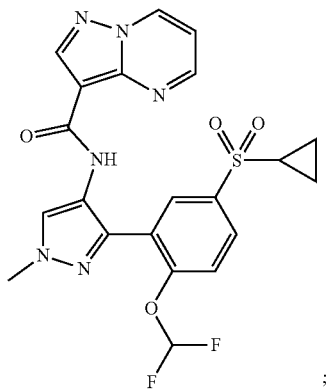
;
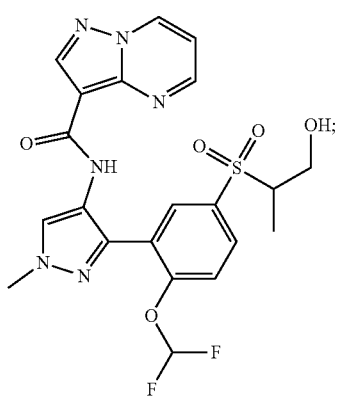
212
-continued
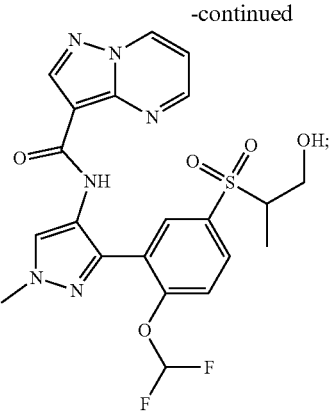
;
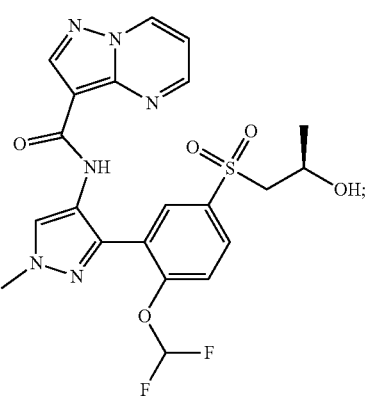
;
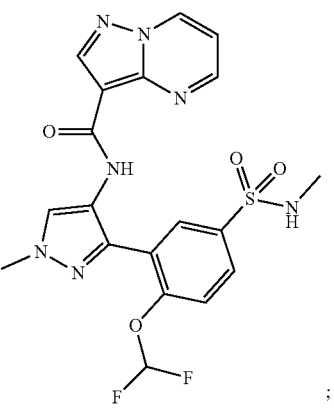
;
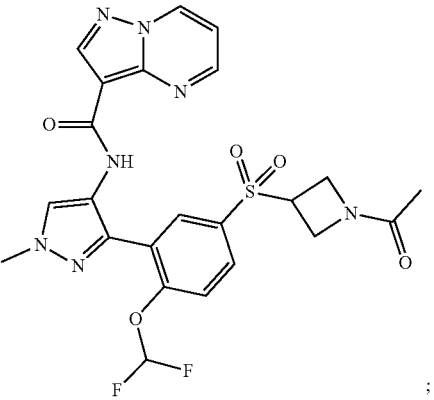
;

213
-continued
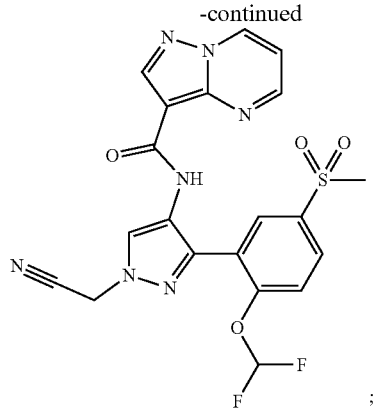
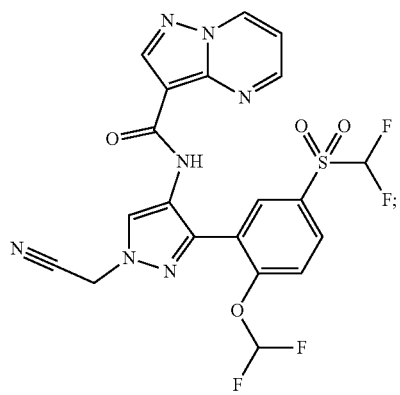
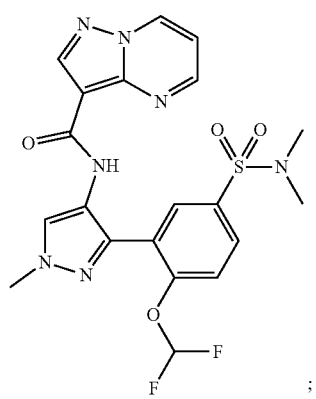
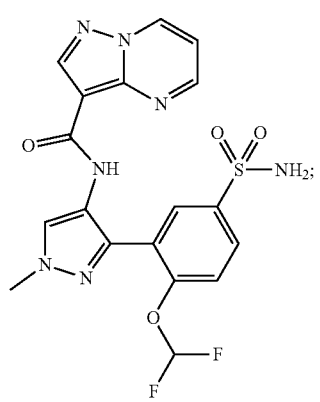
214
-continued
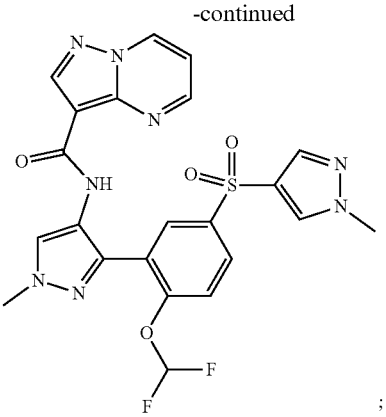
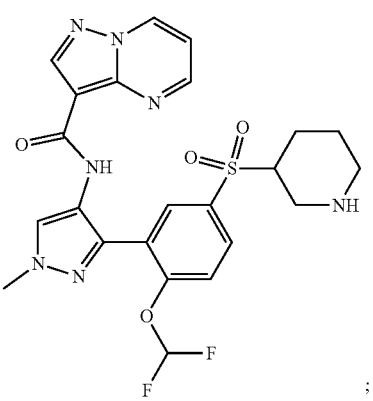
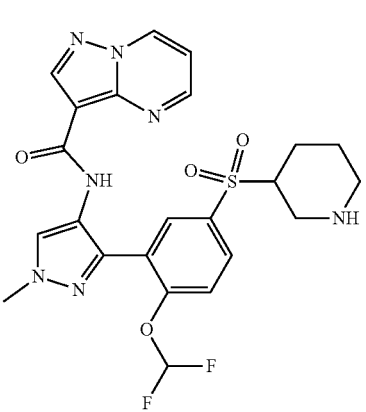
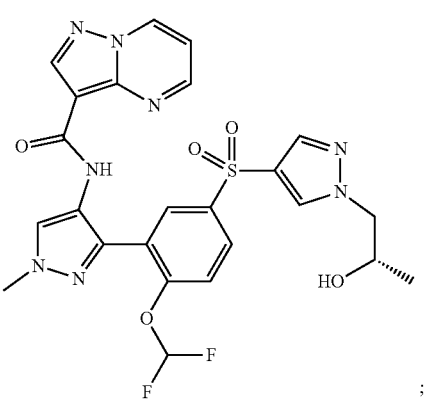

215
-continued
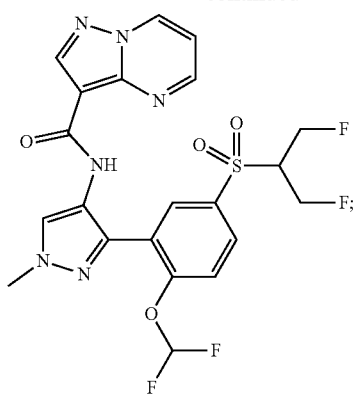
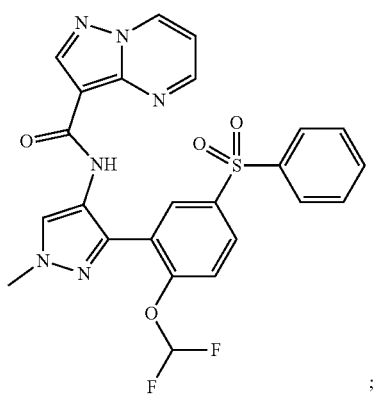
;
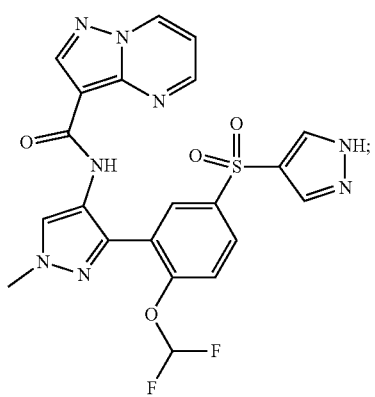
;
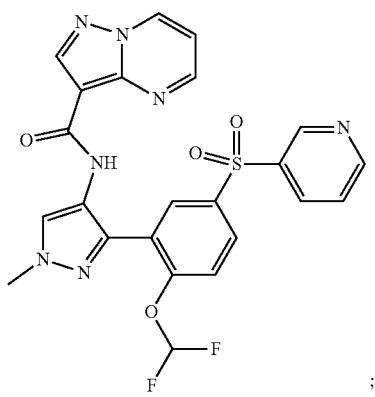
;
216
-continued
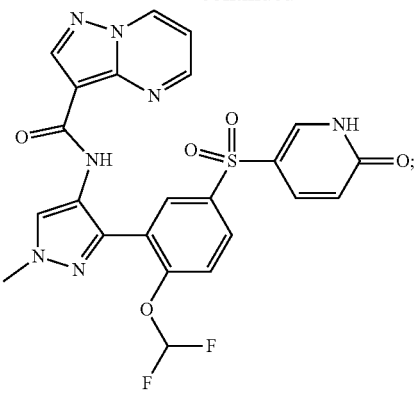
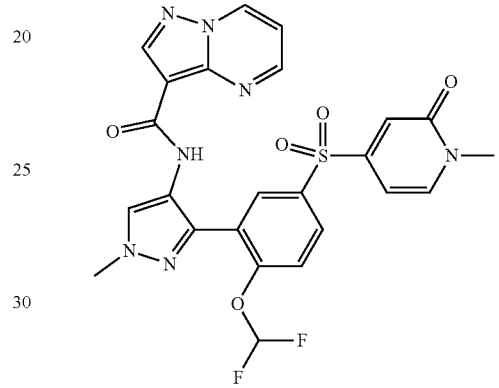
;
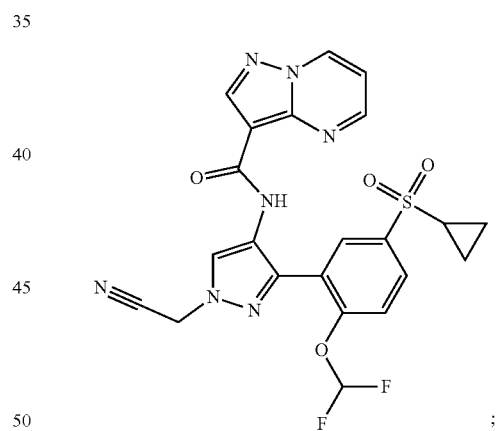
;
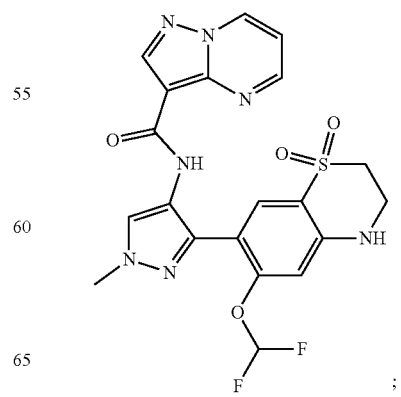
;

217
-continued
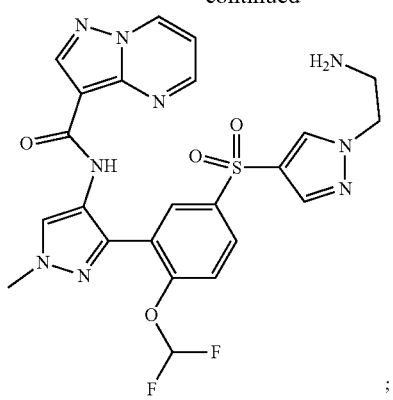
;
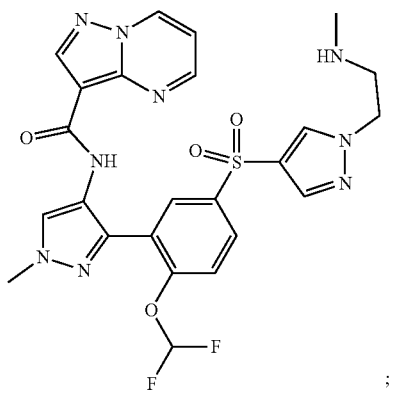
;
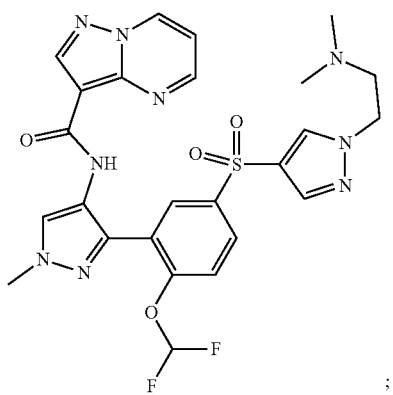
;
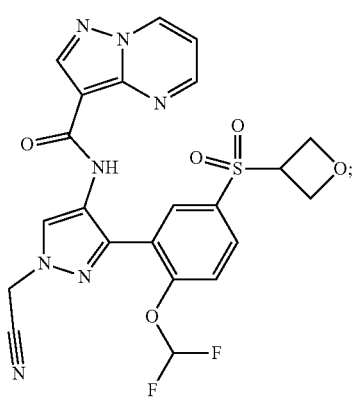
;
218
-continued
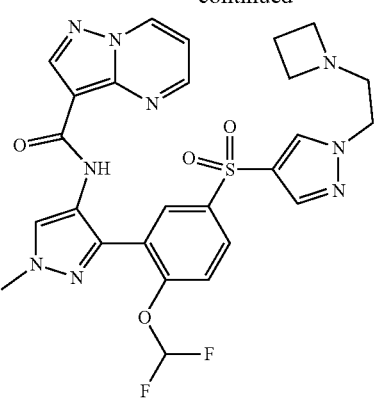
;
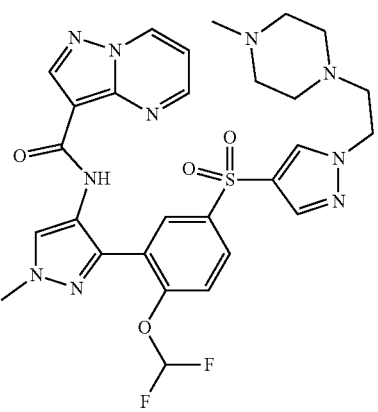
;
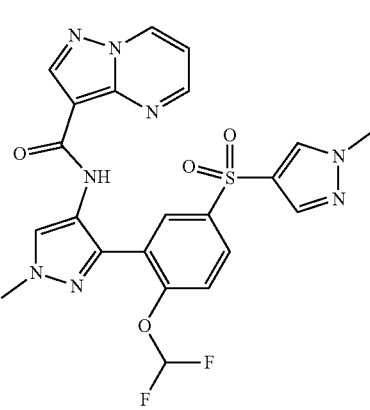
;
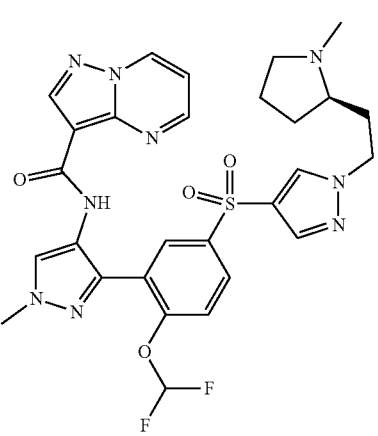
;

219
-continued
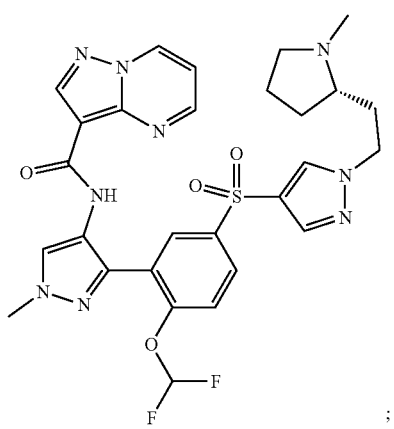
;
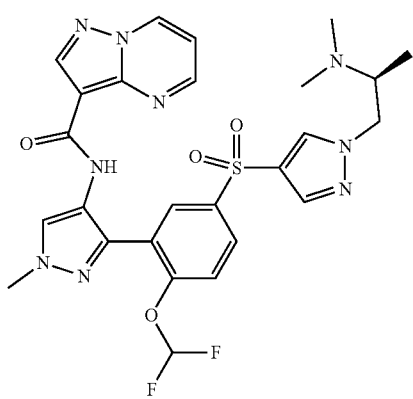
;
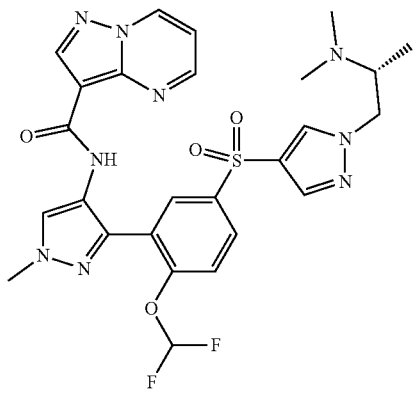
;
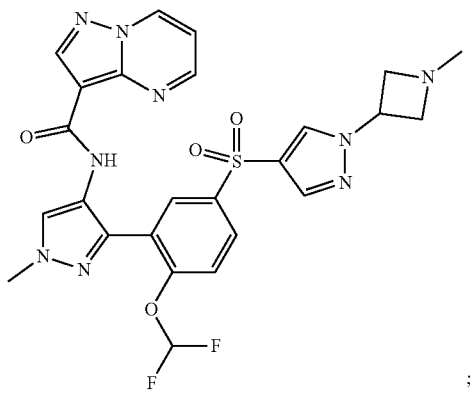
;
220
-continued
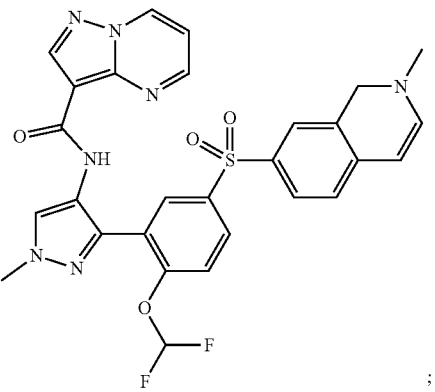
;
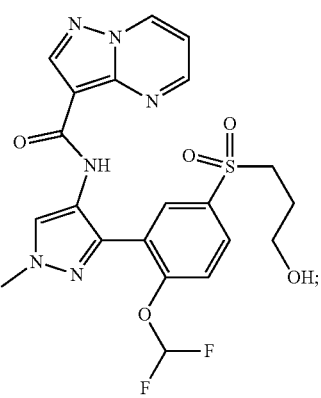
;
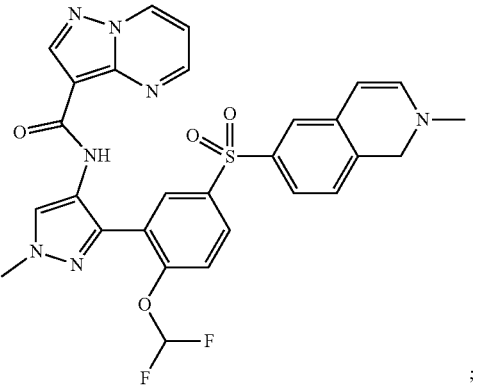
;
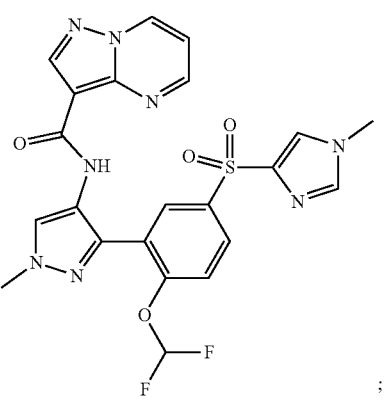
;

-continued
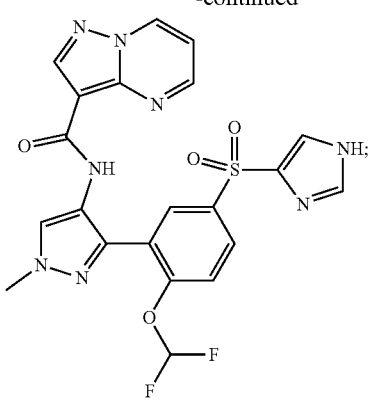
or a pharmaceutically acceptable salt thereof.
2. The compound of claim 1, or a stereoisomer thereof, wherein the compound, or stereoisomer thereof, is selected from the group consisting of:
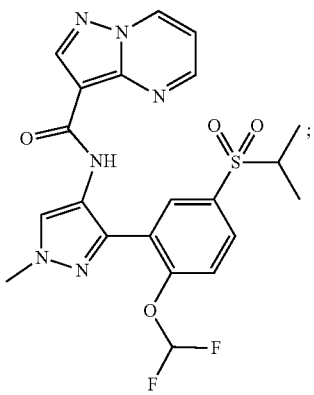
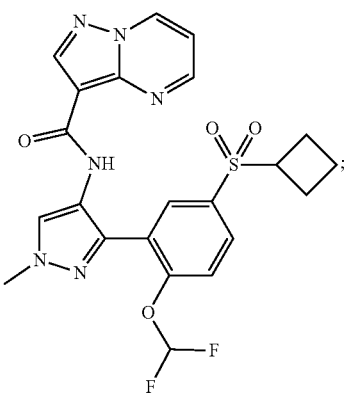
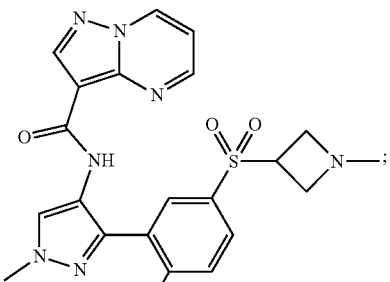
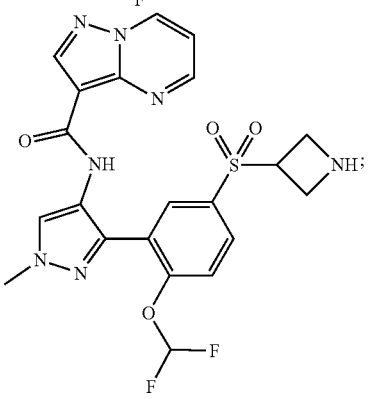

223
-continued
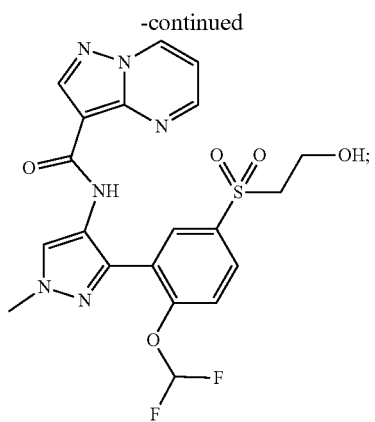
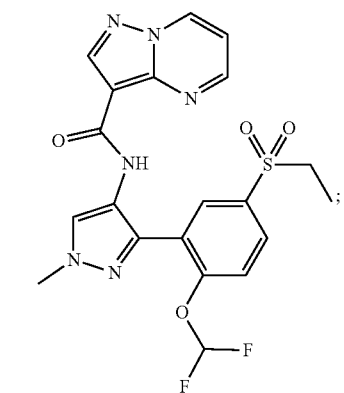
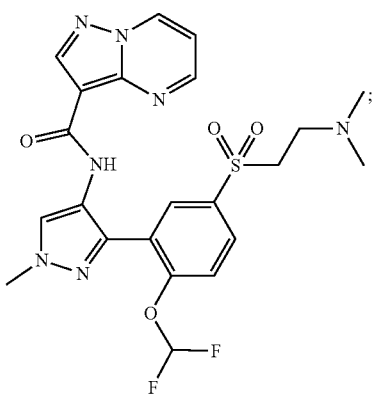
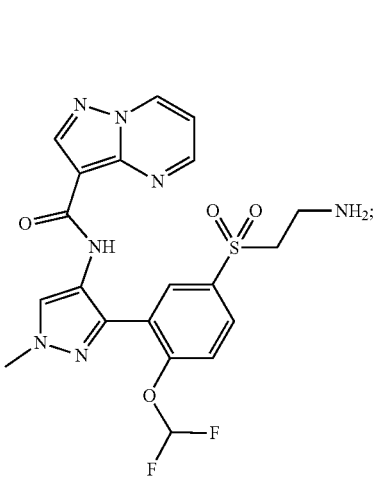
224
-continued
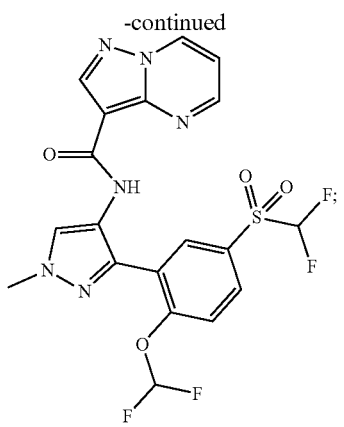
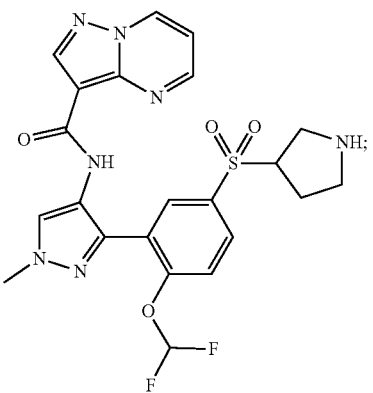
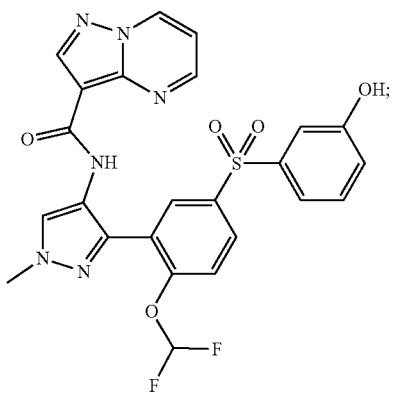
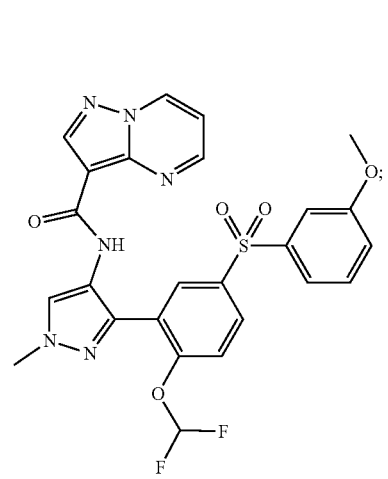

225
-continued
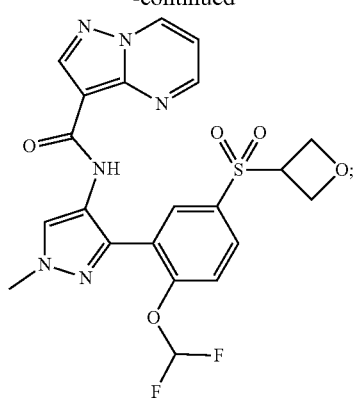
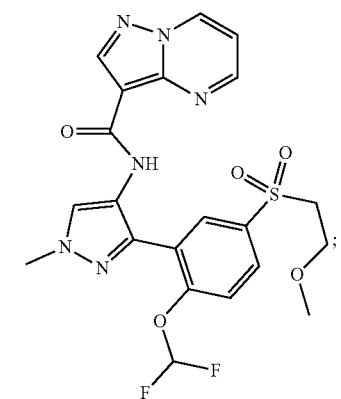
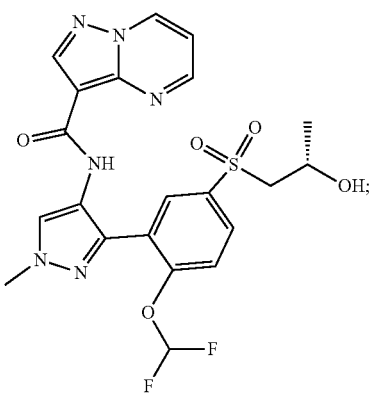
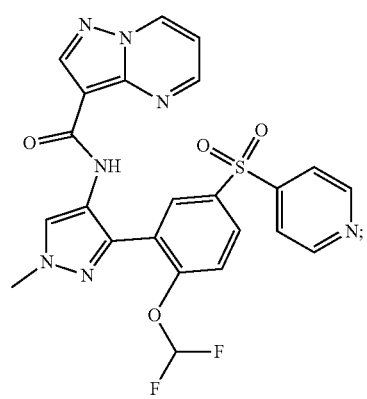
226
-continued
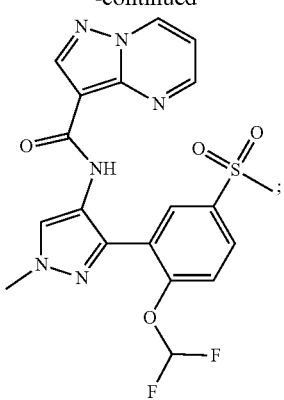
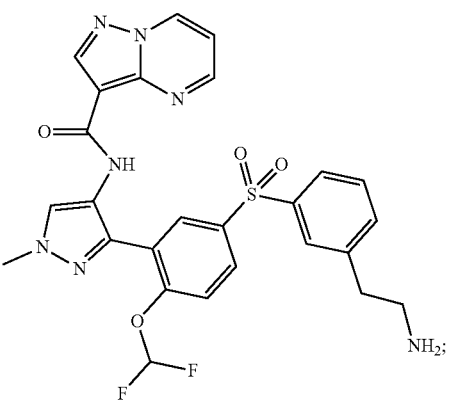
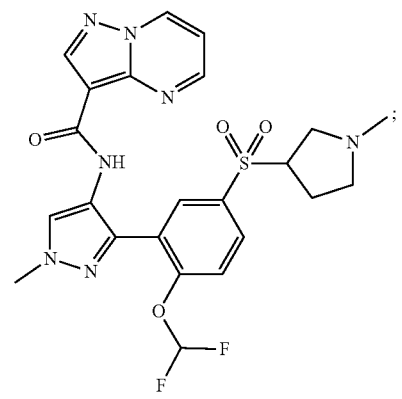
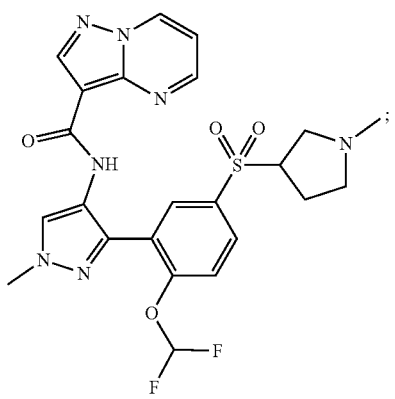

227
-continued
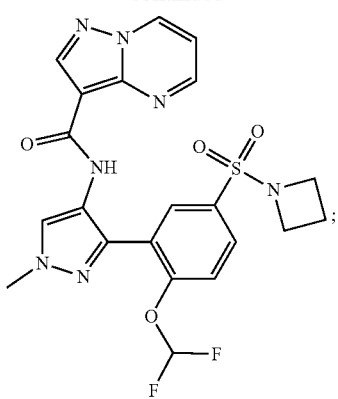
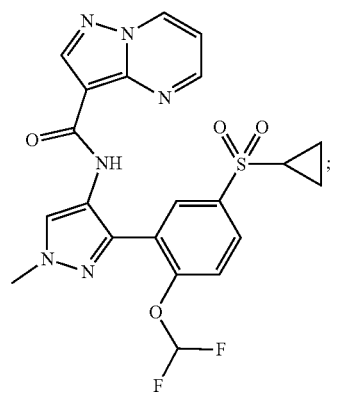
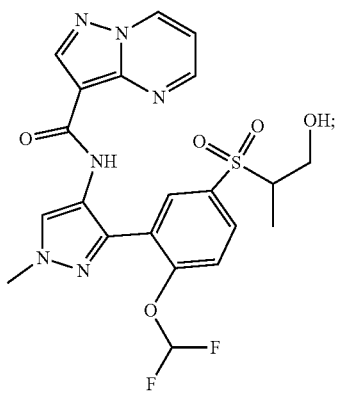
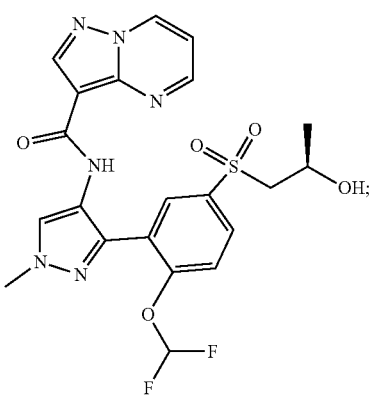
228
-continued
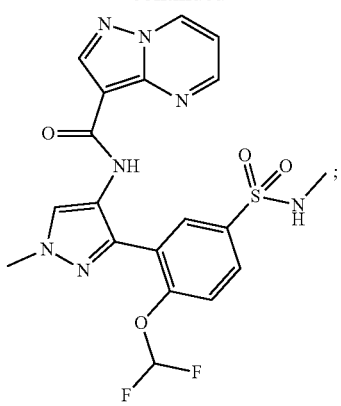
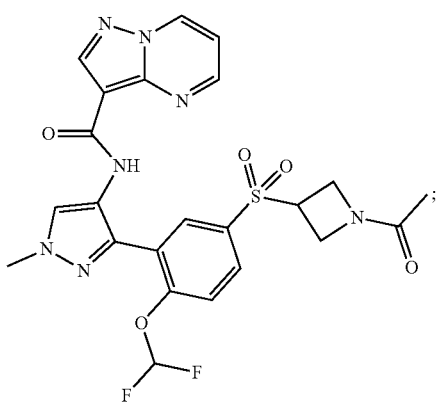
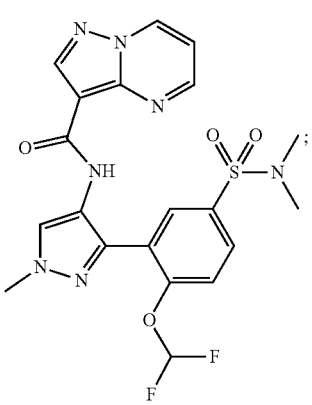
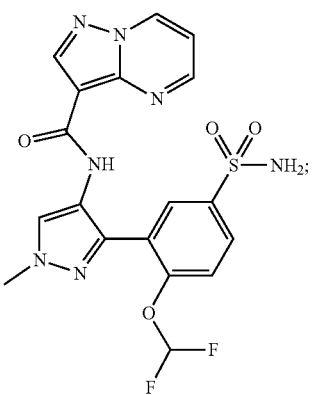

229
-continued
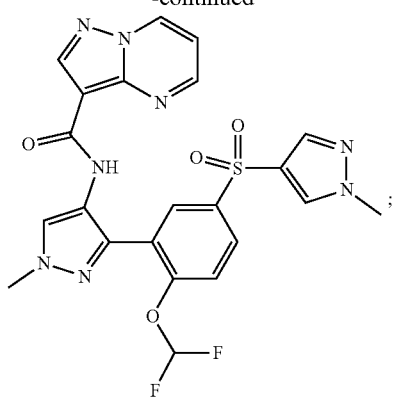
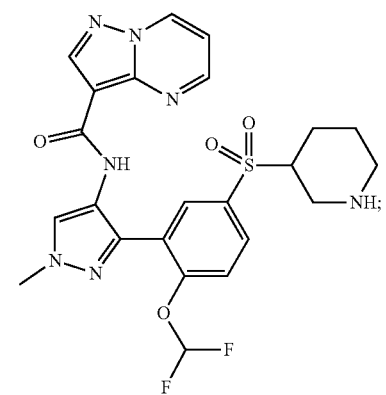
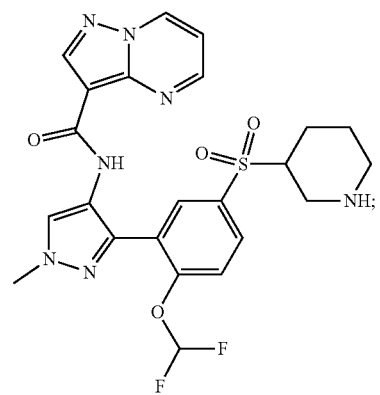
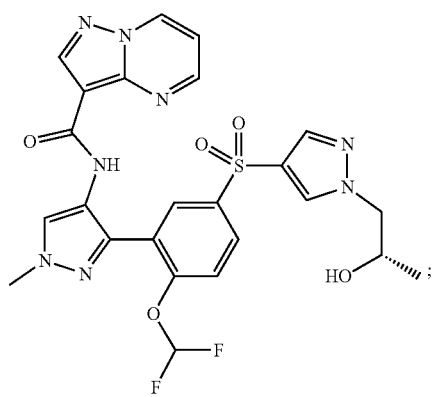
230
-continued
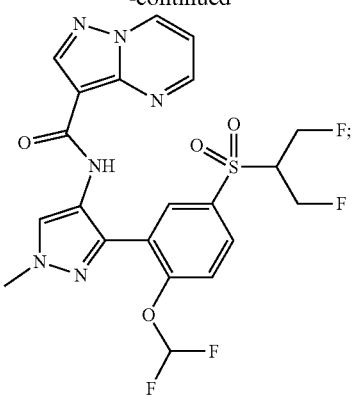
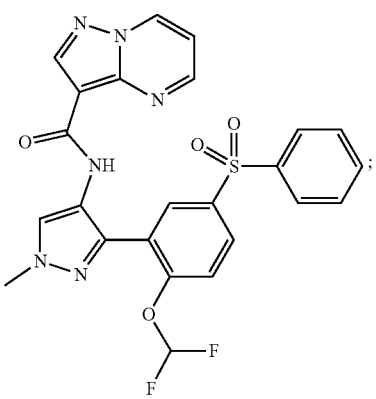
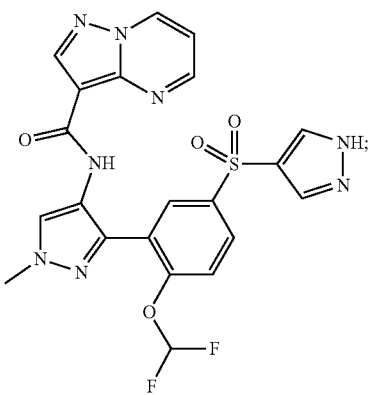
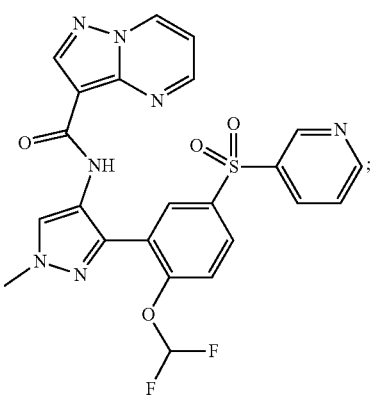

231
-continued
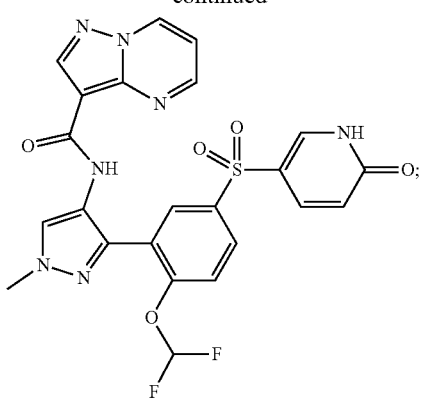
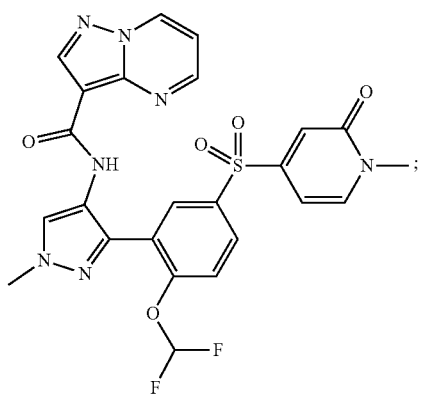
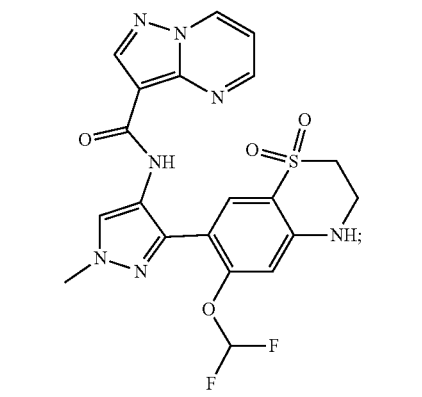
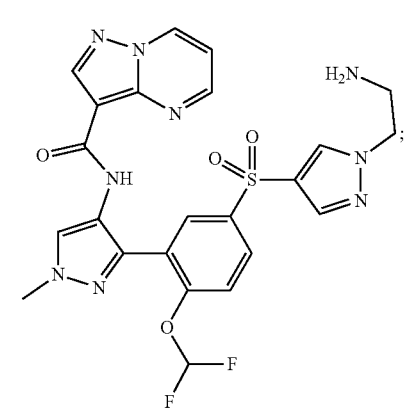
232
-continued
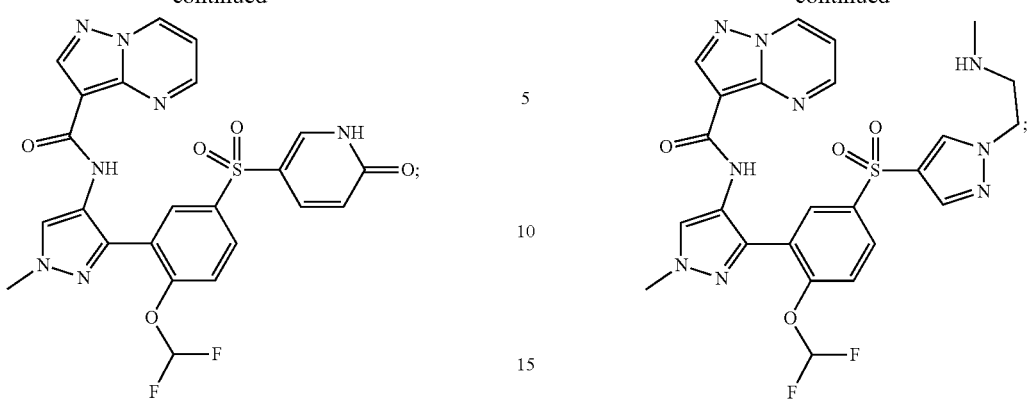
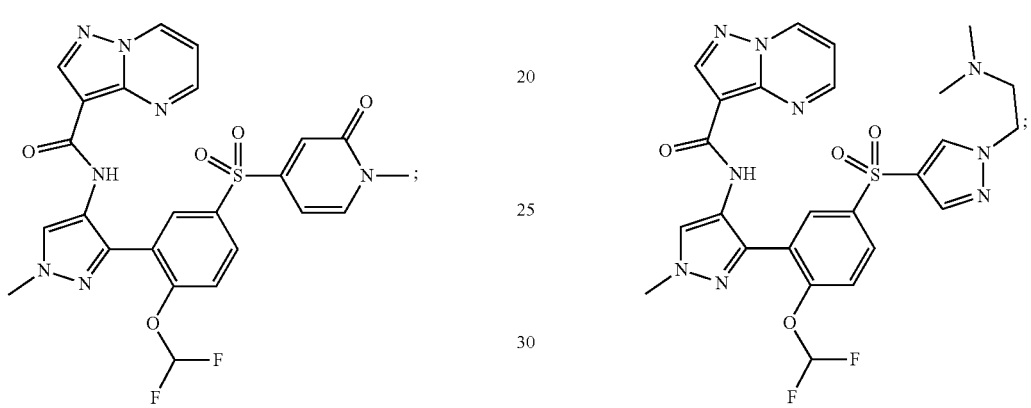
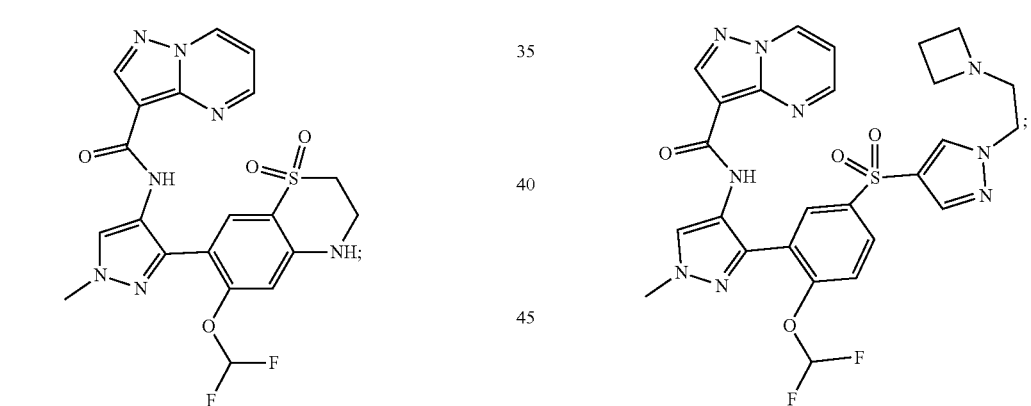
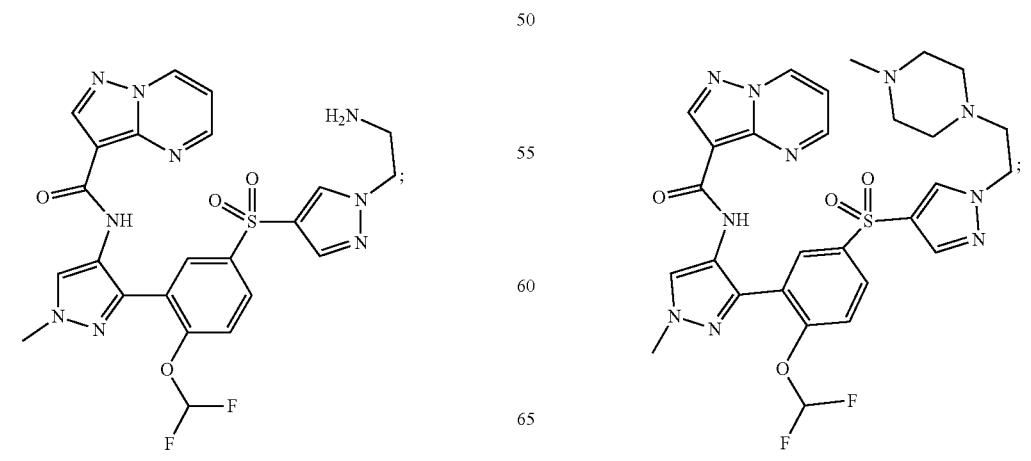

233
-continued
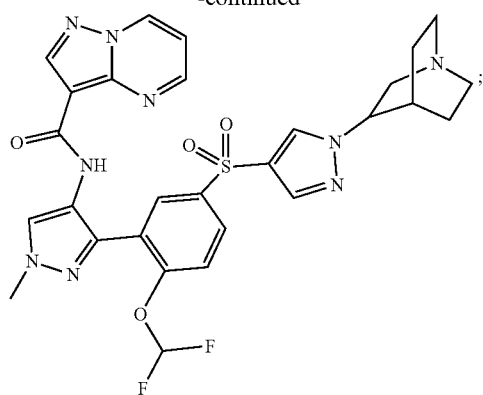
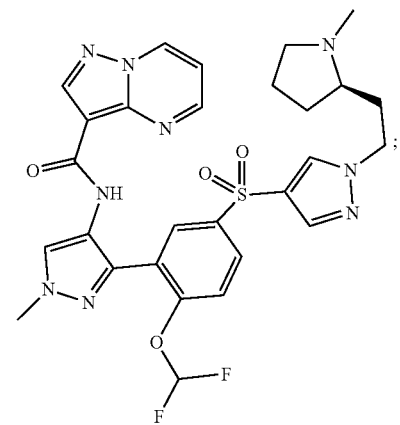
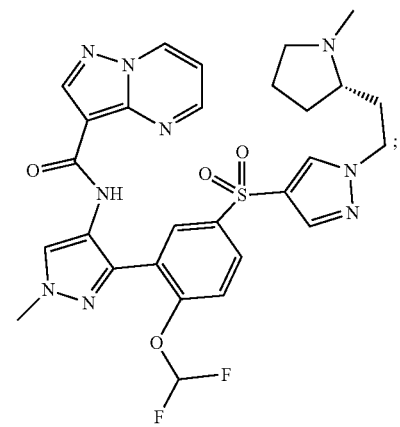
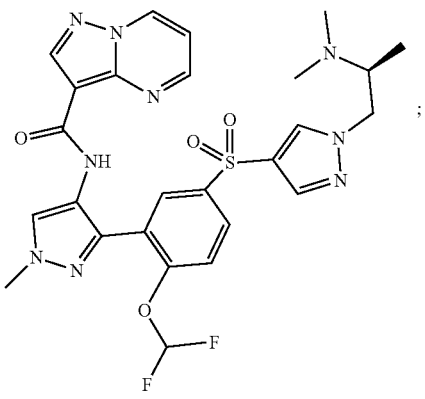
234
-continued
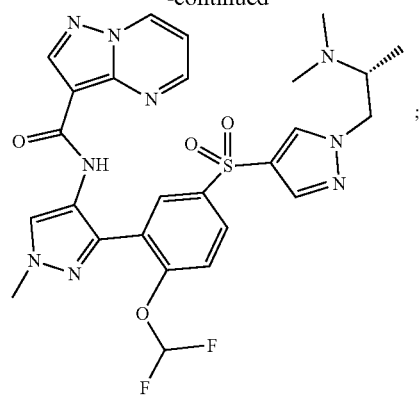
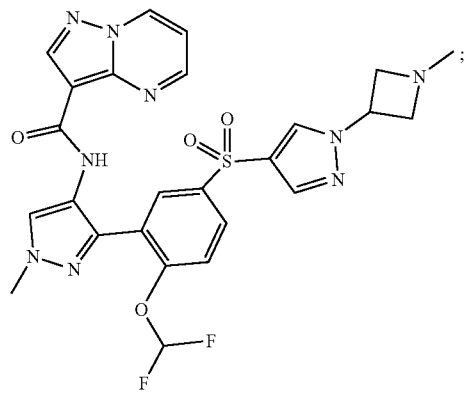
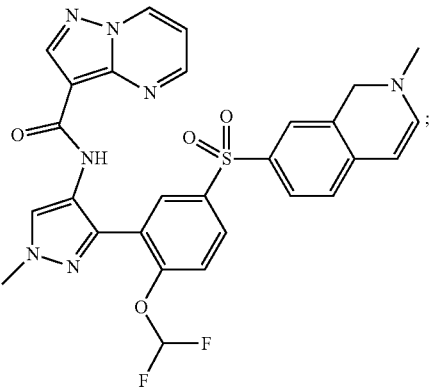
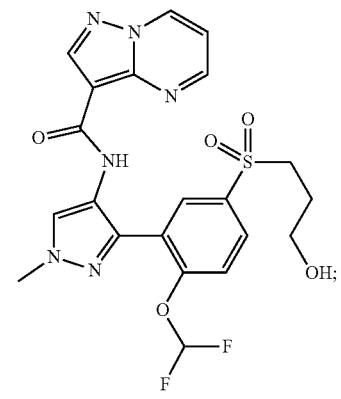

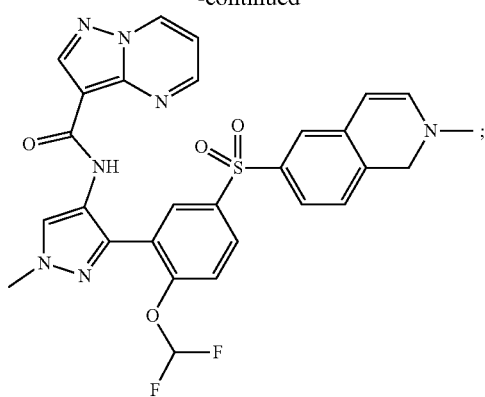
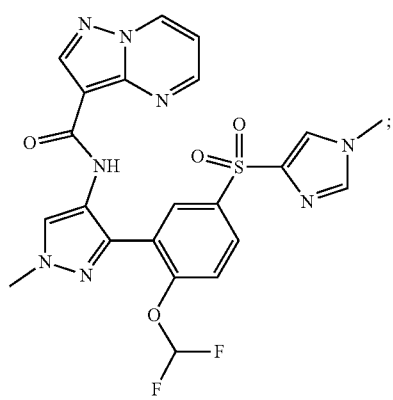
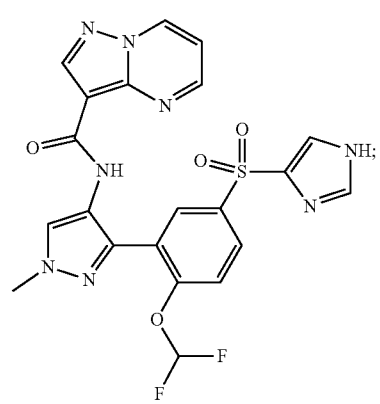
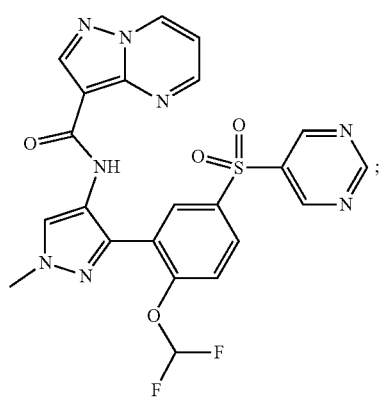
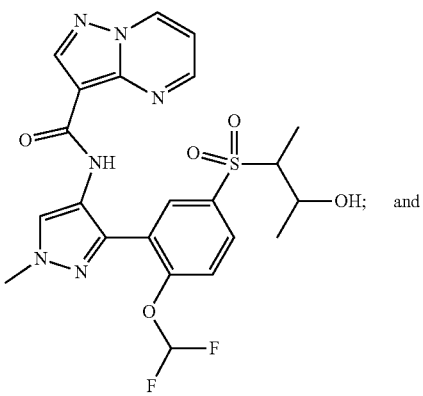
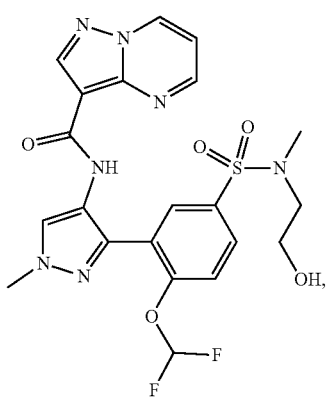
or a pharmaceutically acceptable salt thereof.
3. The compound of claim 2, or a stereoisomer thereof, wherein the compound, or stereoisomer thereof, is selected from the group consisting of:
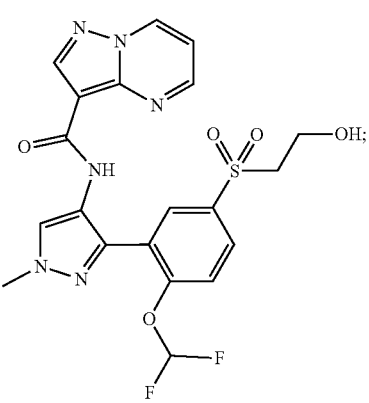 [SMILES: Cn1cc(NC(=O)c2cnn3cccnc23)c(-c2cc(S(=O)(=O)CCO)ccc2OC(F)F)n1]

237
-continued
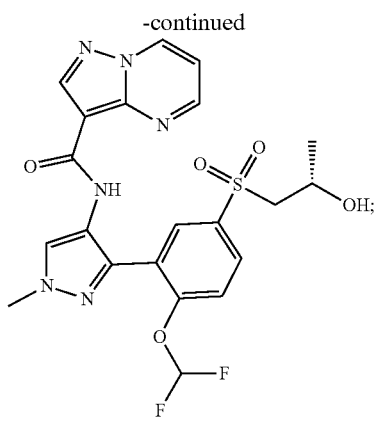
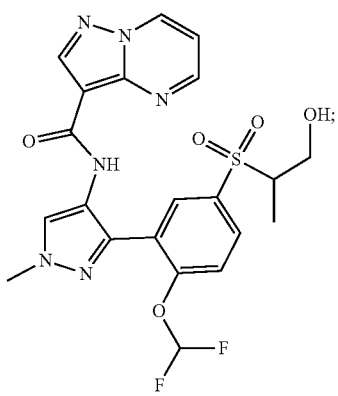 [SMILES: CC(CO)S(=O)(=O)c1ccc(OC(F)F)c(-c2nn(C)cc2NC(=O)c2cnn3cccnc23)c1]
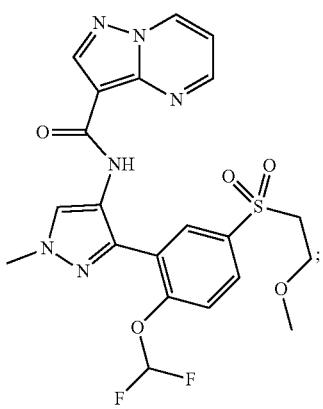
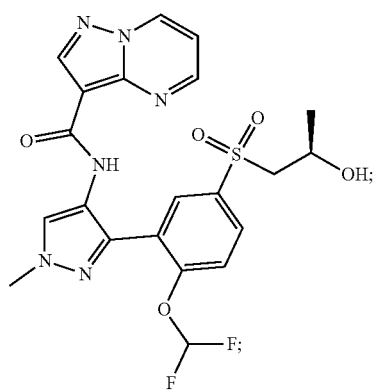 [SMILES: C[C@@H](O)CS(=O)(=O)c1ccc(OC(F)F)c(-c2nn(C)cc2NC(=O)c2cnn3cccnc23)c1]
238
-continued
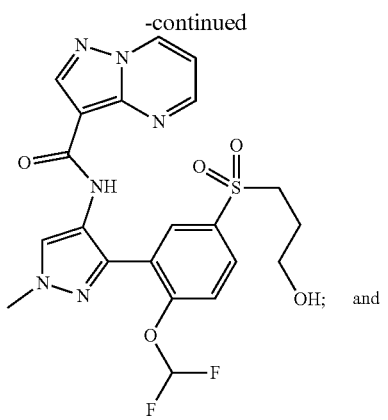
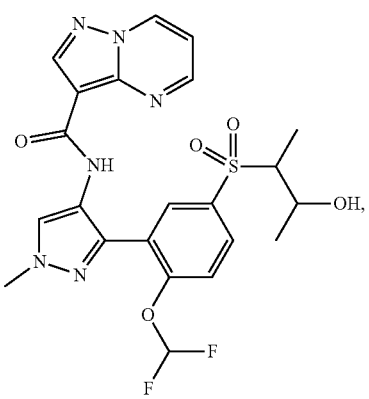
and
or a pharmaceutically acceptable salt thereof.
4. The compound of claim 3, or a stereoisomer thereof, wherein the compound, or stereoisomer thereof, is selected from the group consisting of:
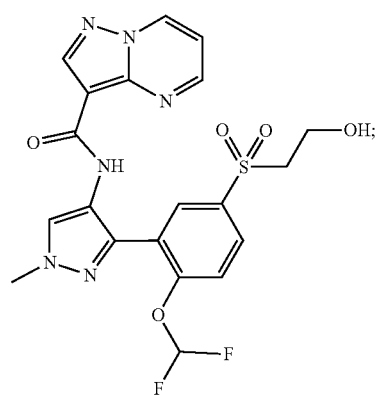

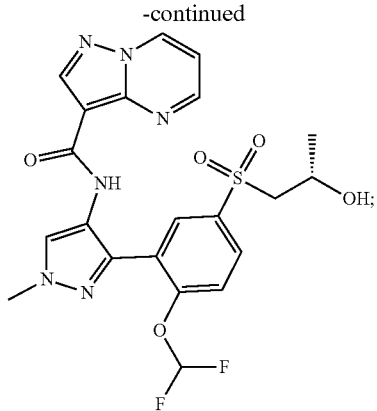
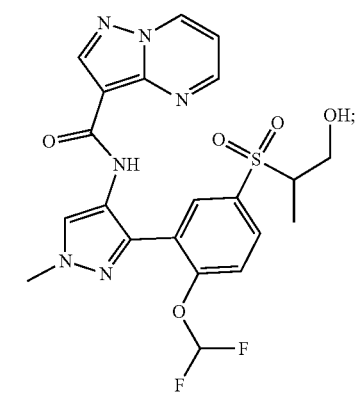
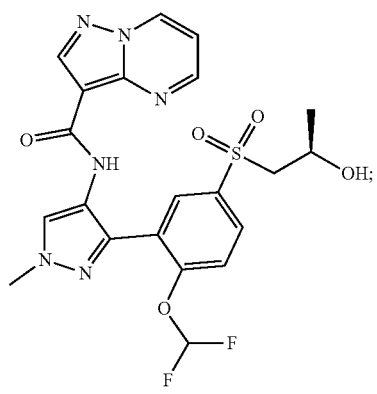
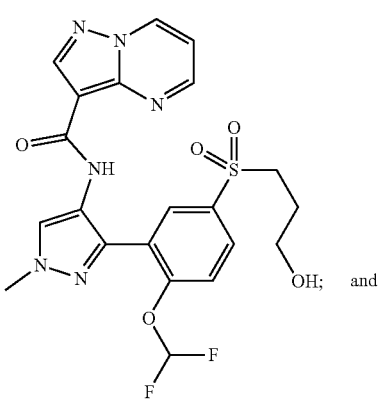
and
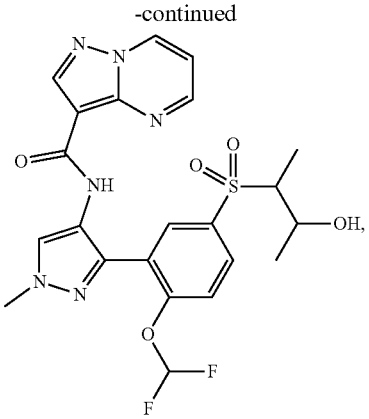
or a pharmaceutically acceptable salt thereof.
5. The compound of claim 1, or a stereoisomer thereof, wherein the compound, or stereoisomer thereof, is selected from the group consisting of:
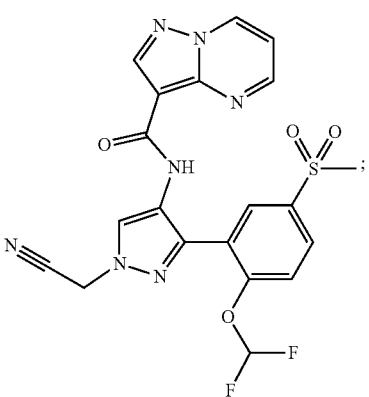
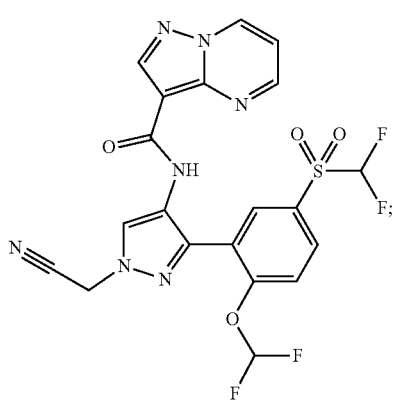

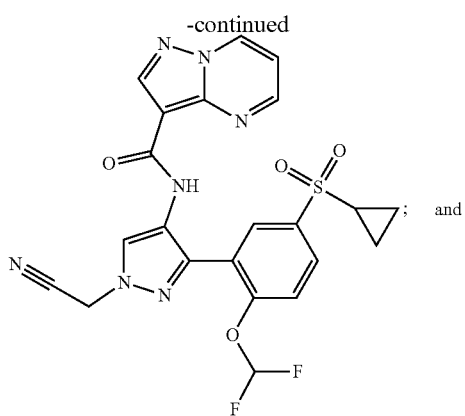

; and

8. The compound

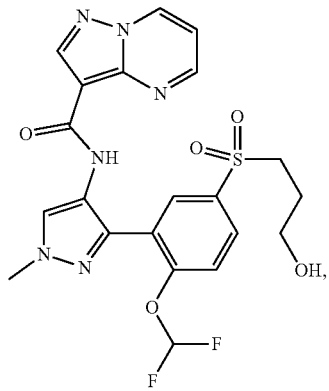

or a pharmaceutically acceptable salt thereof.

9. The compound

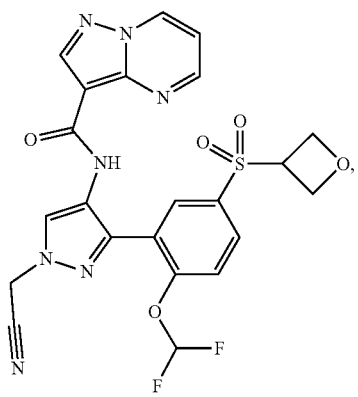

or a pharmaceutically acceptable salt thereof.

6. A pharmaceutical composition comprising a pharmaceutically acceptable carrier, diluent, or excipient and a compound of claim 1, or a pharmaceutically acceptable salt or stereoisomer thereof.

7. The compound

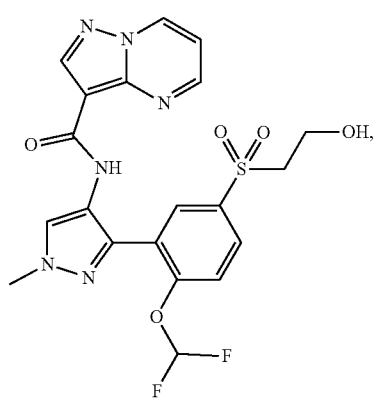

or a pharmaceutically acceptable salt thereof.

or a pharmaceutically acceptable salt thereof.

10. The compound or a pharmaceutically acceptable salt thereof.

11. The compound
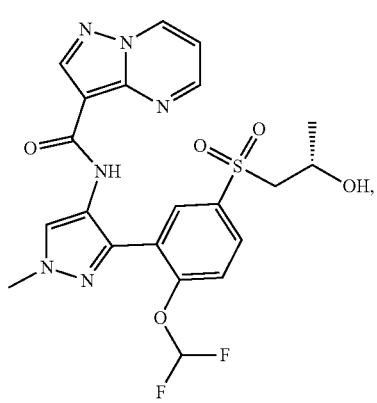 [SMILES: C[C@H](O)CS(=O)(=O)c1ccc(OC(F)F)c(-c2nn(C)cc2NC(=O)c2cnn3cccnc23)c1]
or a pharmaceutically acceptable salt thereof.
12. The compound
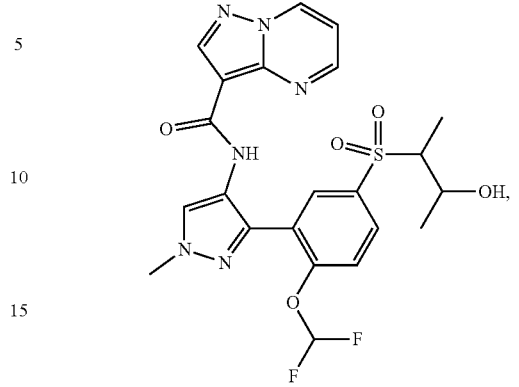
or a pharmaceutically acceptable salt thereof.
* * * * *